US012617784B2

(12) United States Patent
Ma et al.

(10) Patent No.: US 12,617,784 B2
(45) Date of Patent: May 5, 2026

(54) AKT INHIBITOR

(71) Applicant: Nanjing Chia Tai Tianqing Pharmaceutical Co., Ltd., Nanjing (CN)

(72) Inventors: Changyou Ma, Nanjing (CN); He Tian, Nanjing (CN); Jie An, Nanjing (CN); Jianliang Zhao, Nanjing (CN); Donghui Chen, Nanjing (CN); Jian Wu, Nanjing (CN); Dan Xu, Nanjing (CN); Chunxia Zhu, Nanjing (CN); Zhoushan Tian, Nanjing (CN)

(73) Assignee: NANJING CHIA TAI TIANQING PHARMACEUTICAL CO., LTD., Nanjing (CN)

( * ) Notice: Subject to any disclaimer, the term of this patent is extended or adjusted under 35 U.S.C. 154(b) by 971 days.

(21) Appl. No.: 17/426,047

(22) PCT Filed: Jan. 22, 2020

(86) PCT No.: PCT/CN2020/073798

§ 371 (c)(1),
(2) Date: Jul. 27, 2021

(87) PCT Pub. No.: WO2020/156437

PCT Pub. Date: Aug. 6, 2020

(65) Prior Publication Data

US 2022/0144821 A1 May 12, 2022

(30) Foreign Application Priority Data

Jan. 29, 2019 (CN) ......................... 201910084801.3

(51) Int. Cl.
*C07D 471/04* (2006.01)
*C07D 475/06* (2006.01)
*C07D 498/04* (2006.01)
*C07D 519/00* (2006.01)

(52) U.S. Cl.
CPC ......... *C07D 471/04* (2013.01); *C07D 475/06* (2013.01); *C07D 498/04* (2013.01); *C07D 519/00* (2013.01)

(58) Field of Classification Search
CPC .. C07D 471/04; C07D 471/00; C07D 498/00; C07D 498/04; C07D 519/00
See application file for complete search history.

(56) References Cited

FOREIGN PATENT DOCUMENTS

| | | | | |
|---|---|---|---|---|
| CN | 1882347 A | * 12/2006 | ............ B41M 3/008 |
| CN | 102574852 B | 6/2014 | |
| CN | 108503645 A | 9/2018 | |
| JP | 2007512364 A | 5/2007 | |
| JP | 2011509309 A | 3/2011 | |
| JP | 2013508382 A | 3/2013 | |
| JP | 2016500064 A | 1/2016 | |
| JP | 2016500065 A | 1/2016 | |
| JP | 2017526698 A | 9/2017 | |
| JP | 2021522237 A | 8/2021 | |
| KR | 20110137838 A | 12/2011 | |
| WO | 2005051304 A2 | 6/2005 | |
| WO | 2005051304 A3 | 7/2006 | |
| WO | 2009089462 A1 | 7/2009 | |
| WO | 2014078637 A1 | 5/2014 | |

OTHER PUBLICATIONS

Japanese Patent Office, First Office Action for Application No. 2021-543533 issued Dec. 26, 2023; 2 pgs.
European Patent Office, Extended European Search Report, EP20748221.7, Sep. 20, 2022, 8 pages.
Canadian Patent Office, First Office Action for Application No. 3127884 dated Feb. 28, 2024; 6 pgs.
CAS SciFinder, CAS Registry No. 853686-96-1, American Chemical Society, 2021, 1 page.
Korean Patent Office, First Office Action for KR Application No. 10-2021-7027161 issued Feb. 10, 2025; 11 pgs.

* cited by examiner

*Primary Examiner* — Brenda L Coleman
*Assistant Examiner* — Madeline E Braun
(74) *Attorney, Agent, or Firm* — Umberg Zipser LLP

(57) ABSTRACT

An AKT inhibitor is provided, which specifically relates to a compound represented by formula I or a pharmaceutically acceptable salt thereof. The present invention further provides a preparation method thereof, and the use thereof in prevention and/or treatment of a disease mediated by AKT protein kinase.

I

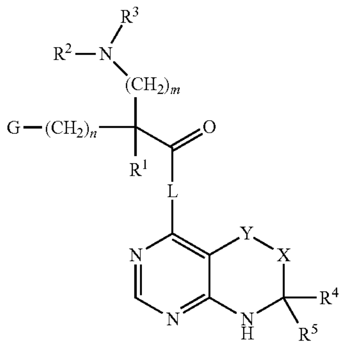

22 Claims, 3 Drawing Sheets

AKT INHIBITOR

CROSS-REFERENCE TO RELATED APPLICATIONS

This application is a U.S. National-Stage entry under 35 U.S.C. § 371 based on International Application No. PCT/CN2020/073798, filed Jan. 22, 2020, which was published under PCT Article 21(2) and which claims the priority of the Chinese patent application with the application number 201910084801.3 filed with the China National Intellectual Property Administration on Jan. 29, 2019, the entire content of which are incorporated in their entirety by reference.

FIELD OF THE INVENTION

The present invention belongs to the field of medicinal chemistry, and specifically relates to an AKT inhibitor, and a preparation method and medical use thereof.

BACKGROUND OF THE INVENTION

The PI3K/AKT/mTOR pathway composed of phosphatidylinositol 3-kinase (PI3K) and its downstream protein AKT (also known as protein kinase B, PKB) and mammalian target of rapamycin (mTOR), as a very important signal transduction pathway in cells, plays an extremely important biological function in the process of cell growth, survival, proliferation, apoptosis, angiogenesis, and autophagy. Abnormal activation of this pathway can cause a series of diseases, including cancer, neuropathy, autoimmune diseases and hemic and lymphatic system diseases.

AKT, a type of serine/threonine kinase, affects cell survival, growth, metabolism, proliferation, migration and differentiation through numerous downstream effectors. Over 50% of human tumors have over-activation of AKT, especially prostate cancer, pancreatic cancer, bladder cancer, ovarian cancer, and breast cancer. Over-activation of AKT can lead to tumorigenesis, tumor metastasis and drug resistance development.

AKT has three subtypes: AKT1, AKT2 and AKT3. As a typical protein kinase, each subtype is composed of an amino-terminal PH domain (Pleckstrin homology domain), a kinase domain that binds ATP in the middle, and a carboxy-terminal regulatory domain. About 80% of the amino acid sequences of the three subtypes are homologous, with large changes only in the junction region of the PH domain and the kinase domain.

Currently, the targeting drugs for the PI3K/AKT/mTOR signal pathway are mainly PI3K inhibitors and mTOR inhibitors, while AKT is at the core of the signal transduction pathway. Inhibition of AKT activity can not only avoid the serious side effects caused by inhibiting upstream PI3K, but also avoid the negative feedback mechanism caused by inhibiting downstream mTOR, which affects the efficacy of the drug. Therefore, searching for effective and selective AKT inhibitors is an important direction of current tumor-targeted drug research and development. CN101631778A discloses a class of cyclopenta[D]pyrimidine derivatives, CN101578273A discloses a class of hydroxylated and methoxylated cyclopenta[D]pyrimidine derivatives, CN101511842A discloses a class of dihydrofuro pyrimidine derivatives, and CN101970415A discloses a class of 5H-cyclopenta[d]pyrimidine derivatives. These compounds have an $IC_{50}$ of inhibiting AKT1 of less than 10 μM.

SUMMARY OF THE INVENTION

In one aspect, the present invention provides a compound represented by formula I or pharmaceutically acceptable salts thereof,

I

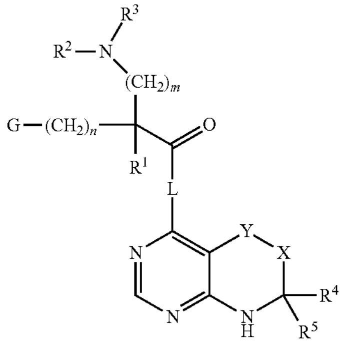

wherein $R^1$ is selected from the group consisting of H, OH, halogen, CN, $NH_2$, $NO_2$, or $C_1$-$C_6$ alkyl optionally substituted by halogen or OH;

$R^2$ and $R^3$ are each independently selected from the group consisting of H, $C_1$-$C_6$ alkyl, $C_3$-$C_6$ cycloalkyl, ($C_3$-$C_6$ cycloalkyl)-($CH_2$)—, ($C_3$-$C_6$ cycloalkyl)-($CH_2CH_2$)—, benzyl, phenethyl, pyrrolidinyl, tetrahydrofuranyl and tetrahydropyranyl, wherein the $C_1$-$C_6$ alkyl, $C_3$-$C_6$ cycloalkyl, ($C_3$-$C_6$ cycloalkyl)-($CH_2$)— or ($C_3$-$C_6$ cycloalkyl)-($CH_2CH_2$)— is optionally substituted by halogen, OH, CN, $NH_2$ or $C_1$-$C_3$ alkoxy, the benzyl or phenethyl is optionally substituted by halogen, OH, CN, $NO_2$, $NH_2$, $C_1$-$C_3$ alkoxy, halogenated $C_1$-$C_3$ alkoxy, $C_1$-$C_3$ alkyl or halogenated $C_1$-$C_3$ alkyl, the pyrrolidinyl, tetrahydrofuranyl or tetrahydropyranyl is optionally substituted by halogen, OH, $C_1$-$C_3$ alkyl, cyclopropylmethyl or $C_1$-$C_4$ alkanoyl; or $R^1$ and $R^2$, together with the atoms to which $R^1$ and $R^2$ are attached, form a 4-7 membered nitrogen-containing heterocyclic ring;

m and n are each independently 0, 1, 2 or 3;

$R^4$ and $R^5$ both are hydrogen or $R^4$ and $R^5$ form =O together;

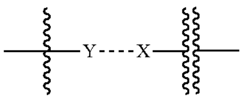

is selected from the group consisting of

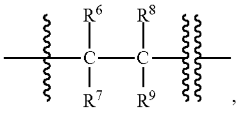
,
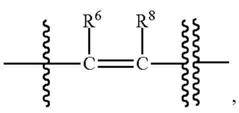
,
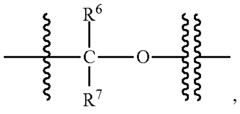
,
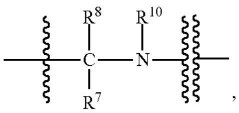
,

-continued

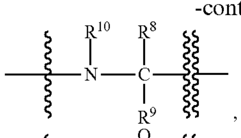,
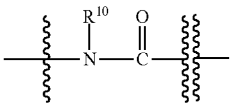,
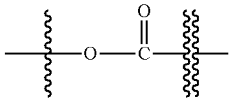,
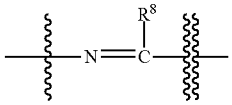 and
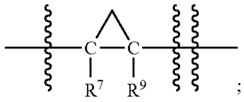;

$R^6$, $R^7$, $R^8$, and $R^9$ are each independently selected from the group consisting of H, CN, $C_1$-$C_6$ alkyl and $C_1$-$C_6$ alkoxy, wherein the $C_1$-$C_6$ alkyl or $C_1$-$C_6$ alkoxy is optionally substituted by halogen, OH, CN or $C_1$-$C_3$ alkoxy;

$R^{10}$ is H or $C_1$-$C_6$ alkyl, wherein the $C_1$-$C_6$ alkyl is optionally substituted by halogen, OH, CN or $C_1$-$C_3$ alkoxy;

L is an optionally substituted 5-12 membered saturated heterocyclic ring containing 1-2 nitrogen atoms;

G is a 6-10 membered aryl or a 5-10 membered heteroaryl optionally substituted by 1-5 $R^{11}$;

$R^{11}$ is independently selected from the group consisting of halogen, OH, CN, $NH_2$, $NO_2$, benzyloxy, —NH($C_1$-$C_6$ alkyl), —N($C_1$-$C_6$ alkyl)$_2$, —C(═O)$NH_2$, —C(═O)NH($C_1$-$C_6$ alkyl), —C(═O)N($C_1$-$C_6$ alkyl)$_2$, —$SO_2$($C_1$-$C_6$ alkyl), $C_1$-$C_6$ alkyl and $C_1$-$C_6$ alkoxy, wherein the $C_1$-$C_6$ alkyl or $C_1$-$C_6$ alkoxy is optionally substituted by halogen;

with the proviso that neither $R^1$ nor $R^2$ is H if $R^1$ and $R^2$, together with the atoms to which $R^1$ and $R^2$ are attached, form a 4-7 membered nitrogen-containing heterocyclic ring.

In some embodiments, $R^1$ is selected from the group consisting of H, OH, and $C_1$-$C_6$ alkyl optionally substituted by halogen or OH; in some preferred embodiments, $R^1$ is selected from the group consisting of H, OH, Me, $CF_3$ and $CH_2OH$; in some more preferred embodiments, $R^1$ is H or OH; in some most preferred embodiments, $R^1$ is H.

In some embodiments, $R^2$ and $R^3$ are each independently selected from the group consisting of H, $C_1$-$C_6$ alkyl, $C_3$-$C_6$ cycloalkyl, ($C_3$-$C_6$ cycloalkyl)-($CH_2$)—, ($C_3$-$C_6$ cycloalkyl)-($CH_2CH_2$)—, benzyl, phenethyl, pyrrolidinyl and tetrahydropyranyl, wherein the $C_1$-$C_6$ alkyl, $C_3$-$C_6$ cycloalkyl, ($C_3$-$C_6$ cycloalkyl)-($CH_2$)— or ($C_3$-$C_6$ cycloalkyl)-($CH_2CH_2$)— is optionally substituted by F, Cl, Br, I, OH, CN, $NH_2$ or $C_1$-$C_3$ alkoxy, the benzyl or phenethyl is optionally substituted by F, Cl, Br, I, OH, OMe, $CF_3$ or Me, and the pyrrolidinyl or tetrahydropyranyl is optionally substituted by F, Cl, Br, I, OH, $C_1$-$C_3$ alkyl, cyclopropylmethyl or $C_1$-$C_4$ alkanoyl.

In some embodiments, $R^2$ and $R^3$ are each independently selected from the group consisting of H, methyl, ethyl, isopropyl, isobutyl, tert-butyl, 3-pentyl, $CH_2OH$, $CH_2CH_2OH$, $CH_2CH_2OMe$, $CF_3$, $CH_2CF_3$, $CH_2CHF_2$, $CH_2CH_2F$, cyclopropyl, cyclopentyl, cyclohexyl, cyclopropyl-($CH_2$)—, cyclopentyl-($CH_2$)—, cyclohexyl-($CH_2$)—, cyclopropyl-($CH_2CH_2$)—, cyclopentyl-($CH_2CH_2$)—, benzyl, 4-fluorobenzyl, 4-chlorobenzyl, 4-fluorophenethyl, 4-chlorophenethyl and tetrahydropyran-4-yl.

In some preferred embodiments, $R^2$ and $R^3$ are each independently selected from the group consisting of H, methyl, ethyl, isopropyl, cyclopropyl, cyclohexyl, cyclopropyl-($CH_2$)—, cyclohexyl-($CH_2$)— and tetrahydropyran-4-yl.

In some more preferred embodiments, $R^2$ and $R^3$ are each independently selected from the group consisting of H, isopropyl and cyclopropyl.

In some embodiments, $R^2$ is H.

In some embodiments, $R^3$ is isopropyl or cyclopropyl.

In some embodiments, $R^2$ is H and $R^5$ is isopropyl or cyclopropyl.

In some embodiments, $R^1$ and $R^2$, together with the atoms to which $R^1$ and $R^2$ are attached, form

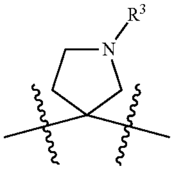,
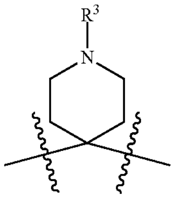 or
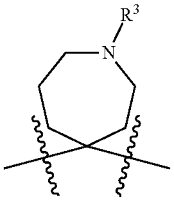, wherein, the definition of $R^3$ is as above.

In some preferred embodiments, $R^1$ and $R^2$, together with the atoms to which $R^1$ and $R^2$ are attached, form

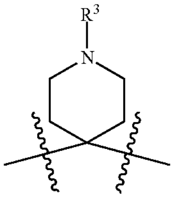, wherein, the definition of $R^3$ is as above.

In some embodiments, m is 0, 1, or 2; in some preferred embodiments, m is 0 or 1; in some more preferred embodiments, m is 1.

In some embodiments, n is 0, 1, or 2; in some preferred embodiments, n is 0 or 1; in some more preferred embodiments, n is 0.

In some embodiments, $R^4$ and $R^5$ both are H.

In some embodiments, $R^4$ and $R^5$ form ═O together.

In some embodiments,

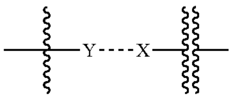

is selected from the group consisting of

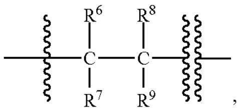,
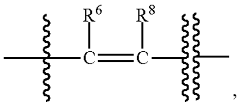,
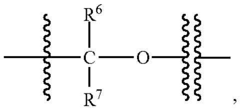,
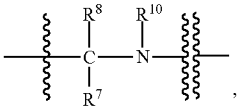,
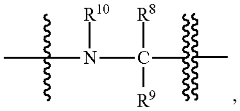,
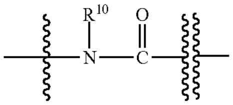,
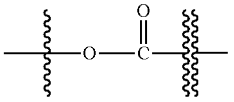 and
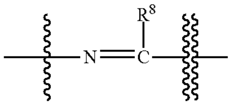.

In some embodiments,

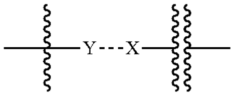

is selected from the group consisting of

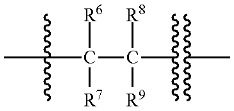,
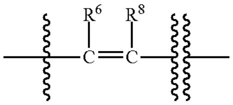,
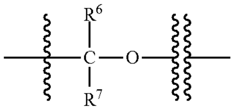,
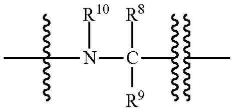 and
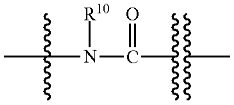.

In some embodiments,

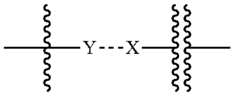

is selected from the group consisting of

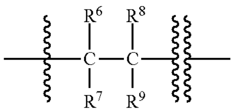,
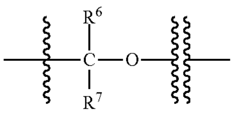 and

-continued

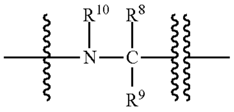.

In some embodiments,

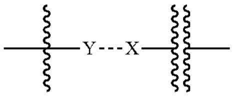

is

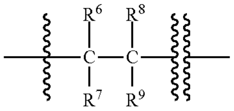, and $R^4$ and $R^5$ form =O together.

In some embodiments,

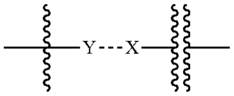

is

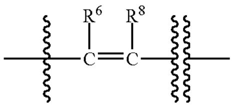, and $R^4$ and $R^5$ form =O together.

In some embodiments,

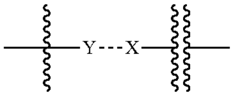

is

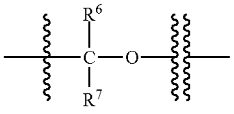, and $R^4$ and $R^5$ form =O together.

In some embodiments,

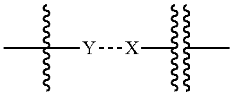

is

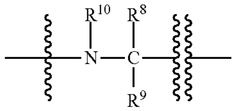

and $R^4$ and $R^5$ form =O together.

In some embodiments,

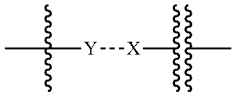

is

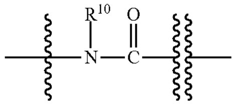

and $R^4$ and $R^5$ both are H.

In some embodiments,

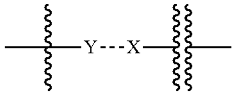

is

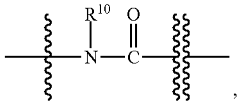

and $R^4$ and $R^5$ form =O together.

In some embodiments, $R^6$, $R^7$, $R^8$, and $R^9$ are each independently selected from the group consisting of H, CN, $C_1$-$C_6$ alkyl and $C_1$-$C_6$ alkoxy, wherein the $C_1$-$C_6$ alkyl or $C_1$-$C_6$ alkoxy is optionally substituted by F, Cl, Br, I, OH, CN or OMe.

In some embodiments, $R^6$, $R^7$, $R^8$, and $R^9$ are each independently selected from the group consisting of H, CN, $C_1$-$C_6$ alkyl and $C_1$-$C_6$ alkoxy, wherein the $C_1$-$C_6$ alkyl or $C_1$-$C_6$ alkoxy is optionally substituted by F, CN or OH.

In some embodiments, $R^6$, $R^7$, $R^8$, and $R^9$ are each independently selected from the group consisting of H, CN, methyl, ethyl, propyl, isopropyl, $CF_3$, $CH_2CF_3$, $CH_2CHF_2$, $CH_2CH_2F$, $CH_2CN$, $CH_2CH_2CN$, $CH_2OH$, $CH_2CH_2OH$, OMe, OEt, $OCH_2CH_2CH_3$ and isopropoxy.

In some embodiments, $R^6$ is selected from the group consisting of H, CN, methyl, ethyl, propyl, isopropyl, $CF_3$, $CH_2CF_3$, $CH_2CHF_2$, $CH_2CH_2F$, $CH_2CN$, $CH_2CH_2CN$, $CH_2OH$, $CH_2CH_2OH$, OMe, OEt, $OCH_2CH_2CH_3$ and isopropoxy; in some preferred embodiments, $R^6$ is selected from the group consisting of H, CN, methyl, ethyl, isopropyl, $CF_3$, $CH_2CH_2OH$, OMe and OEt; in some more preferred embodiments, $R^6$ is selected from the group consisting of H, CN, methyl, $CF_3$ and OMe; in some more preferred embodiments, $R^6$ is selected from the group consisting of CN, methyl, $CF_3$ and OMe; in some more preferred embodiments, $R^6$ is selected from the group consisting of H, CN and methyl; in some more preferred embodiments, $R^6$ is selected from the group consisting of H, $CF_3$ and methyl; in some more preferred embodiments, $R^6$ is methyl or $CF_3$.

In some embodiments, $R^7$ is H.

In some embodiments, $R^8$ is selected from the group consisting of H, CN, methyl, ethyl, propyl, isopropyl, $CF_3$, $CH_2CF_3$, $CH_2CHF_2$, $CH_2CH_2F$, $CH_2CN$, $CH_2CH_2CN$, $CH_2OH$, $CH_2CH_2OH$, OMe, OEt, $OCH_2CH_2CH_3$ and isopropoxy; in some preferred embodiments, $R^8$ is selected from the group consisting of H, CN, methyl, ethyl, isopropyl, $CF_3$, $CH_2CH_2OH$, OMe and OEt; in some more preferred embodiments, $R^8$ is selected from the group consisting of H, CN and methyl; in some more preferred embodiments, $R^8$ is H or CN; in some more preferred embodiments, $R^8$ is H or methyl; in some more preferred embodiments, $R^8$ is H.

In some embodiments, $R^9$ is H.

In some embodiments, $R^{10}$ is H or $C_1$-$C_6$ alkyl, wherein the $C_1$-$C_6$ alkyl is optionally substituted by halogen, OH or CN; in some embodiments, $R^{10}$ is selected from the group consisting of H, methyl, ethyl, propyl, isopropyl, $CF_3$, $CH_2CF_3$, $CH_2CHF_2$, $CH_2CH_2F$, $CH_2CN$, $CH_2CH_2CN$, $CH_2OH$ and $CH_2CH_2OH$; in some preferred embodiments, $R^{10}$ is selected from the group consisting of methyl, ethyl, isopropyl, $CH_2CF_3$, $CH_2CHF_2$, $CH_2CN$ and $CH_2CH_2OH$; in some more preferred embodiments, $R^{10}$ is selected from the group consisting of methyl, ethyl, $CH_2CN$ and $CH_2CH_2OH$; in some more preferred embodiments, $R^{10}$ is methyl.

In some embodiments, L is selected from the group consisting of the following group optionally substituted by one or more $R^{12}$:

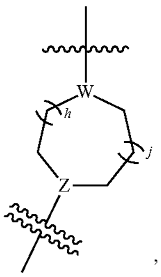

,

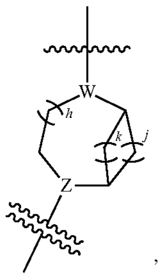

,

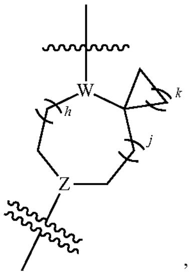

,

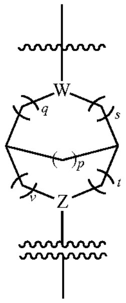

and

-continued

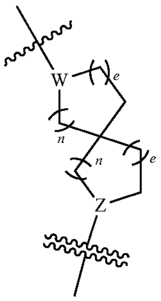

wherein a single wavy line is a position where L is connected to carbonyl, and a double wavy line is a position where L is connected to pyrimidine;

$R^{12}$ is selected from the group consisting of halogen, OH, CN, vinyl, $C_1$-$C_6$ alkyl and $C_1$-$C_6$ alkoxy, wherein the $C_1$-$C_6$ alkyl or $C_1$-$C_6$ alkoxy is optionally substituted by halogen or OH;

h is 0, 1, 2, 3 or 4;

j is 0, 1, 2, or 3;

k is 1, 2, 3, or 4;

q, s, v, and t each independently are 0, 1, or 2, and q, s, v, and t are not 0 simultaneously;

p is 0, 1, 2, or 3;

e is 0, 1, or 2;

u is 1, 2, or 3;

W and Z each independently are N or C, and at least one of W and Z is N.

In some embodiments, $R^{12}$ is selected from the group consisting of F, Cl, Br, I, OH, CN, vinyl, methyl, ethyl, propyl, isopropyl, $CF_3$, $CH_2CF_3$, $CH_2CHF_2$, $CH_2CH_2F$, OMe, OEt, $CH_2OH$, $CH_2CH_2OH$, $OCH_2OH$ and $OCH_2CH_2OH$; in some preferred embodiments, $R^{12}$ is selected from the group consisting of methyl, ethyl, isopropyl, $CF_3$, $CH_2CF_3$, OMe, OEt, $CH_2OH$ and $OCH_2OH$; in some more preferred embodiments, $R^{12}$ is selected from the group consisting of methyl, ethyl and $CF_3$; in some more preferred embodiments, $R^{12}$ is methyl.

In some embodiments, h is 0, 1, 2 or 3 and j is 0, 1, or 2; in some preferred embodiments, h is 0, 1 or 2 and j is 0 or 1; in some more preferred embodiments, h is 0 or 1 and j is 0; in some more preferred embodiments, h is 1 and j is 0.

In some embodiments, k is 1, 2, or 3; in some preferred embodiments, k is 1 or 3; in some more preferred embodiments, k is 1.

In some embodiments, q, s, v, and t each independently are 0 or 1, and q, s, v, and t are not 0 simultaneously; in some preferred embodiments, q, s, v, and t all are 1; in some more preferred embodiments, q and s both are 0, and v and t both are 1; in some more preferred embodiments, q and s both are 1, and v and t both are 0; in some more preferred embodiments, s and v both are 0, and q and t both are 1.

In some embodiments, p is 0, 1, or 2; in some preferred embodiments, p is 0 or 2; in some more preferred embodiments, p is 2.

In some embodiments, e is 0 or 1, and u is 1 or 2; in some preferred embodiments, e is 0 or 1, and u is 1; in some more preferred embodiments, e is 0, and u is 1.

In some embodiments, W is C and Z is N; in some preferred embodiments, W is N and Z is C; in some more preferred embodiments, W and Z both are N.

In some more preferred embodiments, L is selected from the group consisting of the following group optionally substituted by one or more $R^2$:

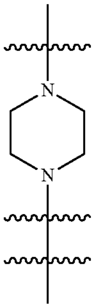, 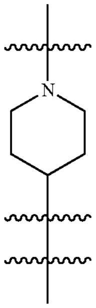, 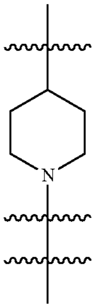, 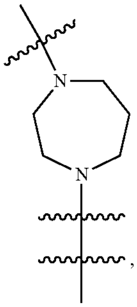,

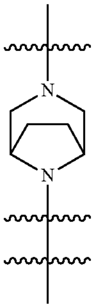, 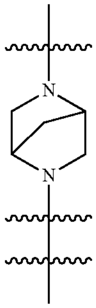, 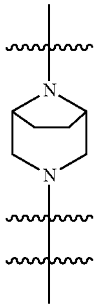, 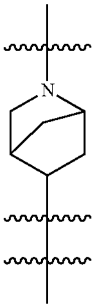,

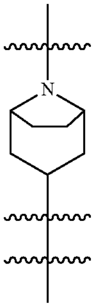, 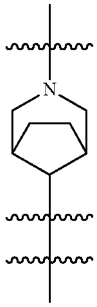, 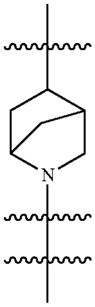, 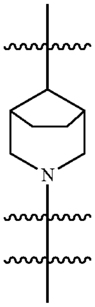,

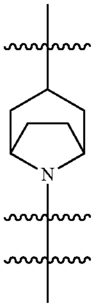, 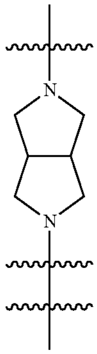, 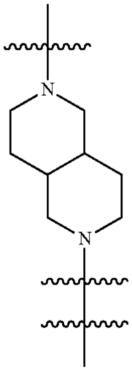,

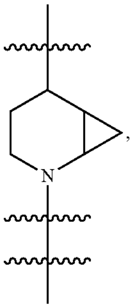, 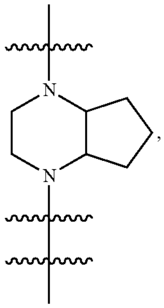, 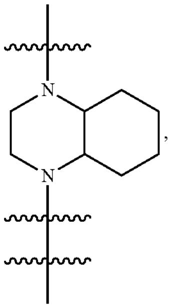,

-continued
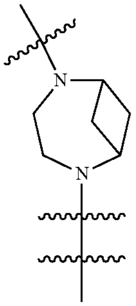,
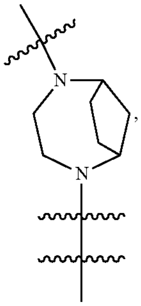,
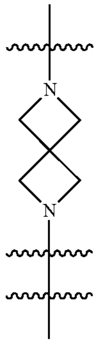
and
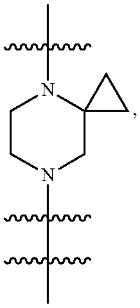,
wherein, the definition of $R^{12}$ is as above.
In some more preferred embodiments, L is selected from the group consisting of the following group optionally substituted by one or more $R^{12}$:
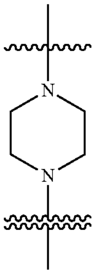,
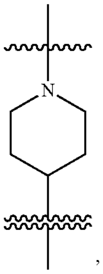,
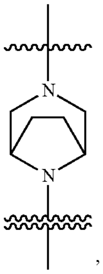,
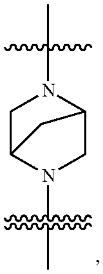,
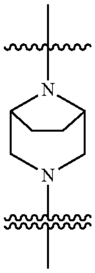,
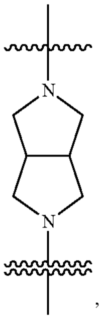,
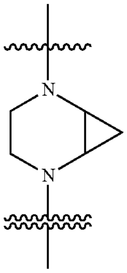,
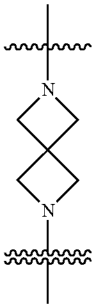
and
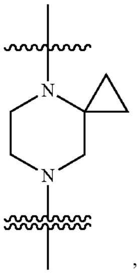,
wherein, the definition of $R^{12}$ is as above.
In some more preferred embodiments, L is selected from the group consisting of
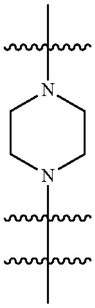,
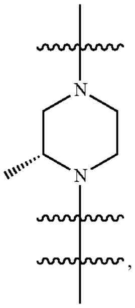,
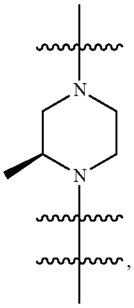,
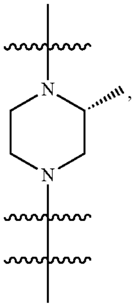,
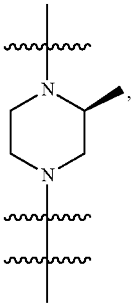,
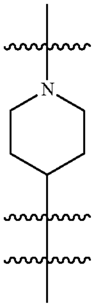,
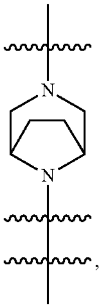,
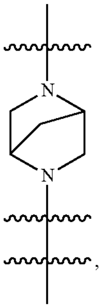,
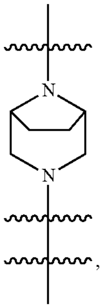,
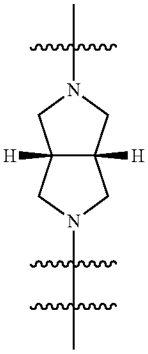,
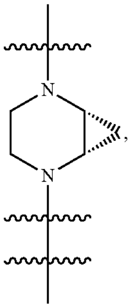,
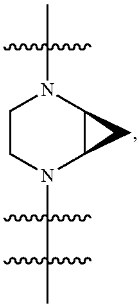,
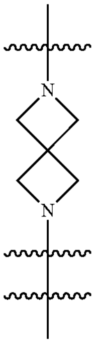
and -continued
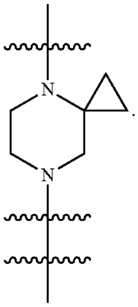
In some more preferred embodiments, L is selected from the group consisting of
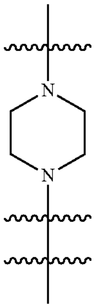,
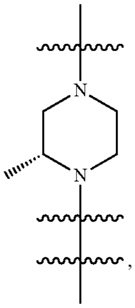,
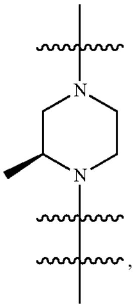,
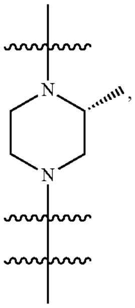,
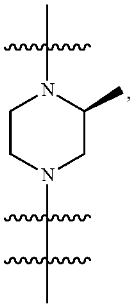,
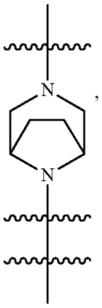,
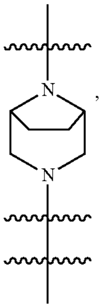,
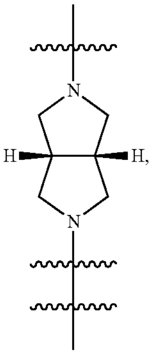,
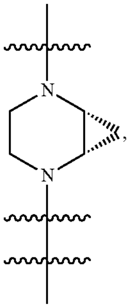,
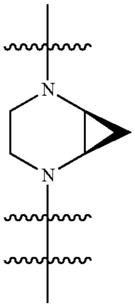 and
-continued
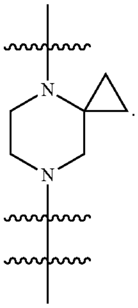
In some more preferred embodiments, L is selected from the group consisting of
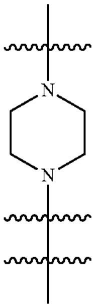,
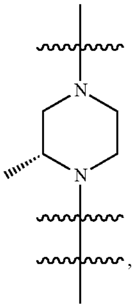,
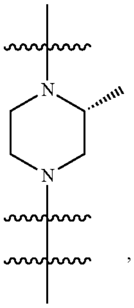,
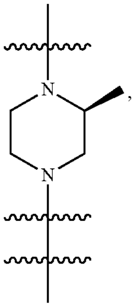,
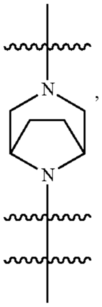,
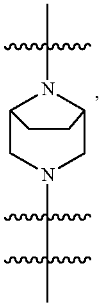,
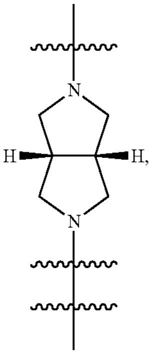,
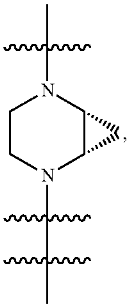,
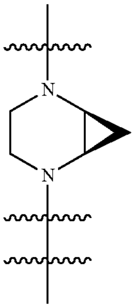 and -continued

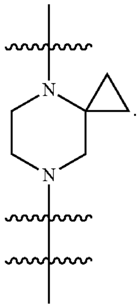

In some embodiments, G is phenyl optionally substituted by 1-5 $R^{11}$, or thienyl or pyridyl optionally substituted by one or more $R^{11}$.

In some embodiments, $R^{11}$ is independently selected from the group consisting of F, Cl, Br, I, OH, CN, $NH_2$, $NO_2$, benzyloxy, methyl, ethyl, isopropyl, $CH_2CF_3$, $CF_3$, SMe, OMe, $OCF_3$, OEt and isopropoxy; in some preferred embodiments, $R^{11}$ is independently selected from the group consisting of F, Cl, Br, CN, benzyloxy, methyl, ethyl, isopropyl, $CF_3$, OMe, SMe and $OCF_3$; in some more preferred embodiments, $R^{11}$ is independently selected from the group consisting of F, Cl and $CF_3$; in some more preferred embodiments, $R^{11}$ is Cl.

In some embodiments, G is selected from the group consisting of phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-methylthiophenyl, 4-trifluoromethoxyphenyl, 4-chloro-3-fluorophenyl, 3,4-difluorophenyl, 2,4-dichlorophenyl and 4-benzyloxyphenyl; in some preferred embodiments, G is selected from the group consisting of 4-chlorophenyl, 4-chloro-3-fluorophenyl, 4-trifluoromethylphenyl and 3,4-difluorophenyl; in some more preferred embodiments, G is 4-chlorophenyl.

In some embodiments, G is thienyl or pyridyl optionally substituted by one or more halogens; in some more preferred embodiments, G is thienyl or pyridyl optionally substituted by one or more F, Cl, Br or I; In some more preferred embodiments, G is selected from the group consisting of

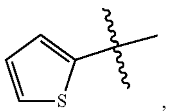
,
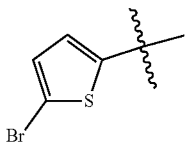
,
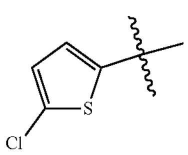
and
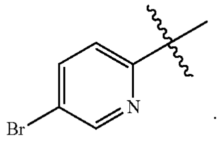

In another aspect, the present invention provides a compound represented by formula II or pharmaceutically acceptable salts thereof,

II

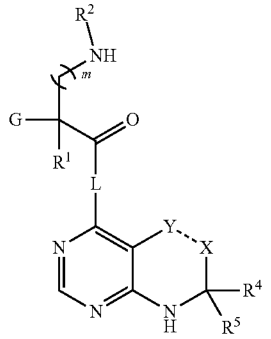

wherein, $R^1$, $R^2$, $R^4$, $R^5$, G, L, m and

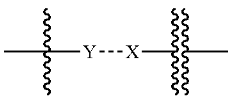

have the same definitions as in the compound represented by formula I.

In another aspect, the present invention provides a compound represented by formula III or pharmaceutically acceptable salts thereof,

III

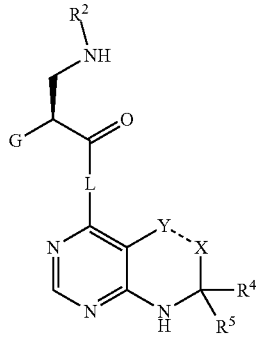

wherein, $R^2$, $R^4$, $R^5$, G, L, and

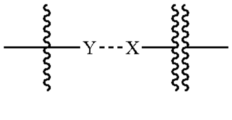

have the same definitions as in the compound represented by formula I.

In another aspect, the present invention provides a compound represented by formula IV or pharmaceutically acceptable salts thereof,

IV

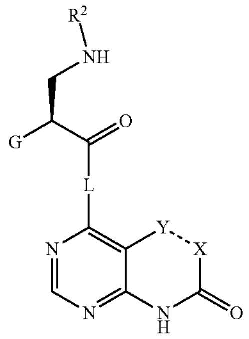

wherein, $R^2$, G, L, and

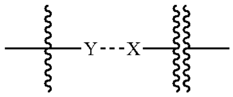

have the same definitions as in the compound represented by formula I.

In another aspect, the present invention provides a compound represented by formula V or pharmaceutically acceptable salts thereof,

V

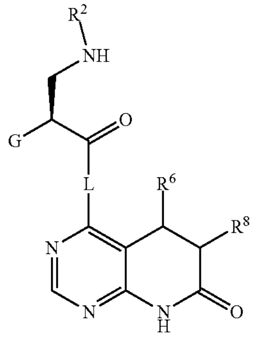

wherein, $R^2$, $R^6$, $R^8$, G, and L have the same definitions as in the compound represented by formula I.

In another aspect, the present invention provides a compound represented by formula VI or pharmaceutically acceptable salts thereof,

VI

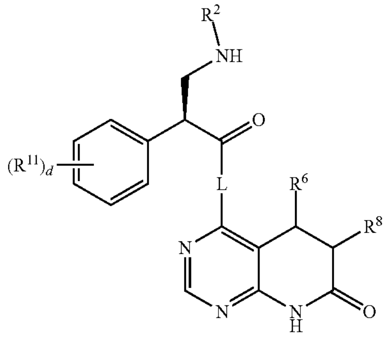

wherein, $R^2$, $R^6$, $R^8$, $R^{11}$ and L have the same definition as in the compound represented by formula I, and d is 0, 1, 2, 3, 4 or 5.

In some embodiments, d is 0, 1, 2 or 5; in some preferred embodiments, d is 0, 1 or 2; in some more preferred embodiments, d is 1 or 2; in some more preferred embodiments, d is 1.

In another aspect, the present invention provides a compound represented by formula VII or pharmaceutically acceptable salts thereof,

VII

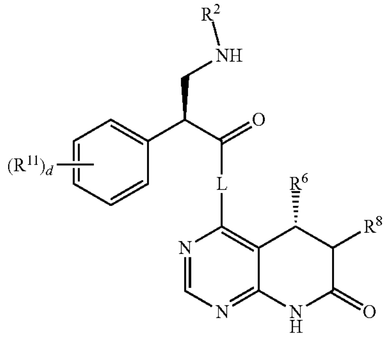

wherein, $R^2$, $R^6$, $R^8$, $R^{11}$ and L have the same definition as in the compound represented by formula I, and d has the same definition as in the compound represented by formula VI.

In another aspect, the present invention provides a compound represented by formula VIII or pharmaceutically acceptable salts thereof,

VIII

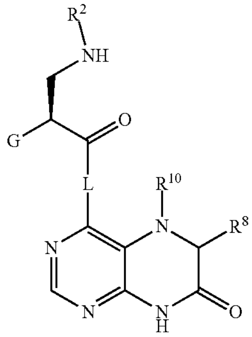

wherein, $R^2$, $R^8$, $R^{10}$, G, and L have the same definitions as in the compound represented by formula I.

In another aspect, the present invention provides a compound represented by formula IX or pharmaceutically acceptable salts thereof,

IX

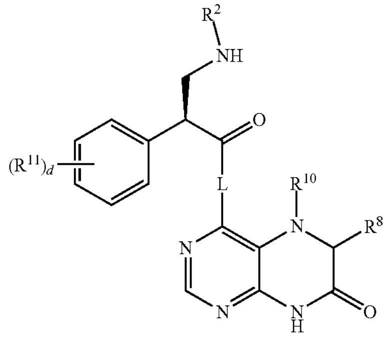

wherein, $R^2$, $R^8$, $R^{10}$, $R^{11}$ and L have the same definition as in the compound represented by formula I, and d has the same definition as in the compound represented by formula VI.

In another aspect, the present invention also provides a compound represented by formula X or pharmaceutically acceptable salts thereof,

X

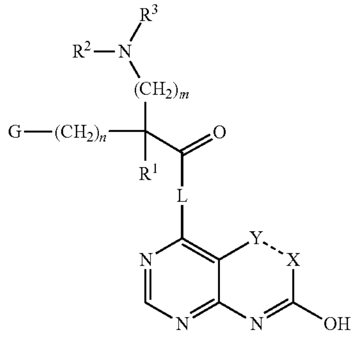

wherein, $R^1$, $R^2$, $R^3$, G, L, m, n and

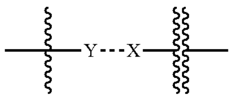

have the same definitions as in the compound represented by formula I.

In another aspect, the present invention also provides a compound represented by formula XI or pharmaceutically acceptable salts thereof,

XI

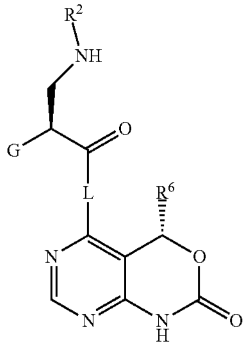

wherein, $R^2$, $R^6$, G, and L have the same definitions as in the compound represented by formula I.

In another aspect, the present invention also provides a compound represented by formula XII or pharmaceutically acceptable salts thereof,

XII

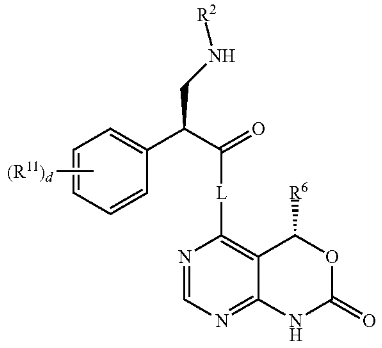

wherein, $R^2$, $R^6$, $R^{11}$ and L have the same definition as in the compound represented by formula I, and d has the same definition as in the compound represented by formula VI.

In another aspect, the present invention provides the following compounds or pharmaceutically acceptable salts thereof:

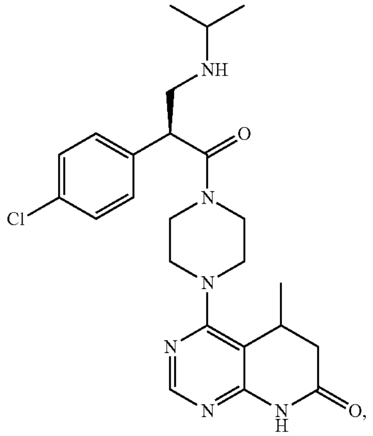

-continued
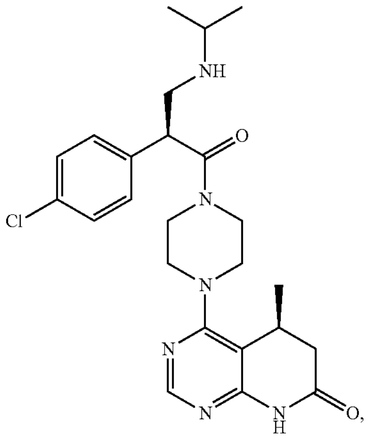
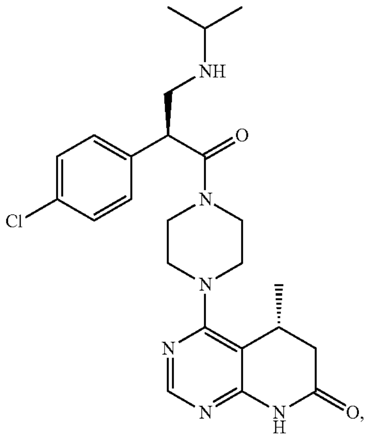
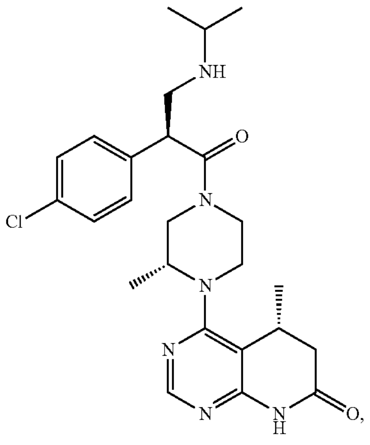
-continued
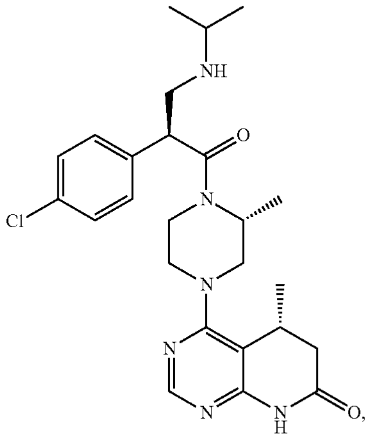
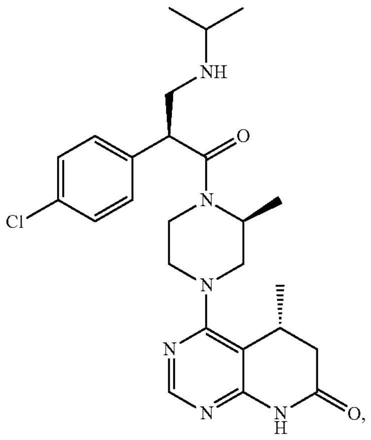
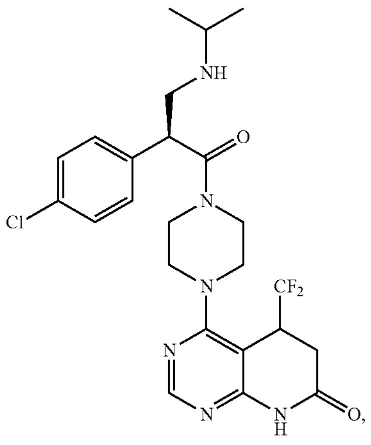

-continued
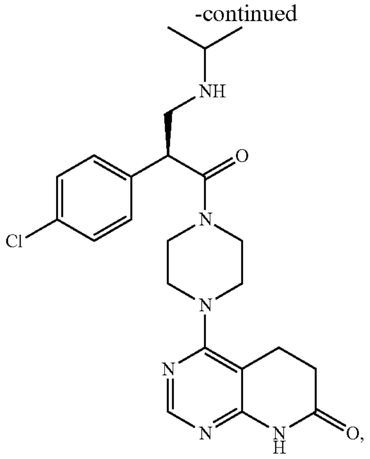
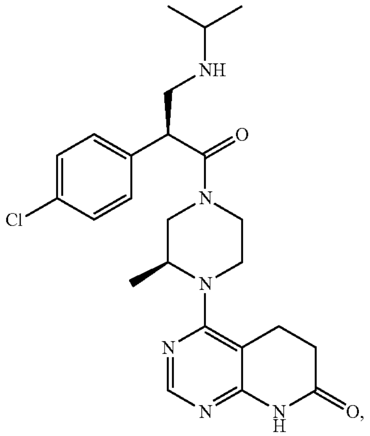
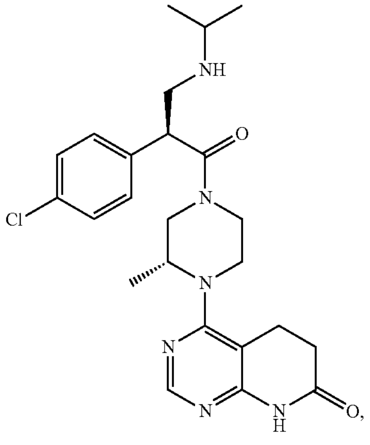
-continued
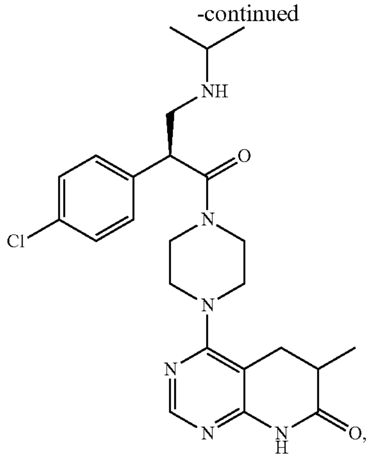
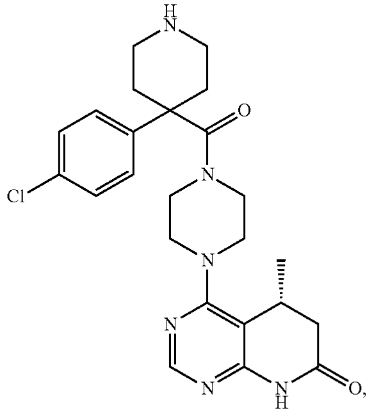
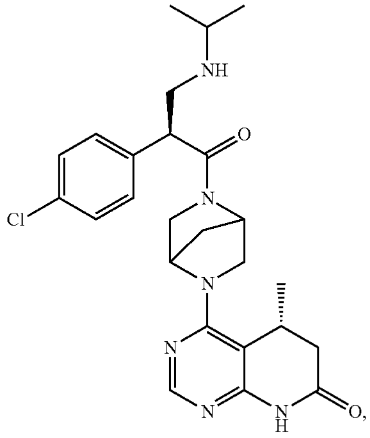
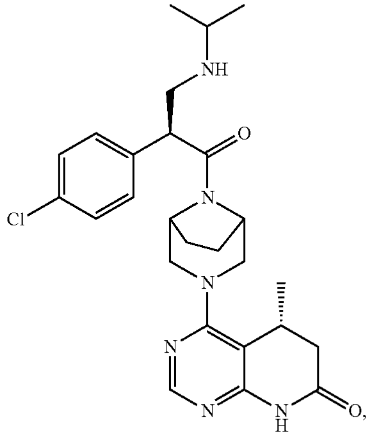

-continued
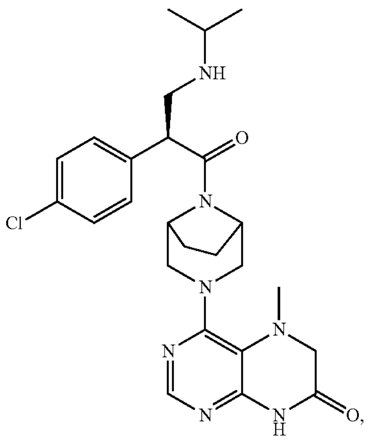
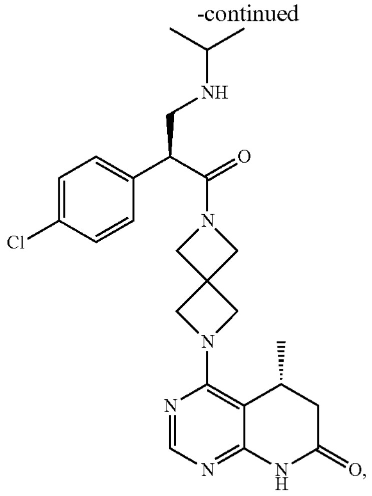
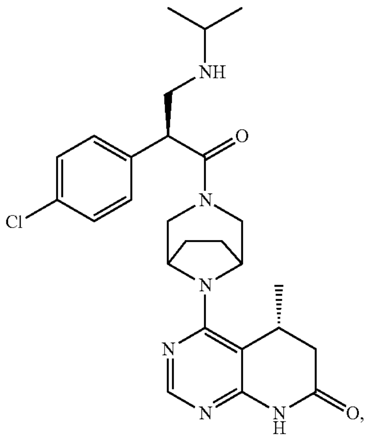
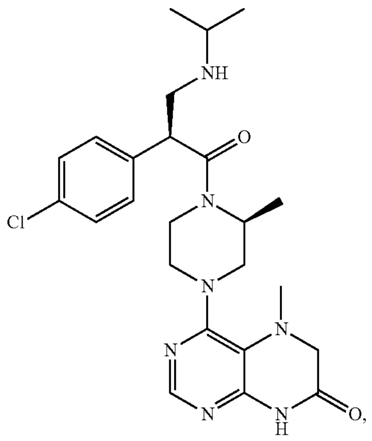
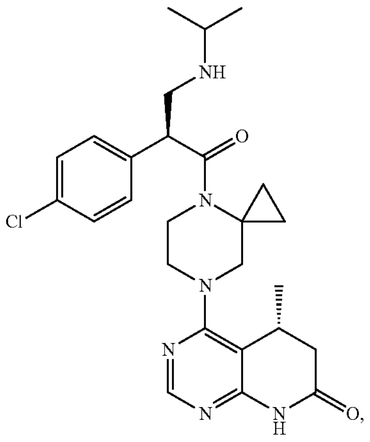
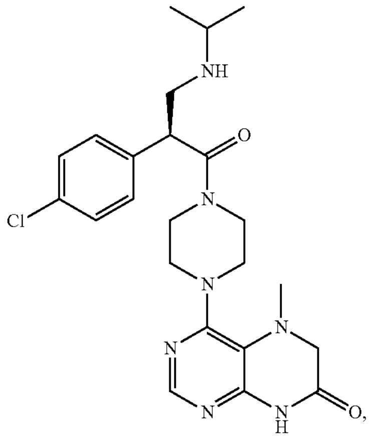

-continued
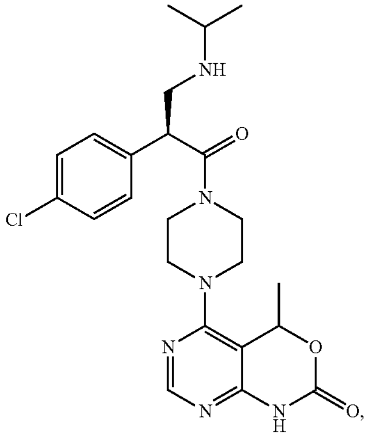
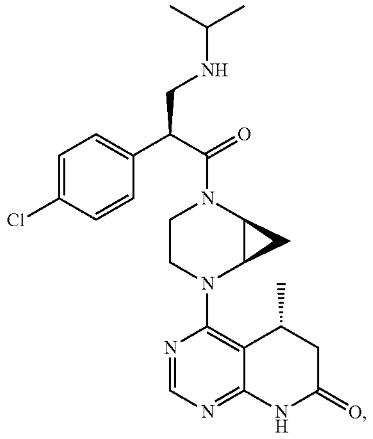
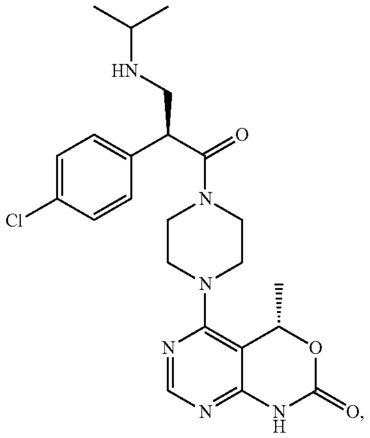
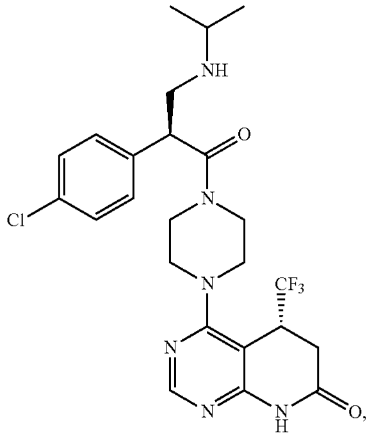
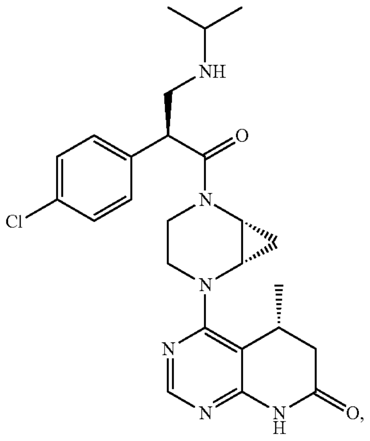
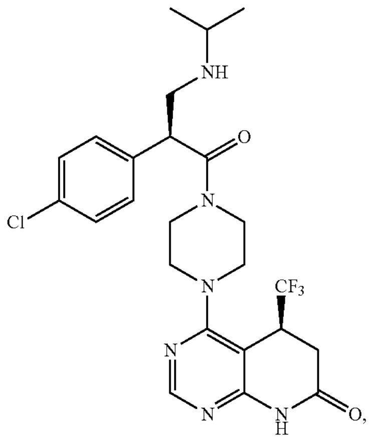

-continued
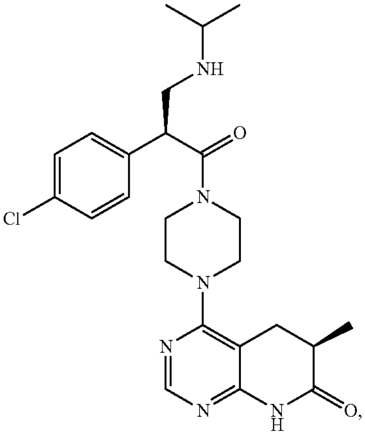
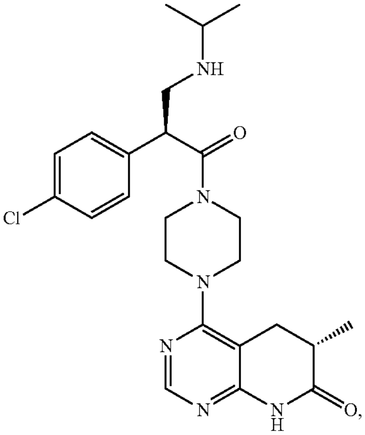
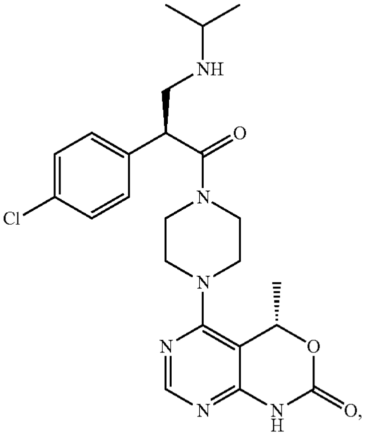
-continued
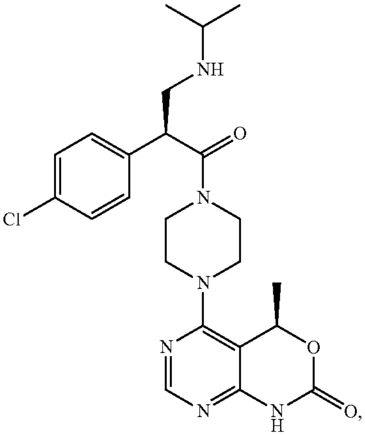
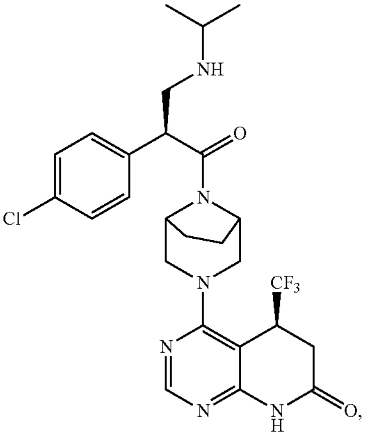
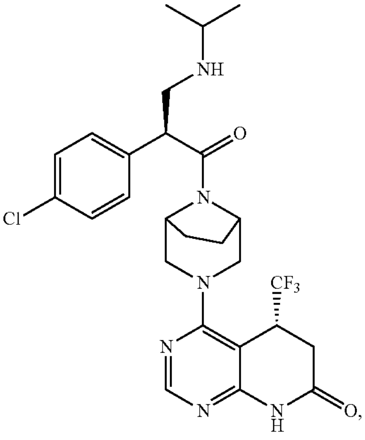

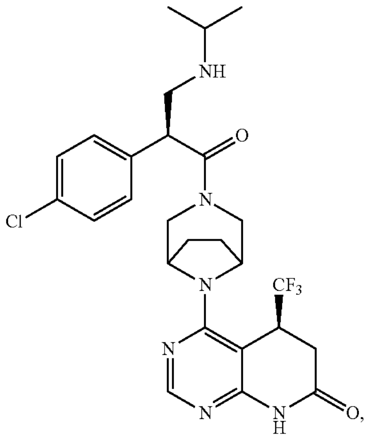
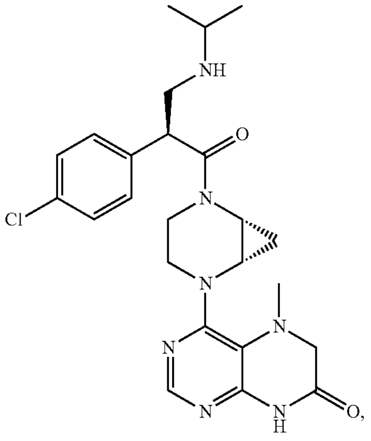
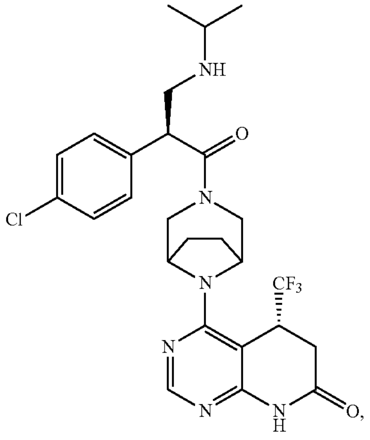
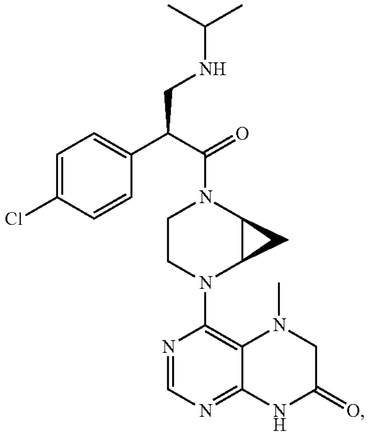
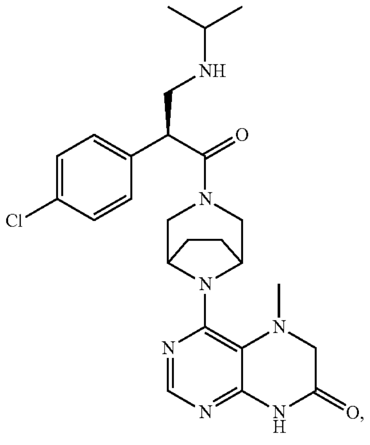
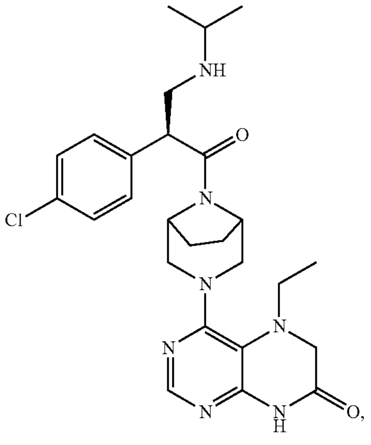

-continued
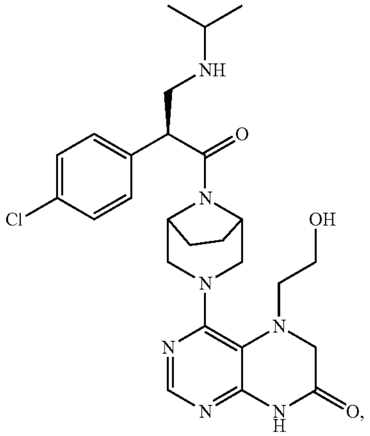
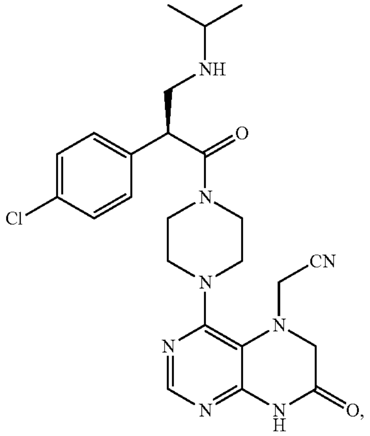
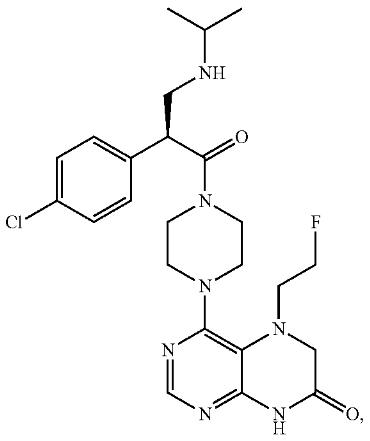
-continued
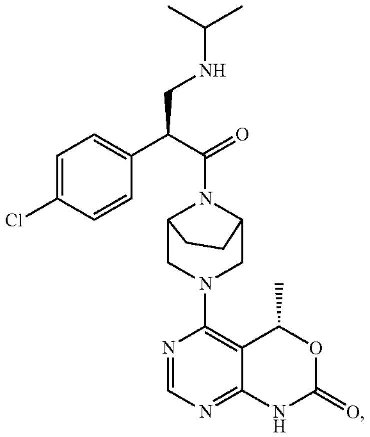
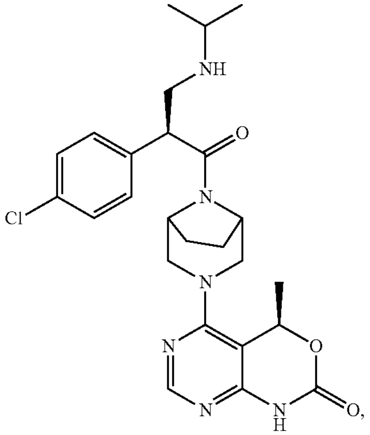
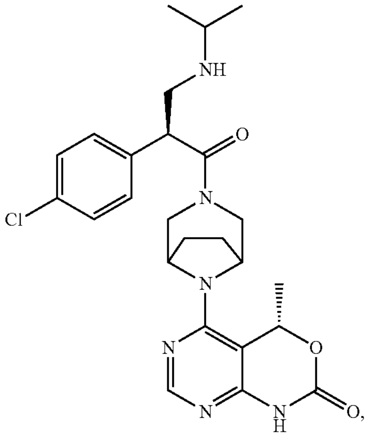

-continued
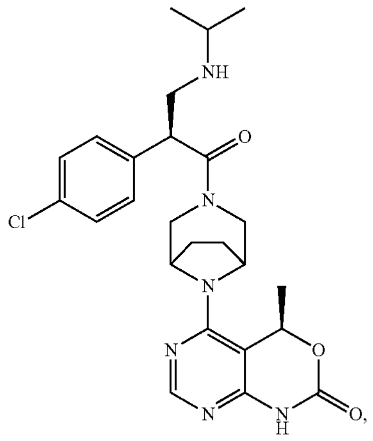
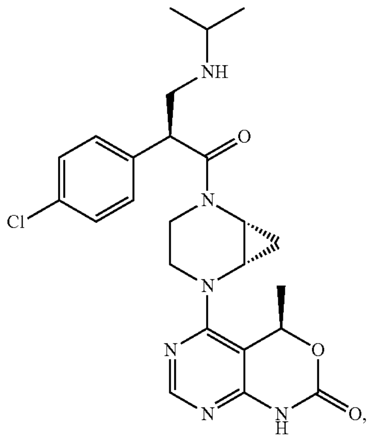
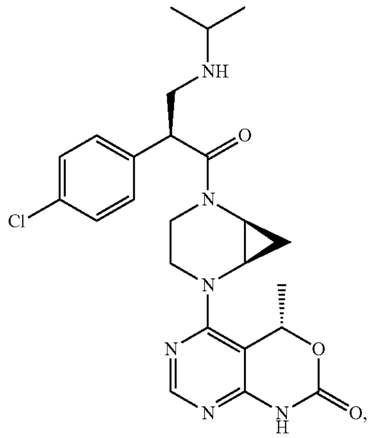
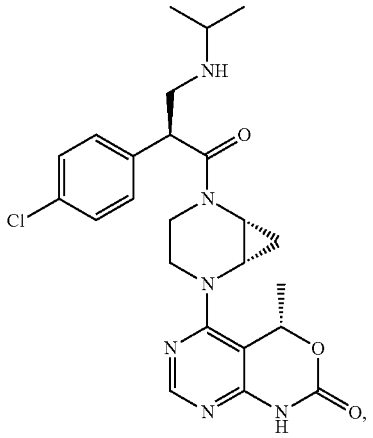
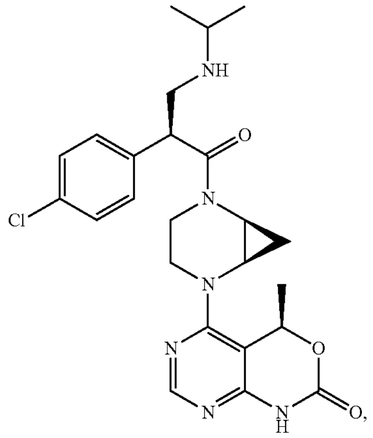
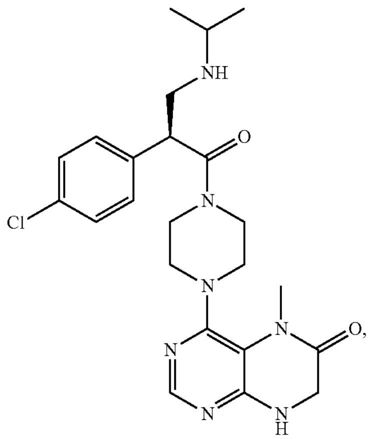

-continued
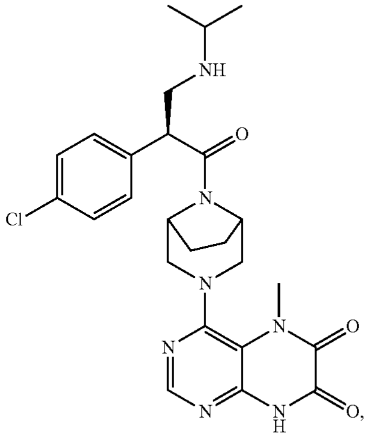
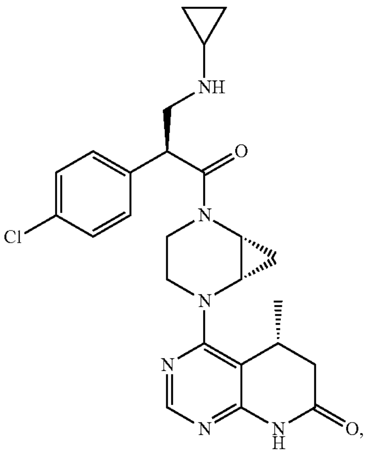
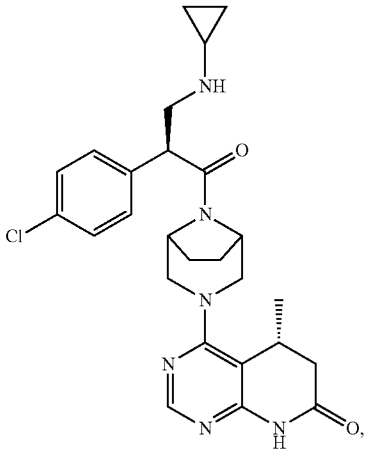
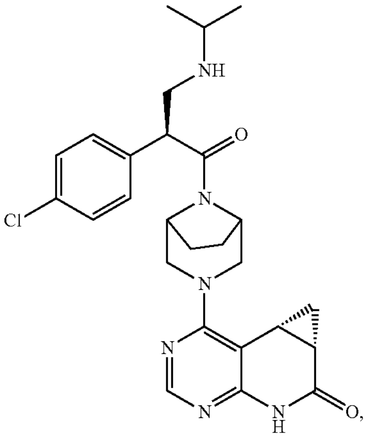
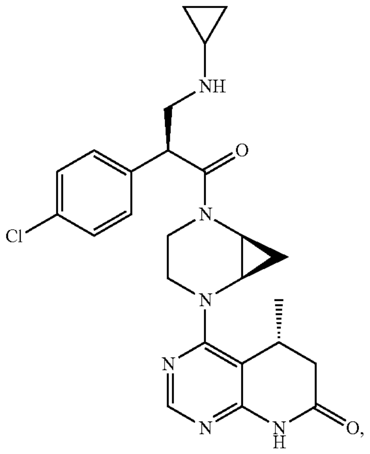
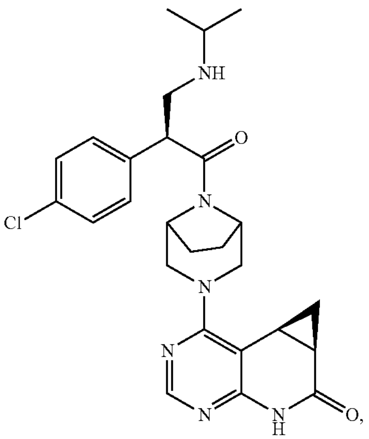
-continued -continued
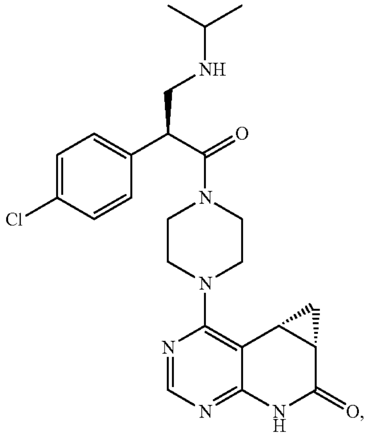
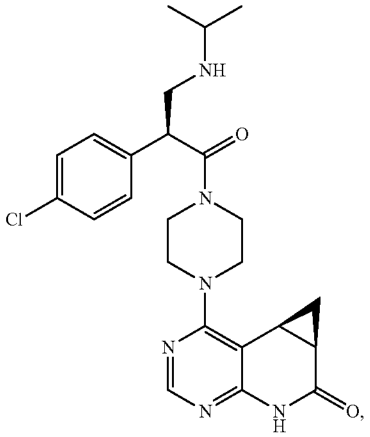
cis-(5R)-4-(5-((S)-2-(4-chlorophenyl)-3-(isopropylamino) propionyl)hexahydropyrrole[3,4-c]pyrrole-2(1H)-yl)-5-methyl-5,8-dihydropyrido[2,3-d]pyrimidin-7(6H)-one, or
trans-(5R)-4-(5-((S)-2-(4-chlorophenyl)-3-(isopropylamino)propionyl)hexahydropyrrole[3,4-c]pyrrole-2(1H)-yl)-5-methyl-5,8-dihydropyrido[2,3-d]pyrimidin-7(6H)-one.
In another aspect, the present invention provides the following compounds:
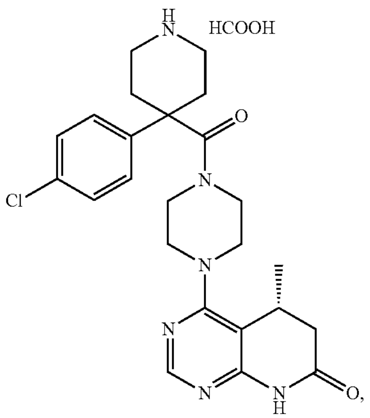
-continued
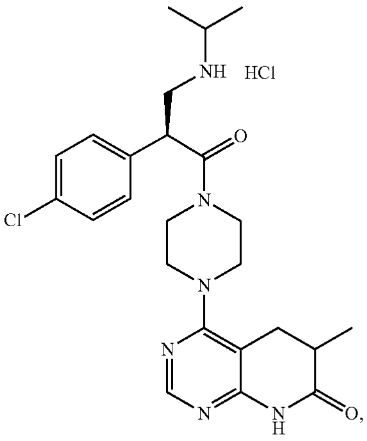
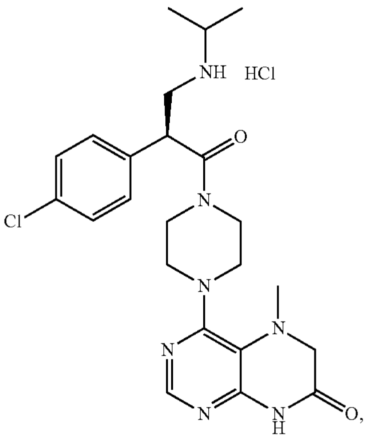
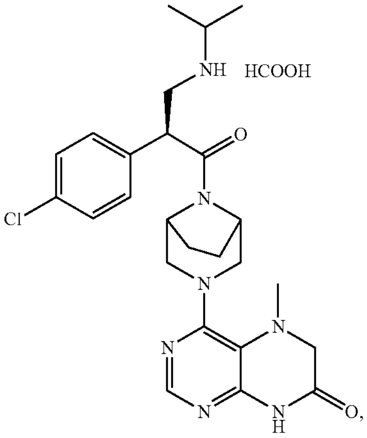
and -continued

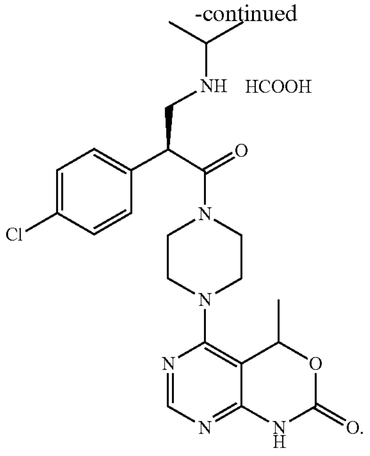

In another aspect, the present invention also provides a pharmaceutical composition comprising a therapeutically effective amount of a compound of formula I, II, III, IV, V, VI, VII, VIII, IX, X, XI or XII or pharmaceutically acceptable salts thereof.

In some embodiments, the present invention also provides a pharmaceutical composition comprising a therapeutically effective amount of a compound of formula I, II, III, IV, V, VI, VII, VIII, IX, X, XI or XII or pharmaceutically acceptable salts thereof, and one or more pharmaceutically acceptable carriers.

The pharmaceutical composition of the present invention can be administered by any suitable routes or methods, for example, by oral or parenteral (for example, intravenous) administration. The therapeutically effective amount of the compound of formula I, II, III, IV, V, VI, VII, VIII, IX, X, XI or XII is from about 0.001 to 20 mg/Kg body weight/day, preferably from 0.01 to 10 mg/Kg body weight/day.

For oral administration, the pharmaceutical composition of the present invention is usually provided in the form of tablet, capsule or solution. The tablet may contain the compound of the present invention or pharmaceutically acceptable salts thereof and a pharmaceutically acceptable carrier. The carrier includes, but is not limited to, diluents, disintegrants, binders, lubricants, colorants or preservatives. The capsule include a hard capsule and a soft capsule.

For parenteral administration, the pharmaceutical composition of the present invention can be administered by intravenous injection, intramuscular injection or subcutaneous injection. It is usually provided as a sterile aqueous solution or suspension or lyophilized powder, and adjusted to suitable pH and isotonicity.

In another aspect, the present invention also provides the use of the compound of formula I, II, III, IV, V, VI, VII, VIII, IX, X, XI or XII in the manufacture of a medicament for preventing and/or treating a disease or condition mediated by AKT protein kinase.

In another aspect, the present invention also provides a method for preventing and/or treating a disease or condition mediated by AKT protein kinase, comprising administering the compound of formula I, II, III, IV, V, VI, VII, VIII, IX, X, XI or XII of the present invention or the pharmaceutical composition of the present invention to a subject in need.

In another aspect, the present invention also provides the compound of formula I, II, III, IV, V, VI, VII, VIII, IX, X, XI or XII of the present invention or the pharmaceutical composition of the present invention for use of preventing and/or treating a disease or condition mediated by AKT protein kinase.

Examples of disease or condition mediated by the AKT protein kinase include, but are not limited to, breast cancer, prostate cancer, or ovarian cancer.

The compound of the present invention has an inhibitory effect on AKT1, AKT2, and AKT3, especially has a significant inhibitory effect on AKT3, has a significant proliferation inhibitory effect on cancer cells, has good pharmacokinetic absorption, and has a significantly better oral absorption effect.

In another aspect, the present invention provides a method for preparing the compound of formula V, including but not limited to the following synthetic schemes:

Synthesis scheme 1

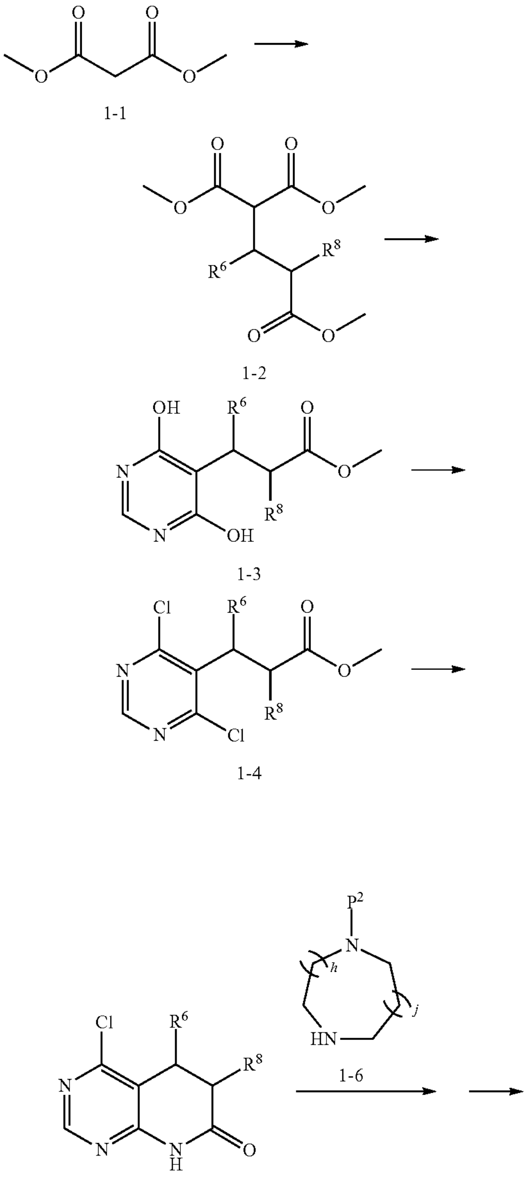
1-1
1-2
1-3
1-4
1-6
1-5

-continued

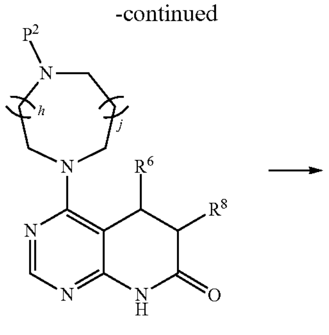

1-7

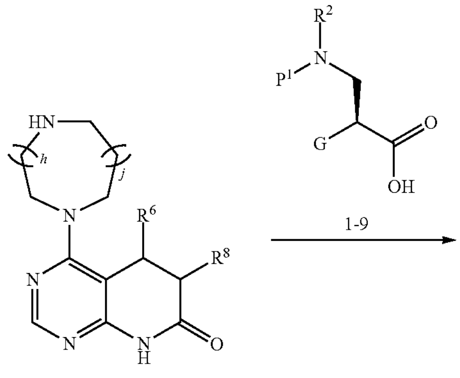

1-8

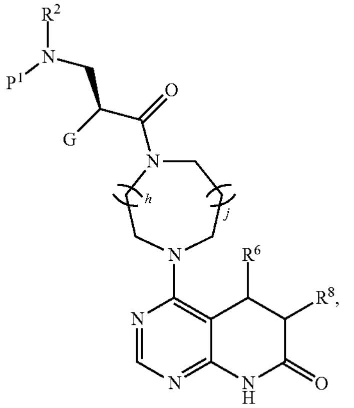

1-10 wherein, $R^2$, $R^6$, $R^8$, G, h, and j are as defined above, $P^1$ is H or an amido protecting group, and $P^2$ is an amido protecting group.

In the presence of a base (such as sodium methoxide) and a solvent (such as methanol), the compound of formula 1-2 is prepared from the compound of formula 1-1; in the presence of a base (such as sodium methoxide) and a solvent (such as methanol), the compound of formula 1-2 is reacted with formamidine acetate to prepare the compound of formula 1-3; in the presence of a base (such as diisopropylethylamine) and a solvent (such as acetonitrile), the compound of formula 1-4 is prepared from the compound of formula 1-3; the compound of formula 1-4 is further reacted to produce the compound of formula 1-5; the compound of formula 1-5 is reacted with the compound of formula 1-6 to prepare the compound of formula 1-7; the protecting group of the compound of formula 1-7 is removed to prepare the compound of formula 1-8; the compound of formula 1-8 is reacted with the compound of formula 1-9 to prepare the compound of formula 1-10. When $P^1$ is an amino protecting group, synthesis scheme 1 further includes a step of removing the amino protecting group.

Synthesis scheme 2

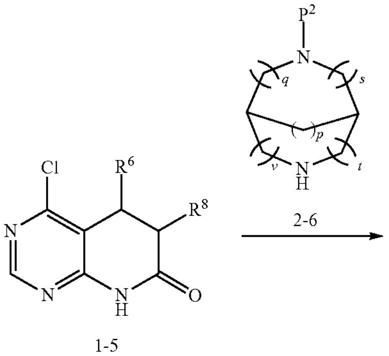

1-5

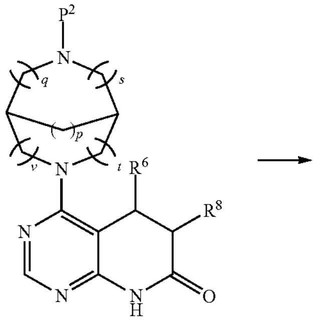

2-7

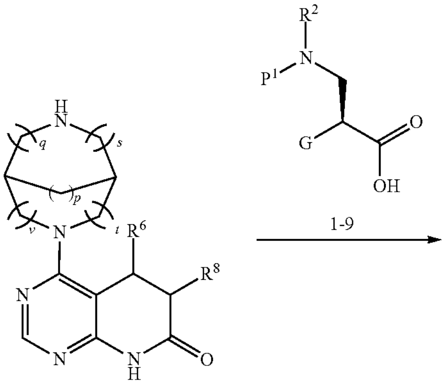

2-8

-continued

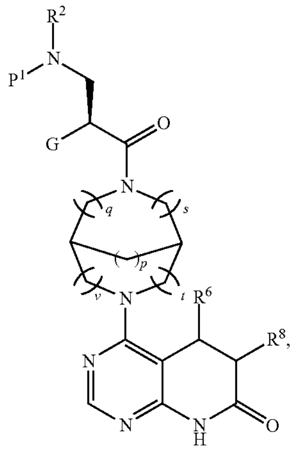

2-10 wherein, $R^2$, $R^6$, $R^8$, CG, q, v, s, t, and p are as defined above, $P^1$ is H or an amido protecting group, and $P^2$ is an amido protecting group.

The compound of formula 1-5 is prepared according to the synthesis scheme 1; the compound of formula 1-5 is reacted with the compound of formula 2-6 to prepare the compound of formula 2-7; the protecting group of the compound of formula 2-7 is removed to prepare the compound of formula 2-8; the compound of formula 2-8 is reacted with the compound of formula 1-9 to prepare the compound of formula 2-10. When $P^1$ is an amido protecting group, synthesis scheme 2 further includes a step of removing the amido protecting group.

Synthesis scheme 3

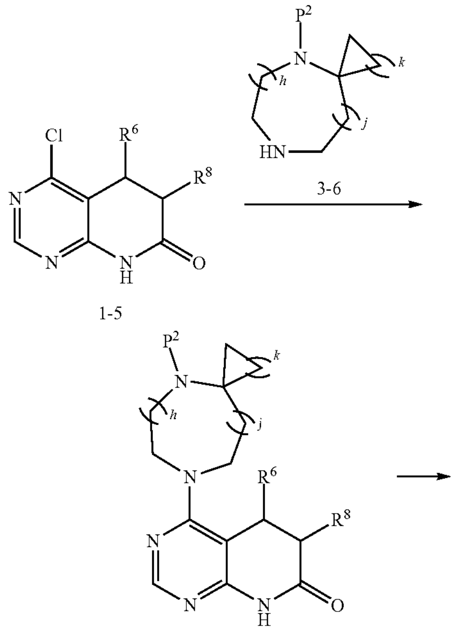

1-5 3-6 3-7

-continued

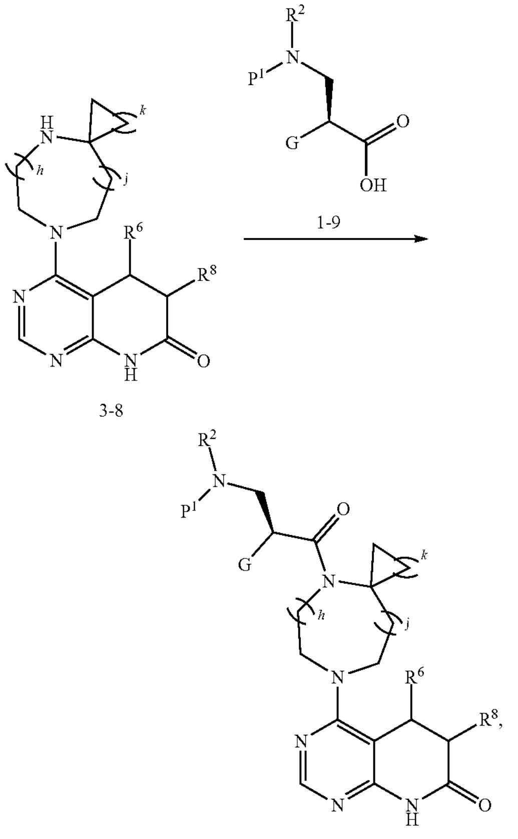

3-8 1-9 3-10 wherein, $R^2$, $R^6$, $R^8$, G, h, j, and k are as defined above, $P^1$ is H or an amido protecting group, and $P^2$ is an amido protecting group.

The compound of formula 1-5 is prepared according to the synthesis scheme 1; the compound of formula 1-5 is reacted with the compound of formula 3-6 to prepare the compound of formula 3-7; the protecting group of the compound of formula 3-7 is removed to prepare the compound of formula 3-8; the compound of formula 3-8 is reacted with the compound of formula 1-9 to prepare the compound of formula 3-10. When $P^1$ is an amido protecting group, synthesis scheme 3 further includes a step of removing the amido protecting group.

Synthesis scheme 4

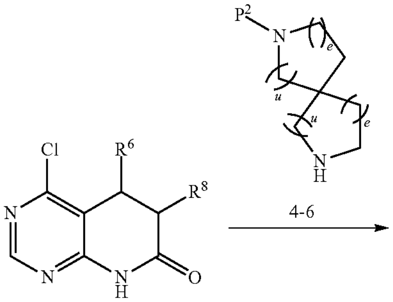

1-5 4-6

-continued

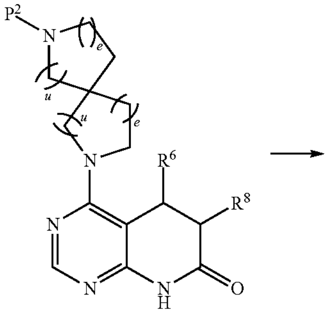

4-7

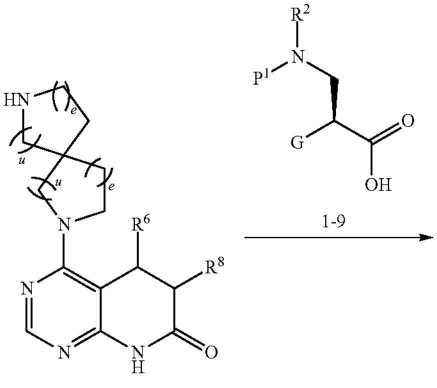

1-9

4-8

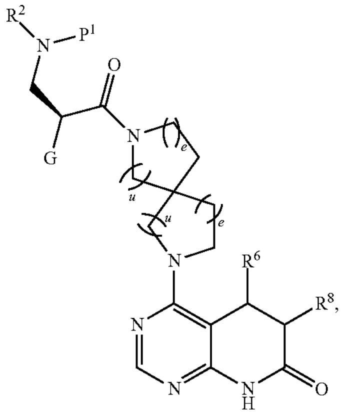

4-10 wherein, $R^2$, $R^6$, $R^8$, e, and u are as defined above, $P^1$ is H or an amido protecting group, and $P^2$ is an amido protecting group.

The compound of formula 1-5 is prepared according to the synthesis scheme 1; the compound of formula 1-5 is reacted with the compound of formula 4-6 to prepare the compound of formula 4-7; the protecting group of the compound of formula 4-7 is removed to prepare the compound of formula 4-8; the compound of formula 4-8 is reacted with the compound of formula 1-9 to prepare the compound of formula 4-10. When $P^1$ is an amido protecting group, synthesis scheme 4 further includes a step of removing the amido protecting group.

In another aspect, the present invention provides a method for preparing the compound of formula VIII, including but not limited to the following synthetic schemes:

Synthesis scheme 5

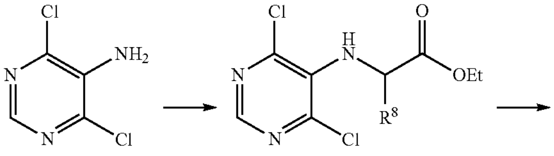

5-1 5-2

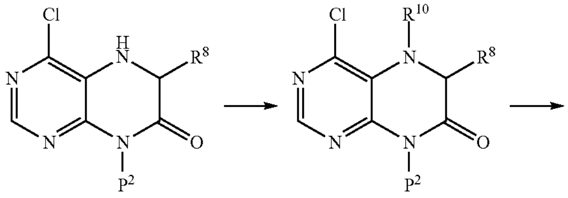

5-3 5-4

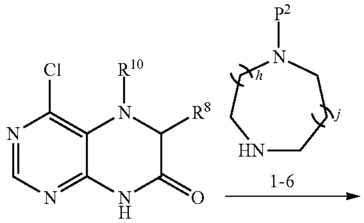

1-6

5-5

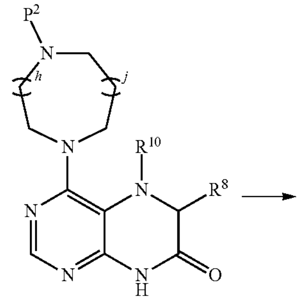

5-7

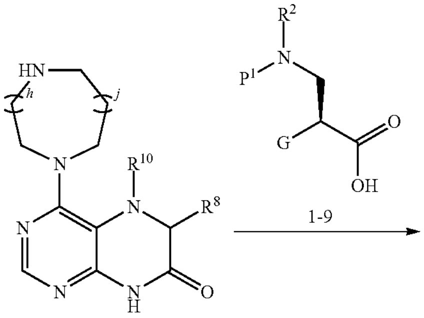

1-9

5-8

-continued

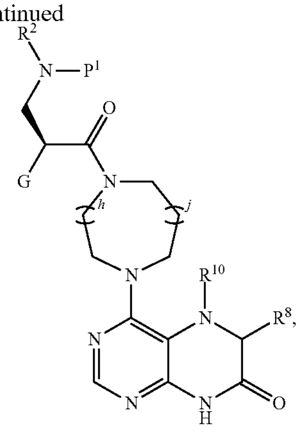

5-10 wherein, $R^2$, $R^{10}$, $R^8$, G, h, and j are as defined above, $P^1$ is H or an amido protecting group, and $P^2$ is an amido protecting group.

In the presence of a base (such as sodium hydride) and a solvent (such as tetrahydrofuran), the compound of formula 5-2 is prepared from the compound of formula 5-1; in the presence of a base (such as triethylamine) and a solvent (such as isopropanol), the compound of formula 5-2 is reacted with $NH_2P^2$ to prepare the compound of formula 5-3; in the presence of a base (such as sodium hydride) and a solvent (such as DNF), the compound of formula 5-4 is prepared from the compound of formula 5-3; the protecting group of the compound of formula 5-4 is removed to prepare the compound of formula 5-5; the compound of formula 5-5 is reacted with the compound of formula 1-6 to prepare the compound of formula 5-7; the protecting group of the compound of formula 5-7 is removed to prepare the compound of formula 5-8; the compound of formula 5-8 is reacted with the compound of formula 1-9 to prepare the compound of formula 5-10. When $P^1$ is an amido protecting group, synthetic scheme 5 further includes a step of removing the protecting group.

Synthesis scheme 6

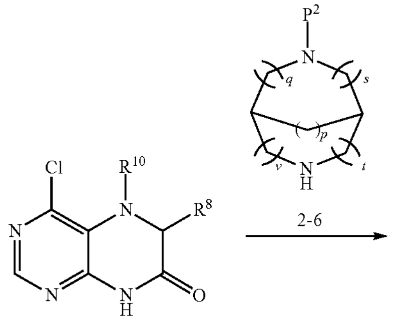

5-5

2-6

-continued

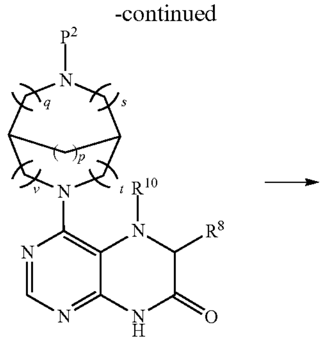

6-7

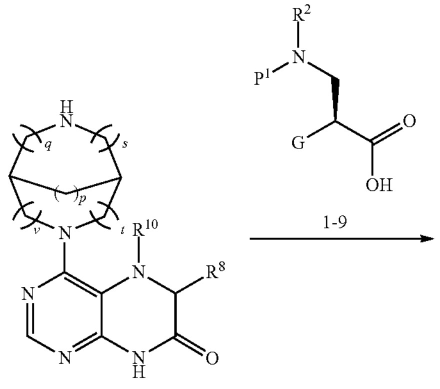

6-8

1-9

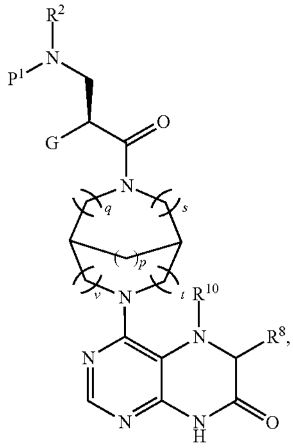

6-10 wherein, $R^2$, $R^{10}$, $R^8$, G, q, s, v, t, and p are as defined above, $P^1$ is H or an amido protecting group, and $P^2$ is an amido protecting group.

The compound of formula 5-5 is prepared according to the synthesis scheme 5; the compound of formula 5-5 is reacted with the compound of formula 2-6 to prepare the compound of formula 6-7; the protecting group of the compound of formula 6-7 is removed to prepare the compound of formula 6-8; the compound of formula 6-8 is reacted with the compound of formula 1-9 to prepare the compound of formula 6-10. When $P^1$ is an amido protecting group, synthesis scheme 6 further includes a step of removing the protecting group.

Synthesis scheme 7

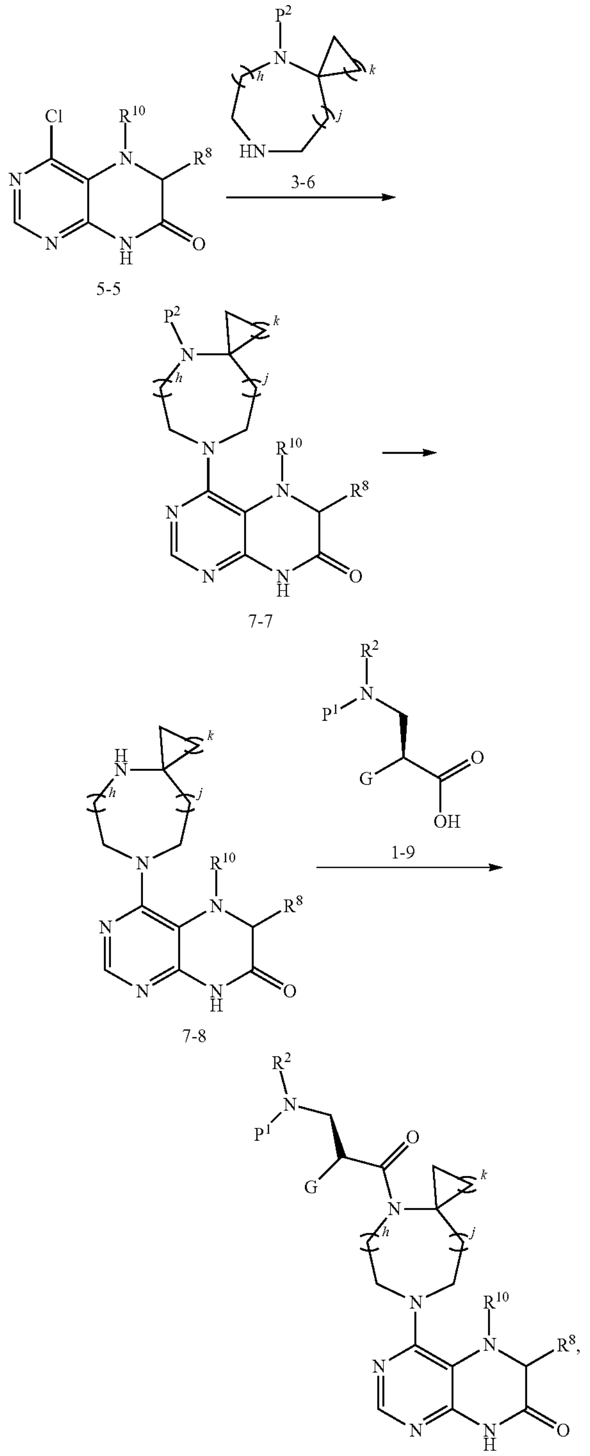

3-6

5-5

7-7

1-9

7-8

7-10 wherein, $R^2$, $R^{10}$, $R^8$, G, h, j, and k are as defined above, $P^1$ is H or an amido protecting group, and $P^2$ is an amido protecting group.

The compound of formula 5-5 is prepared according to the synthesis scheme 5; the compound of formula 5-5 is reacted with the compound of formula 3-6 to prepare the compound of formula 7-7; the protecting group of the compound of formula 7-7 is removed to prepare the compound of formula 7-8; the compound of formula 7-8 is reacted with the compound of formula 1-9 to prepare the compound of formula 7-10. When $P^1$ is an amido protecting group, synthesis scheme 7 further includes a step of removing the protecting group.

Synthesis scheme 8

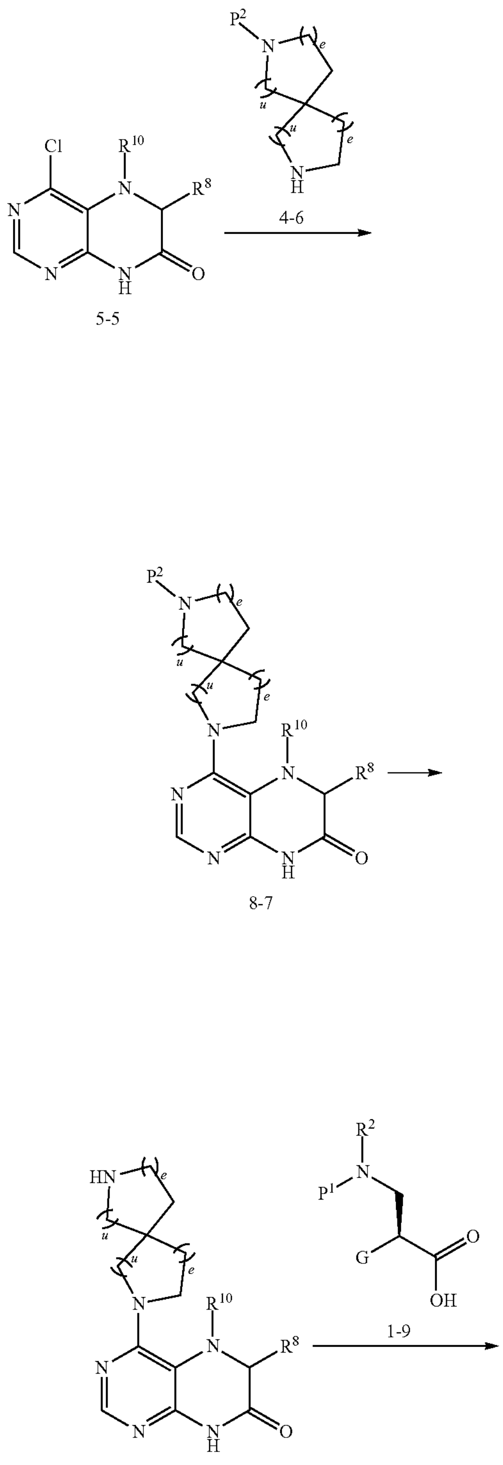

4-6

5-5

8-7

1-9

8-8

-continued

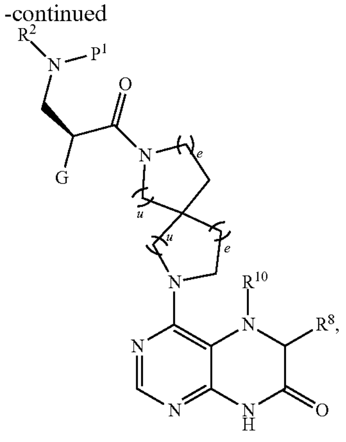

8-10 wherein, $R^2$, $R^{10}$, $R^8$, G, e, and u are as defined above, P is H or an amido protecting group, and $P^2$ is an amido protecting group.

The compound of formula 5-5 is prepared according to the synthesis scheme 5; the compound of formula 5-5 is reacted with the compound of formula 4-6 to prepare the compound of formula 8-7; the protecting group of the compound of formula 8-7 is removed to prepare the compound of formula 8-8; the compound of formula 8-8 is reacted with the compound of formula 1-9 to prepare the compound of formula 8-10. When $P^1$ is an amido protecting group, synthesis scheme 8 further includes a step of removing the protecting group.

Synthesis scheme 9

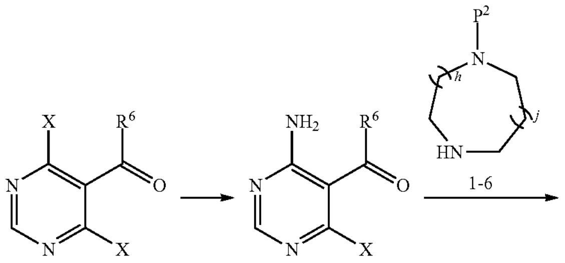

9-1 9-2

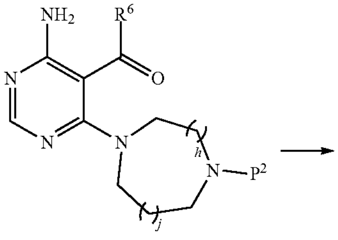

9-3

-continued

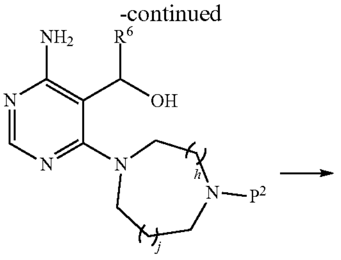

9-4

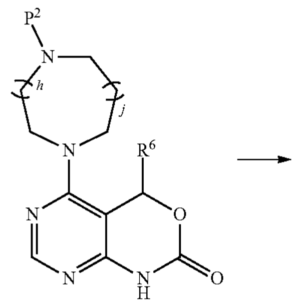

9-5

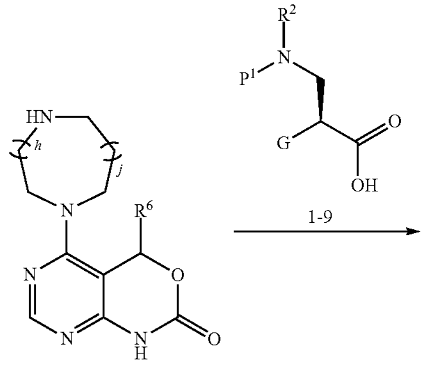

9-6

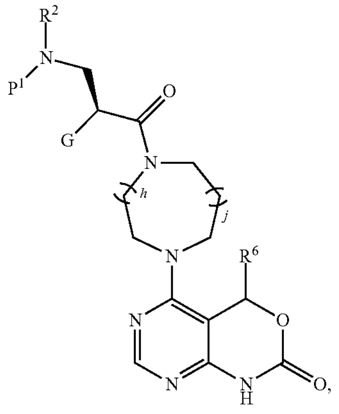

9-7 wherein, X is halogen, $R^6$, h, j, and G are as defined above, $P^1$ is H or an amido protecting group, and $P^2$ is an amido protecting group.

The compound of formula 9-2 is prepared from the compound of formula 9-1; the compound of formula 9-2 is reacted with the compound of formula 1-6 to prepare the compound of formula 9-3; the compound of formula 9-3 is reduced to produce the compound of formula 9-4; the compound of formula 9-4 undergoes a ring-forming reaction to prepare the compound of formula 9-5; the protecting group of the compound of formula 9-5 is removed to produce the compound of formula 9-6 or salts thereof, which is further reacted with the compound of formula 1-9 to prepare the compound of formula 9-7. When $P^1$ is an amido protecting group, synthesis scheme 9 further includes a step of removing the protecting group.

Synthesis scheme 10

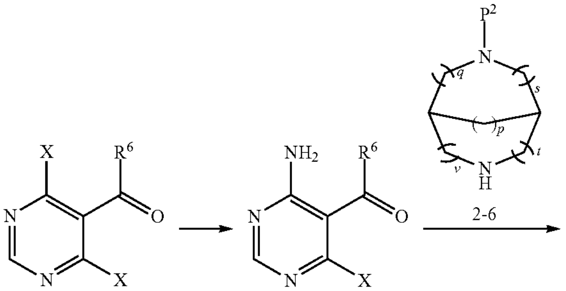

2-6

9-1

9-2

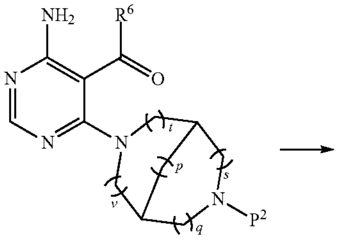

10-3

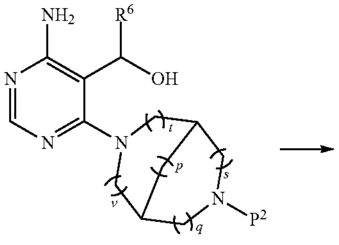

10-4

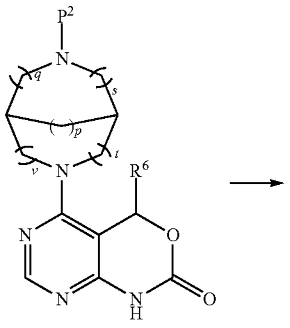

10-5

-continued

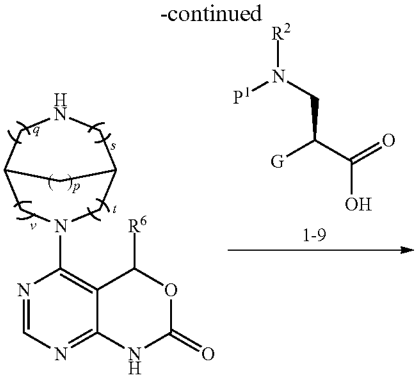

1-9

10-6

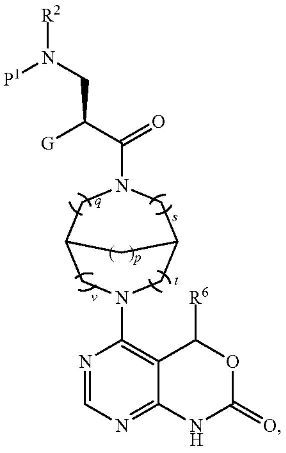

10-7 wherein, X is halogen, $R^6$, q, v, s, t, p and G are as defined above, P is H or an amido protecting group, and $P^2$ is an amido protecting group.

The compound of formula 9-2 is prepared from the compound of formula 9-1; the compound of formula 9-2 is reacted with the compound of formula 2-6 to prepare the compound of formula 10-3; the compound of formula 10-3 is reduced to produce the compound of formula 10-4; the compound of formula 10-4 undergoes a ring-forming reaction to prepare the compound of formula 10-5; the protecting group of the compound of formula 10-5 is removed to produce the compound of formula 10-6 or salts thereof, which is further reacted with the compound of formula 1-9 to prepare the compound of formula 10-7. When $P^1$ is an amido protecting group, synthesis scheme 10 further includes a step of removing the protecting group.

Synthesis scheme 11

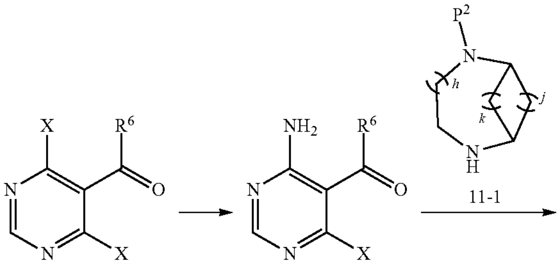

11-1

9-1

9-2

-continued

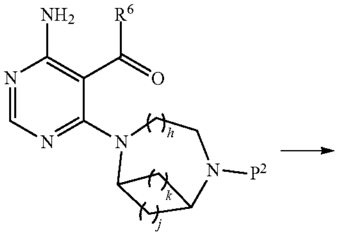

11-2

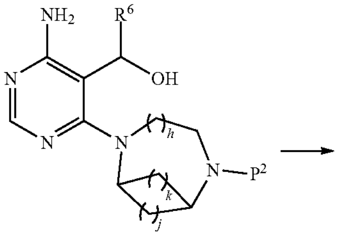

11-3

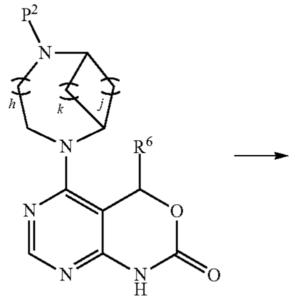

11-4

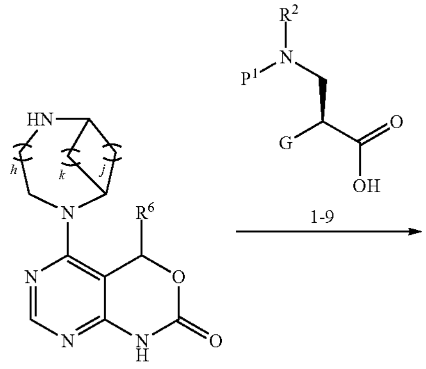

1-9

11-5

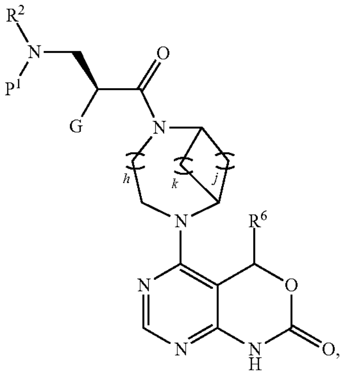

11-6 wherein, X is halogen, $R^6$, h, k, j, and G are as defined above, $P^1$ is H or an amido protecting group, and $P^2$ is an amido protecting group.

The compound of formula 9-2 is prepared from the compound of formula 9-1; the compound of formula 9-2 is reacted with the compound of formula 11-1 to prepare the compound of formula 11-2; the compound of formula 11-2 is reduced to produce the compound of formula 11-3; the compound of formula 11-3 undergoes a ring-forming reaction to prepare the compound of formula 11-4; the protecting group of the compound of formula 11-4 is removed to produce the compound of formula 11-5 or salts thereof, which is further reacted with the compound of formula 1-9 to prepare the compound of formula 11-6. When $P^1$ is an amido protecting group, synthesis scheme 11 further includes a step of removing the protecting group.

Synthesis scheme 12

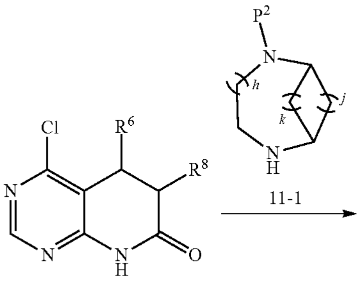

11-1

1-5

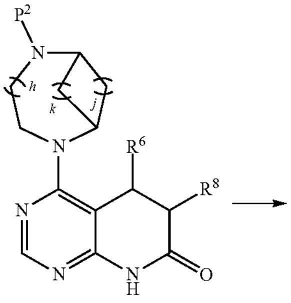

12-1

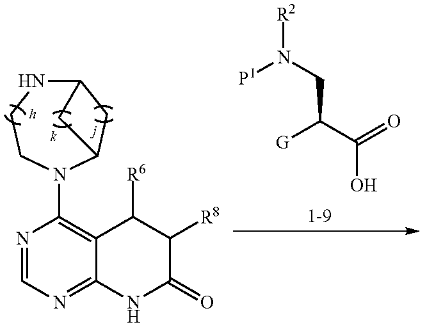

1-9

12-2

-continued

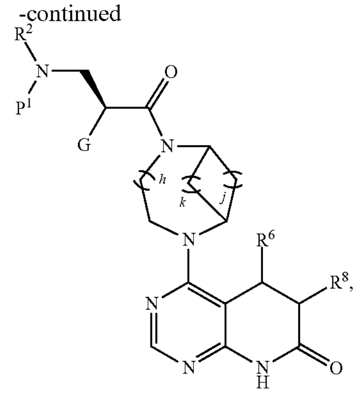

12-3 wherein, $R^6$, $R^8$, h, k, j, and G are as defined above, $P^1$ is H or an amido protecting group, and $P^2$ is an amido protecting group.

The compound of formula 12-1 is prepared by reacting the compound of formula 1-5 with the compound of formula 11-1; the protecting group of the compound of formula 12-1 is removed to prepare the compound of formula 12-2; the compound of formula 12-2 is reacted with the compound of formula 1-9 to prepare the compound of formula 12-3. When $P^1$ is an amido protecting group, synthesis scheme 12 further includes a step of removing the protecting group.

Those skilled in the art could understand that when L is substituted by $R^{12}$, the compound of the present invention can be prepared by referring to the above-mentioned synthesis schemes.

DETAILED DESCRIPTION OF THE INVENTION

Definition

Figure 1:
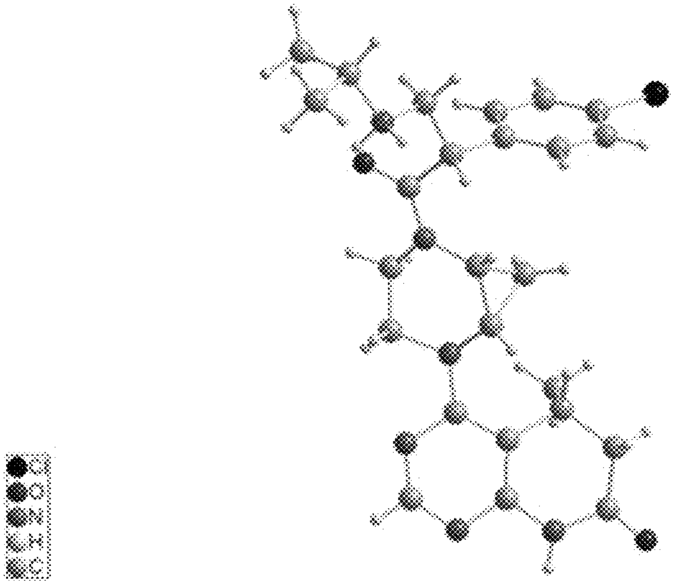
FIG. 1 is a schematic diagram of a single molecule of Isomer 2 of Example 15.

Unless otherwise specified, the following terms used in the specification and claims have the following meanings:

The term "compound" as used herein includes all stereoisomers and tautomers thereof.

The compounds of the invention may be asymmetric, for example, have one or more stereoisomers. Unless otherwise specified, all stereoisomers include, for example, enantiomers and diastereoisomers. The compounds containing asymmetric carbon atoms of the present invention can be separated in an optically active pure form or a racemic form. Compounds in the optically active pure form can be resolved from the racemic mixture thereof, or synthesized by using chiral raw materials or chiral reagents. The racemates, diastereoisomers, and enantiomers are all included in the scope of the present invention.

The compounds of the present invention also include tautomers thereof. Tautomers are derived from the exchange of a single bond with an adjacent double bond, which are accompanied with a transfer of one proton together.

The term "optional" or "optionally" means that the event or situation described later may or may not occur, and the description includes the occurrence of the event or situation and the non-occurrence of the event or situation.

The numerical range as used herein refers to each integer in the given range. For example, "$C_1$-$C_6$" means that the group can have 1 carbon atom, 2 carbon atoms, 3 carbon atoms, 4 carbon atoms, 5 carbon atoms, or 6 carbon atoms; "$C_3$-$C_6$" means that the group can have 3 carbon atoms, 4 carbon atoms, 5 carbon atoms, or 6 carbon atoms.

The term "substituted" means that any one or more hydrogen atoms on a specific atom or group are replaced by substituents, as long as the valence of the specific atom or group is normal and the substituted compound is stable. When the substituent is a keto group (i.e., =O), it means that two hydrogen atoms are replaced. Unless otherwise specified, the type and number of substituents can be arbitrary so long as they are chemically realisable.

When any variable (such as R) occurs more than once in the composition or structure of a compound, its definition in each case is independent. Thus, for example, if a group is substituted by 1-5 R, the group can optionally be substituted with up to 5 R and R has independent options in each case. In addition, combinations of substituents and/or variants thereof are allowed only if stable compounds are formed with such combinations.

The term "alkyl" refers to a saturated aliphatic hydrocarbon group, including linear or branched saturated hydrocarbon groups having the indicated number of carbon atoms. For example, the term "$C_1$-$C_6$ alkyl" includes $C_1$ alkyl, $C_2$ alkyl, $C_3$ alkyl, $C_4$ alkyl, $C_5$ alkyl and $C_6$ alkyl, examples thereof include, but are not limited to, methyl, ethyl, n-propyl, isopropyl, n-butyl, isobutyl, tert-butyl, n-pentyl, 2-pentyl, 3-pentyl, n-hexyl, 2-hexyl, 3-hexyl, etc. It can be a divalent group, such as methylene and ethylene.

The term "alkoxy" refers to a group having an alkyl-O— structure, wherein the alkyl includes a linear or branched saturated monovalent hydrocarbon group. For example, "$C_1$-$C_3$ alkoxy" includes methoxy, ethoxy, n-propoxy, and isopropoxy.

The term "alkanoyl" refers to a group having an RC(=O)— structure, wherein R is H or a saturated aliphatic hydrocarbon group, including linear or branched saturated monovalent hydrocarbon groups. For example, "$C_1$-$C_4$ alkanoyl" includes $C_1$ alkanoyl, $C_2$ alkanoyl, $C_3$ alkanoyl, and $C_4$ alkanoyl. Suitable alkanoyl include formyl, acetyl, n-propionyl, isopropionyl, n-butyryl, isobutyryl and tert-butyryl.

The term "halogenated" refers to being substituted by one or more halogen atoms, and examples of halogen atoms include fluorine atoms, chlorine atoms, bromine atoms and iodine atoms. For example, the term "halogenated $C_1$-$C_3$ alkoxy" refers to a $C_1$-$C_3$ alkoxy substituted by one or more halogen atoms, and examples thereof include, but are not limited to, $OCF_3$, $OCHF_2$, $OCH_2F$, $OCH_2CF_3$, $OCH_2CHF_2$, or $OCF_2CF_3$. For example, the term "halogenated $C_1$-$C_3$ alkyl" refers to a $C_1$-$C_3$ alkyl substituted by one or more halogen atoms, and examples thereof include, but are not limited to, $CF_3$, $CHF_2$, $CH_2F$, $CH_2CF_3$, $CH_2CHF_2$, or $CF_2CF_3$.

The term “cycloalkyl” refers to a monocyclic saturated hydrocarbon system without heteroatoms or double bonds. Examples of the term “$C_3$-$C_6$ cycloalkyl” include, but are not limited to, cyclopropyl, cyclobutyl, cyclopentyl, and cyclohexyl.

The term “aryl” refers to an all-carbon monocyclic or fused polycyclic aromatic ring group with a conjugated π-electron system, which is obtained by removing one hydrogen atom from a single carbon atom of the parent aromatic ring system. For example, an aryl may have 6-20 carbon atoms, 6-14 carbon atoms, or 6-10 carbon atoms. Bicyclic groups containing aromatic rings fused with saturated, partially unsaturated rings, or aromatic carbocyclic rings are also involved. Examples include, but are not limited to, phenyl, naphthyl, anthryl, indene, indane, 1,2-dihydronaphthalene, 1,2,3,4-tetrahydronaphthalene.

The term “heteroaryl” refers to a monovalent aryl containing at least one 5-, 6-, and 7-membered ring with heteroatoms independently selected from the group consisting of nitrogen, oxygen, and sulfur, and includes a fused ring system with 5-10 atoms (at least one of the rings is aromatic). Examples of heteroaryl include, but are not limited to, pyridyl, thienyl, imidazolyl, pyrimidinyl, pyridyl, furyl, pyrazinyl, thiazolyl, quinolinyl, isoquinolinyl, indolyl, benzimidazolyl, imidazopyridyl, benzofuranyl, pyridazinyl, isoindolyl.

The term “membered” refers to the number of backbone atoms constituting the ring. For example, “5-10 membered” means that the number of backbone atoms constituting the ring is 5, 6, 7, 8, 9, or 10. Therefore, for example, pyridine, piperidine, piperazine, and benzene are 6-membered rings, while thiophene and pyrrole are 5-membered rings.

The term “heterocyclic ring” refers to a 5-12 membered saturated non-aromatic system having ring carbon atoms and 1 to 2 ring heteroatoms, wherein the heteroatoms are independently selected from the group consisting of nitrogen, sulfur and oxygen atoms. In heterocyclic groups containing one or more nitrogen atoms, the point of junction may be a carbon or nitrogen atom, as long as the valence is allowable. The heterocyclic ring may be a monocyclic or polycyclic ring system, such as a bicyclic ring, in which two or more rings exist in the form of a fused ring, a bridged ring or a spiro ring, and at least one ring contains one or more heteroatoms.

The substituent $R^{12}$ can bond to any atom on a ring, as long as the valence is allowable. Combinations of substituents and/or variants thereof are allowed only if stable compounds are formed with such combinations. Those skilled in the art can understand that, for any group containing one or more $R^{12}$ substituents, any substitution or substitution pattern that is impossible to exist in space and/or cannot be synthesized will not be introduced.

Single wavy line “⌇” and double wavy line “⌇⌇” both refer to a position where a chemical bond is connected to, and both have the same chemical meaning. Unless otherwise specified, the difference between “⌇” and “⌇⌇” is only the connection position or sequence.

The term “amido protecting group” refers to a protecting group suitable for preventing side reactions at the nitrogen position of the amido. Examples of amino protecting groups include, but are not limited to: Boc, DMB, benzyloxycarbonyl, 9-fluorenylmethyloxycarbonyl, benzyl, formyl, and acetyl.

The term “pharmaceutically acceptable salts” refers to salts that retain the biological efficacy of the free acid and base of a specific compound without biological adverse effects, such as acid (including organic acid and inorganic acid) addition salts or base (including organic base and inorganic base) addition salts.

The pharmaceutically acceptable salts of the present invention can be synthesized from the parent compounds containing acid or basic groups by conventional chemical methods. Generally, such salts are prepared by reacting these compounds in free acid or base form with a stoichiometrically appropriate amount of base or acid in water or an organic solvent or a mixture of both.

The term “effective amount” or “therapeutically effective amount” refers to a sufficient amount of a drug or medicament that is non-toxic but can achieve the desired effect.

The term “pharmaceutically acceptable carrier” refers to those carriers that have no obvious stimulating effect on the body and do not impair the biological activity and performance of the active compounds, including, but not limited to, any diluents, disintegrants, adhesives, glidants, and wetting agents approved by the State Food and Drug Administration that can be used for humans or animals.

The abbreviations used in the claims and specification and meanings thereof are as follows:

M: mol/L mM: mmol/L nM: nmol/L

Boc: tert-butoxycarbonyl

DMB: 2,4-dimethoxybenzyl

NMP: N-methylpyrrolidone

DMAP: p-dimethylaminopyridine

DMF: N, N-dimethylformamide

DEA: diethylamine

PE: petroleum ether

EA: ethyl acetate

HATU: (2-(7-azobenzotriazole)-N,N,N',N'-tetramethylurea hexafluorophosphate)

RT: retention time

SFC: Supercritical Fluid Chromatography h: hour min: minute

TK: Tyrosine Kinase

SEB: fluorescence signal enhancer

HTRF: homogeneous time-resolved fluorescence

DTT: dithiothreitol

NR: not calculated

Preparation Method:

The preparation methods of the compounds of the present invention are described in more detail below, but the scope of the present invention is not limited by these specific preparation methods. In addition, reaction conditions such as reactants, solvents, bases, amounts of compounds used, reaction temperature, reaction time, etc. are not limited to the following examples.

The compounds of the present invention can also be conveniently prepared by combining various synthetic methods described in this specification or known in the art, and such a combination can be easily performed by a person skilled in the art.

Process A:

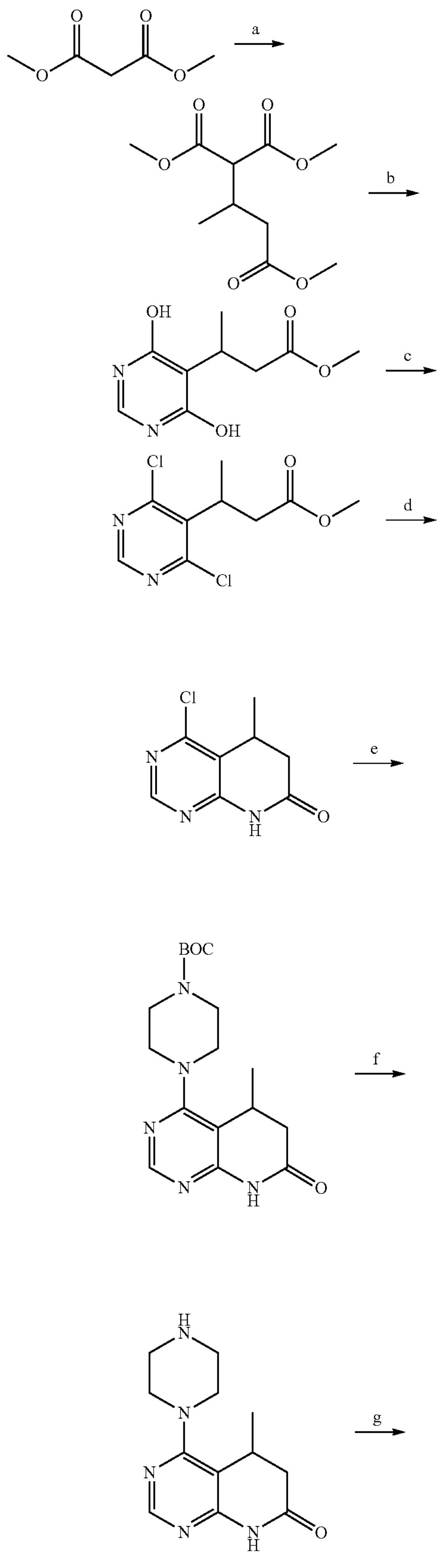

-continued

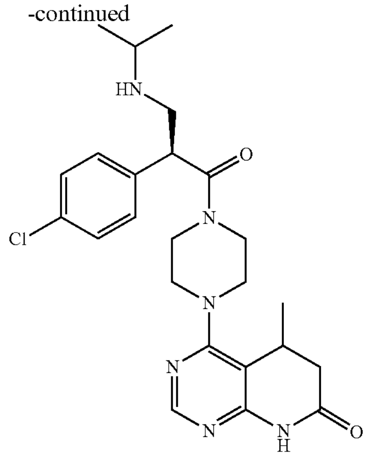

Reaction conditions: a) ethyl crotonate, methanol solution of sodium methoxide (30 wt %), methanol; b) formamidine acetate, methanol solution of sodium methoxide (30 wt %); c) phosphorus oxychloride, diisopropylethylamine, acetonitrile; d) ammonia (25-28 wt %); e) tert-butylpiperazine-1-carboxylate; f) trifluoroacetic acid, dichloromethane; g) (S)-2-(4-chlorophenyl)-3-(isopropylamino)propionic acid, 2-(7-benzotriazole oxide)-N,N,N'N'-tetramethylurea hexaflurophosphate, diisopropylethylamine, dichloromethane.

Example 1

4-(4-((S)-2-(4-chlorophenyl)-3-(isopropylamino) propionyl)piperazin-1-yl)-5-meth yl-5,8-dihydro-pyrido[2,3-d]pyrimidin-7(6H)-one

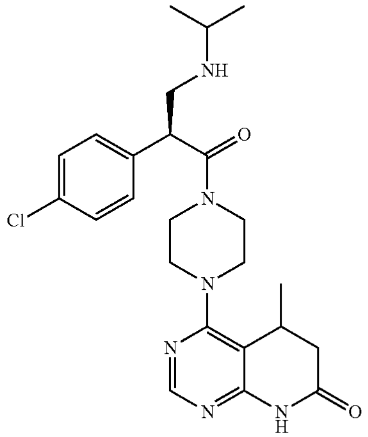

a) trimethyl 2-methylpropane-1,1,3-tricarboxylate

Under the protection of nitrogen, methanol solution of sodium methoxide (30 wt %) (8.16 g) was added to methanol (400 mL) at 20° C. Subsequently, the resulting solution was heated to 70° C., dimethyl malonate (24.64 g) and ethyl crotonate (21.08 g) were mixed uniformly, and then added dropwise to the methanol solution of sodium methoxide, and reacted at 70° C. for 3 hours. After the reaction was complete, the solvent was evaporated under reduced pressure, and ethyl acetate (100 mL) was added and the pH was adjusted to 7 with 4 M hydrochloric acid, and then 100 mL of water was added. The organic phase was separated and concentrated to obtain 45.48 g of yellow liquid, which was used directly in the next step without purification.

$^1$H NMR (400 MHz, DMSO-$d_6$) δ (ppm) 0.93 (d, J=6.8 Hz, 3H), 2.26 (q, J=12.0 Hz, 2H), 2.52-2.58 (m, 1H), 3.56 (d, J=6.8 Hz, 1H), 3.59 (s, 3H), 3.65 (s, 3H), 3.67 (s, 31H).

b) methyl 3-(4,6-dihydroxypyrimidin-5-yl)butyrate

Under protection of nitrogen, methanol solution of sodium methoxide (30 wt %) (97.55 g) was added to methanol (400 mL) at 20° C. Then the resulting solution was cooled to −15° C., and formamidine acetate (22.98 g) was added. The resulting reaction system was reacted for 30 min. Subsequently, trimethyl 2-methylpropane-1,1,3-tricarboxylate (45.72 g) was added dropwise, the temperature was slowly raised to 20° C., and the reaction was continued for 12 hours. After the reaction was completed, the reaction solution was cooled to 0° C., and 4 M hydrochloric acid was added to adjust the pH=2. The solvent was evaporated under reduced pressure, and then 100 mL of water was added at 0° C. to obtain a solid precipitate. The solid was collected by suction filtration. The filter cake was washed with water (50 mL) and dried in vacuum to obtain 29.60 g of yellow solid, which was used directly in the next step without purification. $^1$H NMR (400 MHz, DMSO-$d_6$) δ (ppm) 11.62 (s, 2H), 7.86 (s, 1H), 3.53 (s, 31H), 3.34-3.42 (m, 1H), 2.58-2.70 (m 2H), 1.11 (d, J=6.8 Hz, 3H).

c) methyl 3-(4,6-dichloropyrimidin-5-yl)butyrate

Under the protection of nitrogen, methyl 3-(4,6-dihydroxypyrimidin-5-yl)butyrate (9.1 g) was dispersed in acetonitrile (100 mL) at 22° C., and phosphorus oxychloride (16.03 g) and diisopropylethylamine (7.79 g) were added dropwise successively. The reaction system was obviously exothermic, and the solid was gradually dissolved and clarified, then the temperature was raised to 60° C. and the reaction solution was reacted for 18 hours. After the reaction was completed, the reaction solution was cooled to 0° C., poured into 200 mL ice water, adjusted to pH=7-8 with saturated sodium bicarbonate solution, extracted with ethyl acetate (50 mL×3). The organic phases were combined, and the solvent was evaporated under reduced pressure, and the residue was separated by silica gel column chromatography (petroleum ether: ethyl acetate=4:1, volume ratio) to obtain 8.36 g of brown liquid.

d) 4-chloro-5-methyl-5,8-dihydropyrido[2,3-d]pyrimidin-7(6H)-one

Methyl 3-(4,6-dichloropyrimidin-5-yl)butyrate (4.12 g) and ammonia (25-28 wt %, 25 mL) were added in a 100 mL autoclave at 20° C., and the reaction system was heated to 60° C. and reacted for 18 hours. After the reaction was completed, the reaction solution was cooled to 0° C., filtered with suction, and the filter cake was pulped with 30 mL (petroleum ether: ethyl acetate=10:1, volume ratio) to obtain 1.51 g of a pale yellow solid. $^1$H NMR (300 MHz, DMSO-$d_6$) δ (ppm) 1.09-1.12 (d, J=7.2 Hz, 3H), 2.36-2.49 (m, 1H), 2.92-3.00 (m, 1H), 3.27-3.36 (m, 1H), 8.54 (s, 1H).

e) tert-butyl 4-(5-methyl-7-oxo-5,6,7,8-tetrahydropyrido[2,3-d]pyrimidin-4-yl)piperazine-1-carboxylate Under the protection of nitrogen, 4-chloro-5-methyl-5,8-dihydropyrido[2,3-d]pyrimidin-7(6H)-one (0.42 g) and tert-butylpiperazine-1-carboxylate (10.76 g) were directly heated to 140° C. and stirred for 6 hours. After the reaction was completed, the reaction solution was cooled to 0° C., poured into 30 mL of ice water, adjusted to pH=7 with 4 M hydrochloric acid, and extracted with dichloromethane (20 mL×2). The solvent was evaporated under reduced pressure, and the residue was separated by silica gel column chromatography (dichloromethane:methanol=30:1, volume ratio) to obtain 0.67 g of a pale yellow solid. LC-MS (ESI) m/z: 348, (M+H).

$^1$H NMR (300 MHz, $CDCl_3$) δ (ppm) 8.47 (s, 1H), 8.42 (s, 1H) 3.24-3.61 (m, 9H), 2.56-2.83 (m, 2H) 1.48 (s, 9H), 123-1.26 (d, J=6.9 Hz, 3H).

f) 5-methyl-4-(piperazin-1-yl)-5,8-dihydropyrido[2,3-d]pyrimidin-7(6H)-one tert-butyl 4-(5-methyl-7-oxo-5,6,7,8-tetrahydropyrido[2,3-d]pyrimidin-4-yl)piperazine-1-carboxylate (0.67 g) was dissolved in dichloromethane (10 mL) at 25° C., and trifluoroacetic acid (1.31 g) was added, and the reaction system was reacted for 16 hours. After the reaction was completed, the solvent was evaporated under reduced pressure, and the residue was cooled to 0° C., adjusted to pH=12 with 20% sodium hydroxide solution, extracted with dichloromethane (20 mL×6). The organic phases were combined and evaporated under reduced pressure to remove the solvent, and the residue was separated by silica gel column chromatography (dichloromethane:methanol=20:1, volume ratio) to obtain 0.39 g of a yellow solid, which was directly used in the next step.

g) 4-(4-((S)-2-(4-chlorophenyl)-3-(isopropylamino)propionyl)piperazin-1-yl)-5-methyl-5,8-dihydropyrido[2,3-d]pyrimidin-7(6H)-one Under the protection of nitrogen, 5-methyl-4-(piperazin-1-yl)-5,8-dihydropyrido[2,3-d]pyrimidin-7(6H)-one (0.10 g) and (S)-2-(4-chlorophenyl)-3-(isopropylamino)propionic acid (0.107 g) were dissolved in dichloromethane (5 mL) at 20° C., and then 2-(7-benzotriazole oxide)-N,N,N',N'-tetramethylurea hexafluorophosphate (0.184 g) and diisopropylethylamine (0.078 g) were added separately, and the reaction system was reacted at 25° C. for 16 hours. After the reaction was completed, 10 mL of water was added to the reaction solution. The organic phase was separated and washed with saturated sodium chloride solution (2 mL). After the solvent was evaporated under reduced pressure, the residue was separated by column chromatography (dichloromethane:methanol=25:1, volume ratio) to obtain 0.12 g of a white solid. LC-MS (ESI) m/z: 471 (M+H).

$^1$H NMR (300 MHz, $CDCl_3$) δ (ppm) 1.06-1.28 (m, 6H), 1.30-1.38 (m, 3H) 2.57 (d, J=15.0 Hz, 1H), 2.70-2.78 (m, 4H), 2.80-3.25 (m, 21H), 3.28-3.69 (nm, 7H), 3.86-4.09 (m, 2H), 7.22-7.36 (m, 4H), 8.38 (s, 1H), 8.61 (s, 1H).

Example 2

(S)-4-(4-((S)-2-(4-chlorophenyl)-3-(isopropylamino) propionyl)piperazin-1-yl)-5-methyl-5,8-dihydro-pyrido[2,3-d]pyrimidin-7(6H)-one and (R)-4-(4-((S)-2-(4-chlorophenyl)-3-(isopropylamino) propionyl)piperazin-1-yl)-5-methyl-5,8-dihydropyrido[2,3-d]pyrimidin-7(6H)-one

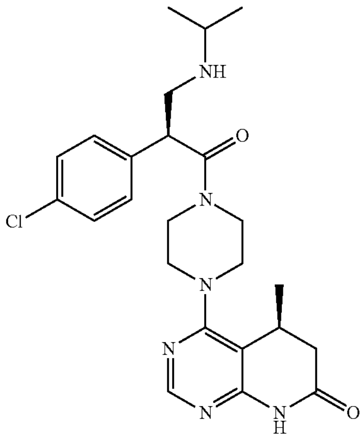

and

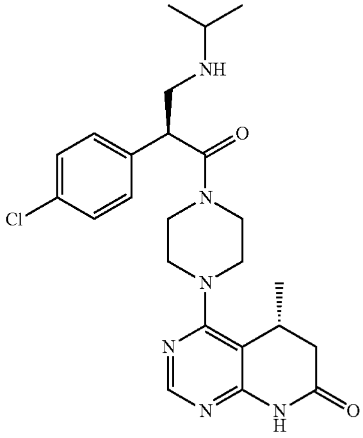

Under the protection of nitrogen, 5-methyl-4-(piperazin-1-yl)-5,8-dihydropyrido[2,3-d]pyrimidin-7(6H)-one (0.49 g) and (S)-2-(4-chlorophenyl)-3-(isopropylamino)propionic acid (0.53 g) were dissolved in N,N-dimethylformamide (20 mL) at 20° C., and then 2-(7-benzotriazole oxide)-N,N,N',N'-tetramethylurea hexafluorophosphate (1.50 g) and diisopropylethylamine (0.51 g) were added separately, and the reaction system was reacted at 25° C. for 4 hours. After the reaction was completed, 100 mL of water was added to the reaction solution. The organic phase was separated and washed with saturated sodium chloride solution (40 mL). After the solvent was evaporated under reduced pressure, the residue was separated by silica gel column chromatography (dichloromethane:methanol=25:1, volume ratio) to obtain 0.59 g of a white solid. After chiral resolution, 0.21 g (de %=100%) of (S) configuration product and 0.19 g (de %=99%) of (R) configuration product were obtained. Resolution instrument: waters SFC200; Column: Daicel Chiralcel OD, 250×30 mm ID, 5 μm; mobile phase A: $CO_2$, mobile phase B: isopropanol (containing 0.1% $NH_3 \cdot H_2O$), A:B=70:30 (volume ratio).

(S) configuration product: LC-MS (ESI m/z: 471 (M+H) $^1$H NMR (300 MHz, DMSO-$d_6$) δ (ppm) 0.93-0.96 (m, 6H), 1.30 (d, J=3.0 Hz, 3H), 2.23-2.36 (m, 1H), 2.61-2.84 (m, 4H), 3.12-3.31 (m, 5H), 3.35-3.49 (m, 2), 3.65-3.78 (m, 3H), 4.21-4.29 (m, 1H), 7.33 (d, J=6.6 Hz, 2H), 7.40 (d, J=6.6 Hz, 2H), 8.38 (s, 1H), 10.66 (s, 1H).

(R) configuration product: LC-MS (ESI m/z: 471 (M+1). $^1$H NMR (300 MHz, DMSO-$d_6$) δ (ppm) 0.95-1.03 (m, 9H), 2.26-2.30 (m, 1H), 2.66-2.79 (m, 1H), 2.82-2.96 (m, 3H), 3.11-3.20 (m, 4H), 3.34-3.47 (m, 3H), 3.62-3.69 (m, 3H), 4.18-4.22 (m, 1H) 7.34 (d, J=6.6 Hz, 2H), 7.42 (d, J=6.6 Hz, 2H), 8.28 (s, 1H), 10.62 (s, 1H).

Process B:

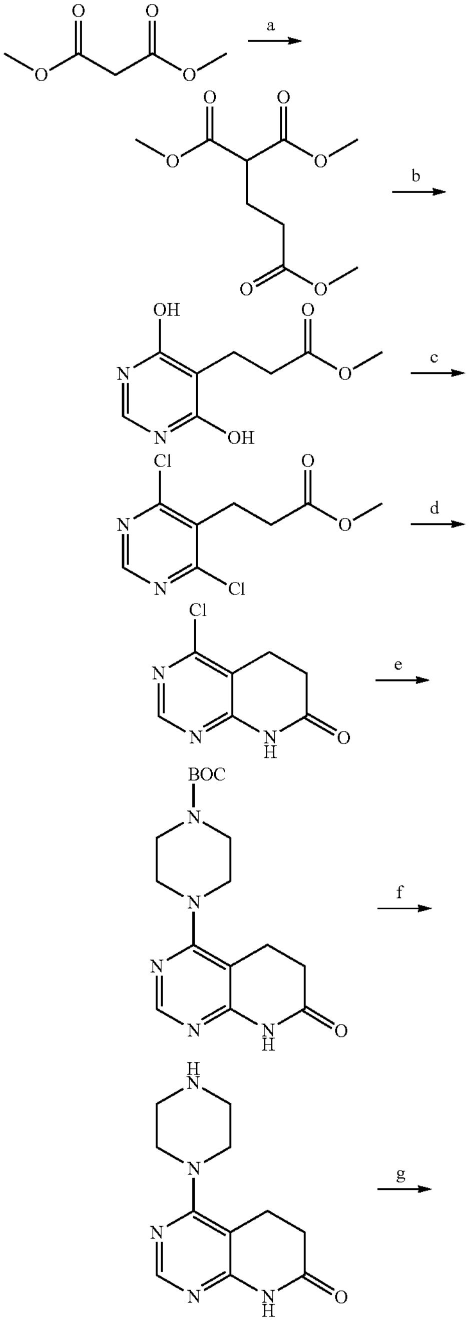

-continued

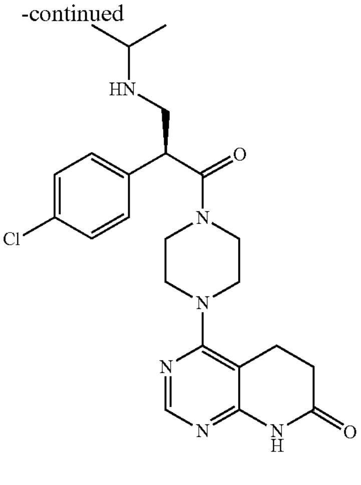

Reaction conditions: a) methyl acrylate, methanol solution of sodium methoxide (30 wt %), methanol; b) formamidine acetate, sodium methoxide, methanol; c) phosphorus oxychloride, diisopropylethylamine, acetonitrile; d) ammonia (25-28 wt %); e) tert-butylpiperazine-1-carboxylate; f) trifluoroacetic acid, dichloromethane; g) (S)-2-(4-chlorophenyl)-3-(isopropylamino)propionic acid, 2-(7-benzotriazole oxide)-N,N,N',N'-tetramethylurea hexafluorophosphate, diisopropylethylamine, dichloromethane.

Example 3

(S)-4-(4-(2-(4-chlorophenyl)-3-(isopropylamino)propionyl)piperazin-1-yl)-5,8-dihydropyrido[2,3-d]pyrimidin-7(6H)-one

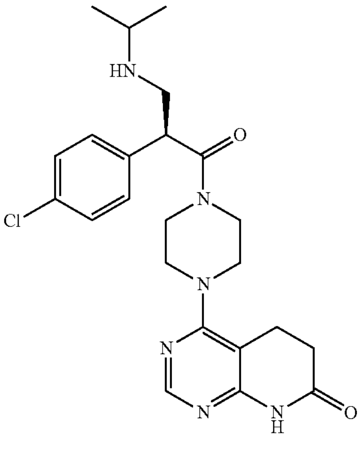 [SMILES: CC(C)NC[C@@H](C(=O)N1CCN(c2ncnc3c2CCC(=O)N3)CC1)c1ccc(Cl)cc1]

Preparation was in accordance with the method described in Example 1, wherein methyl acrylate was used instead of ethyl crotonate.

LC-MS (ESI n/z: 457 (M+H), $^1$H NMR (300 MHz, DMSO-$d_6$) δ (ppm) 0.92-0.96 (m, 6H), 2.42-2.49 (m, 2H), 2.62-278 (m, 5H), 3.08-3.29 (m, 4H), 3.38-3.43 (m, 2H) 3.57-3.65 (m, 3H), 4.21-4.29 (m, 1H) 7.31-7.34 (m, 2H), 7.38-7.40 (m, 2H), 8.27 (s, 1H), 10.53 (s, 1H).

Example 4

4-((R)-4-((S)-2-(4-chlorophenyl)-3-(isopropylamino)propionyl)-2-methylpiperazin-1-yl)-5,8-dihydropyrido[2,3-d]pyrimidin-7(6H)-one

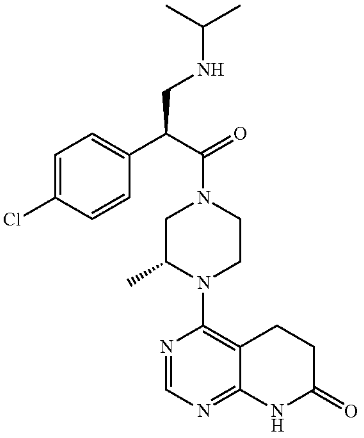 [SMILES: CC(C)NC[C@@H](C(=O)N1CCN(c2ncnc3c2CCC(=O)N3)[C@H](C)C1)c1ccc(Cl)cc1]

Preparation was in accordance with the method as described in Example 3, wherein tert-butyl (R)-3-methylpiperazine-1-carboxylate was used instead of tert-butylpiperazine-1-carboxylate.

LC-MS (ES) m/z: 471 (M+H) $^1$H NMR (300 MHz, DMSO-$d_6$) δ (ppm) 0.75-0.95 (m, 94), 2.40-2.49 (m, 3H), 2.51-2.61 (m, 4H), 2.85-3.36 (m, 5H), 3.62-3.76 (m, 1H), 3.91-3.96 (m, 1H), 4.14-4.19 (m, 2H) 7.29-7.42 (m, 4H), 8.26 (d, J=7.2 Hz, 1H), 10.54 (s, 1H).

Example 5

4-((S)-4-((S)-2-(4-chlorophenyl)-3-(isopropylamino)propionyl)-2-methylpiperazin-1-yl)-5,8-dihydropyrido[2,3-d]pyrimidin-7(6H)-one

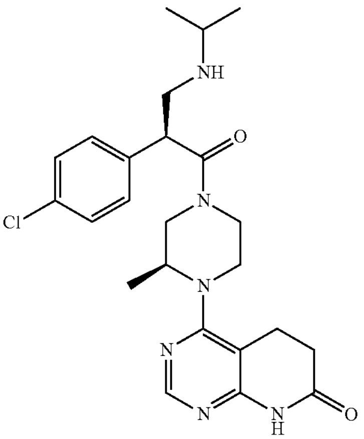 [SMILES: CC(C)NC[C@@H](C(=O)N1CCN(c2ncnc3c2CCC(=O)N3)[C@@H](C)C1)c1ccc(Cl)cc1]

Preparation was in accordance with the method as described in Example 3, wherein tert-butyl (S)-3-methylpiperazine-1-carboxylate was used instead of tert-butylpiperazine-1-carboxylate.

LC-MS (ESI) m/z: 471 (M+H) $^1$H NMR (300 MHz, DMSO-$d_6$) δ (ppm) 1.10-1.33 (m, 9H), 2.42-2.49 (m, 2H)

2.67-2.76 (m, 4H), 2.84-3.05 (m, 4H) 3.51-3.58 (m, 3H) 3.91-4.19 (m, 21H) 4.28-4.54 (m, 1H) 7.32-7.45 (m, 4H), 8.27 (s, 1H), 10.53 (s, 1H).

Process C:

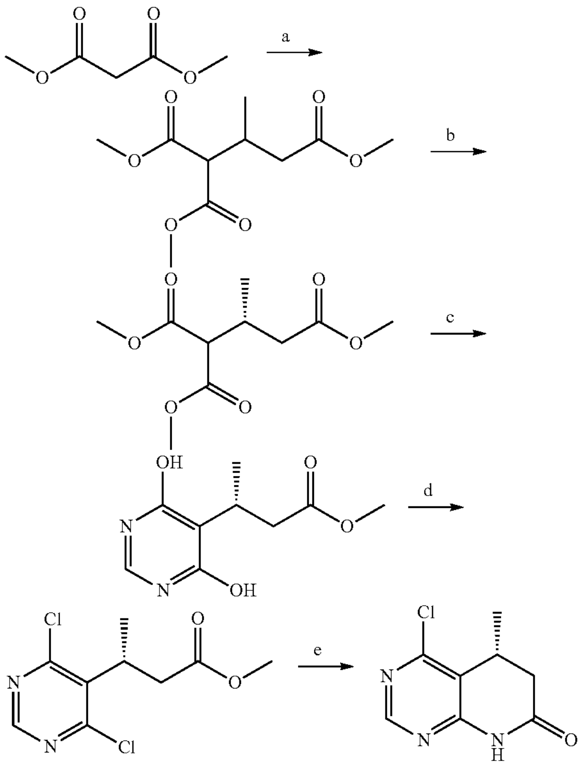

Reaction conditions: a) ethyl crotonate, methanol solution of sodium methoxide (30 wt %), methanol; b) disodium hydrogen phosphate, deionized water, hydrochloric acid, lipase (Candida rugosa), sodium hydroxide; c) formamidine acetate, sodium methoxide, methanol; d) phosphorus oxychloride, diisopropylethylamine, acetonitrile; e) ammonia (25-28 wt %).

Intermediate (R)-4-chloro-5-methyl-5,8-dihydropyrido[2,3-d]pyrimidin-7(6H)-one

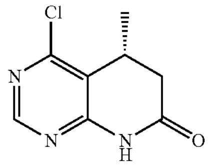

a) Trimethyl 2-methylpropane-1,1,3-tricarboxylate

Under the protection of nitrogen, methanol solution of sodium methoxide (30 wt %, 50.32 g) was added to methanol (900 mL) at 20° C. Subsequently, the resulting solution was heated to 70° C. Dimethyl malonate (461.12 g) and ethyl crotonate (349.46 g) were mixed uniformly, and then added dropwise to the methanol solution of sodium methoxide, and reacted at 70° C. for 3 hours. After the reaction was complete, the solvent was evaporated under reduced pressure, and ethyl acetate (1 L) was added and the pH was adjusted to 7-8 with 4 M hydrochloric acid, and then 500 mL of water was added. The organic phase was separated and concentrated to obtain 777.68 g of yellow liquid.

$^1$H NMR (400 MHz, DMSO-$d_6$) δ (ppm) 3.67 (s, 3H) 3.65 (s, 3H), 3.59 (s, 3H), 3.56 (d, J=6.8 Hz, 1H), 2.45-2.58 (m, 2H), 2.23-2.29 (m, 1H), 0.93 (d, J=6.8 Hz, 3H).

b) trimethyl (R)-2-Methylpropane-1,1,3-tricarboxylate

Disodium hydrogen phosphate (4.5 g) was dissolved in 1.5 L of deionized water at 25° C., and the pH was adjusted to 7.05 with 2 N hydrochloric acid. Trimethyl 2-methylpropane-1,1,3-tricarboxylate (150.46 g) and lipase (*Candida rugosa,* 40 g, added in 6 days) were added, and the pH was adjusted to 7.0-7.6 with 2 N sodium hydroxide solution. The reaction was carried out at 35° C. for 6 days. The chiral test result is ee %>98% (Chiral test conditions: Chiralpak IC, 4.6×250 mm, 5 μm, n-hexane:ethanol=9:1, volume ratio). The reaction solution was cooled to 10° C., adjusted to pH=3-4 with 3 M hydrochloric acid, and then 500 mL ethyl acetate was added. Following filtrating with suction, the obtained filter cake was washed with ethyl acetate (600 mL), separated, and washed with saturated sodium bicarbonate aqueous solution (100 mL). The organic phase was then separated and concentrated to obtain 26.89 g of pale yellow liquid.

$^1$H NMR (400 MHz, $CDCl_3$) δ (ppm) 3.74 (s, 6H), 3.68 (s, 3H), 3.46 (d, J=7.2 Hz, 1H), 2.71-2.79 (m, 1H), 2.54 (dd, J=15.6, 4.8 Hz, 1H), 2.32 (dd, J=16.0, 8.4 Hz, 1H), 1.06 (d, J=6.8 Hz, 3H).

c) methyl (R)-3-(4,6-Dihydroxypyrimidin-5-yl)butyrate

Under protection of nitrogen, formamidine acetate (11.33 g) was dissolved in methanol (200 mL) at 20° C., cooled to 0° C., and methanol solution of sodium methoxide (30%, 55.62 g) was added dropwise, and reacted at 0° C. for 60 min. A methanol (60 mL) solution of trimethyl (R)-2-methylpropane-1,1,3-tricarboxylate (24.07 g) was added dropwise. The temperature was naturally raised to 20° C. and the reaction solution was reacted for 10 hours. After the reaction was completed, the reaction solution was cooled to 0° C., and 3 N hydrochloric acid was added to adjust the pH to 5-6. The solvent was evaporated under reduced pressure, and then the residue was cooled to 0° C., and 3 N hydrochloric acid was added to adjust the pH=3 to obtain a solid precipitate. The solid was collected by suction filtration. The filter cake was washed with ice water (100 mL) and dried in vacuum to obtain 18.79 g of a white solid, which was used directly in the next step.

d) methyl (R)-3-(4,6-Dichloropyrimidin-5-yl)butyrate

Under the protection of nitrogen, methyl (R)-3-(4,6-dihydroxypyrimidin-5-yl)butyrate (14.63 g) was dispersed in acetonitrile (70 mL) at 22° C., and phosphorus oxychloride (26.42 g) and diisopropylethylamine (12.51 g) were added dropwise successively. The reaction system was obviously exothermic, and then the temperature was raised to 60° C. The solid was gradually dissolved and clarified, and the reaction solution was continued for 18 hours. After the reaction was completed, the reaction solution was cooled to 0° C., and 100 mL ethyl acetate was added. The pH was adjusted to 7-8 with saturated sodium bicarbonate solution, and the reaction solution was extracted with ethyl acetate (50 mL×3), and evaporated under reduced pressure to remove the organic phase to obtain 13.89 g of a yellow solid, which was used directly in the next step.

e) (R)-4-chloro-5-methyl-5,8-dihydropyrido[2,3-d]pyrimidin-7(6H)-one

Methyl (R)-3-(4,6-dichloropyrimidin-5-yl)butyrate (13.89 g) and ammonia (25-28 wt %, 70 mL) were added in a 100 mL autoclave at 20° C., and the reaction system was heated to 50° C. and reacted for 18 hours. After the reaction was completed, the reaction solution was cooled to 0° C., filtered with suction, and the filter cake was pulped with 30 mL (petroleum ether: ethyl acetate=10:1, volume ratio) to obtain 7.32 g of a pale yellow solid.

LC-MS (ESI) m/z: 0.198 (M+H) $^1$H NMR (300 MHz, $CDCl_3$) δ (ppm) 1.30 (d, J=7.2 Hz, 3H), 2.65-2.69 m, 1H), 2.86-2.92 (m, 1H), 3.47-3.54 (m, 1H), 8.64 (s, 1H), 10.10 (s, 1H).

Process D:

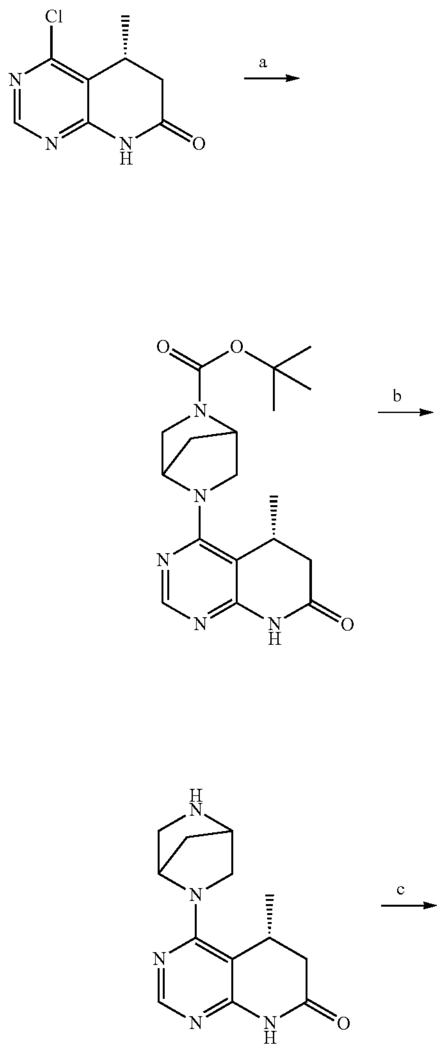

-continued

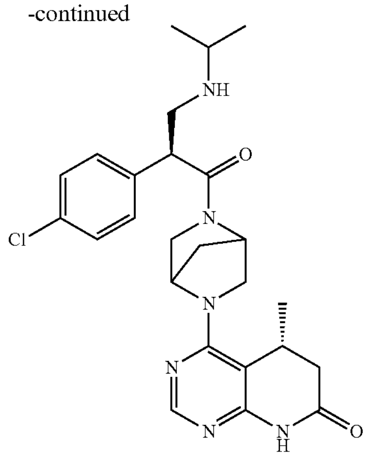

Reaction conditions: a) tert-butyl, 2,5-diazabicyclo[2.2.1]heptane-2-carboxylate, 4-dimethylaminopyridine, N-methylpyrrolidone; b) hydrogen chloride/1,4-dioxane (4.0M), dioxane; c) (S)-2-(4-chlorophenyl)-3-(isopropylamino)propionic acid, 2-(7-benzotriazole oxide)-N,N,N',N'-tetramethylurea hexafluorophosphate, diisopropylethylamine, N,N-dimethylformamide.

Example 6

(5R)-4-(5-((S)-2-(4-chlorophenyl)-3-(isopropylamino)propionyl)-2,5-diazabicyclo[2.2.1]heptan-2-yl)-5-methyl-5,8-dihydropyrido[2,3-d]pyrimidin-7(6H)-one

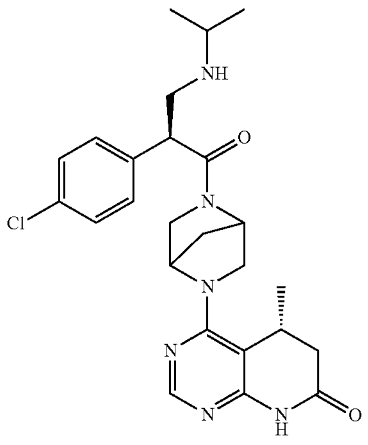 [SMILES: CC(C)NC[C@@H](C(=O)N1CC2CC1CN2c1ncnc2c1[C@H](C)CC(=O)N2)c1ccc(Cl)cc1]

a) tert-butyl 4-(5-methyl-7-oxo-5,6,7,8-tetrahydropyrido[2,3-d]pyrimidin-4-yl)piperazine-1-carboxylate Under the protection of nitrogen, (R)-4-chloro-5-methyl-5,8-dihydropyrido[2,3-d]pyrimidin-7(6H)-one (0.30 g), tert-butyl 2,5-diazabicyclo[2.2.1]heptane-2-carboxylate (1.21 g) and 4-dimethylaminopyridine (0.58 g) were dissolved in N-methylpyrrolidone at 22° C., heated to 140° C., and reacted for 6 hours. After the reaction was completed, the reaction solution was cooled to 0° C., poured into 30 mL of ice water, adjusted to pH=4-5 with 4 M hydrochloric acid, and extracted with ethyl acetate (20 mL×2). The organic phases were washed with saturated sodium chloride solution (10 mL×3) and evaporated under reduced pressure, and the residue was separated by silica gel column chromatography (petroleum ether: ethyl acetate=1:1, volume ratio) to obtain 0.33 g of a pale yellow solid. LC-MS (ESI) m/z: 360 (M+H).

b)(5R)-4-(2,5-diazabicyclo[2.2.1]heptan-2-yl)-5-methyl-5,8-dihydropyrido[2,3-d]pyrimidin-7(6H)-one Tert-butyl 4-(5-methyl-7-oxo-5,6,7,8-tetrahydropyrido[2,3-d]pyrimidin-4-yl)piperazine-1-carboxylate (0.28 g) was dissolved in dioxane (3 mL) at 25° C., and hydrogen chloride/1,4-dioxane (4.0 M, 1.91 g) was added to react for 16 hours. After the reaction was completed, the reaction solution was concentrated to remove the solvent, cooled to 0° C., adjusted to pH=12 with 20% sodium hydroxide solution, and extracted with dichloromethane (20 mL×8). The organic phase was evaporated under reduced pressure to obtain 0.15 g of a brown solid, which was directly used in the next step.

c)(5R)-4-(5-((S)-2-(4-chlorophenyl)-3-(isopropylamino)propionyl)-2,5-diazabicyclo[2.2.1]heptan-2-yl)-5-methyl-5,8-dihydropyrido[2,3-d]pyrimidin-7(6H)-one Under the protection of nitrogen, tert-butyl 4-(5-methyl-7-oxo-5,6,7,8-tetrahydropyrido[2,3-d]pyrimidin-4-yl)piperazine-1-carboxylate (0.15 g) and (S)-2-(4-chlorophenyl)-3-(isopropylamino)propionic acid (0.157 g) were dissolved in N,N-dimethylformamide (5 mL) at 20° C., and then 2-(7-benzotriazole oxide)-N,N,N',N'-tetramethylurea hexafluorophosphate (0.26 g) and diisopropylethylamine (0.29 g) were added separately. The reaction system was reacted at 25° C. for 16 hours. After the reaction was completed, 10 mL of water was added to the reaction solution. The organic phase was separated and washed with saturated sodium chloride solution (2 mL). After the organic phase was evaporated under reduced pressure, the residue was separated by silica gel column chromatography (dichloromethane:methanol=20:1, volume ratio) to obtain 0.037 g of a wheat color solid.

LC-MS (ESI) m/z. 483 (M+H), $^1$H NNR (300 MHz DMSO $d_6$) δ (ppm) 0.68-1.24 (m, 10H), 1.75-2.38 (m, 3H), 2.54-2.61 (m, 4H), 3.08-3.28 (m, 2H) 3.59-3.61 (m, 2H), 3.87-4.16 (m, 2H) 4.72-4.97 (m, 2H) 7.31-7.38 (m, 4H), 8.10 (d, J=23.1 Hz, 11H), 10.36 (d, J=11.41 Hz, 1H).

Example 7

(R)-4-((R)-4-((S)-2-(4-chlorophenyl)-3-(isopropylamino)propionyl)-2-methylpiperazin-1-yl)-5-methyl-5,8-dihydropyrido[2,3-d]pyrimidin-7(6H)-one

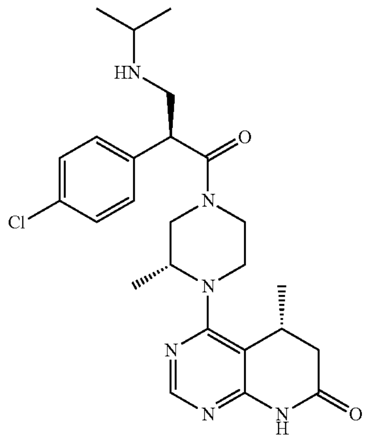 [SMILES: CC(C)NC[C@@H](C(=O)N1CCN(c2ncnc3c2[C@H](C)CC(=O)N3)[C@H](C)C1)c1ccc(Cl)cc1]

Preparation was in accordance with the method as described in Example 6, wherein (R)-4-Boc-2-methylpiperazine was used instead of tert-butyl 2,5-diazabicyclo[2.2.1]heptane-2-carboxylate.

LC-MS (ESI) m/z: 485 (M+H). $^1$H NMR (300 MHz, DMSO-$d_6$) δ (ppm) 0.94-1.04 (m, 12H), 2.24-229 (m, 1H) 2.67-2.93 (m, 5H), 3.06-3.19 (m, 5H), 3.57-3.62 (m, 3H), 4.21-4.24 (m, 1H), 7.32-7.44 (m, 4H), 8.26 (s, 1H) 10.61 (s, 1H).

Example 8

(R)-4-((R)-4-((S)-2-(4-chlorophenyl)-3-(isopropylamino)propionyl)-3-methylpiperazin-1-yl)-5-methyl-5,8-dihydropyrido[2,3-d]pyrimidin-7(6H)-one

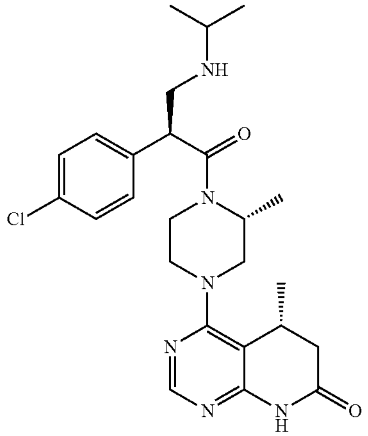 [SMILES: CC(C)NC[C@@H](C(=O)N1CCN(c2ncnc3c2[C@H](C)CC(=O)N3)C[C@H]1C)c1ccc(Cl)cc1]

Preparation was in accordance with the method as described in Example 6, wherein (R)-1-N-Boc-2-methylpiperazine was used instead of tert-butyl 2,5-diazabicyclo[2.2.1]heptane-2-carboxylate.

LC-MS (ESI) m/z: 485 (M+H). $^1$H NMR (300 MHz, $CDCl_3$) δ (ppm) 8.37 (d, J=12.0 Hz 1H), 828 (s, 1H), 7.36 (d, J=6.0 Hz, 2H), 7.26 (d, J=6.0 Hz, 2H), 4.59-4.95 (m, 1H), 408-4.31 (m, 2H), 3.15-3.82 (m, 6H), 2.72-3.09 (m, 4H), 2.52-258 (m, 1H), 2.32-2.39 (m, 1H), 1.10-138 (m, 12H).

Example 9

(R)-4-((S)-4-((R)-2-(4-chlorophenyl)-3-(isopropylamino)propionyl)-3-methylpiperazin-1-yl)-5-methyl-5,8-dihydropyrido[2,3-d]pyrimidin-7(6H)-one

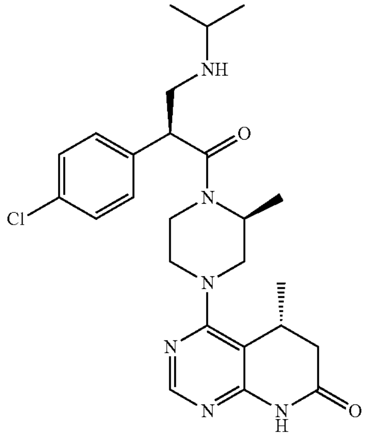

Preparation was in accordance with the method as described in Example 6, wherein (S)-1-N-Boc-2-methylpiperazine was used instead of tert-butyl 2,5-diazabicyclo[2.2.1]heptane-2-carboxylate.

LC-MS (ESI) m/z: 485 (M+H). $^1$H NMR (400 MHz, $CDCl_3$) δ (ppm) 8.35 (d, J=16.0 Hz, 1H), 7.41-7.28 (m, 3H), 7.26-7.21 (m, 1H), 4.89 (d, J=6.8 Hz, 1H), 4.76-4.49 (m, 1H), 375-3.65 (m, 1H), 3.64-3.54 (m, 1H), 3.51-3.49 (m, 1H), 3.44-3.34 (m, 1H), 3.34-3.17 (m, 3H), 3.17-3.09 (m, 1H), 3.06-2.96 (m, 1H), 2.89-2.49 (m, 3H), 1.44-1.29 (m, 7H), 1.25-1.06 (m, 5H).

Example 10

(R)-4-(8-((S)-2-(4-chlorophenyl)-3-(isopropylamino) propionyl)-3,8-diazabicyclo[3.2.1]octan-3-yl)-5-methyl-5,8-dihydropyrido[2,3-d]pyrimidin-7(6H)-one

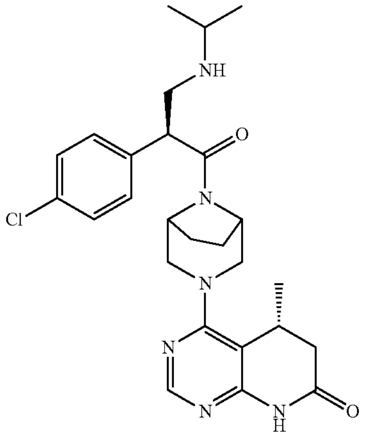

Preparation was in accordance with the method as described in Example 6, wherein tert-butyl 3,8-diazabicyclo [3.2.1]octan-8-formate was used instead of tert-butyl 2,5-diazabicyclo[2.2.1]heptane-2-carboxylate.

LC-MS (ESI) m/z: 497 (M+H), $^1$H NMR (400 MHz, $CDCl_3$) δ (ppm) 8.35 (d, J=16.0 Hz, 1H), 7.41-7.28 (m, 3H), 7.26-7.21 (m, 1H), 4.83 (s, 1H), 4.51-4.30 (m, 2H), 4.25-4.22 (m, 1H), 4.10-4.03 (m, 1H) 3.92-3.84 (m, 1H), 3.73-3.62 (m, 1H), 3.50-3.26 (m, 3H), 3.24-3.21 (1, 1H), 3.20-2.85 (m, 2H), 2.75-2.62 (m, 1H), 2.49-2.41 (m, 1H), 2.20-1.90 (m, 1H), 1.88-1.60 (m, 3H), 1.44-1.29 (m, 6H), 1.25-1.06 (m, 3H).

Example 11

(R)-4-(3-((S)-2-(4-chlorophenyl)-3-(isopropylamino) propionyl)-3,8-diazabicyclo[3.2.1]octan-8-yl)-5-methyl-5,8-dihydropyrido[2,3-d]pyrimidin-7(6H)-one

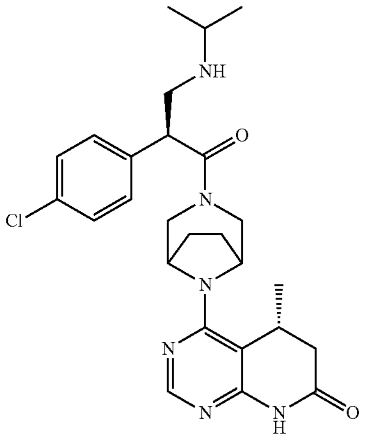 [SMILES: CC(C)NC[C@@H](C(=O)N1CC2CCC(C1)N2c1ncnc2c1[C@H](C)CC(=O)N2)c1ccc(Cl)cc1]

Preparation was in accordance with the method as described in Example 6, wherein tert-butyl 3,8-diazabicyclo [3.2.1]octan-3-formate was used instead of tert-butyl 2,5-diazabicyclo[2.2.1]heptane-2-carboxylate.

LC-MS (ESI) m/z: 497 (M+H). $^1$H NMR (400 MHz, $CDCl_3$) δ (ppm) 8.66 (s, 1H), 8.28 (d, J=5.2 Hz, 1H), 7.15-7.38 (m, 4H), 4.31-4.56 (m, 3H), 3.93 (s, 1H), 3.49-3.66 (m, 2H), 3.15-3.31 (m, 2H), 2.70-3.01 (m, 4H), 2.26-2.50 (m, 1H), 1.74-2.03 (m, 3H), 1.57-1.67 (m, 1H), 1.43-1.50 (m, 1H) 1.03-1.26 (m, 9H).

Example 12

(R)-4-(4-((S)-2-(4-chlorophenyl)-3-(isopropylamino) propionyl)-4,7-diazaspiro[2.5]octan-7-yl)-5-methyl-5,8-dihydropyrido[2,3-d]pyrimidin-7(6H)-one

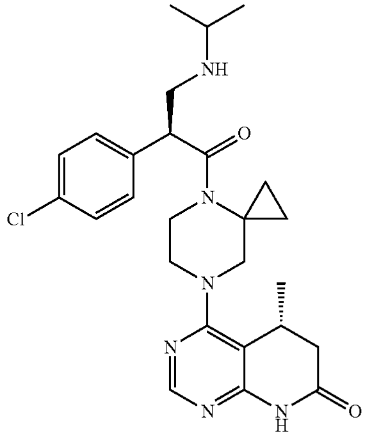 [SMILES: CC(C)NC[C@@H](C(=O)N1CCN(c2ncnc3c2[C@H](C)CC(=O)N3)CC12CC2)c1ccc(Cl)cc1]

Preparation was in accordance with the method as described in Example 6, wherein tert-butyl 4,7-diazaspiro [2.5]octan-4-formate was used instead of tert-butyl 2,5-diazabicyclo[2.2.1]heptane-2-carboxylate.

LC-MS (ESI) m/z=497 (M+H). $^1$H NMR (400 MHz, DMSO-$d_6$) δ 10.58 (s, 1H), 8.22 (s, 1H), 7.33-7.38 (m, 4H), 4.37 (s, 1H), 3.40-4.15 (m, 4H), 2.97-3.09 (m, 3H), 2.57-2.90 (m, 4H), 2.24-2.32 (m, 1H), 0.44-1.13 (m, 13H).

Example 13

(5R)-4-(5-((S)-2-(4-chlorophenyl)-3-(isopropylamino)propionyl)hexahydropyrrolo[3,4-c]pyrrole-2(1H)-yl)-5-methyl-5,8-dihydropyrido[2,3-d]pyrimidin-7(6H)-one

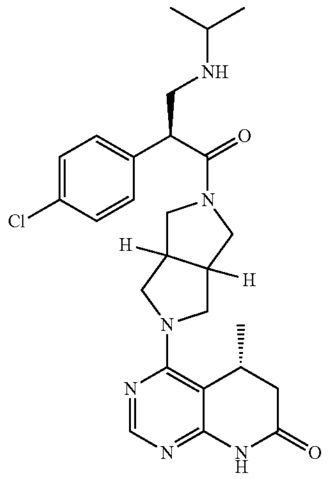 [SMILES: CC(C)NC[C@@H](C(=O)N1CC2CN(c3ncnc4c3[C@H](C)CC(=O)N4)CC2C1)c1ccc(Cl)cc1]

Preparation was in accordance with the method as described in Example 6, wherein tert-butyl hexahydropyrrolo[3,4-c]pyrrole-2(1H)-formate was used instead of tert-butyl 2,5-diazabicyclo[2.2.1]heptane-2-carboxylate. The final product was prepared and resolved to obtain a cis-isomer and a trans-isomer. Chiral resolution conditions: resolution instrument: waters SFC200; column: Daicel Chiralcel AD, 250×30 mm ID, 5 μm; mobile phase A: $CO_2$, mobile phase B: ethanol (containing 0.1% ammonia), A:B=65:35 (volume ratio). The product with a retention time of 8-10 min was collected as the cis isomer, and the product with a retention time of 11-13 min was collected as the trans-isomer.

cis-isomer: LC-MS (ESI) m/z: 497. (M+H). $^1$H NMR 300 MHz, DMSO-$d_6$) δ (ppm) 10.31 (d, J=6.91 Hz, 1H), 8.08 (d, J=13.5 Hz, 1H), 7.28-7.38 (m, 4H), 3.76-3.93 (m, 3H), 3.56-3.72 (m, 2H) 3.45-3.52 (m, 2H) 3.38-3.40 (m, 2H), 3.13-3.24 (m, 2H), 3.03-3.07 (m, 1H), 2.84-2.90 (m, 2H), 2.57-2.78 (m, 3H), 2.17-2.26 (m, 1H), 1.04 (d, J=5.1 Hz, 2H), 0.87-0.93 (m, 7H).

trans-isomer: LC-MS (ESI) m/z: 497. (M+H). $^1$H NMR (300 MHz, DMSO-$d_6$) δ (ppm) 10.31 (d, J==7.8 Hz, 1H), 8.08 (d, J=13.2 Hz, 1H), 7.28-7.40 (m, 4H), 3.82-3.94 (m, 2H), 3.68-379 (m, 1H), 3.47-3.63 (m, 2H), 3.07-3.22 (m, 3H) 2.62-3.02 (m, 5H), 2.18-2.27 (m, 1H) 1.20-1.29 (m, 31H) 1.05 (d, J=5.4 Hz, 1H), 0.90-0.96 (m, 6H), 0.81-0.86 (m, 3H).

Example 14

(R)-4-(6-((S)-2-(4-chlorophenyl)-3-(isopropylamino)propionyl)-2,6-diazaspiro[3.3]heptan-2-yl)-5-methyl-5,8-dihydropyrido[2,3-d]pyrimidin-7(6H)-one

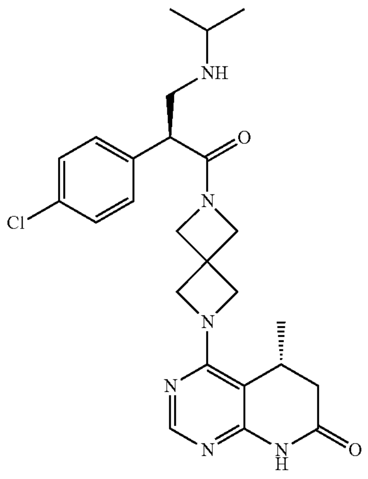 [SMILES: CC(C)NC[C@@H](C(=O)N1CC2(C1)CN(c1ncnc3c1[C@H](C)CC(=O)N3)C2)c1ccc(Cl)cc1]

Preparation was in accordance with the method as described in Example 6, wherein tert-butyl 2,6-diazaspiro[3.3]hepta-2-formate was used instead of tert-butyl 2,5-diazabicyclo[2.2.1]heptane-2-carboxylate.

LC-MS (ESD n/z 483 (M+H). $^1$H NMR (400 MHz, DMSO-$d_6$) δ (ppm) 10.38 (s, 1H), 8.09 (s, 1H), 7.36-7.38 (m, 2H) 7.30-7.32 (m, 2H), 4.48 (d, J=9.6 Hz, 1H), 4.35 (s, 2H), 4.26 (s, 2H), 3.98-408 (m, 3H), 3.63-3.67 (m, 1H), 3.00-3.10 (m, 2H) 2.61-2.73 (m, 4H), 2.23 (d, J=16.0 Hz, 1H) 1.02 (d, J=7.2 Hz, 3H), 0.91-0.93 (m, 6H).

Process E:

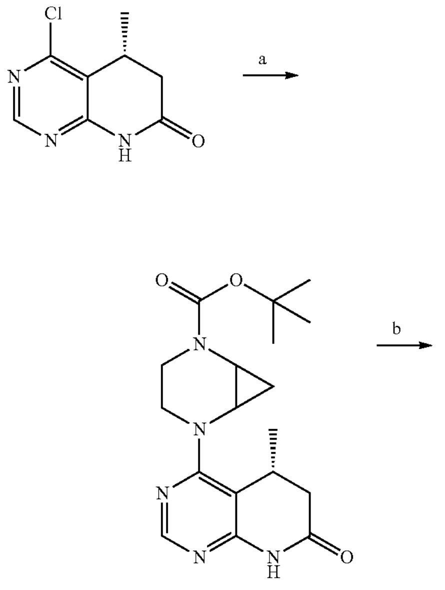

-continued

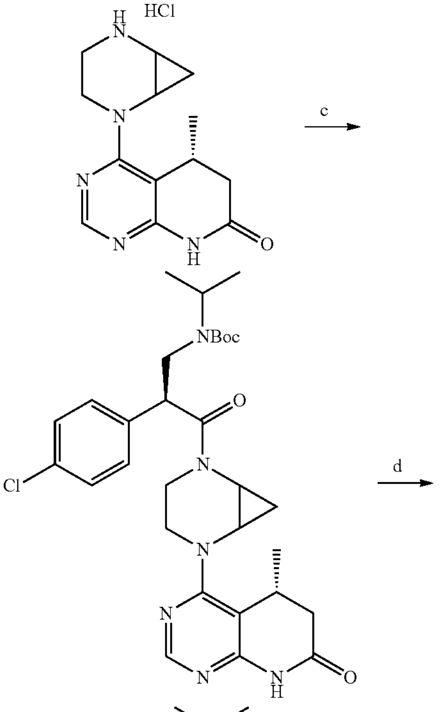

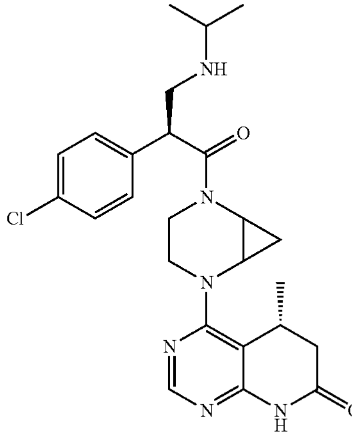

and

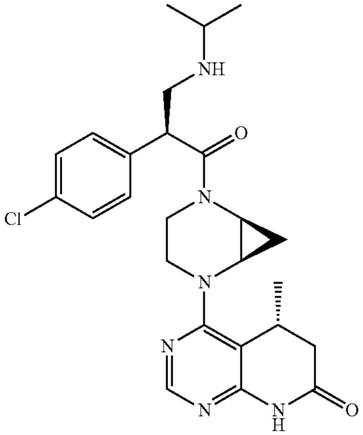

Reaction conditions: a) tert-butyl, 2,5-diazabicyclo[4.1.0]heptane-2-carboxylate, N-methylpyrrolidone, 4-dimethylaminopyridine; b) hydrogen chloride/1,4-dioxane (4.0M), dichloromethane; c) (S)-3-((tert-butoxycarbonyl)(isopropyl)amino)-2-(4-chlorophenyl)-propionic acid, 2-(7-benzotriazole oxide)-N,N,N',N'-tetramethylurea hexafluorophosphate, 4-dimethylaminopyridine, N,N-dimethylformamide; d) trifluoroacetic acid, dichloromethane.

Example 15

(R)-4-((1S,6R)-5-((S)-2-(4-chlorophenyl)-3-(isopropylamino)propionyl)-2,5-diaza bicyclo[4.1.0]heptan-2-yl)-5-methyl-5,8-dihydropyrido[2,3-d]pyrimidin-7(6H)-one or (R)-4-((1R,6S)-5-((S)-2-(4-chlorophenyl)-3-(isopropylamino)propionyl)-2,5-diaza bicyclo[4.1.0]heptan-2-yl)-5-methyl-5,8-dihydropyrido[2,3-d]pyrimidin-7(6H)-one Isomer 1

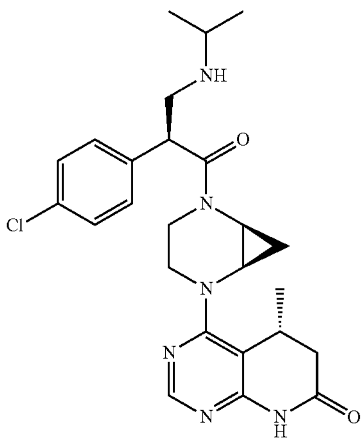

and

Isomer 2

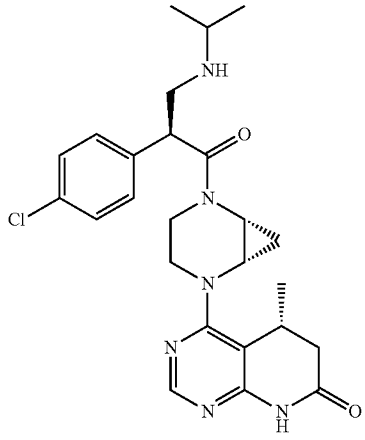

a) tert-butyl 5-((R)-5-methyl-7-oxo-5,6,7,8-tetrahydropyrido[2,3-d]pyrimidin-4-yl)-2,5-diazabicyclo [4.1.0]heptan-2-carboxylate Under the protection of nitrogen, (R)-4-chloro-5-methyl-5,8-dihydropyrido[2,3-d]pyrimidin-7(6H)-one (0.21 g), tert-butyl 2,5-diazabicyclo[4.1.0]heptane-2-carboxylate (0.31 g) and 4-dimethylaminopyridine (0.39 g) were dissolved in N-methylpyrrolidone (5 mL) at 22° C., heated to 140° C., and reacted for 3 hours. After the reaction was completed, the reaction solution was cooled to 20° C., poured into 20 mL of ice water, extracted with ethyl acetate (20 mL×2), and washed with saturated sodium chloride solution (10 mL×3). The solvent was evaporated under reduced pressure, and the residue was separated by silica gel column chromatography (petroleum ether: ethyl acetate=3:1-1:1, volume ratio) to obtain 0.28 g of a pale yellow liquid. LC-MS (ESI) m/z: 360 (M+H).

b)(5R)-4-(2,5-diazabicyclo[4.1.0]heptan-2-yl)-5-methyl-5,8-dihydropyrido[2,3-d]pyrimidin-7(6H)-one hydrochloride Tert-butyl 5-((R)-5-methyl-7-oxo-5,6,7,8-tetrahydropyrido[2,3-d]pyrimidin-4-yl)-2,5-diazabicyclo[4.1.0]heptane-2-carboxylate (0.28 g) was dissolved in dichloromethane (5 mL) at 20° C., and hydrogen chloride/1,4-dioxane (4.0 mL) was added to react for 1 hours. After the reaction was completed, the reaction solution was evaporated to remove the solvent under reduced pressure to obtain 0.23 g of a yellow solid, which was directly used in the next step.

c) tert-butyl (2S)-2-(4-chlorophenyl)-3-(5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(isopropyl)carbamate Under the protection of nitrogen, (5R)-4-(2,5-diazabicyclo[4.1.0]heptan-2-yl)-5-methyl-5,8-dihydropyrido[2,3-d] pyrimidin-7 (6H)-one hydrochloride (0.20 g) and (S)-3-((tert-butoxycarbonyl)(isopropyl)amino)-2-(4-chlorophenyl)-propionic acid (0.22 g) were dissolved in N,N-dimethylformamide (5 mL) at 20° C., and then 2-(7-benzotriazole oxide)-N,N,N',N'-tetramethylurea hexafluorophosphate (0.59 g) and 4-dimethylaminopyridine (0.48 g) were added separately, and reacted at 25° C. for 4 hours. After the reaction was completed, 20 ml of water was added to the reaction solution, and the reaction solution was extracted with ethyl acetate (10 mL×3). The organic phase was washed with saturated sodium chloride solution (10 mL×2) and evaporated under reduced pressure. 0.18 g of a yellow solid was then obtained through a separation by column chromatography (dichloromethane:methanol=50:1). LC-MS (ESI) m/z: 583 (M+H).

d)(R)-4-((1S,6R)-5-((S)-2-(4-chlorophenyl)-3-(isopropylamino)propionyl)-2,5-diazabicyclo[4.1.0]heptan-2-yl)-5-methyl-5,8-dihydropyrido[2,3- d]pyrimidin-7(6H)-one or (R)-4-((1R,6S)-5-((S)-2-(4-chlorophenyl)-3-(isopropylamino)propionyl)-2,5-diaza bicyclo[4.1.0]heptan-2-yl)-5-methyl-5,8-dihydropyrido[2,3-d]pyrimidin-7(6H)-one Tert-butyl (2S)-2-(4-chlorophenyl)-3-(5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(isopropyl) carba mate (0.18 g) was dissolved in dichloromethane (2 mL) at 20° C., and trifluoroacetic acid (0.86 mL) was added to react for 3 hours. After the reaction was completed, dichloromethane (10 mL) was added to the reaction solution, and 2 M sodium hydroxide solution was added dropwise at 0° C. to adjust pH=12. After separation, the organic phase was washed with saturated sodium chloride solution (5 mL), and dried with anhydrous sodium sulfate. The organic phase was evaporated under reduced pressure to obtain 0.10 g of a yellow solid. After high-performance preparative liquid chromatography resolution, an isomer 1 (3 mg) and an isomer 2 (12 mg) were obtained.

HPLC conditions: Column: Agilent 5 μm prep-C18 50×21.2 mm, mobile phase A: water (containing 0.1% ammonia); mobile phase B:methanol. Gradient: time 0-10 min, phase B: 60-70% (volume ratio).

isomer 1: $RT_1$=53 min, LC-MS (ESI) m/z: 483 (M+H).

isomer 2: $RT_2$=5.9 min; LC-MS (ESI) m/z: 483 (M+H); $^1$H NMR 400 MHz, $CDCl_3$) δ (ppm) 8.27 (d, J=7.6 Hz, 1H), 7.92 (s, 1H), 7.27-730 (m, 4H), 4.23-4.29 (m, 1H), 3.90-3.95 (m, 1H), 3.81-3.85 (m, 1H), 3.69-372 (m, 1H), 3.44-3.59 (m, 1H) 3.20-3.38 (m, 3H), 3.01-3.05 (m, 1H), 2.70-285 (m, 3H)) 2.47-2.57 (m, 1H), 2.21-2.25 (m, 1H), 1.25-1.28 (m, 3H), 1.03-1.11 (m, 6H), 0.82-0.90 (m, 2H).

Configuration Measurement by the Single Crystal Diffraction:

Single crystal preparation: 30.0 mg of the compound of isomer 2 and 2.0 mL of isopropanol were added in a 5 mL screw-top glass bottle, stirred for 5 min. The solid was dissolved and clarified. 3.9 mg of oxalic acid dihydrate was weighed and added to the above glass bottle. A white solid was gradually precipitated out in the glass bottle. After stirring at room temperature for 3 hours, a large amount of white solid was deposited in the glass bottle. 1.0 mL of methanol was added to the glass bottle, and the white solid gradually disappeared, while the solution became clarified. Stirring was continued for 1 h. The solution was filtered through a 0.22 μm microporous membrane into a 3 mL screw-top glass bottle, and the mouth of the glass bottle was covered with plastic wrap. The plastic wrap were pierced at the mouth of the bottle with a needle to form 8 small holes, and the mixture was allowed to stand at room temperature for 7 days to obtain an oxalate single crystal of the compound of isomer 2.

Single Crystal Diffraction Experiment:

Single crystal X-ray diffractometer: BRUKER D8 VENTURE PHOTON II

Wavelength: Ga K α (λ=1.34139 Å)

Test temperature: 190K

Computer program for structural analysis: SHELXL-2018

Single crystal data: molecular formula: $C_{55}H_{72}Cl_2N_{12}O_9$; molecular weight: 1116.14; crystal system: hexagonal crystal system; space group: P 61; unit cell parameters: a=25.8406(15)Å, b=25.8406(15)Å, c=45.916(3)Å, α=90°, β=90°, γ=120°; unit cell volume: V=26552(4)$Å^3$; number of molecular formulas contained in unit cell: Z=12; calculated density: $D_{calc}$=0.838 g/$cm^3$; R($F_o$): 0.0730; RW($F_o^2$): 0.2069; goodness of fit (S): 1.034; Flack parameter: 0.066 (9).

Figure 2:
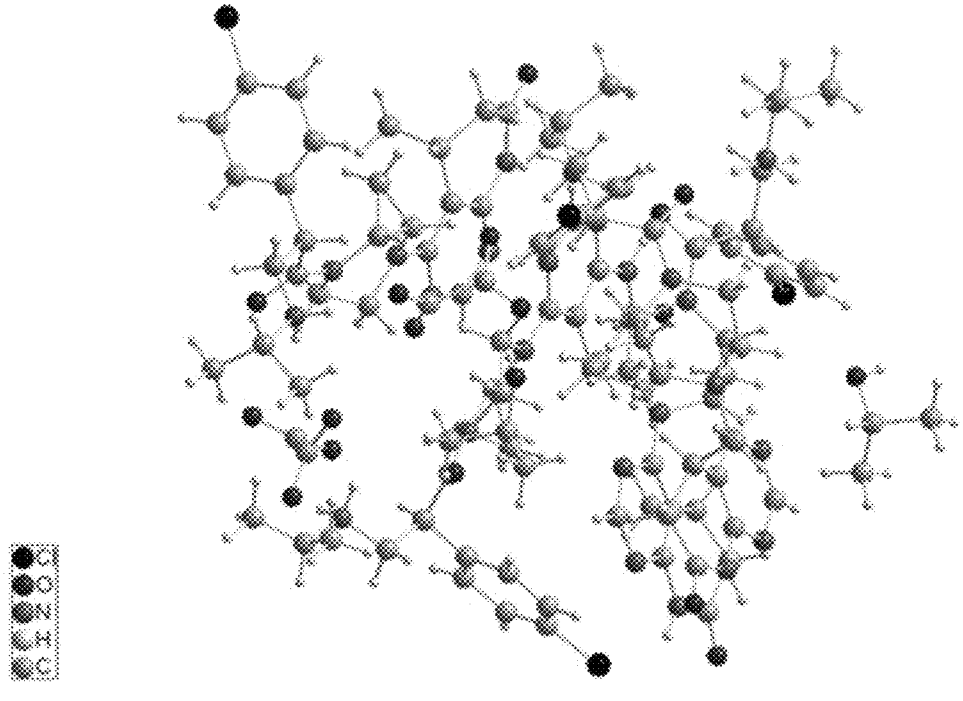
FIG. 2 is a schematic diagram of a asymmetric structural unit of a single crystal of Isomer 2 of Example 15.

Structure description: Single crystal X-ray diffraction and structure analysis show that the obtained single crystal is an oxalate isopropanol complex of isomer 2. The asymmetric structural unit of the crystal contains four isomer 2 molecules, two oxalic acid molecules and two isopropanol molecules, wherein isomer 2 and oxalic acid form oxalate. The single molecule schematic diagram of the compound of isomer 2 is shown in FIG. 1, and the asymmetric structural unit of the oxalate single crystal is shown in FIG. 2. The structural formula is as follows:

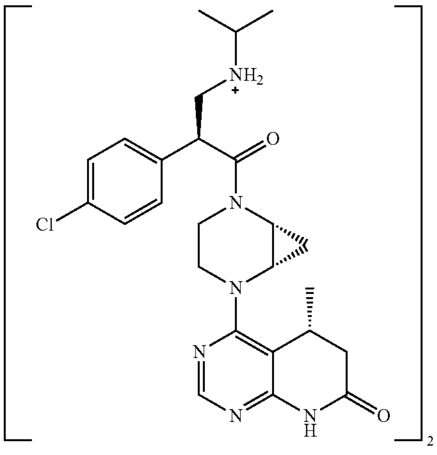

.

-continued

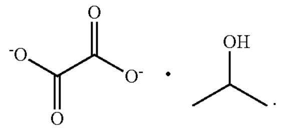

Process F:

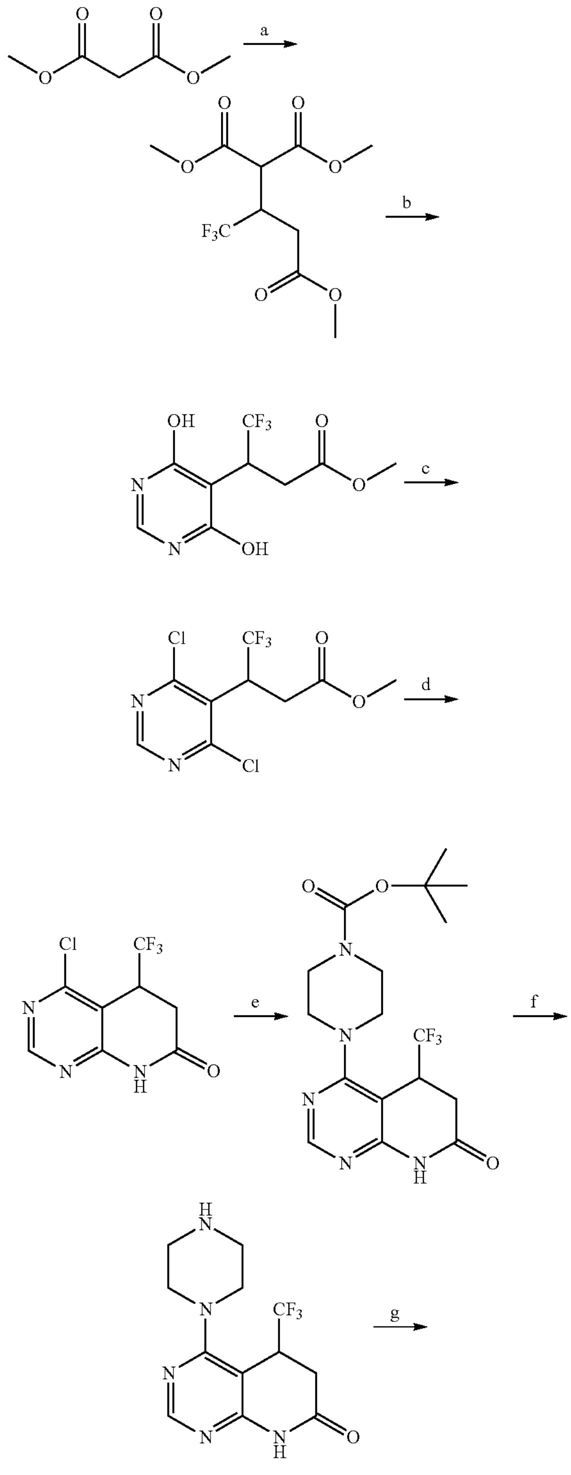

-continued

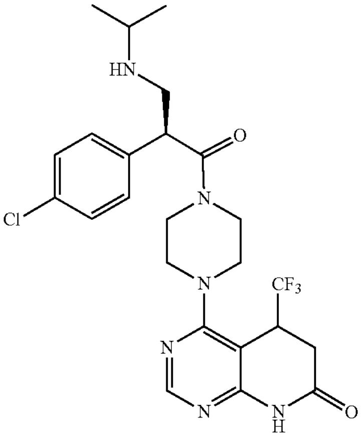

Reaction conditions: a) methyl 4,4,4-trifluoro-2-crotonate, methanol solution of sodium methoxide (30 wt %); b) formamidine acetate, methanol solution of sodium methoxide (30 wt %); c) phosphorus oxychloride, diisopropylethylamine, acetonitrile; d) ammonia (25-28 wt %); e) tert-butylpiperazine-1-carboxylate; f) trifluoroacetic acid, dichloromethane; g) (S)-2-(4-chlorophenyl)-3-(isopropylamino)propionic acid, 2-(7-benzotriazole oxide)-N,N,N′,N′-tetramethylurea hexafluorophosphate, diisopropylethylamine, dichloromethane.

Example 16

4-(4-((S)-2-(4-chlorophenyl)-3-(isopropylamino)propionyl)piperazin-1-yl)-5-(trifluoromethyl)-5,8-dihydropyrido[2,3-d]pyrimidin-7(6H)-one

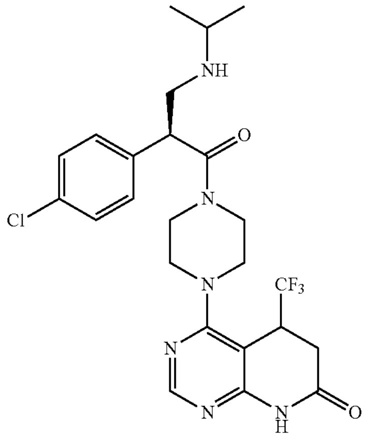

According to the process F, preparation was in accordance with the method as described in Example 1. LC-MS (ESI) m/z: 525 (M+H).

Isomer separation: chiral resolution of the above-mentioned title compound was carried out by supercritical fluid chromatography to obtain an isomer 1 and an isomer 2. Resolution instruments and conditions: waters SFC200; Column: Daicel Chiralcel AS, 250×30 mm ID, 5 μm; Mobile phase: A is $CO_2$, B is ethanol (0.1% $NH_3H_2O$); A: B=85:15 (volume ratio); flow rate: 60 mL/min, column temperature: 38° C.

Isomer 1:
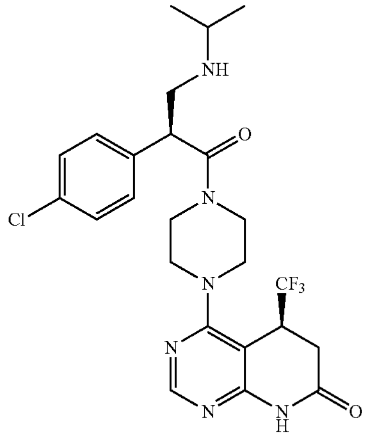 [SMILES: CC(C)NC[C@@H](C(=O)N1CCN(c2ncnc3c2[C@@H](C(F)(F)F)CC(=O)N3)CC1)c1ccc(Cl)cc1]
LCMS (ESI) m/z: 525 (M+H). $^1$HNMR (400 MHz, DMSO-$d_6$) δ (ppm) 0.91-0.95, (m, 6H), 2.59-2.78 (m, 4H) 3.07-3.12 (m, 1H), 3.20-3.31 (m, 4H), 3.37-3.50 (m, 3H), 3.69-3.75 (m, 2H), 4.08-4.19 m, 2H), 7.35 (dd, =25.2, 8.0 Hz, 4H), 8.36 (s, 1H), 10.90 (s, 1H).
Isomer 2:
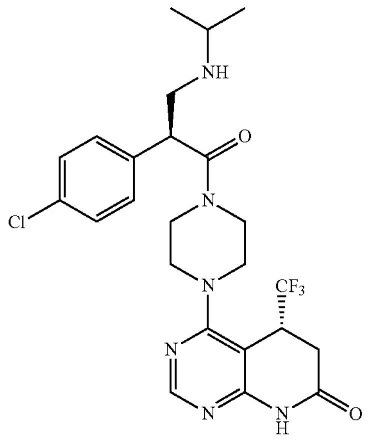
LCMS (ESI) m/z: 525 (M+H) $^1$HNMR (300 MHz, DMSO-$d_6$) δ (ppm) 0.93-1.06 (m, 6H), 2.58-2.72 (m, 4H), 3.06-3.31 (m, 4H), 3.45-3.68 (m, 6H), 4.11-4.20 (m, 2H) 7.31-7.43 (m, 4H), 8.34 (d, J=16.0 Hz, 1H), 10.92 (s, 1H).
Process G:
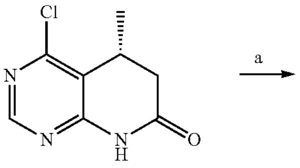
-continued
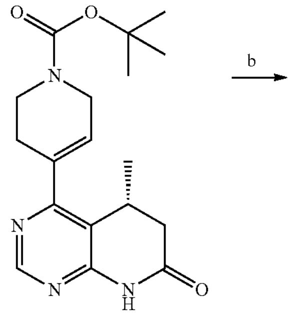
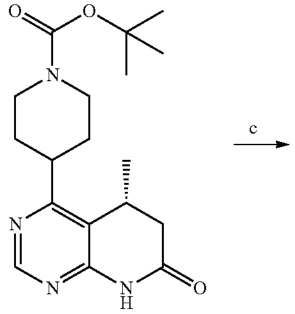
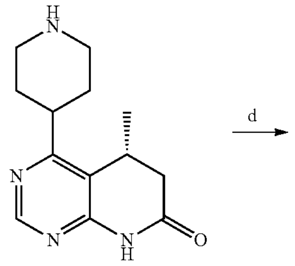
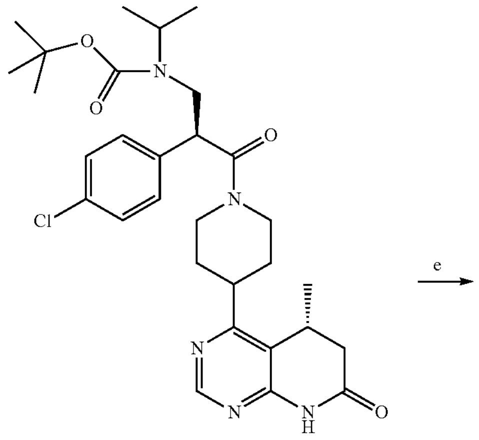

-continued

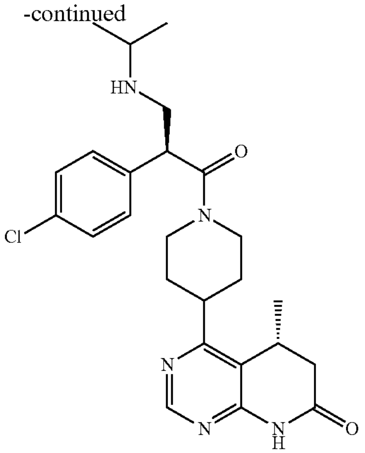

Reaction conditions: a) tert-butyl, 4-(4,4,5,5-tetramethyl-1,3,2-dioxaborolan-2-yl)-3,6-dihydropyridine-1(2H)-carboxylate, dioxane, cesium carbonate, water, tetrakis(triphenylphosphine)palladium; b) methanol, formic acid, palladium on carbon (5%), hydrogen; c) dichloromethane, hydrogen chloride/1,4-dioxane solution (4.0M); d) (S)-3-((tert-butoxycarbonyl)(isopropyl)amino)-2-(4-chlorophenyl)propionic acid, N,N-dimethylformamide, 2-(7-benzotriazole oxide)-N,N,N′,N′-tetramethylurea hexafluorophosphate, diisopropylethylamine; e) dichlormethane, hydrogen chloride/1,4-dioxane solution (4.0M).

Example 17

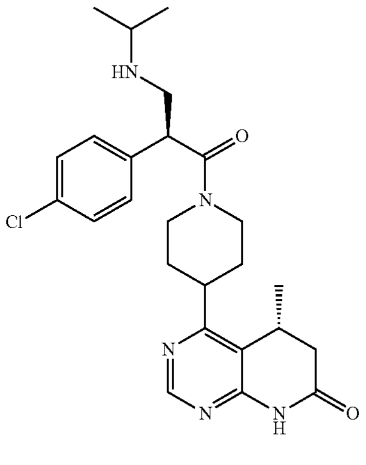 [SMILES: CC(C)NC[C@@H](C(=O)N1CCC(c2ncnc3c2[C@H](C)CC(=O)N3)CC1)c1ccc(Cl)cc1]

a) tert-butyl (R)-4-(5-methyl-7-oxo-5,6,7,8-tetrahydropyrido[2,3-d]pyrimidin-4-yl)-3,6-dihydro pyridine-1(2H))-formate Under the protection of nitrogen, (R)-4-chloro-5-methyl-5,8-dihydropyrido[2,3-d]pyrimidin-7(6H)-one (0.60 g) and tert-butyl 4-(4,4,5,5-tetramethyl-1,3,2-dioxaborolan-2-yl)-3,6-dihydropyridine-1(2H)-carboxylate (1.03 g) were dissolved in dioxane (20 mL) at 22° C., and cesium carbonate and water (5 mL) were added, and finally tetrakis(triphenylphosphine)palladium (0.35 g) was added and reacted at 100° C. for 7 hours. After the reaction was completed, the reaction solution was cooled to 20° C., poured into 20 mL of ice water, and extracted with ethyl acetate (20 mL). The organic phase was evaporated under reduced pressure, and the residue was separated by silica gel column chromatography (petroleum ether: ethyl acetate=4:1, volume ratio) to obtain 0.81 g of a pale yellow solid. MS (ESI) m/z: 345 (M+H).

b) tert-butyl (R)-4-(5-Methyl-7-oxo-5,6,7,8-tetrahydropyrido[2,3-d]pyrimidin-4-yl)piperidine-1-carboxylate Tert-butyl (R)-4-(5-methyl-7-oxo-5,6,7,8-tetrahydropyrido[2,3-d]pyrimidin-4-yl)-3,6-dihydro pyridine-1(2H))-formate (0.75 g) was dissolved in methanol (50 mL) at 20° C., and formic acid (0.11 g) and 0.30 g of palladium on carbon (5%) were added. The reaction system was replaced with nitrogen for 3 times and filled with hydrogen, and reacted at 60° C. for 16 hours. After the reaction was completed, the reaction solution was cooled to 10° C., palladium-carbon was filtered with suction, and the filtrate was evaporated under reduced pressure to remove the solvent to obtain 0.66 g of a colorless oily product. MS (ESI) m/z: 347 (M+H).

c) (R)-5-methyl-4-(piperidin-4-yl)-5,8-dihydropyrido[2,3-d]pyrimidin-7(6H)-one

Tert-butyl (R)-4-(5-methyl-7-oxo-5,6,7,8-tetrahydropyrido[2,3-d]pyrimidin-4-yl)piperidine-1-carboxylate (0.63 g) was dissolved in dichloromethane (10 mL) at 25° C., and hydrogen chloride/1,4-dioxane solution (4.0 M) (10 mL) was added to react for 2 hours. After the reaction was completed, the reaction solution was concentrated to remove the solvent, cooled to 0° C., adjusted to pH=12 by adding 20% sodium hydroxide solution, and extracted with ethyl acetate (10 mL×3). The organic phase was washed with saturated sodium chloride solution and evaporated under reduced pressure to obtain 0.346 g of a yellow solid, which was directly used in the next step.

d) tert-butyl (S)-2-(4-chlorophenyl)-3-(4-((R)-5-methyl-7-oxo-5,6,7,8-tetrahydropyrido[2,3-d]pyrimidin-4-yl)piperidin-1-yl)-3-oxopropyl)(isopropyl) carbamate Under the protection of nitrogen, (R)-5-methyl-4-(piperidin-4-yl)-5,8-dihydropyrido[2,3-d]pyrimidin-7(6H)-one (0.302 g) and (S)-3-((tert-butoxycarbonyl)(isopropyl) amino)-2-(4-chlorophenyl)propionic acid (0.308 g) were dissolved in N,N-dimethylformamide (5 mL) at 20° C., and then 2-(7-benzotriazole oxide)-N,N,N',N'-tetramethylurea hexafluorophosphate (0.86 g) and diisopropylethylamine (0.76 g) were added separately, and reacted at 20° C. for 3 hours. After the reaction was completed, 30 mL of water was added to the reaction solution. Ethyl acetate (50 mL) was added for extraction. After separation, the organic phase was washed with saturated sodium chloride solution (10 mL×2) and evaporated under reduced pressure, and the residue was separated by silica gel column chromatography (dichloromethane:methanol=25:1, volume ratio) to obtain 0.339 g of a white solid, which is directly used for the next step.

e) (R)-4-(1-((S)-2-(4-chlorophenyl)-3-(isopropylamino)propionyl)piperidin-4-yl)-5-methyl-5,8-dihydropyrido[2,3-d]pyrimidin-7(6H)-one Tert-butyl (S)-2-(4-chlorophenyl)-3-(4-((R)-5-methyl-7-oxo-5,6,7,8-tetrahydropyrido[2,3-d]pyrimidin-4-yl)piperidin-1-yl)-3-oxopropyl)(isopropyl)carbamate (0.320 g) was dissolved in dichloromethane (3 mL) at 25° C., and hydrogen chloride/1,4-dioxane solution (4.0 M) (2.9 mL) was added to react for 2 hours. After the reaction was completed, the reaction solution was evaporated under reduced pressure to remove the solvent, cooled to 0° C., adjusted to pH=12 by adding 20% sodium hydroxide, and extracted with ethyl acetate (10 mL×3). The resultant was washed with saturated sodium chloride solution (15 mL). The organic phase was evaporated under reduced pressure to obtain 0.176 g of a white solid.

LC-MS (ESI) m/z: 470 (M+H). $^{1}$H NMR (400 MHz, DMSO-$d_6$) δ (ppm) 0.83-0.97 (m, 6H), 1.03-1.10 (m, 3H), 1.24-1.43 (m, 2H), 1.57-1.95 (m, 2H), 2.29-2.35 (m, 1H), 2.51-2.87 (m, 5H), 3.01-3.19 (m, 3H), 3.35-3.41 (m, 1H), 4.02-4.21 (m, 2H) 4.51-4.62 (m, 1H) 7.32-7.43 (m, 4H), 8.50-8.61 (m, 1H) 10.85 (s, 1H).

Process H:

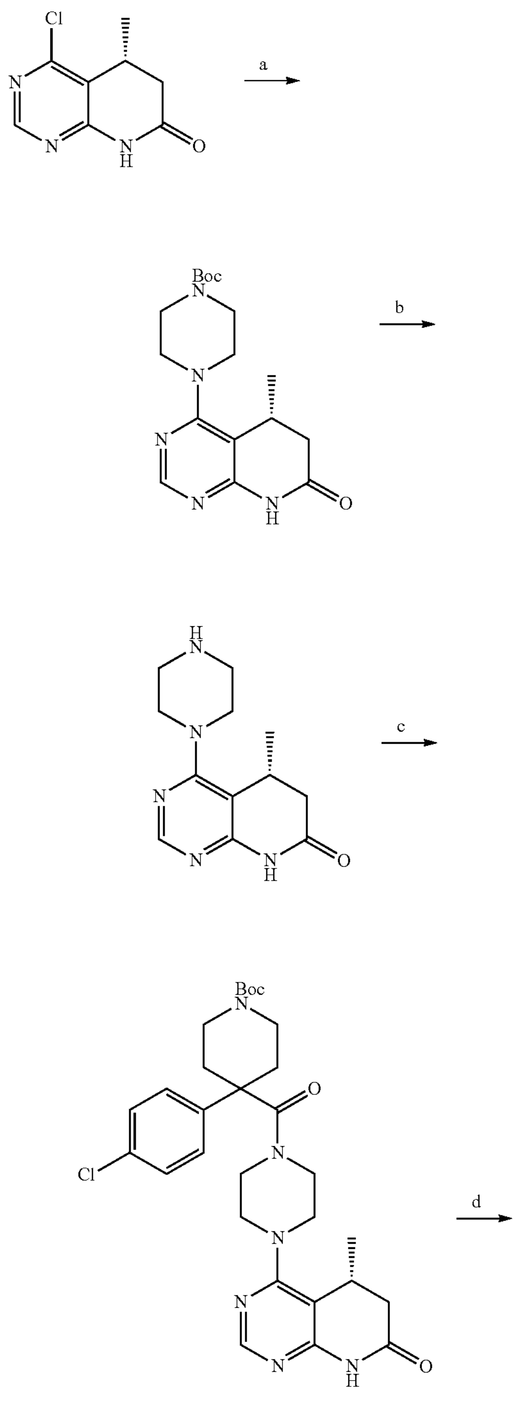

-continued

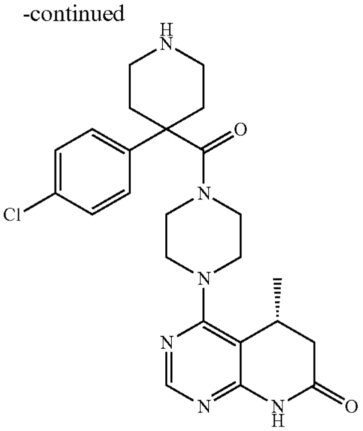

Reaction conditions: a) tert-butylpiperazine-1-carboxylate, N-methylpyrrolidione, 4-dimethylaminopyridine; b) dichloromethane, hydrogen chloride/1,4-dioxane solution (4.0M); c) diisopropylethylamine, N,N-dimethylformamide, 2-(7-benzotriazole oxide)-N,N,N',N'-tetramethylurea hexafluorophosphate, 1-(tert-Butoxycarbonyl)-4-(4-chlorophenyl)piperidine-4-carboxylic acid; d) dichloromethane, hydrogen chloride/1,4-dioxane solution (4.0M).

Example 18

(R)-4-(4-(4-(4-chlorophenyl)piperidin-4-carbonyl)piperazin-1-yl)-5-methyl-5,6-dihydropyrido[2,3-d]pyrimidin-7(8H)-one formate

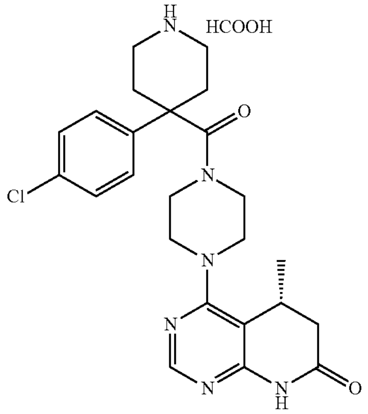 [SMILES: C[C@@H]1CC(=O)Nc2ncnc(N3CCN(C(=O)C4(c5ccc(Cl)cc5)CCNCC4)CC3)c21 ; "HCOOH"]

a) tert-Butyl (R)-4-(5-Methyl-7-oxo-5,6,7,8-tetrahydropyrido[2,3-d]pyrimidin-4-yl)piperazine-1-carboxylate (R)-4-chloro-5-methyl-5,6-dihydropyrido[2,3-d]pyrimidin-7(8H)-one (400 mg), tert-butylpiperazine-1-carboxylate (1.8 g) and 4-dimethylaminopyridine (494 mg) were dissolved in N-methylpyrrolidone (10 mL) at 20° C. The reaction solution was replaced with nitrogen three times, and heated to 150° C. under the protection of nitrogen and reacted for 4 hours. After the reaction was completed, the reaction solution was poured into 20 mL of ethyl acetate, washed with water (2 mL×2), and then washed with 0.5 M diluted hydrochloric acid to pH=5-6. After separation, the organic phase was dried with anhydrous sodium sulfate and concentrated to obtain a crude product. The crude product was separated and purified by Flash Column Chromatography (eluent: petroleum ether/ethyl acetate=2:1, volume ratio) to obtain 0.6 g of a white solid. LC-MS (ESI) m/z: 348 (M+H).

b) (R)-5-methyl-4-(piperazin-1-yl)-5,6-dihydro-pyrido[2,3-d]pyrimidin-7(8H)-one (R)-4-(5-methyl-7-oxo-5,6,7,8-tetrahydropyrido[2,3-d]pyrimidin-4-yl)tert-butylpiperazine-1-carboxylate (0.6 g) was dissolved in dichloromethane (2 mL) at 18° C., and hydrogen chloride/1,4-dioxane solution (4.0 M, 5 mL) was added dropwise and reacted at 18° C. for 2 hours. After the reaction was completed, the solvent was evaporated from the reaction solution under reduced pressure to obtain an oily target product. The product was dissolved in dichloromethane and sodium hydroxide solid was added. The mixture was stirred until the oily substance was dissolved. The solid was removed by filtration. The residue was concentrated to obtain a white solid (0.3 g), which was used directly for the next step.

c) tert-butyl (R)-4-(4-chlorophenyl)-4-(4-(5-methyl-7-oxo-5,6,7,8-tetrahydropyrido[2,3-d]pyrimidin-4-yl))piperazine-1-carbonyl)piperidin-1-carboxylate(R)-5-Methyl-4-(piperazin-1-yl)-5,6-dihydropyrido[2,3-d]pyrimidin-7(8H)-one (150 mg), (1-tert-butoxycarbonyl)-4-(4-chlorophenyl) piperidin-4-carboxylic acid (247 mg), diisopropylethylamine (235 mg) and 2-(7-benzotriazole oxide))-N,N,N',N'-tetramethylurea hexafluorophosphate (346 mL) were dissolved in N,N-dimethylformamide (3 mL) at 18° C., and reacted at 18° C. for 12 hours. After the reaction was completed, the reaction solution was poured into ethyl acetate (20 mL) and washed with water (5 mL×3). The organic phase was evaporated under reduced pressure to obtain a crude product. The crude product was separated by silica gel column (eluent: petroleum ether/ethyl acetate=1:2, volume ratio) and purified to obtain 280 mg of the colorless oily target product, which was directly used in the next step.

d) (R)-4-(4-(4-(4-chlorophenyl)piperidin-4-carbonyl)piperazin-1-yl)-5-methyl-5,8-dihydropyrido[2,3-d]pyrimidin-7(6H)-one formate Tert-butyl (R)-4-(4-chlorophenyl)-4-(4-(5-methyl-7-oxo-5,6,7,8-tetrahydropyrido[2,3-d]pyrimidin-4-yl))piperazine-1-carbonyl)piperidin-1-carboxylate (280 mg) was dissolved in dichloromethane (5 mL) at 15° C., and hydrogen chloride/1,4-dioxane solution (4.0 M, 5 mL) was added to react at 15° C. for 1.5 hours. After the reaction was completed, the reaction solution was concentrated to obtain a white crude product. The crude product was separated by high performance liquid chromatography to obtain 60 mg of the target product. HPLC conditions: Column: Kromasil 10 μm C18 50×250 mm, mobile phase A: water (containing 0.1% formic acid), mobile phase B:methanol. Gradient: time 0-10 min, phase B 20%; 10-30 min, phase B 20-50%; 30-40 min, phase B 50% (volume ratio), RT=31.4 min.

LC-MS (ESI) m/z=469[M+H]. $^1$HNMR (400 MHz, DMSO-$d_6$) δ (ppm) 10.62 (s, 1H), 8.41 (s, 1H), 8.26 (s, 1H), 7.48 (d, J=8.3 Hz, 2H), 7.29 (d, J=8.3 Hz, 2H), 2.74-3.74 m, 12H), 2.49-2.50 (m, 2H), 2.22-2.26 (m, 3H), 1.96-2.00 (m, 2H), 0.97-0.99 (m, 3H).

Process I:

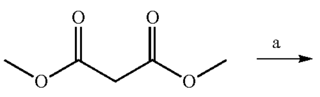

-continued

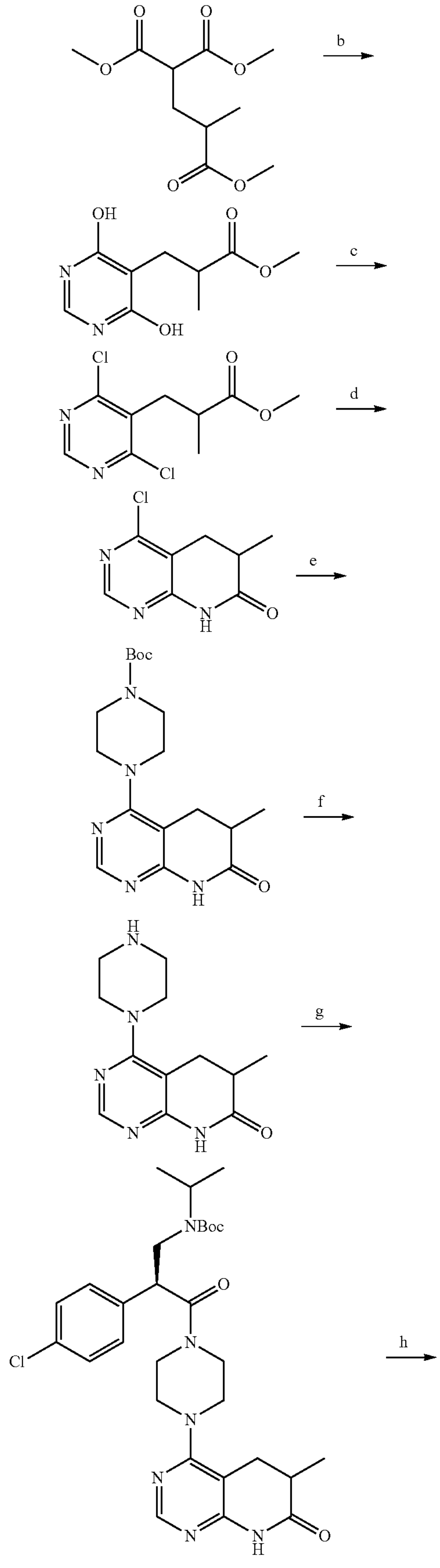

-continued

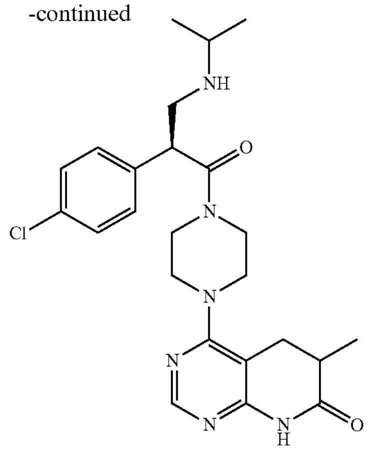

Reaction conditions: a) methyl methacrylate, sodium methoxide, methanol; b) formamidine acetate, sodium methoxide, methanol; c) phosphorus oxychloride, diisopropylethylamine, acetonitrile; d) ammonia (25-28 wt %); e) tert-butylpiperazine-1-carboxylate, N-N-lutidine-4-amine, N-methylpyrrolidone; f) hydrogen chloride/1,4-dioxane solution (4.0M); g) (S)-3-((tert-butoxycarbonyl)(isopropyl)amino)-2-(4-chlorophenyl)propionic acid, diisopropylethylamine, 2-(7-benzotriazole oxide)N,N,N',N'-tetramethylurea hexafluorophosphate, N,N-dimethylformamide; h) hydrogen chloride/1,4-dioxane solution (4.0M).

Example 19

4-(4-((S)-2-(4-chlorophenyl)-3-(isopropylamino) propyl)piperazin-1-yl)-6-methyl-5,8-dihydropyrido [2,3-d]pyrimidin-7(6H)-one hydrochloride

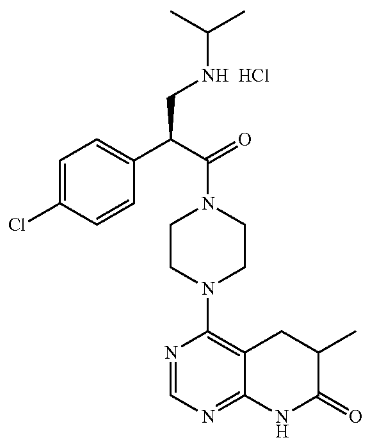 [SMILES: CC(C)NC[C@@H](C(=O)N1CCN(c2ncnc3c2CC(C)C(=O)N3)CC1)c1ccc(Cl)cc1 ; Cl]

a) 1,1,3-trimethylbutane tricarboxylic acid

Under the protection of nitrogen, sodium methoxide (2.45 g) was dispersed in methanol (50 mL) at 20° C., and dimethyl malonate (5 g) and methyl methacrylate (3.75 g) were added, the temperature was raised to 60° C., and the reaction was carried out for 16 hours. After the reaction was completed, the reaction solution was evaporated to remove the solvent under reduced pressure to obtain 5 g of yellow liquid, which was directly used in the next step.

b) methyl 3-(4,6-dihydroxypyrimidin-5-yl)-2-methylpropionate

Under the protection of nitrogen, sodium methoxide (11.67 g) was dissolved in methanol (30 mL) at 20° C., which was cooled to 0° C. Under stirring, formamidine acetate (2.44 g) was added and reacted for 30 min, and then 1,1,3-trimethylbutane tricarboxylic acid (5 g) was added dropwise, and the reaction was carried out at 20° C. for 16 hours. After the reaction was completed, isopropanol hydrochloride (4.0 M) was added to the reaction solution to adjust the pH=5. The solvent was evaporated under reduced pressure, and the residue was cooled to 0° C. Solids were precipitated out and filtered with suction. The filter cake was washed with water (50 mL), and the filter cake was dried to obtain 3.7 g of a pale yellow solid, which was used directly in the next step.

c) methyl 3-(4,6-dichloropyrimidin-5-yl)-2-methylpropionate

Under the protection of nitrogen, methyl 3-(4,6-dihydroxypyrimidin-5-yl)-2-methylpropionate (3 g) was dispersed in acetonitrile (60 mL) at 22° C., and phosphorus oxychloride (2.91 mL) and diisopropylethylamine (1.18 mL) were added dropwise successively. The reaction system was obviously exothermic, and the solid was gradually dissolved and clarified, then the temperature was raised to 90° C. and the reaction was carried out for 16 hours. After the reaction was completed, the reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel column chromatography (petroleum ether: ethyl acetate=10:1, volume ratio) to obtain 1.50 g of a white solid, which was directly used in the next step.

d) 4-chloro-6-methyl-5,8-dihydropyrido[2,3-d]pyrimidin-7(6H)-one

Methyl 3-(4,6-dichloropyrimidin-5-yl)-2-methylpropionate (1.5 g) was added to ammonia (3 mL) at 20° C. and reacted at 20° C. for 16 hours. After the reaction was completed, the reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel column chromatography (petroleum ether: ethyl acetate=4:1, volume ratio) to obtain 0.30 g of a white solid. LC-MS (ESI) m/z: 199 (M+H).

e) tert-butyl 4-(6-methyl-7-oxo-5,6,7,8-tetrahydropyrido[2,3-d]pyrimidin-4-yl)piperazine-1-carboxylate Tert-butylpiperazine-1-carboxylate (0.28 g) and N,N-lutidine-4-amine (0.31 g) were added to a solution of 4-chloro-6-methyl-5,8-dihydropyrido[2,3-d]pyrimidin-7(6H)-one (0.1 g) in N-methylpyrrolidone (3 mL) at 20° C., and the reaction mixture was stirred at 150° C. for 3 hours. After the reaction was completed, the reaction solution was poured into water (100 mL), and ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel plate chromatography (petroleum ether: ethyl acetate=1:1, volume ratio) to obtain 0.31 g of a white solid. LC-MS (ESI) m/z: 348.2 (M+H).

f) 6-methyl-4-(piperazin-1-yl)-5,8-dihydropyrido[2,3-d]pyrimidin-7(6H)-one

Hydrogen chloride/1,4-dioxane solution (4.0 M, 10 mL) was added to tert-butyl 4-(6-methyl-7-oxo-5,6,7,8-tetrahydropyrido[2,3-d]pyrimidin-4-yl)piperazine-1-carboxylate (0.1 g) at 20° C., and the reaction mixture was stirred at 20° C. for 3 hours. After the reaction was completed, the solvent was evaporated under reduced pressure to obtain a near-white solid (0.1 g). LC-MS (ESI) m/z: 248.2 (M+H).

g) tert-butyl (2S)-2-(4-chlorophenyl)-3-(4-(6-methyl-7-oxo-5,6,7,8-tetrahydropyridine[2,3-d]pyrimidin-4-yl)piperazin-1-yl)-3-oxopropyl(isopropyl) carbamate (S)-3-((tert-butoxycarbonyl)(isopropyl)amino)-2-(4-chlorophenyl)propionic acid (0.17 g) and diisopropylethylamine (0.16 g) were added to a solution of 6-methyl-4-(piperazin-1-yl)-5,8-dihydropyrido[2,3-d]pyrimidin-7(6H)-one (0.1 g) in N,N-dimethylformamide (10 mL) at 20° C. The reaction mixture was stirred for 2 min. 2-(7-benzotriazole oxide)-N,N,N',N'-tetramethylurea hexafluorophosphate (0.23 g) was added at 20° C., and the reaction mixture was stirred at 20° C. for 1 hour. After the reaction was completed, the reaction solution was poured into water (100 mL), and ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel plate chromatography (petroleum ether: ethyl acetate=1:2, volume ratio) to obtain 0.08 g of a white solid, which was directly used in the next step.

h) 4-(4-((S)-2-(4-chlorophenyl)-3-(isopropylamino)propionyl)piperazin-1-yl)-6-meth yl-5,8-dihydropyrido[2,3-d]pyrimidin-7(6H)-one hydrochloride At 20° C., hydrogen chloride/1,4-dioxane solution (4.0 M, 3 mL) was added to tert-butyl (2R)-2-(4-chlorophenyl)-3-(4-(6-methyl-7-oxo-5,6,7,8-tetrahydropyrido[2,3-d]pyrimidin-4-yl)piperazin-1-yl)-3-oxopropyl(isopropyl)carbamate (0.2 g). The reaction mixture was stirred at 20° C. for 3 hours. After the reaction was completed, the reaction solution was evaporated under reduced pressure to remove the solvent and the resultant was separated by HPLC to obtain 0.06 g of a near-white solid.

LC-MS (ESI) m/z: 471 (M+H). $^1$H NMR (400 MHz, MeOD) δ 8.42 (d, J=4.5 Hz, 1H), 7.54-7.33 (m, 4H), 4.64-4.52 (m, 1H), 3.96-3.81 (m, 2H), 3.79-3.73 (m, 2H), 3.70-3.66 (m, 2H), 3.63-3.56 (m, 1H), 3.51-3.40 (m, 2H), 3.24-3.16 (m, 1H), 3.09-2.94 (m, 1H), 2.84 (s, 1H), 2.79-2.66 (m, 2H), 1.44-1.35 (m, 6H), 1.33-1.25 (m, 3H).

Isomer Separation:

The above-mentioned title compound was chirally resolved by supercritical fluid chromatography. Resolution instrument and conditions: Waters SFC200; Column: Daicel Chiralcel AS, 250×30 mm ID, 5 μm; Mobile phase: A is $CO_2$, B is methanol (0.1% $NH_3H_2O$), A:B=90:10 (volume ratio); flow rate 60 mL/min, column temperature 38° C.

Isomer 1:

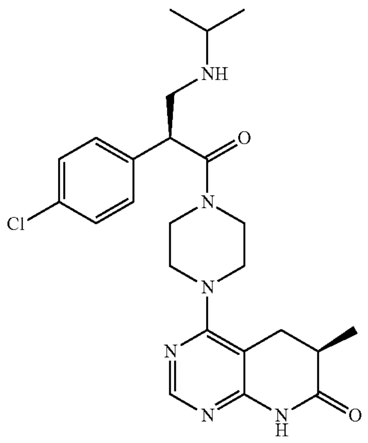 [SMILES: CC(C)NC[C@@H](C(=O)N1CCN(c2ncnc3c2C[C@@H](C)C(=O)N3)CC1)c1ccc(Cl)cc1]

LCMS ESD r/z: 471 (M+H). $^1$H NMR (400 MHz, $CDCl_3$) δ 836 (s, 1H) 7.86 (s, 1H), 7.32-7.37 (m, 2H), 7.21-7.27 (m, 2H), 4.18 (s, 1H) 3.89-4.00 (m, 1H), 3.65-3.74 (m, 1H), 3.53-3.64 (m, 2H), 3.44-3.52 (m, 1H), 3.35-3.42 (m, 2H), 3.27-3.34 (m, 2H), 2.87-2.94 (m, 1H) 2.74-2.82 (m, 2H), 2.57-2.64 (m, 1H), 2.47-2.54 (m, 1H), 1.32 (d, J=6.6 Hz, 3H), 1.07-1.19 (m, 6H),

Isomer 2:

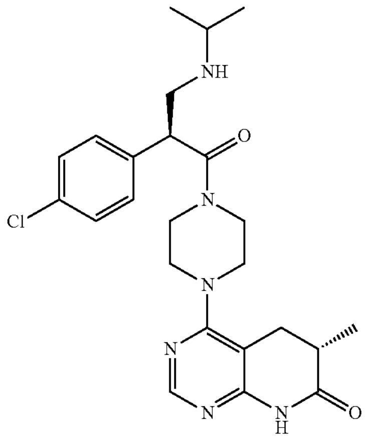 [SMILES: CC(C)NC[C@@H](C(=O)N1CCN(c2ncnc3c2C[C@H](C)C(=O)N3)CC1)c1ccc(Cl)cc1]

LCMS (ESI) m/z: 471 (M+H). $^1$H NMR (400 MHz, $CDCl_3$) δ 8.37 (s, 1H), 7.33-7.38 (m, 2H), 7.21-7.27 (m, 2H), 4.09 (s, 1H), 3.83-3.91 (m, 1H), 3.62-3.72 (m, 1H), 3.47 s, 3H) 3.26-3.34 (m, 2H), 3.12-3.21 (m, 1H), 2.69-2.98 (m, 5H), 2.50-2.66 (m, 2H), 1.32 (d, J=6.71 Hz, 3H), 1.11 (dd, J=14.8, 6.2 Hz, 6H).

Process J:

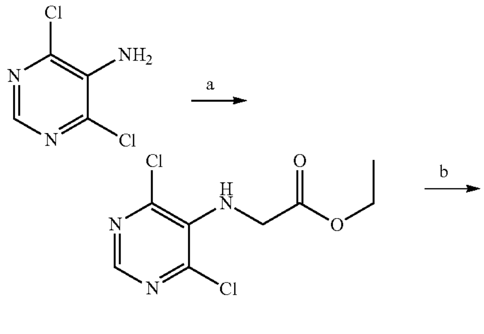

-continued

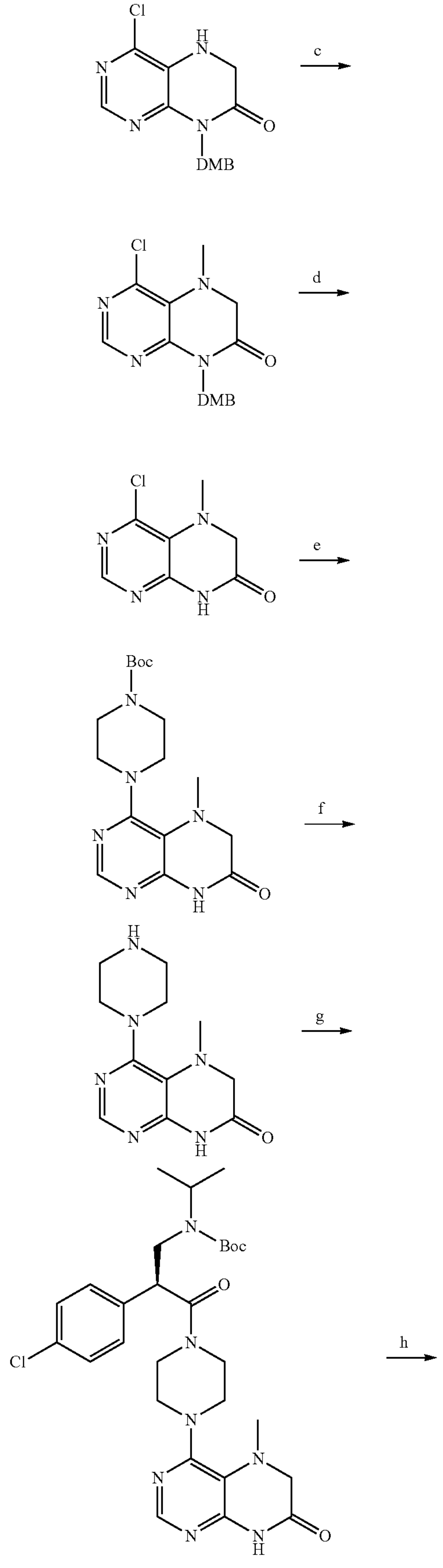

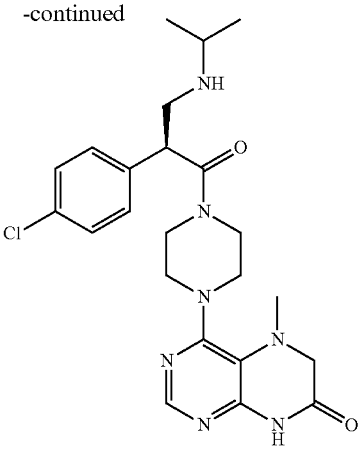

Reaction conditions: a) Ethyl bromoacetate, sodium hydride, tetrabutylammonium iodide, tetrahydrofuran; b) 2,4 dimethoxybenzylamine, triethylamine, isopropanol; c) methyl iodide, sodium hydride, N,N-dimethylformamide; d) trifluoroacetic acid; e) tert-butylpiperazine-1-carboxylate, 4-dimethylaminopyridine, N-methylpyrrolidone; f) hydrogen chloride/1,4-dioxane solution (4.0M); g) (S)-3-((tert-butoxycarbonyl)(isopropyl)amino)-2-(4-chlorophenyl)propionic acid, diisopropylethylamine, 2-(7-benzotriazole oxide)-N,N,N',N'-tetramethylurea hexafluorophosphate, N,N-dimethylformamide; h) hydrogen chloride/1,4-dioxane solution (4.0M).

Example 20

(S)-4-(4-(2-(4-chlorophenyl)-3-(isopropylamino)propionyl)piperazin-1-yl)-5-meth yl-5,8-dihydropteridine-7(6H)-one hydrochloride

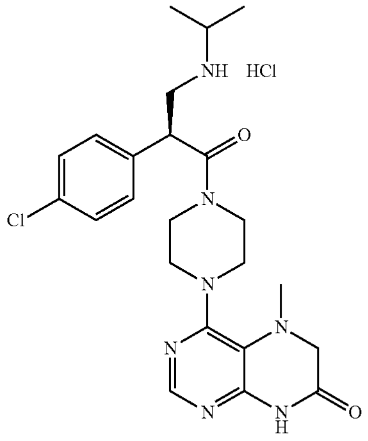 [SMILES: CC(C)NC[C@@H](C(=O)N1CCN(c2ncnc3c2N(C)CC(=O)N3)CC1)c1ccc(Cl)cc1 ; Cl]

a) ethyl 2-((4,6-dichloropyrimidin-5-yl)amino)acetate

Sodium hydride (2.93 g) was added to a solution of 4,6-dichloro-5-aminopyrimidine (10.0 g) in tetrahydrofuran (100 mL) at 0° C. The reaction mixture was stirred for 2 min. The temperature was raised to 20° C. and ethyl bromoacetate (12.22 g) was added, followed by tetrabutylammonium iodide (27.03 g). The reaction mixture was stirred at 20° C. for 16 hours. After the reaction was completed, the reaction solution was poured into water (100 mL), stirred for 30 min, and then ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel column chromatography (petroleum ether: ethyl acetate=20:1, volume ratio) to obtain 6.5 g of a colorless oily product, which was directly used in the next step.

b) 4-chloro-8-(2,4-dimethoxybenzyl)-5,8-dihydropteridine-7(6H)-one

At 20° C., 2,4-dimethoxybenzylamine (3.67 g) was added to a solution of ethyl 2-((4,6-dichloropyrimidin-5-yl)amino) acetate (5 g) in isopropanol (150 mL), and then triethylamine (4.45 g) was added. The reaction mixture was stirred at 80° C. for 18 hours. After the reaction was completed, the reaction solution was filtered, and the filter cake was washed with ethanol and dried under reduced pressure to obtain 5.0 g of a near-white solid, which was directly used in the next step.

c) 4-chloro-8-(2,4-dimethoxybenzyl)-5-methyl-5,8-dihydropteridine-7(6H)-one

At 0° C., methyl iodide (1.68 g) was added to a solution of 4-chloro-8-(2,4-dimethoxybenzyl)-5,6-dihydropteridine-7(8H)-one (3.3 g) in N,N-dimethylformamide (30 mL), and the reaction mixture was stirred for 20 min. The temperature was maintained at 0° C. and sodium hydride (0.47 g) was added. The reaction mixture was stirred at 0° C. for 3 hours. After the reaction was completed, the reaction solution was poured into water (100 mL), and ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel column chromatography (petroleum ether: ethyl acetate=5:1, volume ratio) to obtain 1.5 g of a white solid, which was directly used in the next step.

d) 4-chloro-5-methyl-5,8-dihydropteridine-7(6H)-one

At 20° C., trifluoroacetic acid (20 mL) was added to 4-chloro-8-(2,4-dimethoxybenzyl)-5-methyl-5,6-dihydropteridine-7(8H)-one (5 g). The reaction mixture was stirred at 60° C. for 16 hours. After the reaction was completed, the solvent was evaporated under reduced pressure to obtain a near-purple solid (1.0 g). LC-MS (ESI) m/z: 199.1 (M+H). $^1$H NMR (300 MHz, DMSO-$d_6$) δ (ppm) 11.60 (s, 1H), 8.35 (s, 1H), 3.77 (s, 2H), 2.85 (s, 3H).

e) tert-butyl 4-(5-methyl-7-oxo-5,6,7,8-tetrahydropteridine-4-yl) piperazine-1-carboxylate Tert-butylpiperazine-1-carboxylate (0.85 g) and 4-dimethylaminopyridine (0.93 g) were added to a solution of 4-chloro-5-methyl-5,8-dihydropteridine-7(6H)-one (0.3 g) in N-methylpyrrolidone (5 mL) at 20° C. The reaction mixture was stirred at 150° C. for 3 hours. After the reaction was completed, the reaction solution was poured into water (100 mL), and ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel plate chromatography (petroleum ether: ethyl acetate=1:1, volume ratio) to obtain 0.27 g of a white solid, which was directly used in the next step.

f) 5-methyl-4-(piperazin-1-yl)-5,8-dihydropteridine-7(6H)-one

Hydrogen chloride/1,4-dioxane solution (4.0 M, 3 mL) was added to tert-butyl 4-(5-methyl-7-oxo-5,6,7,8-tetrahydropteridine-4-yl)piperazine-1-carboxylate (0.1 g) at 20° C., and the reaction mixture was stirred at 20° C. for 3 hours. After the reaction was completed, the solvent was evaporated under reduced pressure to obtain a near-white solid (0.1 g).

g) tert-Butyl (S)-2-(4-chlorophenyl)-3-(4-(5-methyl-7-oxo-5,6,7,8-tetrahydropteridine-4-yl)piperazin-1-yl)-3-oxopropyl(isopropyl)carbamate At 20° C., (S)-3-((tert-butoxycarbonyl)(isopropyl) amino)-2-(4-chlorophenyl)propionic acid (0.17 g) and diisopropylethylamine (0.16 g) were added to a solution of 5-methyl-4-(piperazin-1-yl)-5,6-dihydropteridine-7(8H)-one (0.1 g) in N,N-dimethylformamide (10 mL). The reaction mixture was stirred for 2 min. Then 2-(7-benzotriazole oxide)-N,N,N',N'-tetramethylurea hexafluorophosphate (0.23 g) was added at 20° C., and the reaction mixture was stirred at 20° C. for 1 hour. After the reaction was completed, the reaction solution was poured into water (100 mL), and ethyl acetate (100 mL) was added for extraction. The organic phase was washed with saturated sodium chloride solution (100 mL×3), and dried with anhydrous sodium sulfate. The solvent was evaporated under reduced pressure. The product was purified by silica gel plate chromatography (petroleum ether: ethyl acetate=1:1.5, volume ratio) to obtain 0.08 g of a white solid. LC-MS (ESI) m/z: 572 (M+H).

h) (S)-4-(4-(2-(4-chlorophenyl)-3-(isopropylamino) propionyl)piperazin-1-yl)-5-methyl-5,8-dihydropteridine-7(6H)-one hydrochloride At 20° C., hydrogen chloride/1,4-dioxane solution (4.0 M, 3 mL) was added to tert-butyl (S)-(2-(4-chlorophenyl)-3-(4-(5-methyl-7-oxo-5,6,7,8-tetrahydropteridine-4-yl)piperazine-1-yl)-3-oxopropyl(isopropyl)carbamate (0.08 g). The reaction mixture was stirred at 20° C. for 3 hours. After the reaction was completed, the reaction solution was evaporated under reduced pressure to remove the solvent and the resultant was separated by HPLC to obtain 0.02 g of a near-white solid.

LC-MS (ESI) m/z: 472 (M+H), $^1$H NMR (300 MHz, DMSO-$d_6$) δ (ppm) 10.94 (s, 1H), 8.12 (s, 1H), 7.46-7.51 (m, 2H), 7.37-7.43 (m, 2H), 4.68-4.74 (m, 1H), 3.81-3.91 (m, 2H), 3.64-3.74 (m, 2H), 3.59-3.63 (m, 2H), 3.52-3.59 (m, 4H), 3.25-3.34 (m, 2H), 2.95-3.03 (m, 1H), 2.48 (s, 3H), 1.20-1.28 (m, 6H).

Example 21

4-(8-((S)-2-(4-chlorophenyl)-3-(isopropylamino)propionyl)-3,8-diazabicyclo[3.2.1]octan-3-yl)-5-methyl-5,8-dihydropteridine-7(6H)-one formate

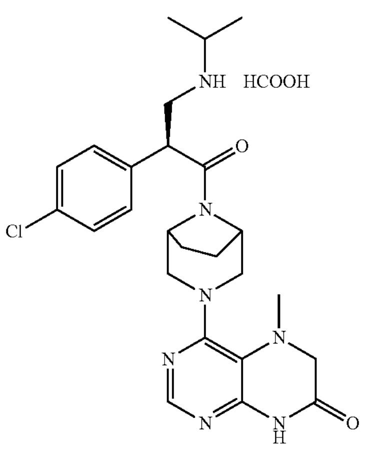 [SMILES: CC(C)NC[C@@H](C(=O)N1C2CCC1CN(c1ncnc3c1N(C)CC(=O)N3)C2)c1ccc(Cl)cc1 ; "HCOOH"]

Preparation was in accordance with the method as described in Example 20, wherein tert-butyl 3,8-diazabicyclo[3.2.1]octane-8-carboxylate was used instead of tert-butylpiperazine-1-carboxylate. The HPLC conditions for target product: Column: Agilent 5 μm prep-C18 50×21.2 mm, mobile phase A: water (containing 0.1% formic acid); mobile phase B: acetonitrile. Gradient: time 0-10 min, phase B 5-75% (volume ratio), RT=3.4 min.

LC-MS (ES) m/z: 498 (M+H). $^1$H NMR 400 MHz, DMSO-$d_6$) δ (ppm) 10.89 (s, 1H), 8.27 (s, 1H), 8.10 (d, J=25.6 Hz, 1H), 7.31-7.48 (m, 4H), 4.48-4.68 (m, 3H), 4.09-4.30 (m, 2H), 3.50-3.60 (m, 3H), 3.11-3.24 (m, 2H), 2.62-2.84 (m, 3H), 2.37-2.47 (m, 3H), 1.49-1.88 (m, 4H), 0.89-1.02 (m, 61-1).

Example 22

4-((S)-4-((S)-2-(4-chlorophenyl)-3-(isopropylamino)propionyl)-3-methylpiperazin-1-yl)-5-methyl-5,8-dihydropteridine-7(6H)-one

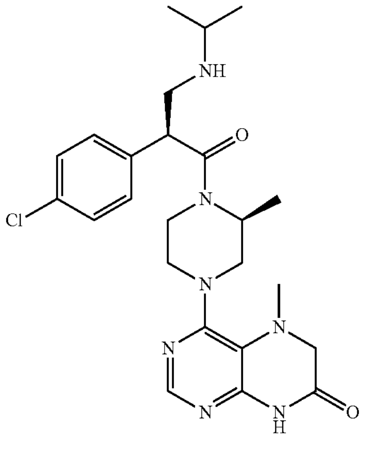

Preparation was in accordance with the method as described in Example 20, wherein (S)-1-N-Boc-2-methylpiperazine was used instead of tert-butylpiperazine-1-carboxylate. The final product was adjusted to pH=9 by adding 10% sodium hydroxide solution at 0° C., and extracted with dichloromethane (10 mL×3). The organic phase was washed with saturated sodium chloride solution (15 mL), dried with anhydrous sodium sulfate, and evaporated under reduced pressure to obtain 70 mg of a white solid.

LC-MS (ESI) m/z: 486 (M+H) $^1$H NNR (400 MHz, DMSO-$d_6$) δ (ppm) 10.88 (s, 1H), 8.09 (d, J=5.6 Hz, 1H), 7.35-7.42 (m, 3H), 7.27 (d, J=8.4 Hz, 1H), 4.55-4.74 (m, 3H), 4.44-4.53 (m, 1H), 4.31-4.39 (m, 1H), 4.16-4.26 (m, 1H), 4.00-4.10 (m, 1H), 3.87-3.96 (m, 1H), 3.04-3.16 (m, 2H), 2.87-296 (m, 1H), 2.77-285 (m, 1H), 2.56-2.63 (m, 2H), 2.42-2.47 m, 3H), 1.18-1.29 (m, 3N), 0.90-0.96 (m, 6H).

Process K:

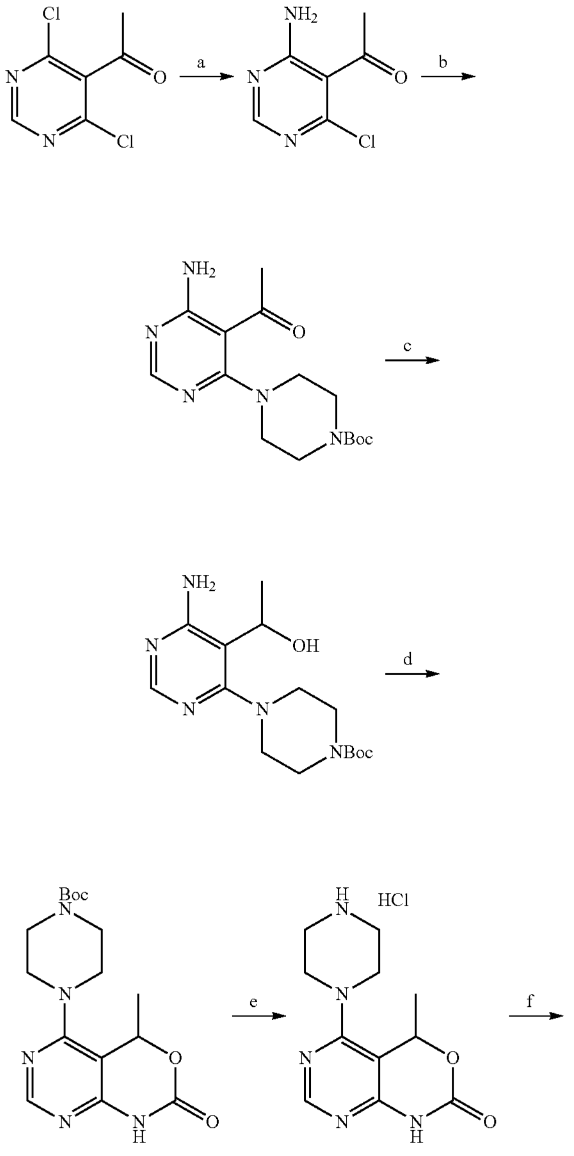

-continued

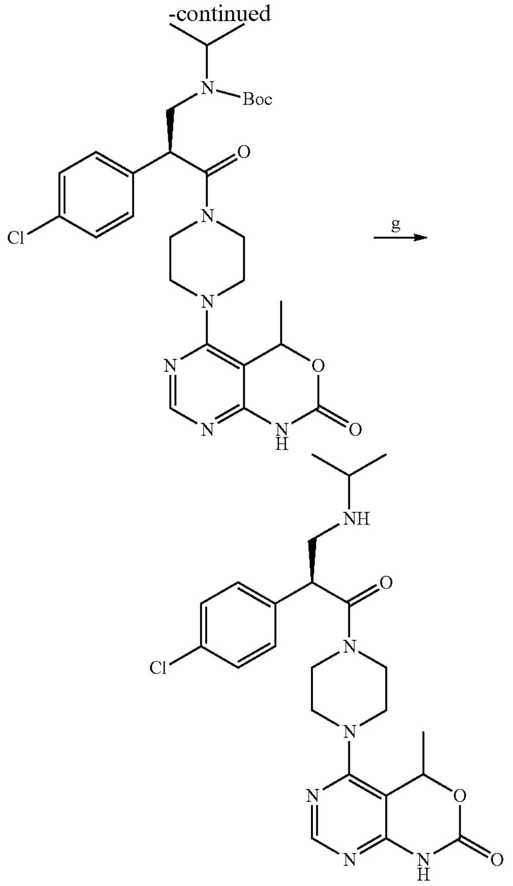

Reagents: a) ammonia (25-28 wt %), tetrahydrofuran; b) acetonitrile, tert-butylpiperazine-1-carboxylate, N,N-diisopropylethylamine; c) sodium borohydride, methanol, saturated aqueous ammonium chloride solution; d) trichloromethyl carbonate, N,N-diisopropylethylamine, tetrahydrofuran; e) dichloromethane, hydrogen chloride/1,4-dioxane solution (4.0 M); f) (S)-3-((tert-butoxycarbonyl)(isopropyl)amino)-2-(4-chlorophenyl)propionic acid, N,N-diisopropylethylamine, N,N-dimethylformamide, 2-(7-azobenzotriazole)-N,N,N′,N′-tetramethylurea hexafluorophosphate; g) dichloromethane, hydrogen chloride/1,4-dioxane solution (4.0 M).

Example 23

5-(4-((S)-2-(4-chlorophenyl)-3-(isopropylamino) propionyl)piperazin-1-yl)-4-meth yl-1,4-dihydro-2H-pyrimido[4,5-d][1,3]oxazin-2-one formate

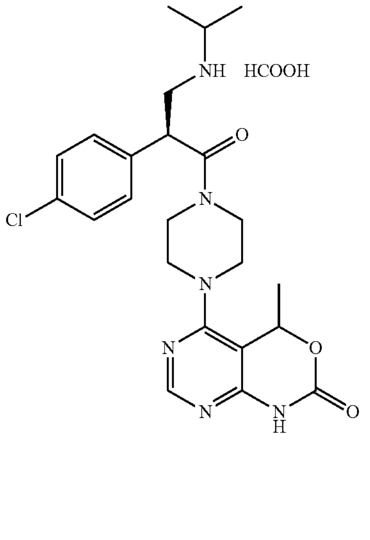 [SMILES: CC(C)NC[C@@H](C(=O)N1CCN(c2ncnc3c2C(C)OC(=O)N3)CC1)c1ccc(Cl)cc1 ; "HCOOH"]

a) 1-(4-amino-6-chloropyrimidin-5-yl)ethanone

At 20° C., 1-(4,6-dichloropyrimidin-5-yl)ethanone (2.5 g) was dissolved in tetrahydrofuran (15 mL), and ammonia (9 g) was added. The reaction solution was stirred at 20° C. for 5 hours, then concentrated and diluted with a small amount of water, and filtered with suction to obtain a white solid, which was dried in vacuum to obtain 2 g of a white solid, which was directly used in the next step.

b) tert-butyl 4-(5-acetyl-6-aminopyrimidin-4-yl) piperazine-1-carboxylate 1-(4-Amino-6-chloropyrimidin-5-yl)ethanone (2 g) and N,N-diisopropylethylamine (3 g) were dissolved in acetonitrile (20 mL) at 20° C. Then 1-(4-amino-6-chloropyrimidin-5-yl)ethanone was added, and the reaction solution was stirred at 40° C. for 5 hours. After the reaction was completed, the solvent was evaporated under reduced pressure to obtain a crude product. The crude product was separated and purified by a silica gel column chromatography (ethyl acetate: petroleum ether=1:1, volume ratio) to obtain 3.2 g of a pale yellow solid, which was directly used in the next step.

c) tert-butyl 4-(6-amino-5-(1-hydroxyethyl)pyrimidin-4-yl)piperazine-1-carboxylate Tert-butyl 4-(5-acetyl-6-aminopyrimidin-4-yl)piperazine-1-carboxylate (1.5 g) was dissolved in methanol (15 mL) at 20° C. and cool to −10° C. Then sodium borohydride (1 g) was added in batches. After the addition was completed, the reaction solution was slowly warmed to 20° C. and stirred for another 3 hours. After the reaction was completed, the reaction solution was quenched with saturated aqueous solution of ammonium chloride. The reaction solution was concentrated and pulped with ethyl acetate (20 mL×2). The mother liquor is concentrated to obtain an oily crude product. The crude product was separated and purified by silica gel column chromatography (dichloromethane:methanol=1:30, volume ratio) to obtain 400 mg of a white oily product. LC-MS (ESI): m/z=324 [M+H].

d) tert-butyl 4-(4-methyl-2-oxo-1,4-dihydro-2H-pyrimido[4,5-d][1,3]oxazin-5-yl)piperazine-1-carboxylate At 20° C., tert-butyl 4-(6-amino-5-(1-hydroxyethyl)pyrimidine-4-yl)piperazine-1-carboxylate (300 mg) and N,N-diisopropylethylamine (282 mg) were dissolved in tetrahydrofuran (3 mL). Then the temperature was lowered to −5° C. and trichloromethyl carbonate was slowly added, and stirred at −5° C. for 0.5 hour. The temperature was then slowly raised to 18° C. and the reaction solution was stirred for 1.5 hours. After the reaction was completed, the reaction was quenched with aqueous sodium bicarbonate solution and extracted with ethyl acetate (10 mL×3). The organic phases were combined and dried with anhydrous sodium sulfate, filtered, and concentrated to obtain an oily crude. The crude was separated and purified by silica gel column chromatography (petroleum ether: ethyl acetate=1:1, volume ratio) to obtain 108 mg of a white solid. LC-MS (ESI) m/z=350[M+H].

e) 4-methyl-5-(piperazin-1-yl)-1,4-dihydro-2H-pyrimido[4,5-d][1,3]oxazin-2-one hydrochloride At 20° C., tert-butyl 4-(4-methyl-2-oxo-1,4-dihydro-2H-pyrimido[4,5-d][1,3]oxazin-5-yl)piperazine-1-carboxylate (100 mg) was dissolved in dichloromethane (3 mL) and added with hydrogen chloride/1,4-dioxane solution (4.0 M, 3 mL) under stirring. The reaction solution was stirred at 20° C. for 1 hour, and a white solid was precipitated out. The reaction solution was evaporated to remove the solvent under reduced pressure to obtain 80 mg of white solid target product, which was directly used in the next step.

f) tert-butyl (2S)-2-(4-chlorophenyl)-3-(4-(4-methyl-2-oxo-1,4-dihydro-2H-pyrimido[4,5-d][1,3]oxazin-5-yl)piperazin-1-yl)-3-oxopropyl)(isopropyl) carbamate At 20° C., 4-methyl-5-(piperazin-1-yl)-1H-pyrimido[4,5-d][1,3]oxazine-2(4H)-one (80 mg), (S)-3-((tert-butoxycarbonyl)(isopropyl)amino)-2-(4-chlorophenyl)propionic acid (100 mg), N,N-diisopropylethylamine (113 mg) and 2-(7-azobenzotriazole)-N,N,N',N'-tetramethylurea hexafluorophosphate (167 mg) were dissolved in anhydrous N,N-Dimethylformamide (2.5 mL). The reaction solution was stirred at 20° C. for 12 hours. After the reaction was completed, the reaction solution was poured into ethyl acetate (20 mL) and washed twice with water and once with sodium chloride aqueous solution. The organic phase was concentrated to obtain a crude product. The crude product was separated and purified by silica gel column chromatography (petroleum ether: ethyl acetate=1:1, volume ratio) to obtain 130 mg of a white solid. LC-MS (ESI) m/z=573[M+H].

g) 5-(4-((S)-2-(4-chlorophenyl)-3-(isopropylamino) propionyl)piperazin-1-yl)-4-methyl-1,4-dihydro-2H-pyrimido[4,5-d][1,3]oxazin-2-one formate Tert-butyl (2S)-2-(4-chlorophenyl)-3-(4-(4-methyl-2-oxo-1,4-dihydro-1H-pyrimido[4,5-d][1,3])oxazin-5-yl)piperazin-1-yl)-3-oxopropyl)(isopropyl)carbamate (130 mg) was dissolved in dichloromethane (2 mL) at 20° C. Under stirring, hydrogen chloride/1,4-dioxane solution (4.0 M, 2 mL) was added, and the reaction solution was stirred at 20° C. for 2 hours. After the reaction was completed, the reaction solution was cooled to 0° C., and 10% sodium hydroxide solution was added to adjust pH=9, and dichloromethane (10 mL×3) was added for extraction. The organic phase was washed with saturated sodium chloride solution (15 mL), dried with anhydrous sodium sulfate and evaporated under reduced pressure. The residue was separated and purified by high performance preparative liquid chromatography to obtain 32 mg of a white solid. HPLC conditions: Column: Agilent 5 μm prep-C18 50×21.2 mm, mobile phase A: water (containing 0.1% formic acid); mobile phase B: acetonitrile, gradient: time 0-10 min, phase B 5-45% (volume ratio), RT=3.7 min.

LC-MS (ESI): m/z=473 [M+H]. $^1$H NMR (400 MHz, DMSO-$d_6$) δ (ppm) 8.22-8.31 (m, 2H), 7.37-7.45 (m, 2H), 7.28-7.36 (m, 2H), 5.68-5.81 (m, 1H), 4.18-4.28 (m, 1H) 3.41-3.78 (m, 8H) 3.03-3.26 (m, 3H), 2.89-3.01 (m, 1H), 2.74-2.83 (m, 1H). 2.64-2.72 (m, 1H). 1.33-2.49 (m, 3H). 0.89-1.04 (m, 6H).

Isomer Separation:

The above-mentioned title compound was chirally resolved by supercritical fluid chromatography. Resolution instrument and conditions: Waters SFC200; Column: Daicel Chiralcel AD, 250×30 mm ID, 5 μm; Mobile phase: A is $CO_2$, B is methanol (0.1% $NH_3H_2O$), A:B=65:35 (volume ratio); flow rate 60 mL/min, column temperature 38° C.

Isomer 1:

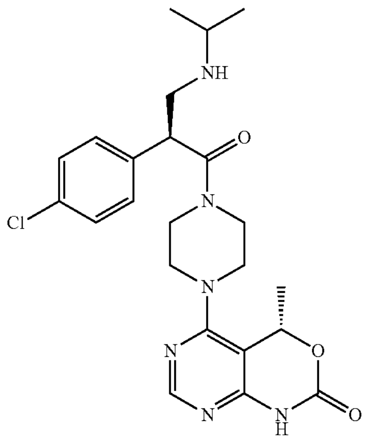

LCMS (ESI): m/z=473 (M+H). $^1$H NMR (400 MHz, DMSO-$d_6$) δ 8.28 (s, 1H), 7.47-7.23 (m, 4H), 5.76 (d, J=6.3 Hz, 1H), 4.15 (s, 1H) 3.75-3.44 (m, 6H), 3.28-3.20 (m, 2H), 3.15-3.04 (m, 2H), 2.74-2.58 (m, 2H), 1.41 (d, J=6.2 Hz, 3H), 0.93 (t, J=6.9 Hz, 6H).

Isomer 2:

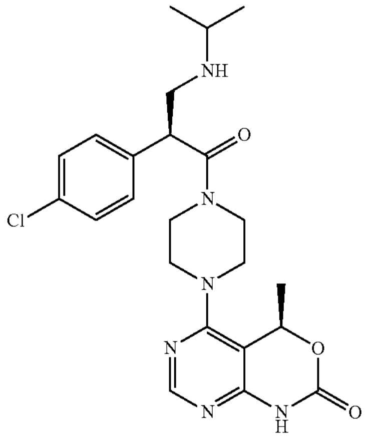 [SMILES: CC(C)NC[C@@H](C(=O)N1CCN(c2ncnc3c2[C@@H](C)OC(=O)N3)CC1)c1ccc(Cl)cc1]

LCMS (ESI): M/Z=473 (M+H). $^1$H NMR (400 MHz, DMSO-$d_6$) δ 10.85 (s, 1H), 8.29 (s, 1H), 7.43 (dd, J=42.1, 8.2 Hz, 4H), 5.75 (q, J=6.2 Hz, 1H), 4.76-4.54 (m, 1H), 3.79-3.39 (m, 8H), 3.32-3.20 (m, 2H) 3.10-2.85 (m, 2H) 1.43 (d, 1=6.41 Hz, 3H), 1.25 (t, J=5.6 Hz, 6H).

Example 24

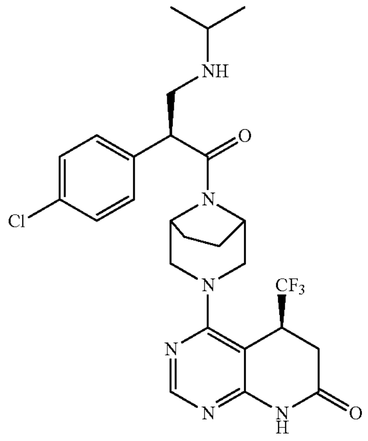

and isomer 1

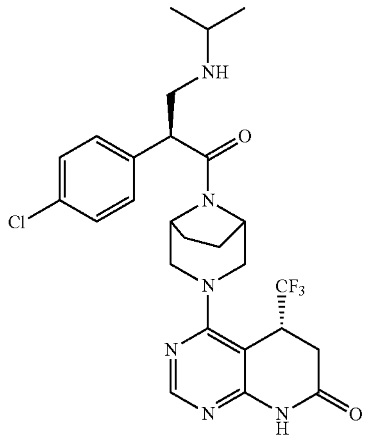

isomer 2

Preparation was in accordance with the method according to the method described in Process F, wherein tert-butyl 3,8-diazabicyclo[3.2.1]octane-8-formate was used instead of tert-butylpiperazine-1-carboxylate. The final product was separated by supercritical fluid chromatography to obtain an isomer 1 and an isomer 2. Resolution instrument and conditions: waters SFC200; Column: Daicel Chiralcel OD, 250×30 mm ID, 5 μm; Mobile phase: A is $CO_2$, B is ethanol (0.1% $NH_3H_2O$); A:B=70:30 (volume ratio); flow rate 60 mL/min, column temperature 38° C.

isomer 1: LCMS (ESI) m/z: 551 (M+H). $^1$HNMR (300 MHz, DMSO-$d_6$) δ (ppm): 1.28-1.11 (m, 6H), 2.10-1.47 (m, 6H), 3.18-275 (m, 7H), 4.28-3.65 (m, 5H), 4.85-4.83 (1H), 7.41-7.25 (m, 4H), 8.42-8.33 (m, 1H).

isomer 2: LCMS (ESI) m/z: 551 M+H). $^1$HNMR (300 MHz, DMSO-$d_6$) δ (ppm) 2.28-1.20 (m, 13H), 3.43-2.89 (m, 6H), 4.37-3.71 (m, 5H), 4.86-4.81 (m, 1H), 7.39-7.27 (m, 4H), 8.36 (s, 1H).

Example 25

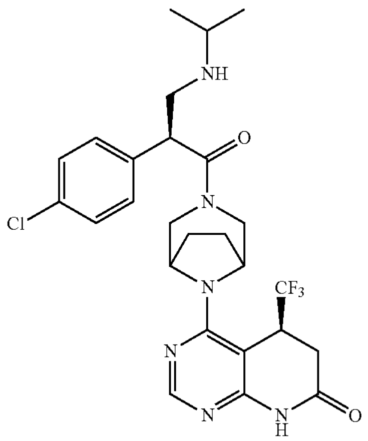

and isomer 1

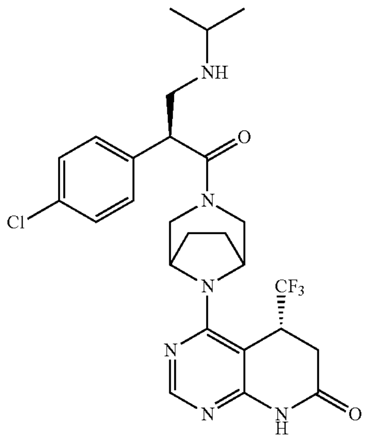

isomer 2

Preparation was in accordance with the method according to the method described in Process F, wherein tert-butyl 3,8-diazabicyclo[3.2.1]octane-3-formate was used instead of tert-butylpiperazine-1-carboxylate. The final product was separated by supercritical fluid chromatography to obtain an isomer 1 and an isomer 2. Resolution instrument and conditions: waters SFC200; Column: Daicel Chiralcel OZ, 250×30 mm ID, 5 μm; Mobile phase: A is $CO_2$, B is ethanol (0.1% $NH_3H_2O$); A:B=60:40 (volume ratio); flow rate 60 mL/min, column temperature 38° C.

Isomer 1:

LCMS (ESI) m/z: 551 (M+H). $^1$HNMR (400 MHz, DMSO-$d_6$) δ (ppm): 0.98-0.92 (m, 6H), 1.96-1.57 (m, 3H), 2.87-2.59 (m, 5H), 3.29-3.12 (m, 2H), 3.63-3.42 (m, 2H), 3.99 (s, 1H), 4.67-4.24 (m, 5H), 7.46-7.27 (m, 4H), 8.30 (d, J=3.6 Hz, 1H), 10.84 (s, 1H).

Isomer 2:

LCMS (ESI) m/z: 551 (M+H). $^1$HNMR (400 MHz, DMSO-$d_6$) δ (ppm): 0.98-0.89 (m, 6H), 2.03-1.54 (m, 4H), 2.76-2.57 (m, 4H), 3.27-2.95 (m, 4H), 3.70-3.67 (m, 1H), 3.99-3.95 (m, 1H), 467-4.20 (m, 4H), 7.45-7.27 (m, 4H), 8.28 (s, 1H), 10.83 (s, 1H).

Example 26

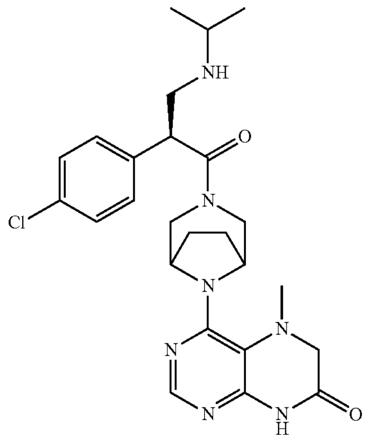 [SMILES: CC(C)NC[C@@H](C(=O)N1CC2CCC(C1)N2c1ncnc2c1N(C)CC(=O)N2)c1ccc(Cl)cc1]

Preparation was in accordance with the method according to the method described in Process J, wherein tert-butyl 3,8-diazabicyclo[3.2.1]octane-3-formate was used instead of tert-butylpiperazine-1-carboxylate.

LCMS (ESI) m/z=498 (M+H) $^1$H NMR (400 MHz, DMSO-$d_6$) δ 10.86 (s, 1H), 8.06-8.15 (m, 1H), 7.23-7.47 (m, 4H), 4.85-5.09 (m, 2H), 4.11-4.31 (m, 2H), 3.92-4.04 (m, 1H), 3.54-3.62 (m, 2H), 3.05-3.17 (m, 1H), 2.8-2.95 (m, 1H), 2.72-2.82 (m, 1H), 2.55-2.63 (m, 1H), 241 (s, 3H), 1.91 (s, 1H), 1.61-1.77 (m, 1H), 1.40-1.55 (m, 1H), 1.22-1.33 (m, 1H), 0.84-1.01 (m, 6H), 0.40-053 (m, 1H).

Example 27

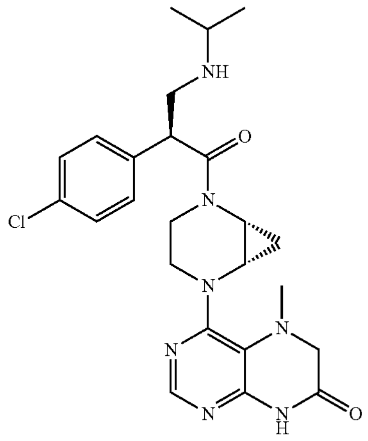

and isomer 1

-continued

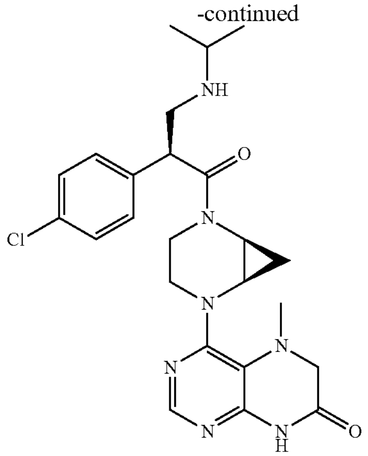

isomer 2

Preparation was in accordance with the method according to the method described in Scheme J, wherein tert-butyl 2,5-diazabicyclo[4.1.0]heptan-2-carboxylate was used instead of tert-butylpiperazine-1-carboxylate. The final product was separated by supercritical fluid chromatography to obtain an isomer 1 and an isomer 2. Resolution instrument and conditions: Waters SFC200; Column: Daicel Chiralcel OZ, 250×30 mm ID, 5 μm; Mobile phase: A is $CO_2$, B is ethanol (0.1% $NH_3H_2O$); A:B=60:40 (volume ratio); flow rate 60 mL/min, column temperature 38° C.

UltraPerformance Convergence Chromatographic Conditions:

Column: Daicel Chiralcel AD, 2.1×150 mm I.D., 3 μm, mobile phase A: $CO_2$, mobile phase B: ethanol (0.1% DEA), gradient: time 0-8 min, phase B 5-40% (volume ratio); flow rate: 1 mL/min; column temperature 40° C. Isomer 1: RT=4.0 min; Isomer 2: RT=4.8 min.

isomer 1: LCMS (ESI): m/z 484 (M+H). $^1$H NMR (400 MHz, DMSO-$d_6$) δ 10.97 (s, 1H), 8.17-8.25 (m, 1H), 7.38-7.52 (m, 4H), 4.44-4.51 (m, 1H), 4.20-4.38 (m, 1H), 3.65-3.78 (m, 1H), 3.50-363 (m, 4H), 3.13-3.33 (m, 3H), 2.69-286 (m, 2H), 2.49-2.58 (m, 3H), 1.44-1.51 (m, 1H), 0.93-1.06 (m, 7H), 0.51 (d, J=5.6 Hz, 1H).

isomer 2: LCMS (ESI): m/z=484 (M+H). $^1$H NMR (400 MHz, DMSO-$d_6$) δ 10.89 (s, 1H), 7.99-8.19 (m, 1H), 7.16-7.47 (m, 4H), 4.07-4.36 (m, 2H), 3.56-3.69 (m, 2H), 3.39-3.54 (m, 3H), 3.03-3.25 (m, 3H), 2.71-2.79 (m, 1H), 2.57-2.69 (m, 2H), 2.27-2.32 (m, 3H), 1.23-1.35 (m, 1H), 0.80-1.02 (m, 6H), 0.66 (q, J=4.9 Hz, 1H).

Example 28

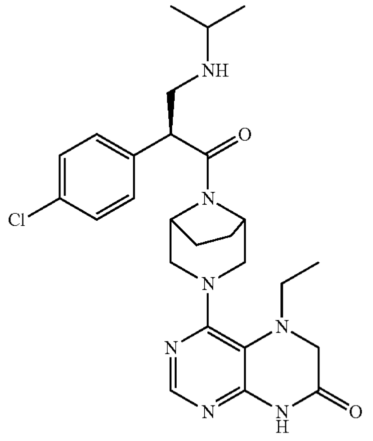 [SMILES: CCN1CC(=O)Nc2ncnc(N3CC4CCC(C3)N4C(=O)[C@H](CNC(C)C)c3ccc(Cl)cc3)c21]

Preparation was in accordance with the method described in Process J, wherein ethyl iodide was used instead of methyl iodide, and tert-butyl 3,8-diazabicyclo[3.2.1]octane-8-carboxylate was used instead of tert-butylpiperazine-1-carboxylate.

LCMS (ESI): m/z=512 (M+H). $^1$H NMR (400 MHz, DMSO-$d_6$) δ 10.88 (s, 1H), 8.15 (d, J=26.0 Hz, 1H), 7.54-7.39 (m, 4H), 4.71-4.52 (m, 4H), 4.26-4.19 (m, 1H), 4.15-4.06 (m, 1H), 3.75-3.57 (m, 2H), 3.29-3.11 (m, 2H), 3.01-2.93 (m, 1H), 2.85-2.78 (m, 1H), 2.72-2.64 (m, 4H), 2.09-1.98 (m, 1H), 1.96-1.86 (m, 1H), 1.88-1.59 (m, 3H), 1.04-0.87 (m, 7H).

Example 29

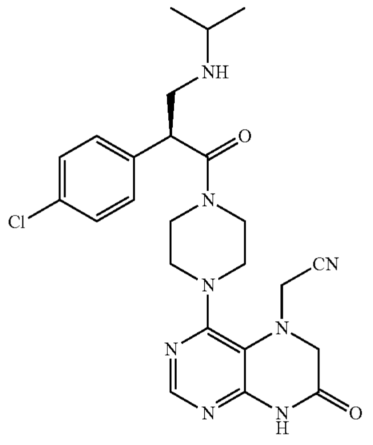 [SMILES: CC(C)NC[C@@H](C(=O)N1CCN(c2ncnc3c2N(CC#N)CC(=O)N3)CC1)c1ccc(Cl)cc1]

Preparation was in accordance with the method described in Process J, wherein bromoacetonitrile was used instead of methyl iodide.

LCMS (ESI) m/z: 523 (M+H). $^1$H NMR (400 MHz, DMSO-$d_6$) δ 11.02 (s, 1H), 8.16 (d, J=22.9 Hz, 1H), 7.38 (dd, J=11.8, 2.4 Hz, 4H), 4.61-4.44 (m, 2H), 4.34-4.08 (m, 3H), 4.05-3.94 (m, 2H), 3.85-3.80 (m, 2H), 3.23-3.01 (m, 2H), 2.77-2.66 (m, 2H), 1.90-1.53 (m, 4H), 0.94 (t, J=5.6 Hz, 6H).

Example 30

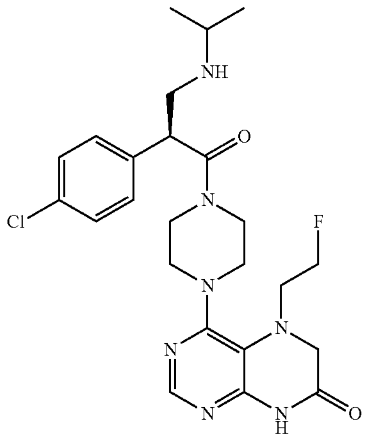 [SMILES: CC(C)NC[C@@H](C(=O)N1CCN(c2ncnc3c2N(CCF)CC(=O)N3)CC1)c1ccc(Cl)cc1]

Preparation was in accordance with the method described in Process J, wherein 1-fluoro-2-iodoethane was used instead of methyl iodide.

LCMS ESD n/z: 530 (M+H). $^1$H NMR (400 MHz, DMSO-$d_6$) δ 8.28 (d, J=53 Hz, 1H), 8.05-8.5 (m, 1H), 7.33-7.49 (m, 4H), 4.22-4.70 (m, 8H), 3.48-3.74 (m, 1H), 3.21-3.43 (m, 2H), 2.88-3.16 (m, 3H), 2.74-2.86 (m, 1H), 1.44-2.02 (m, 4H), 0.97-1.11 (m, 6H).

Process J-1:

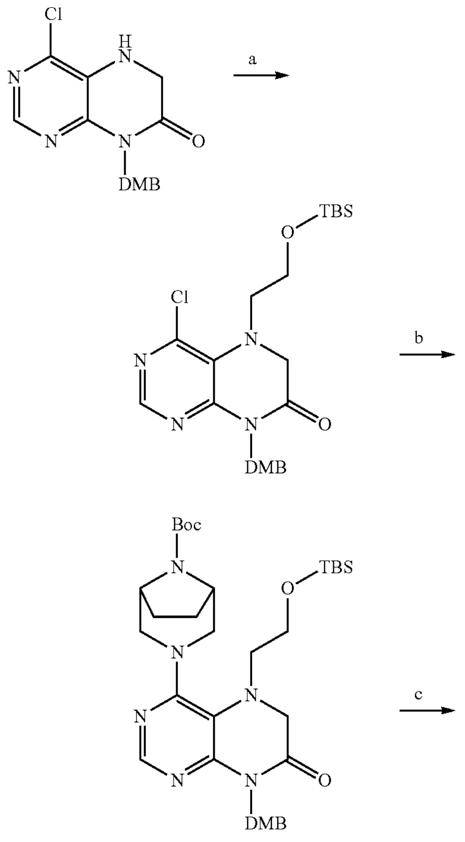

-continued

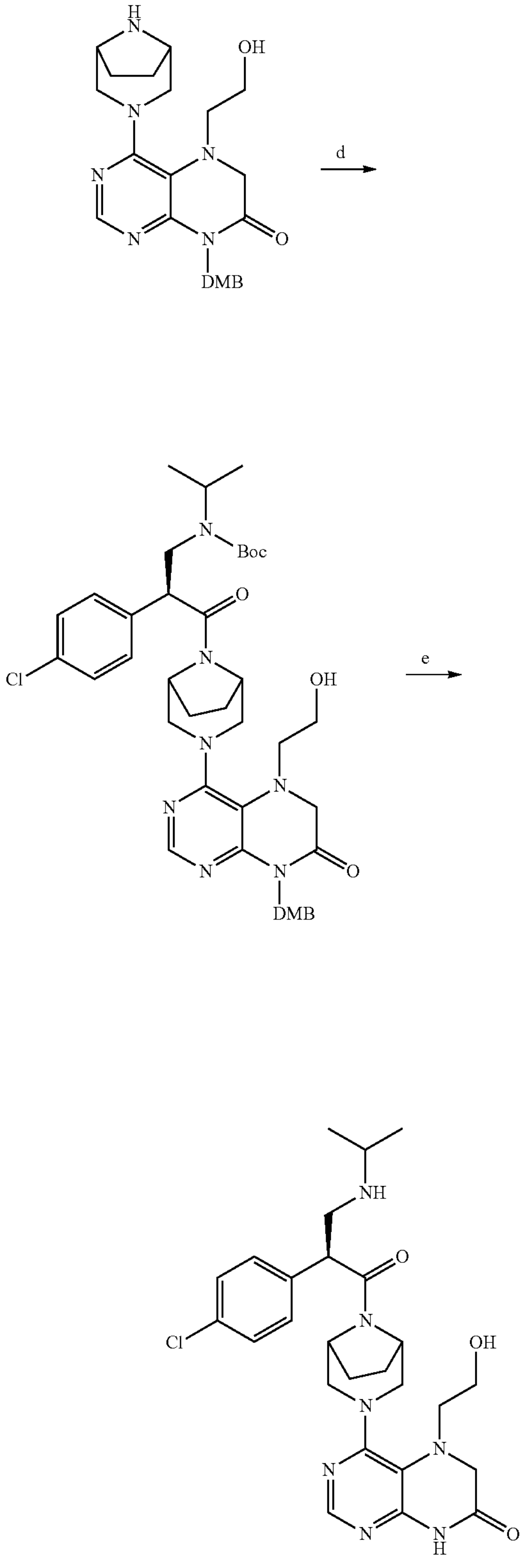

Reaction conditions: a) dimethyl tert-butyl (2-iodoethoxy) silane, sodium hydride, N,N-dimethylformamide; b) tert-butyl 3,8-diazabicyclo[3.2.1]octane-8-formate, 4-dimethylaminopyridine, N-methylpyrrolidone; c) hydrogen chloride/dioxane solution; d) (S)-3-((tert-butoxycarbonyl)(isopropyl)amino)-2-(4-chlorophenyl)propionic acid, diisopropylethylamine, 2-(7-benzotriazole oxide)-N,N,N′,N′-tetramethylurea hexafluorophosphate, N,N-dimethylformamide; e) trifluoroacetic acid, dichloromethane.

Example 31

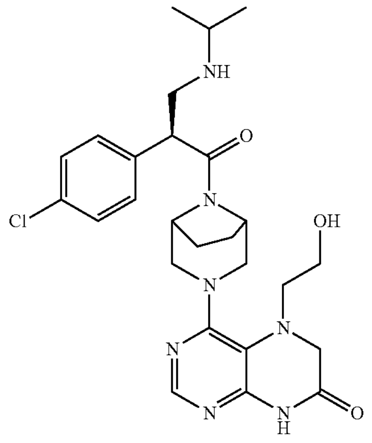 [SMILES: CC(C)NC[C@@H](C(=O)N1C2CCC1CN(c1ncnc3c1N(CCO)CC(=O)N3)C2)c1ccc(Cl)cc1]

a) 5-(2-((tert-butyldimethylsilyl)oxyethyl)-4-chloro-8-(2,4-dimethoxybenzyl)-5,8-dihydropteridine-7(6H)-one At 0° C., sodium hydride (0.53 g) was added to a solution of 4-chloro-8-(2,4-dimethoxybenzyl)-5,8-dihydropteridine-7(6H)-one (2.2 g) in N,N-dimethylformamide (30 mL). The reaction mixture was stirred for 20 min. Dimethyl tert-butyl (2-iodoethoxy)silane (2.82 g) was added at 0° C. The reaction mixture was stirred at 0° C. for 3 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel column chromatography (petroleum ether: ethyl acetate=5:1) to obtain 0.8 g of a white solid product.

b) 5-(2-((tert-butyldimethylsilyl)oxyethyl)-4-(8-tert-butyloxycarbonyl-3,8-diazabicyclo[3,2,1]octan-3-yl)-8-(2,4-dimethoxybenzyl)-5,8-dihydropteridine-7(6H)-one Tert-butyl 3,8-diazabicyclo[3.2.1]octane-8-formate (0.85 g) and 4-dimethylaminopyridine (0.17 g) were added to a solution of the product of step a) (0.2 g) in N-methylpyrrolidone at 20° C. The reaction mixture was stirred at 150° C. for 3 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel plate chromatography (petroleum ether: ethyl acetate=1:1) to obtain 0.08 g of a white solid product.

c) 4-(3,8-diazabicyclo[3.2.1]octane-3-yl)-8-(2,4-dimethoxybenzyl)-5-(2-hydroxyethyl)-5,8-dihydropteridine-7(6H)-one Hydrogen chloride/dioxane solution (3 mL) was added to the product of step b) (0.08 g) at 20° C. The reaction mixture was stirred at 20° C. for 3 hours. The reaction solution was spin-dried to obtain a near-white solid (0.06 g).

d) tert-butyl ((S)-2-(4-chlorophenyl)-3-3-(8-(2,4-dimethoxybenzyl)-5-(2-hydroxyethyl)-7-oxo-5,6,7,8-tetrahydropteridine-4-yl)-3,8-diazabicyclo[3.2.1]octane-8-carbamate)-3-oxopropyl(isopropyl)ester (S)-3-((tert-butoxycarbonyl)(isopropyl)amino)-2-(4-chlorophenyl)propionic acid (0.04 g) and diisopropylethylamine (0.03 g) were added to a solution of the product of step c) (0.06 g) in N,N-dimethylformamide (10 mL) at 20° C. The reaction mixture was stirred for 2 min. 2-(7-benzotriazole oxide)-N,N,N',N'-tetramethylurea hexafluorophosphate (0.04 g) was added at 20° C., and the reaction mixture was stirred at 20° C. for 1 hour. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel plate chromatography (petroleum ether: ethyl acetate=1:2) to obtain 0.04 g of a white solid product.

e) 4-8-((S)-2-(4-chlorophenyl)-3-(isopropylamino)propionyl)-3,8-diazabicyclo[3.2.1]octan-3-yl)-5-(2-hydroxyethyl)-5,6-dihydropteridine-7(8H)- one Trifluoroacetic acid (3 mL) was added to the product of step d) (40 mg) at 20° C. The reaction mixture was stirred at 60° C. for 3 hours. The reaction solution was spin-dried, and $NaHCO_3$ was added and stirred for 20 min, and a near-white solid product (10 mg) was obtained by filtration.

LCMS (ESI) m/z: 528 (M+H). $^1H$ NMR: (400 MHz, DMSO-$d_6$) δ 10.78 (d, J=19.6 Hz, 1H), 8.07 (d, J=29.4 Hz, 1H), 7.30-7.51 (m, 4H), 4.61-4.70 (m, 1H), 4.384-4.54 (m, 1H), 4.26-4.36 (m, 1H), 4.04-4.25 (m, 1H), 3.49-3.78 (m, 6H), 2.97-3.23 (m, 4H), 2.82-2.91 (m, 1H), 2.63-2.80 (m, 1H), 1.62-202 (m, 4H), 1.27-117 (m, 81H).

Example 32

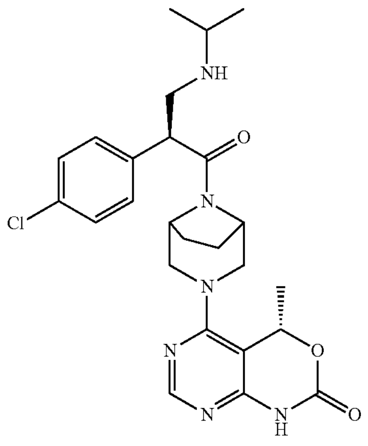

and isomer 1

-continued

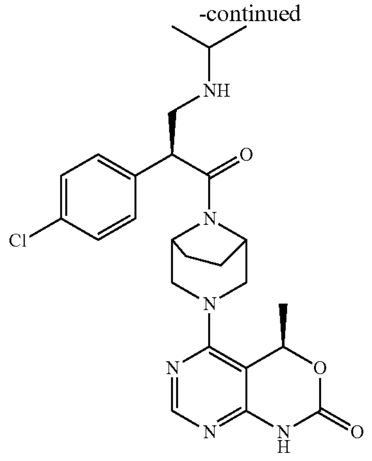

isomer 2

Preparation was in accordance with the method described in Process K, wherein tert-butyl 3,8-diazabicyclo[3.2.1]octane-8-formate was used instead of tert-butylpiperazine-1-carboxylate. The final product was separated by supercritical fluid chromatography to obtain an isomer 1 and an isomer 2. Resolution instrument and conditions: waters SFC200; Column: Daicel Chiralcel OZ, 250×30 mm ID, 5 μm; Mobile phase: A is $CO_2$, B is isopropanol (0.1% $NH_3H_2O$); A: B=60:40 (volume ratio); flow rate 60 mL/min, column temperature 38° C.

UltraPerformance Convergence Chromatographic conditions: Column: Daicel Chiralcel AD, 2.1×150 mm ID, 3 μm, mobile phase A: $CO_2$, mobile phase B: isopropanol (0.1% DEA), gradient: time 0-8 min, phase B 5-40% (volume ratio); flow rate: 1 mL/min; column temperature 40° C. Isomer 1: RT=4.3 min; Isomer 2: RT=4.5 min.

Isomer 1:

LCMS (ESI) m/z: 499 (M+H). $^1H$ NMR (400 MHz, DMSO-$d_6$) δ 8.23 (cd, J=11.7 Hz, 1H), 7.50-7.21 (m, 4H), 5.79-5.59 (m, 1H), 4.64-4.47 (m, 2H), 4.08-3.94 (m, 2H), 3.70-3.40 (m, 2H), 3.31-3.20 (m, 2H), 3.16-3.06 (m, 1H), 2.82 (d, J=9.2 Hz, 0.5H) 2.75-2.62 (m, 2H), 2.17 (d, J=8.7 Hz, 0.5H) 1.96-1.49 (m, 4H), 1.46-128 (m, 3H), 0.98-0.87 (m, 6H).

Isomer 2:

LCMS (ESI) m/z: 499 (M+H). $^1H$ NMR (400 MHz, DMSO-$d_6$) δ 8.24 (d, J=16.4 Hz, 1H), 7.53-7.21 (m, 4H), 5.81-5.65 (m, 1H), 4.73-4.60 (m, 2H), 4.46 (d, J=4.9 Hz, 0.5H), 4.19 (d, J=5.1 Hz, 0.5H), 4.03 (d, J=9.3 Hz, 0.5H), 3.76 (d, J=9.3 Hz, 0.5H), 3.70-3.49 (m, 3H), 0.21-3.16 (m, 1H) 3.06-2.92 (m, 2H) 2.11-1.86 (m, 1.5H) 1.84-1.52 (m, 4H), 1.48-1.33 (m, 3.5H), 1.30-1.22 (m, 6H).

Example 33

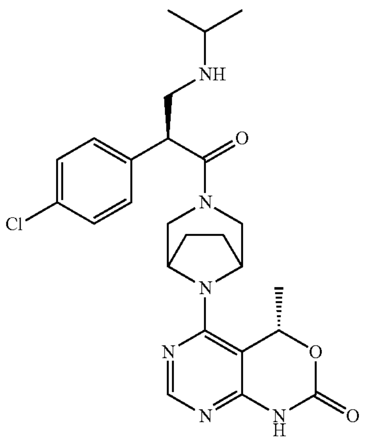

and isomer 1

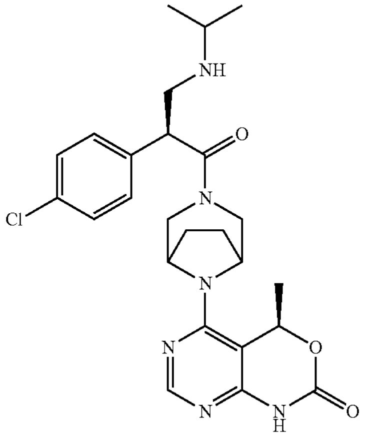

isomer 2

Preparation was in accordance with the method described in Process K, wherein tert-butyl 3,8-diazabicyclo[3.2.1] octane-3-formate was used instead of tert-butylpiperazine-1-carboxylate. The final product was separated by super-critical fluid chromatography to obtain an isomer 1 and an isomer 2. Resolution instrument and conditions: waters SFC200; Column: Daicel Chiralcel OZ, 250×30 mm ID, 5 μm; Mobile phase: A is $CO_2$, B is ethanol (0.1% $NH_3H_2O$); A:B=60:40 (volume ratio); flow rate 60 mL/min, column temperature 38° C.

UltraPerformance Convergence Chromatographic conditions: Column: Daicel Chiralcel AD, 2.1×150 mm ID, 3 μm, mobile phase A: $CO_2$, mobile phase B: ethanol (0.1% DEA), gradient: time 0-8 min, phase B 5-40% (volume ratio); flow rate: 1 mL/min; column temperature 40° C. Isomer 1: RT=4.6 min; Isomer 2: RT=5.0 min.

Isomer 1:

LCMS (ESI) m/z: 499 (M+H). $^1$H NMR (400 MHz, DMSO-$d_6$) δ 10.87 (s, 1H), 8.23 (d, J=11.7 Hz, 1H), 7.50-7.21 (m, 4H), 5.80-5.76 (m, 1H), 4.68-4.64 (m, 1H), 4.44-4.39 (m, 1H, 4.33-4.14 (m, 2H), 4.07-3.88 (m, 2H), 3.66-3.62 (m, 1H), 3.16-2.88 (m, 2H), 2.79-2.55 (m, 4H), 2.01-1.77 (m, 1H), 1.72-1.49 (m, 2H), 1.48-1.36 (m, 2H), 1.31-1.18 (m, 1H), 1.04-0.85 (m, 4H), 0.54-0.44 (m, 1H).

Isomer 2:

LCMS (ESI) m/z. 499 M+H). $^1$H NMR (400 MHz, DMSO-$d_6$) δ 10.69 (s, 1H), 8.24 (d, J=3.8 Hz, H), 7.53-7.21 (m, 4H), 5.80-5.76 (m, 1H), 4.64-4.48 (m, 1H), 4.43-4.42 (m, 1H, 4.27-4.18 (m, 1H), 4.02-32 (m, 1H) 3.68-3.60 (m, 1H), 3.21-3.02 (m, 1H), 2.95-2.64 (m, 4H), 2.02-1.70 (m, 2H), 1.60-1.22 (m, 5H), 1.04-0.83 (m, 6H), 0.43-0.40 (m, 0.14).

Example 34

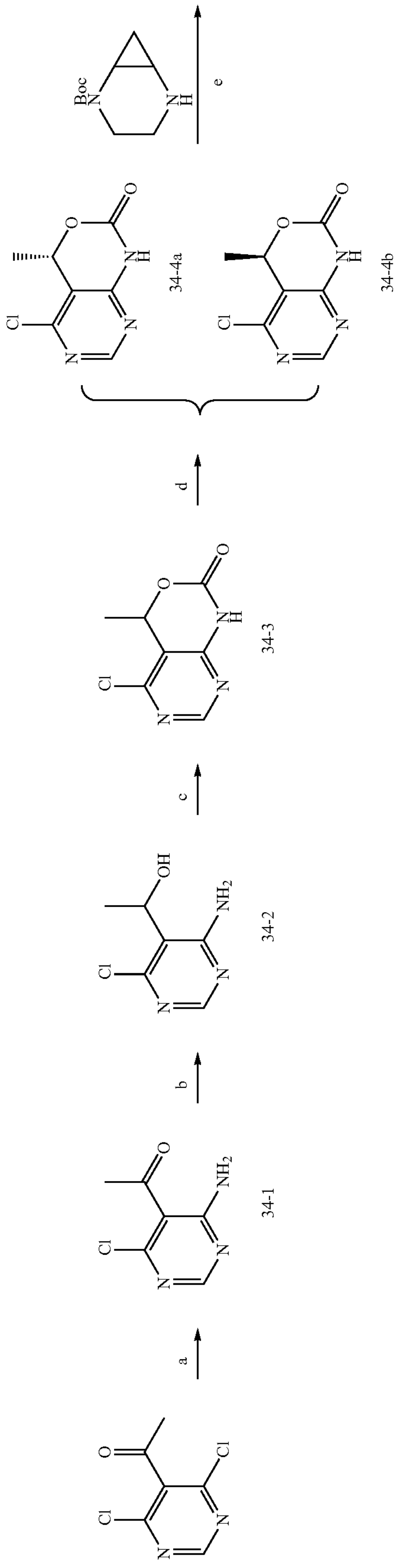
34-1
34-2
34-3
34-4a
34-4b

-continued
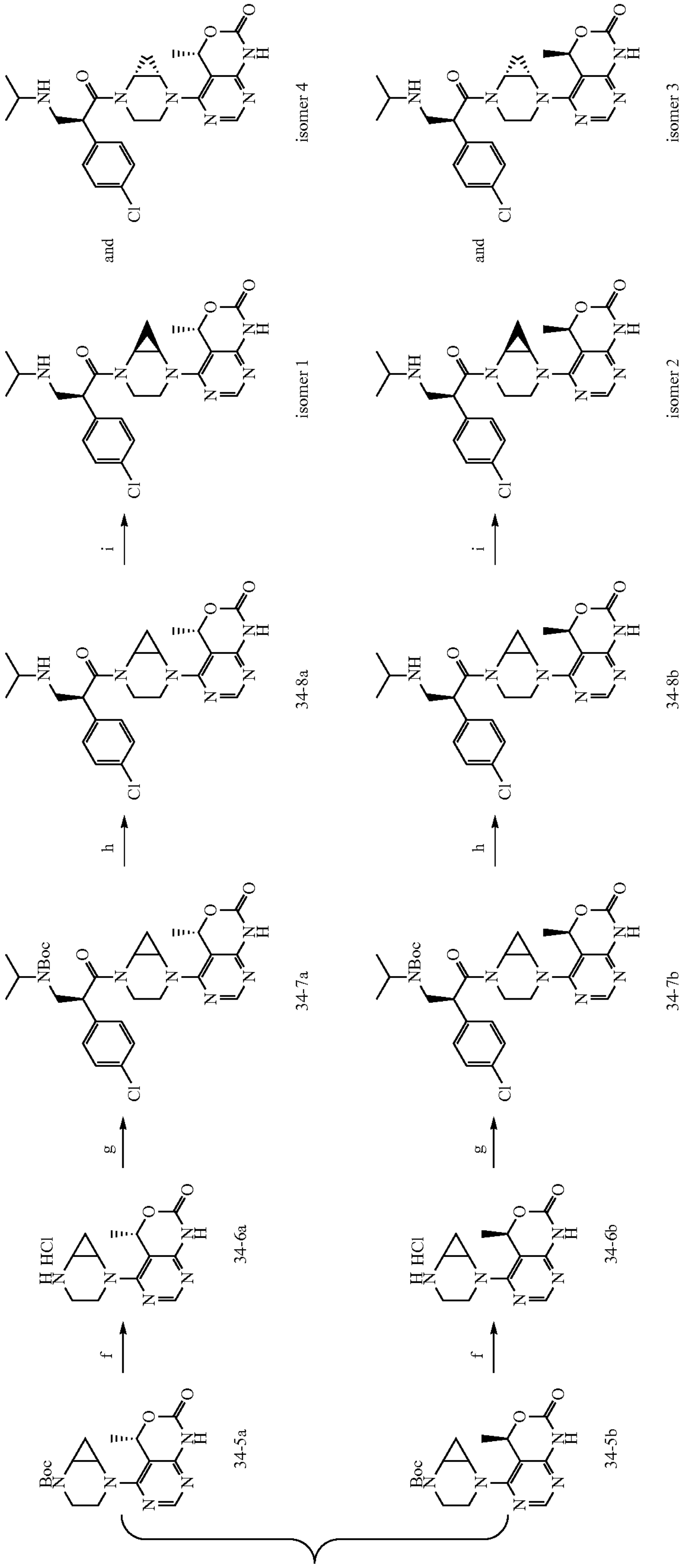
34-5a 34-6a 34-7a 34-8a isomer 1 and isomer 4
34-5b 34-6b 34-7b 34-8b isomer 2 and isomer 3 a) 1-(4-amino-6-chloropyrimidin-5-yl)ethanone (Compound 34-1)

At 20° C., 1-(4,6-dichloropyrimidin-5-yl)ethanone (25 g) was dissolved in tetrahydrofuran (15 mL), and ammonia (9 g) was added. The reaction solution was stirred at 20° C. for 5 hours, then concentrated and diluted with a small amount of water, and filtered with suction to obtain a white solid, which was dried in vacuum to obtain 2 g of a white solid, which was directly used in the next step.

b) 1-(4-Amino-6-chloropyrimidin-5-yl)ethane-1-ol (Compound 34-2)

1-(4-Amino-6-chloropyrimidin-5-yl)ethanone (1.5 g) was dissolved in methanol (15 mL) at 20° C. and cooled to −10° C. Then sodium borohydride (1 g) was added in batches. After the addition was completed, the reaction solution was slowly warmed to 200° C. and stirred for another 3 hours. After the reaction was completed, the reaction solution was quenched with saturated aqueous solution of ammonium chloride. The reaction solution was concentrated and pulped with ethyl acetate (20 mL×2). The mother liquor is concentrated to obtain an oily crude product. The crude product was separated by a chromatographic column to obtain 400 mg of a white oily product. LC-MS (ESI) m/z: 174 (M+H).

c) 5-Chloro-4-methyl-1,4-dihydro-2H-pyrimidin[4,5-d][1,3]oxazin-2-one (Compound 34-3)

At 20° C., 1-(4-amino-6-chloropyrimidin-5-yl)ethane-1-ol (300 mg) and N,N-diisopropylethylamine (282 mg) were dissolved in tetrahydrofuran (3 mL). Then the temperature was lowered to −5° C. and bis(trichloromethyl) carbonate (300 mg) was slowly added, and stirred at −5° C. for 0.5 hours. The temperature was then slowly raised to 18° C. and the reaction solution was stirred for 1.5 hours. After the reaction was completed, the reaction was quenched with aqueous sodium bicarbonate solution and extracted with ethyl acetate (10 mL×3). The organic phases were combined and dried with anhydrous sodium sulfate, filtered, and concentrated to obtain an oily crude. The crude product was separated and purified by column chromatography to obtain 108 mg of a white solid. LC/MS (ESI) m/z: 200 (M+H).

d) (S)-5-chloro-4-methyl-1,4-dihydro-2H-pyrimidin[4,5-d][1,3]oxazin-2-one (Compound 34-4a) and (R)-5-chloro-4-methyl-1,4-dihydro-2H-pyrimidin[4,5-d][1,3]oxazin-2-one (Compound 34-4b)

The compound 34-3 was resolved by SFC chiral column to obtain the desired target products Compound 34-4a and Compound 34-4b.

SFC chiral resolution conditions are as follows: instrument: waters SFC200; separation column: Daicel Chiralcel AD, 250×50 mm ID, 10 μm; mobile phase: A: $CO_2$, B:methanol (0.1% $NH_3H_2O$), A: B=65:35 (volume ratio); flow rate: 150 mL/min; Pressure: 100 bar; Column temperature: 38° C.; Detection wavelength: 220 nm; Cycle time: 14 min; Sample pretreatment: 10 g dissolved in 300 ml MeOH; Injection volume: 16 ml.

Post-treatment: The sample was concentrated at 40° C. and lyophilized to obtain the title Compound 34-4a and Compound 34-4b, respectively.

Route 1: Preparation of Isomer 1 and Isomer 4 e) tert-butyl 5-((S)-4-methyl-2-oxo-1,4-dihydro-2H-pyrimidin[4,5-d][1,3]oxazin-5-yl)-2,5-diazabicyclo[4.1.0]heptane-2-carboxylate (Compound 34-5a)

Compound 34-4a (2 g) and tert-butyl 2,5-diazabicyclo[4.1.0]heptane-2-carboxylate (3.58 g) were dissolved in anhydrous MeCN (20 mL), and DIEA (3.89 g) was added, and the reaction solution was purged with nitrogen, and the tube was sealed and stirred at 95° C. for 6 hours. After the reaction was completed, the reaction solution was concentrated to obtain the crude product of the target product. The crude product was dissolved in DCM, washed with water and concentrated to obtain the crude product, which was separated and purified by column chromatography (EA:PE=1:1) to obtain 3.2 g of a pale brown solid.

f)(4S)-5-(2,5-diazabicyclo[4.1.0]heptan-2-yl)-4-methyl-1,4-dihydro-2H-pyrimido[4,5-d][1,3]oxazin-2-one hydrochloride (Compound 34-6a)

The product of step e) (3.2 g) was dissolved in HCl/i-PrOH (10 mL), and stirred at room temperature for 2 h. After the reaction was completed, the reaction solution was concentrated to obtain a crude product, which was used directly in the next step without purification.

g) Compound 34-7a

The product of step f) (3.3 g), (S)-3-((tert-butoxycarbonyl)(isopropyl)amino)-2-(4-chlorophenyl)propionic acid (4.9 g), HATU (6.32 g) and DIPEA (4.3 g) were dissolved in anhydrous DMF (50 mL). The reaction solution was stirred at room temperature for 12 hours. After the reaction was completed, the reaction solution was poured into 100 mL of ethyl acetate and washed with water (20 mL×3) and 10 mL of saturated sodium chloride solution. The organic phase was dried and concentrated to obtain a crude product. The crude product was separated and purified by column chromatography (PE:EA=1:1) to obtain 7.2 g of brown solid. MS (ESI) m/z: 585 (M+H).

h) Compound 34-8a

The product of step g) (7.2 g) was dissolved in MeOH (25 mL), then HCl/dioxane (70 mL) was added, and the reaction solution was stirred at room temperature for 2 h, and then concentrated to obtain a red oily crude product. The crude product was dissolved in MeOH (20 mL) and freed with $Na_2CO_3$ and concentrated to obtain 6 g of a crude product.

i) Isomer 1 and Isomer 4

The compound 34-8a was resolved by SFC chiral column to obtain isomer 1 and isomer 4.

SFC chiral resolution conditions: instrument: waters SFC200; separation column: Daicel Chiralcel AD, 250×50 mm ID, 10 μm; mobile phase: A: $CO_2$, B: MeOH (0.1% $NH_3H_2O$), A:B=75:25; flow rate: 70 mL/min; Pressure: 100 bar; Column temperature: 38° C.; Detection wavelength: 254 nm; Cycle time: 5 min; Sample pretreatment: 10 g dissolved in 200 ml MeOH; Injection volume: 16 ml.

Post-treatment: The sample was concentrated at 40° C. and lyophilized to obtain the title compound isomer 1 and isomer 4, respectively.

Route 2: Preparation of Isomer 2 and Isomer 3

Using compound 34-4b as a raw material, according to the method described in Route 1, isomer 2 and isomer 3 were prepared respectively.

isomer 1 LCMS m/z: 485 (M+H). $^1$H NMR (400 MHz, DMSO-$d_6$) δ 10.70 (s, 1H), 8.23 (s, 1H), 7.46 (d, J=8.5 Hz. 2H), 7.39 (d, J=8.6 Hz, 2H), 6.13 (q, J=6.6 Hz, 1H), 4.51 (s, 1H), 4.42-4.30 (m, 1H), 3.53-3.45 (m, 1H), 3.28-3.06 (m, 5H), 3.01-2.59 (m, 3H, 1.52-1.34 (m, 4H), 1.08-0.97 (m, 6H), 0.93-0.84 (s, 1H).

isomer 4: LCMS m/z: 485 (M+H). $^1$H NMR (400 MHz, DMSO-$d_6$), δ 10.73 (S, 1H) 8.23 (s, 1H), 7.41-7.32 (m, 4H), 6.14 (q, J=8.0 Hz, 1H), 4.40-4.36 (m, 1H), 4.19-4.11 (m, 1H), 3.62-3.51 (m, 2H), 3.49-3.35 (m, 1H), 3.24-3.05 (m, 4H), 2.73-2.63 (m, 2H), 1.45 (d, J=8.0 Hz. 1H), 1.33 (d, J=8.0 Hz, 2H), 1.12 (q. J=4.01 Hz, 1H), 0.95-0.88 (m, 6H), 0.26 (q, J=4.0 Hz, 1H).

isomer 2: LCMS m/z: 485 (M+H). $^1$H NMR (400 MHz, DMSO-$d_6$) δ 10.86 s, 1H), 8.27 (s, 1H), 7.54-7.27 (m, 4H), 6.32-6.18 (m, 1H), 4.69-4.52 (m, 1H), 4.27-3.97 (m, 2H), 3.66-3.43 (m, 2H), 3.29-2.92 (m, 6H), 2.61-2.55 (m, 1H), 1.63-1.58 (m, 1H), 1.53-1.28 (m, 3H), 1.28-1.12 (m, 6H).

isomer 3: LCMS m/z: 485 (M+H). $^1$H NMR (400 MHz, DMSO-$d_6$) δ 10.71 (s, 1H), 8.18 (s, 1H), 7.46-7.39 (m, 1H). 7.36-7.28 (m, 3H), 6.00 (q, J=6.4 Hz, 1H), 4.53 (s, 1H), 4.46-4.33 (m, 1H), 3.56-3.44 (m, 2H), 3.26-3.09 (m, 5H), 3.00-2.71 (m, 2H), 1.43-1.38 (m, 3H), 1.10-0.93 (m, 7H), −0.07-−0.11 (m, 1H).

Configuration Measurement by the Single Crystal Diffraction:

(1) Configuration Measurement of Isomer 1

Single crystal preparation: the compound of isomer 1 (50.0 mg) and 3.0 ml isopropanol were weighted in a 5 ml screw-top glass bottle, and stirred for 5 min. The solid was dissolved and clarified. 13.0 mg of oxalic acid dihydrate was weighed and added to the above glass bottle. A white solid was gradually precipitated out the glass bottle. After stirring at room temperature for 3 hours, a large amount of white solid was deposited in the glass bottle. 1.5 mL of methanol and 0.2 mL purified water were added to the glass bottle, and the white solid gradually disappeared, while the solution became clarified. Stirring was continued for 1 h. The solution was filtered through a 0.22 μm microporous membrane into a 20 ml screw-top glass bottle, and the mouth of the glass bottle was covered with plastic wrap. The plastic wrap were pierced at the mouth of the bottle with a needle to form 8 small holes, and the mixture was allowed to stand at room temperature for 10 days to obtain an oxalate single crystal of the compound of isomer 1.

Single Crystal Diffraction Experiment:

Single crystal X-ray diffractometer: BRUKER KAPPA APEX-II CCD

Wavelength: Cu Kα (λ=1.54178 Å)

Test temperature: 296K

Computer program for structural analysis: SHELXL-2018

Single crystal data: molecular formula: $C_{50}H_{60}Cl_2N_{12}O_{10}$; molecular weight: 1060.00; crystal system: orthorhombic crystal system; space group: C 2 2 2; unit cell parameters: a=15.719(2)Å, b=17.411(2)Å, c=48.335(6) Å, α=90°, β=90°, γ=90°; unit cell volume: V=13228(3)$Å^3$; number of molecular formulas contained in unit cell: Z=8; calculated density: $D_{calc}$=1.064 g/$cm^3$; $R(F_o)$: 0.0612; $R_W(F_o^2)$: 0.1856; goodness of fit (S): 1.023; Flack parameter: 0.040(11).

Figure 3:
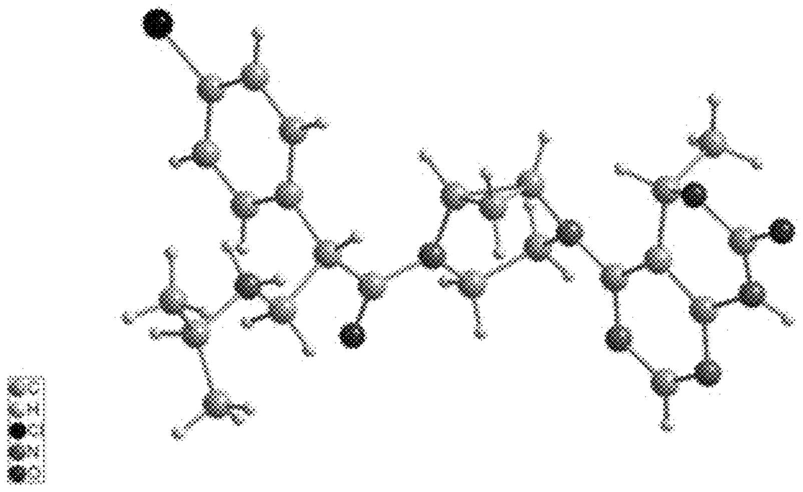
FIG. 3 is a schematic diagram of a single molecule of Isomer 1 of Example 34.
Figure 4:
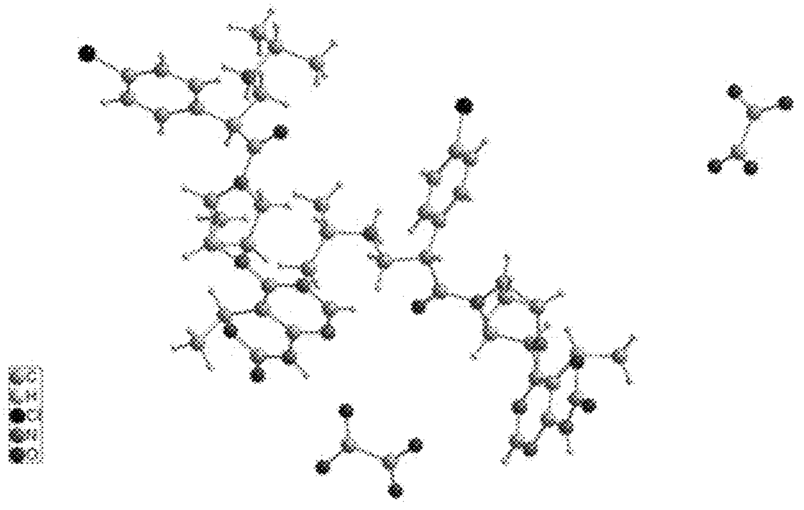
FIG. 4 is a schematic diagram of a asymmetric structural unit of a single crystal of Isomer 1 of Example 34.

Structure description: Single crystal X-ray diffraction and structure analysis show that the obtained single crystal is an oxalate of isomer 1. The asymmetric structural unit of the crystal contains two isomer molecules and one oxalic acid molecule. The single molecule schematic diagram of compound isomer 1 is shown in FIG. 3, and the single crystal of oxalate is shown in FIG. 4. The structural formula is as follow:

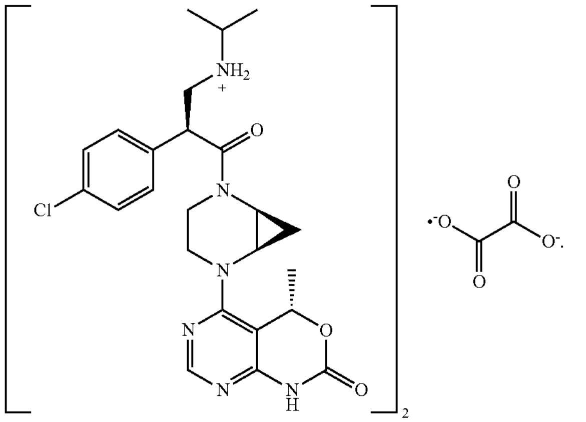

(2) Configuration Measurement of Isomer 3

Single crystal preparation: The oxalate single crystal of isomer 3 was prepared according to the method described in the preparation of single crystal of isomer 1 above.

Single Crystal Diffraction Experiment:

Single crystal X-ray diffractometer: BRUKER D8 VENTURE PHOTON II

Wavelength: Ga K α (λ=1.34139 Å)

Test temperature: 173K

Computer program for structural analysis: SHELXL-2018

Single crystal data: molecular formula: $C_{52}H_{64}Cl_2N_{12}O_{15}$; molecular weight: 1168.05; crystal system: monoclinic system; space group: P $2_1$/c; unit cell parameters: a=20.1588(13)Å, b=21.4744(14)Å, c=14.4055 (9)Å, α=90°, β=98.259(3)°, γ=90°; unit cell volume: V=6171.4(7)$Å^3$; number of molecular formulas contained in unit cell: Z=4; calculated density: $D_{calc}$=1.257 g/$cm^3$; $R(F_o)$: 0.0634; $R_W(F_o^2)$: 0.2016; goodness of fit (S): 1.053.

Figure 5:
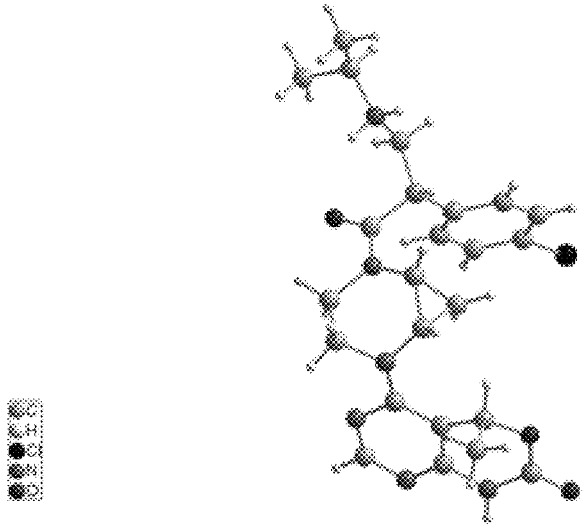
FIG. 5 is a schematic diagram of t single molecule of Isomer 3 of Example 34.
Figure 6:
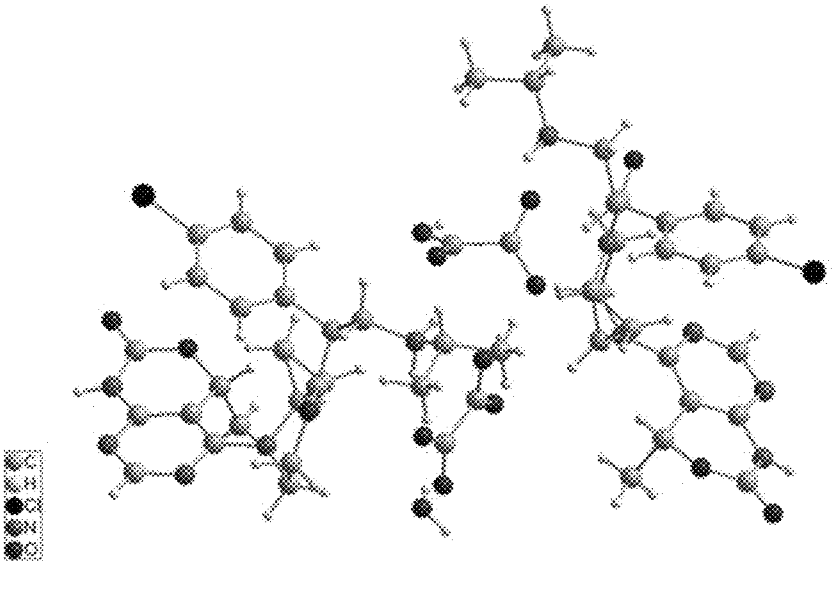
FIG. 6 is a schematic diagram of a asymmetric structural unit of a single crystal of Isomer 3 of Example 34.

Structure description: Single crystal X-ray diffraction and structure analysis show that the obtained single crystal is an oxalate hydrate of isomer 3. The asymmetric structural unit of the crystal contains three isomer 3 molecules, two oxalic acid molecules and one water molecule, wherein isomer 3 and oxalic acid form oxalate. The single molecule schematic diagram of the compound of isomer 3 is shown in FIG. 5, and the asymmetric structural unit of the oxalate single crystal is shown in FIG. 6. The structural formula is as follow:

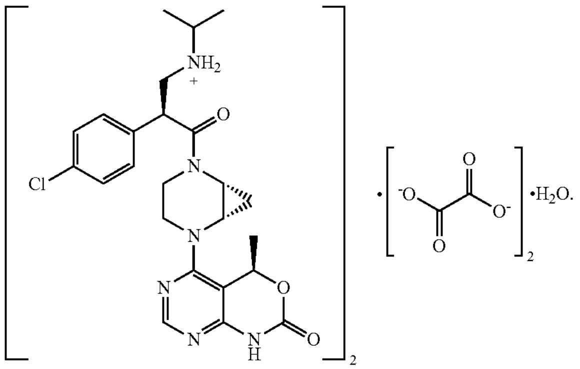

Process L:

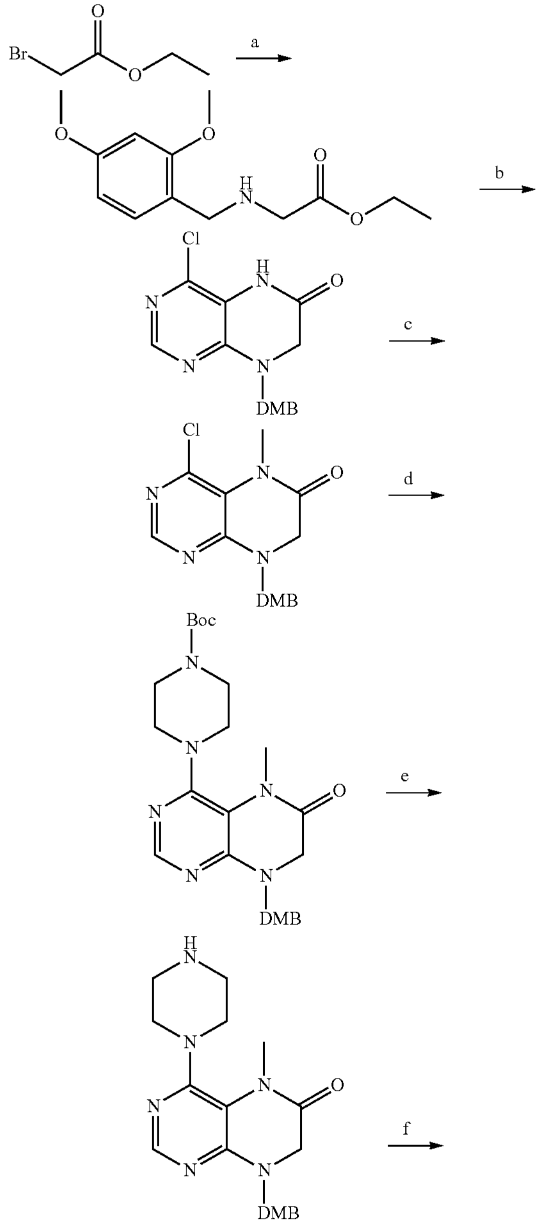

-continued

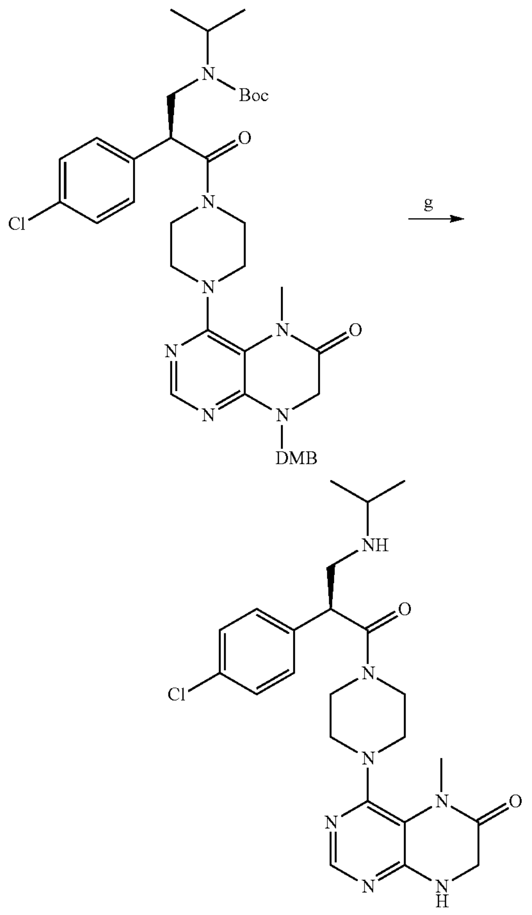

Reaction conditions: a) (2,4-dimethoxyphenyl)methylamine, triethylamine, tetrahydrofuran; b) 4,6-dichlorpyrimidin-5-amine, triethylamine, isopropanol; c) methyl iodide, sodium hydride, N,N-dimethylformamide; d) tert-butylpiperazine-1-carboxylate, 4-dimethylaminopyridine, N-methylpyrrolidone; e) Hydrogen chloride/dioxane solution; f) (S)-3-((tert-butoxycarbonyl)(isopropyl)amino)-2-(4-chlorophenyl)propionic acid, diisopropylethylamine, 2-(7-benzotriazole oxide)-N,N,N′,N′-tetramethylurea hexafluorophosphate, N,N-dimethylformamide; g) trifluoroacetic acid.

Example 35

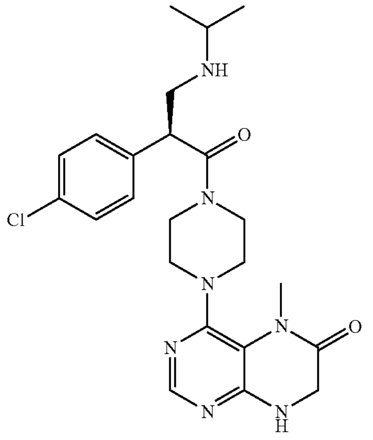 [SMILES: CC(C)NC[C@@H](C(=O)N1CCN(c2ncnc3c2N(C)C(=O)CN3)CC1)c1ccc(Cl)cc1]

a) ethyl 2-(2,4-dimethoxybenzyl)aminoacetate

Triethylamine (0.6 g) and (2,4-dimethoxyphenyl)methylamine (1.0 g) were added to a solution of ethyl bromoacetate (1.0 g) in THF (10 mL) at 0° C. The reaction mixture was stirred at room temperature for 3 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel column chromatography (petroleum ether: ethyl acetate=3:1) to obtain 1.3 g of a white solid product.

b) 4-chloro-8-(2,4-dimethoxybenzyl)-7,8-dihydropteridine-6(5H)-one

Triethylamine (1.56 g) and 4,6-dichloropyrimidin-5-amine (0.84 g) were added to a solution of ethyl 2-(2,4-dimethoxybenzyl)aminoacetate (1.3 g) in isopropanol (10 mL) at 0° C. The reaction mixture was stirred at 90° C. for 3 hours. The reaction solution was filtered to obtain 0.7 g of a white solid product.

c) 4-chloro-8-(2,4-dimethoxybenzyl)-5-methyl-7,8-dihydropteridine-6(5H)-one

At 0° C., sodium hydride (76.7 mg) was added to a solution of 4-chloro-8-(2,4-dimethoxybenzyl)-7,8-dihydropteridine-6(5H)-one (0.5 g) in N,N-dimethylformamide (5 mL). The reaction mixture was stirred for 20 min. Methyl iodide (255 mg) was added at 0° C. The reaction mixture was stirred at 0° C. for 3 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel column chromatography (petroleum ether: ethyl acetate=5:1) to obtain 0.5 g of a white solid product.

d) 4-(8-(2,4-dimethoxybenzyl)-5-methyl-6-oxo-5,6,7,8-tetrahydropteridine-4-yl)piperazine-1-carboxylate Tert-butylpiperazine-1-carboxylate (0.53 g) and 4-dimethylaminopyridine (0.52 g) were added to a solution of 4-chloro-8-(2,4-dimethoxybenzyl)-5-methyl-7,8-dihydropteridine-6(5H)-one (0.5 g) in N-methylpyrrolidone (10 mL) at 20° C. The reaction mixture was stirred at 150° C. for 3 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel plate chromatography (petroleum ether: ethyl acetate=1:1) to obtain 0.5 g of a white solid product.

e) 8-(2,4-Dimethoxybenzyl)-5-methyl-4-(piperazin-1-yl)-7,8-dihydropteridine-6(5H)-one Hydrogen chloride/dioxane solution (5 mL) was added to 4-(8-(2,4-dimethoxybenzyl)-5-methyl-6-oxo-5,6,7,8-tetrahydropteridine-4-yl)piper azine-1-carboxylate (0.1 g) at 20° C. The reaction mixture was stirred at 20° C. for 3 hours. The reaction solution was spin-dried to obtain a near-white solid (0.1 g).

f)(S)-tert-butyl(2-(4-chlorophenyl)-3-(4-(8-(2,4-dimethoxybenzyl)-5-methyl-6-oxo-5,6,7,8-tetrahydropteridine-4-yl)piperazin-1-yl)-3-oxopropyl)(isopropyl)carbamate (S)-3-((tert-butoxycarbonyl)(isopropyl)amino)-2-(4-chlorophenyl)propionic acid (0.12 g) and diisopropylethylamine (0.10 g) were added to a solution of 8-(2,4-dimethoxybenzyl)-5-methyl-4-(piperazin-1-yl)-7,8-dihydropteridine-6(5H)-one (0.1 g) in N,N-dimethylformamide (10 mL) at 20° C. The reaction mixture was stirred for 2 min. 2-(7-benzotriazole oxide)-N,N,N',N'-tetramethylurea hexafluorophosphate (0.12 g) was added at 20° C., and the reaction mixture was stirred at 20° C. for 1 hour. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel plate chromatography (petroleum ether: ethyl acetate=1:2) to obtain 0.1 g of a white solid product.

g)(S)-4-(4-(2-(4-chlorophenyl)-3-(isopropylamino)propionyl)piperazin-1-yl)-5-methyl-7,8-dihydropteridine-6(5H)-one Trifluoroacetic acid (5 mL) was added to (S)-tert-butyl (2-(4-chlorophenyl)-3-(4-(8-(2,4-dimethoxybenzyl)-5-methyl-6-oxo-5,6,7,8-tetrahydropteridine-4-yl)piperazin-1-yl)-3-oxopropyl)(isopropyl)carbamate (100 mg) at 20° C. The reaction mixture was stirred at 60° C. for 3 hours. The reaction solution was spin-dried to obtain a near-white solid (20 mg).

LCMS (ESI) m/z: 472 (M+H) $^1H$ NMR (400 MHz, $CDCl_3$) δ 7.89 (s, 1H), 7.22-7.29 (m, 2H), 7.10-7.18 (m, 2H), 4.08-4.17 (m, 1H), 3.86 (s, 2H), 3.32-3.45 (m, 2H), 315-3.30 (m, 3H), 3.08 (s, 3H) 2.82-293 (m, 2H), 2.51-2.78 (m, 4H), 1.21-1.31 (nm, 2H), 1.03-1.12 (m, 6H).

Process M:

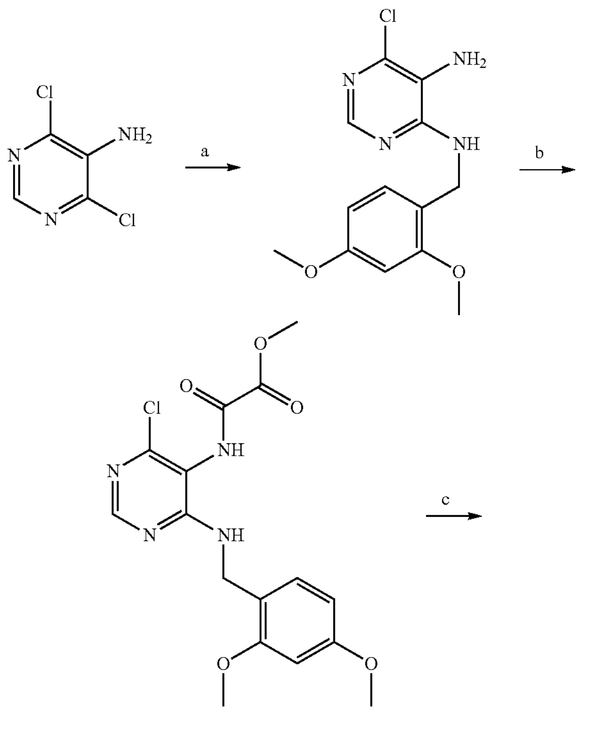

-continued

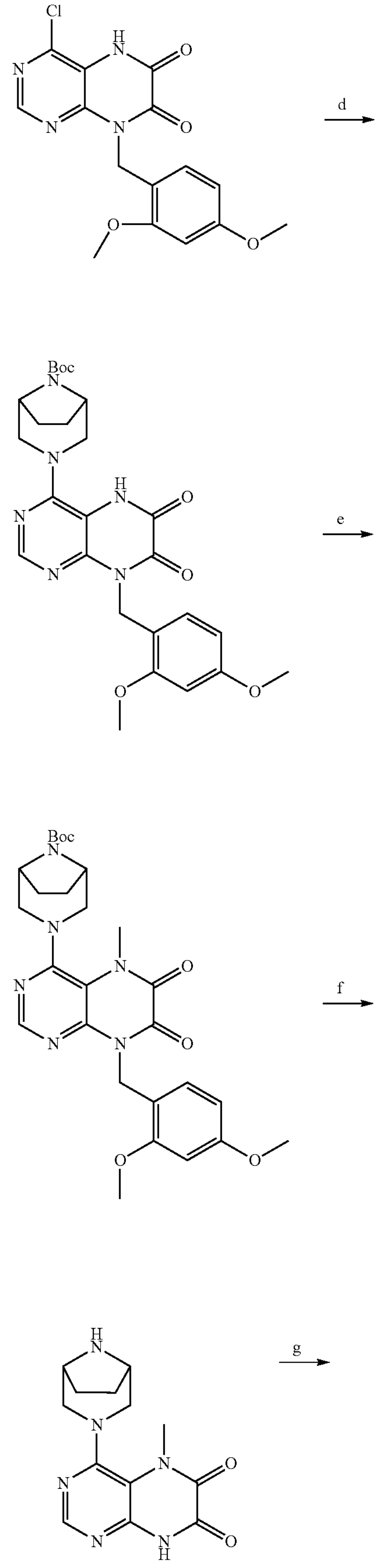

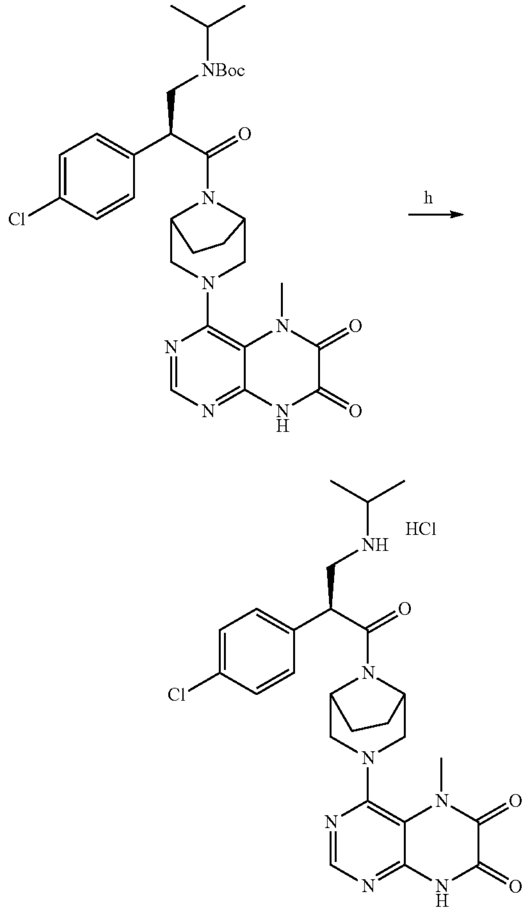

Reaction conditions: a) 2,4-dimethoxybenzylamine, N,N-diisopropylethylamine, acetonitrile; b) tetrahydrofuran, potassium carbonate, methyl 2-chloro-2-oxoacetate; c) N,N-diisopropylethylamine, ethanol; d) tert-butyl 3,8-diazabicyclo[3.2.1]octane-8-carboxylate, N,N-diisopropylethylamine, acetonitrile; e) N,N-dimethylformamide, potassium carbonate, methyl iodide; f) trifluoroacetic acid; g) (S)-3-((tert-butoxycarbonyl)(isopropyl)amino)-2-(4-chlorophenyl)propionic acid, N,N-diisopropylethylamine, N,N-dimethylformamide, HATU; h) dichloromethane, hydrogen chloride/isopropanol solution.

Example 36

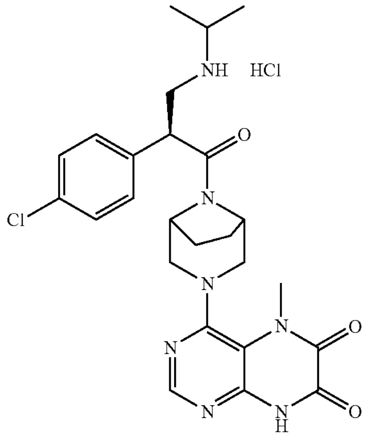 [SMILES: CC(C)NC[C@@H](C(=O)N1C2CCC1CN(c1ncnc3[nH]c(=O)c(=O)n(C)c13)C2)c1ccc(Cl)cc1 ; Cl]

a) 6-chloro-N-(2,4-dimethoxybenzyl)pyrimidin-4,5-diamine 4,6-Dichloropyrimidin-5-amine (2 g), N,N-diisopropylethylamine (4.7 g) and 2,4-dimethoxybenzylamine (2.45 g) were dissolved in acetonitrile (20 mL). The reaction solution was stirred at 90° C. for 5 hours, and then concentrated to obtain a crude product, which was then dissolved in dichloromethane and washed with a small amount of water. The organic phase was dried by rotary evaporation to obtain the crude product. The crude product was separated and purified by column chromatography (PE:EA=1:1), and concentrated to obtain a pale yellow solid target product (3.5 g).

b) methyl 2-((4-chloro-6-(((2,4-dimethoxybenzyl) amino)pyrimidin-5-yl) amino)-2-oxoacetate 6-chloro-N-(2,4-dimethoxybenzyl)pyrimidin-4,5-diamine (1.5 g), potassium carbonate (1.1 g) and methyl 2-chloro-2-oxoacetate (623 mg) were dissolved in anhydrous ethanol (20 mL). The reaction solution was stirred at 20° C. for 3 hours. The reaction solution was poured into 30 mL ethyl acetate and washed with water (10 mL×2). The organic phase was concentrated to a constant weight to obtain a crude product. The crude product was purified and pulped with (PE:EA=3:1) to obtain a white solid product (1.6 g).

c) 4-chloro-8-(2,4-dimethoxybenzyl)-5,8-dihydropteridine-6,7-dione

Methyl 2-((4-chloro-6-(((2,4-dimethoxybenzyl)amino) pyrimidin-5-yl)amino)-2-oxoacetate (1 g) was dissolved in anhydrous ethanol (10 mL), and N,N-diisopropylethylamine (1.02 g) was added. The reaction solution was stirred at 90° C.-110° C. for 2 hours under the protection of nitrogen. Then the reaction solution was concentrated to obtain a crude product. The crude product was dissolved in dichloromethane, adjusted to weak acidity with dilute hydrochloric acid, and washed with water to remove salts. The organic phase was concentrated to obtain a crude product. The crude product was then purified and pulped with (PE:EA=3:1) to obtain a white oily product (800 mg).

$^1$H NMR (400 MHz, DMSO-$d_6$) δ 12.15 (s, 1H), 0.47 (s, 1H), 6.88 (d, J=8.4 Hz, 1H), 6.59 (d, J=2, Hz, 1H), 6.32 (dd, J=8.4, 2.3 Hz, 1H), 5.21 (s, 2H), 3.84 (s, 3H), 3.72 (s, 3H).

d) tert-butyl-3-(8-(2,4-dimethoxybenzyl)-6,7-dioxo-5,6,7,8-tetrahydropteridine-4-yl)-3,8-diazabicyclo [3.2.1]octane-8-carboxylate 4-chloro-8-(2,4-dimethoxybenzyl)-5,8-dihydropteridine-6,7-dione (250 mg), tert-butyl (1R,5S)-3,8-diazabicyclo [3.2.1]octane-8-carboxylate (456 mg) and N,N-diisopropylethylamine (278 mg) were dissolved in anhydrous acetonitrile (5 mL). Under the protection of nitrogen, the reaction solution was sealed and stirred at 90° C. for 3 hours. Then the reaction solution was concentrated to obtain an oily crude substance. The oily crude substance was dissolved in ethyl acetate (30 mL), adjusted to pH=3-4 with dilute hydrochloric acid, washed with water to pH=5-6, and concentrated to obtain a crude product. The crude product was separated and purified by column chromatography (PE: EA=1:1) to obtain 200 mg of a white solid, m/z=525 (M+H).

e) tert-butyl-3-(8-(2,4-dimethoxybenzyl)-5-methyl-6,7-dioxo-5,6,7,8-tetrahydropteridine-4-yl)-3,8-diazabicyclo[3.2.1]octane-8-carboxylate Tert-butyl-3-(8-(2,4-dimethoxybenzyl)-6,7-dioxo-5,6,7,8-tetrahydropteridine-4-yl)-3,8-diazabicyclo[3.2.1]octan-8-carboxylate (180 mg), methyl iodide (146 mg) and potassium carbonate (142 mg) were dissolved in anhydrous DMF (3 mL). The reaction solution was stirred at 20° C. for 1 hour, then poured into 30 mL EA and washed with water (10 mL×2) and saturated sodium chloride solution (10 mL), and the organic phase was concentrated to obtain a crude product. The crude product was separated and purified by column chromatography (PE:EA=3:1) to obtain 180 mg of a pale yellow solid.

f) 4-((1R,5S)-3,8-diazabicyclo[3.2.1]octane-3-yl)-5-methyl-5,8-dihydropteridine-6,7-dione Tert-butyl-3-(8-(2,4-dimethoxybenzyl)-5-methyl-6,7-dioxo-5,6,7,8-tetrahydropyrid in-4-yl)-3,8-diazabicyclo [3.2.1]octane-8-carboxylate (120 mg) was dissolved in anhydrous DCM (1 mL), and TFA (2 mL) was added dropwise and the reaction solution was stirred at room temperature for 3 hours. The reaction solution was red. The reaction solution was directly concentrated to obtain a crude product, which was adjusted to pH=8-9 with sodium bicarbonate solution, then concentrated, dissolved in THF, and filtered to remove salts, and the residue was separated by column chromatography (DCM:MeOH=10:1) to obtain 60 mg of an oily product.

g) tert-butyl ((S)-2-(4-chlorophenyl)-3-3-(5-methyl-6,7-dioxo-5,6,7,8-tetrahydropteridine-4-yl)-3,8-diazabicyclo[3.2.1]octane-8-yl)-3-oxopropyl carbamate (isopropyl)

Compound 4-(3,8-diazabicyclo[3.2.1]octane-3-yl)-5-methyl-5,8-dihydropteridine-6,7-dione (60 mg), (S)-3-((tert-butoxycarbonyl)(isopropyl)amino)-2-(4-chlorophenyl)propionic acid (90 mg), (2-(7-azobenzotriazole)-N,N,N',N'-tetramethylurea hexafluorophosphate (130 mg), and N,N-diisopropylethylamine (102 mg) were dissolved in anhydrous DMF (2 mL). The reaction solution was stirred at room temperature for 3 hours, and then poured into 20 mL of ethyl acetate and washed with water (50 mL×2). The organic phase was dried with anhydrous sodium sulfate and concentrated to obtain a crude product. The crude product was separated and purified by silica gel column chromatography (DCM:MeOH=10:1) to obtain 120 mg of an oily product.

h) 4-(8-((S)-2-(4-chlorophenyl)-3-(isopropylamino) propionyl)-3,8-diazabicyclo[3.2.1]octan-3-yl)-5-methyl-5,8-dihydropteridine-6,7-dione Tert-butyl ((S)-2-(4-chlorophenyl)-3-3-(5-methyl-6,7-dioxo-5,6,7,8-tetrahydropteridine-4-yl)-3,8-diazabicyclo [3.2.1]octane-8-yl)-3-oxopropyl carbamate (isopropyl) was dissolved in DCM (2 mL), and HCl/i-PrOH (2 mL) was added dropwise. The reaction solution was stirred at room temperature for 3 h, and then concentrated to obtain a crude product. The crude product was separated by HPLC and lyophilized to obtain 14 mg of a white solid. m/z: 499 (M+H).

$^1$H NMR (400 MHz, $CD_3OD$) δ 8.32 (J=25.7 Hz, 1H), 7.68-7.32 (m, 4H), 5.14 (m, 1H), 4.71-4.28 (m, 3H), 4.12-

3.92 (m, 3H), 3.80-3.40 (m, 3H), 3.23-3.15 (m, 2H), 2.24-2.16 (m, 1H), 1.92-1.82 (m, 2H), 1.80-1.70 (m, 1H), 1.48-1.16 (m, 8H).

Example 37

Process N:

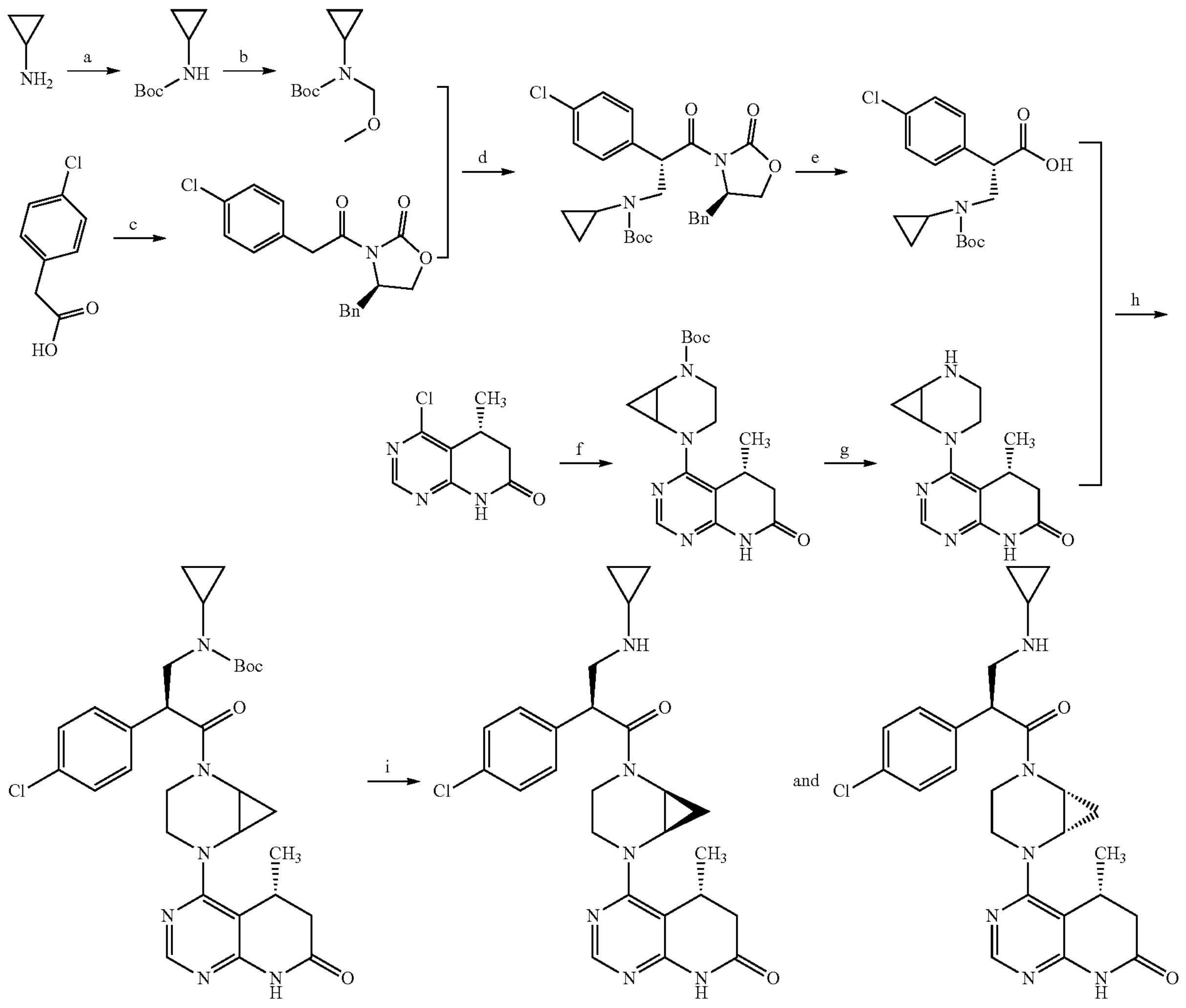

isomer 1 isomer 2

Reaction conditions: a) triethylamine, di-tert-butyl dicarbonate, dichloromethane; b) sodium bis(trimethylsilyl)amide (2.0 mol/L in tetrahydrofuran), bromomethyl methyl ether, 2-methyltetrahydrofuran; c) (R)-4-benzyloxazolidin-2-one, diisopropylethylamine, trimethylacetyl chloride, toluene; d) Titanium tetrachloride (1 mol/L in toluene), diisopropylethylamine, dichloromethane; e) Hydrogen peroxide solution (30%), lithium hydroxide monohydrate, tetrahydrofuran, water; f) tert-butyl 2,5-diazabicyclo[4.1.0]heptane-2-carboxylate, 4-dimethylaminopyridine, N-methylpyrrolidone; g) Hydrogen chloride/dioxane solution (4.0 M); h) 2-(7-benzotriazole oxide)-N,N,N′,N′,-tetramethylurea hexafluorophosphate, diisopropylethylamine, N,N-dimethylformamide; i) Hydrogen chloride/dioxane solution (4.0 M).

a) tert-butyl cyclopropyl carbamate

Under the protection of nitrogen, cyclopropylamine (9.3 g) and triethylamine (19.7 g) were dissolved in dichloromethane (100 mL) at 20° C., and di-tert-butyl dicarbonate (35.48 g) was added dropwise at 0° C. The reaction was carried out at 20° C. for 16 hours. After the reaction was completed, the solvent was removed to obtain 24.3 g of colorless liquid. $^1H$ NMR (400 MHz, $CDCl_3$) δ (ppm) 0.47-0.50 (m, 2H), 0.66-0.72 (m, 2H), 1.44 (s, 9H), 2.53 (m, 1H), 4.79 (s, 1H).

b) tert-butyl cyclopropyl (methoxymethyl) carbamate

Under the protection of nitrogen, tert-butyl cyclopropyl carbamate (24.3 g) was dissolved in 2-methyltetrahydrofuran (100 mL), and sodium bis(trimethylsilyl)amide (120 mL) was added dropwise at 0° C. The reaction solution was stirred at 0° C. for 1 hour, and bromomethyl methyl ether (35.7 g) was added dropwise at 0° C. The reaction solution was stirred at 0° C. for 6 hours and poured into 50 g of ice water, separated, and extracted with ethyl acetate (100 mL×2). The reaction solution was directly concentrated to obtain 29.1 g of a colorless liquid product, which was directly used in the next step without purification.

c) (R)-4-benzyl-3-(2-(4-(chlorophenyl)acetyl)oxazolidin-2-one

Under the protection of nitrogen, 2-(4-chlorophenyl)acetic acid (50 g), (R)-4-benzyloxazolidin-2-one (45.5 g) and diisopropylethylamine (127.3 g) dissolved in toluene (600 mL) at 15° C. and then trimethylacetyl chloride (38.4 g) was added dropwise. The reaction solution was stirred under refluxing for 16 hours, then poured into 200 mL of water, separated, washed with 120 mL of saturated sodium chloride solution. The organic phase was dried and concentrated to obtain a crude product. The crude product was separated and purified by column chromatography (PE:EA=5:1) to obtain 32 g of a white solid. $^1$H NMR (400 MHz, DMSO-$d_6$) δ (ppm) 2.88-3.02 (m, 2H), 4.12-4.37 (m, 4H), 4.64-4.70 (m, 1H), 7.13-7.16 (m 2H), 7.23-7.32 (m, 5H), 7.39-7.42 (m, 2H).

d) tert-butyl ((S)-3-((R)-4-benzyl-2-oxazolidin-3-yl)-2-(4-chlorophenyl)-3-oxopropyl)(cyclopropyl) carbamate Under the protection of nitrogen, (R)-4-benzyl-3-(2-(4-(chlorophenyl)acetyl)oxazolidin-2-one (3.48 g) was dissolved in dichloromethane (60 mL), and titanium tetrachloride toluene solution (13 mL) was added dropwise at 0° C. The reaction solution was stirred at 0° C. for 2 hours. DIPEA (1.49 g) was added dropwise and the reaction solution was stirred at 0° C. for 1.5 hours, and tert-butyl cyclopropyl (methoxymethyl)carbamate (2.77 g) was added dropwise. The reaction solution was stirred at 0° C. for 6 h, and the reaction was completed. Then the reaction solution was poured into 30 mL of saturated ammonium chloride solution, separated, and washed with 120 mL of saturated sodium chloride solution. The organic phase was dried and concentrated to obtain a crude product. The crude product was separated and purified by silica gel column chromatography (PE:EA=10:1) to obtain 2.50 g of a colorless oily product.

e)(S)-3-((tert-butoxycarbonyl)(cyclopropyl)amino)-2-(4-chlorophenyl)propionic acid Lithium hydroxide monohydrate (0.63 g) was dissolved in water (18 mL), and tetrahydrofuran (20 mL) was added, and hydrogen peroxide (1.6 mL) was added dropwise at 0° C. Tert-butyl ((S)-3-((R)-4-benzyl-2-oxazolidine-3-yl)-2-(4-chlorophenyl)-3-oxopropyl)(cyclopropyl)carbamate (2.50 g) was added at 0° C. The reaction solution was stirred at 0° C. for 3 h, and a saturated solution of sodium sulfite (15 mL) was added to the reaction solution, reacted for 1.5 h, adjusted to pH=3-4 with a saturated solution of potassium bisulfate, extracted with ethyl acetate (30 mL×2), and separated. The organic phase was dried and concentrated to obtain a crude product. The crude product was separated and purified by column chromatography (PE:EA=1:1) to obtain 1.26 g of a colorless solid. $^1$H NMR (400 MHz, DMSO-$d_6$) δ (ppm): 0.45-0.48 (m, 2H), 0.60-0.64 (m, 2H), 1.30 (s, 9H), 2.19 (s, 1H), 3.61 (d, J=7.6 Hz, 1H), 3.95 (t, J=8.0 Hz, 1H), 7.37 (dd, J=26.8, 8.8 Hz, 4H), 12.7 (s, 1H).

f) 5-((R)-5-methyl-7-oxo-5,6,7,8-tetrahydropyrido[2,3-d]pyrimidin-4-yl)-2,5-diazabicyclo[4.1.0]heptan-2-carboxylate Under the protection of nitrogen, (R)-4-chloro-5-methyl-5,8-dihydropyrido[2,3-d]pyrimidin-7(6H)-one (300 mg), tert-butyl 2,5-diazabicyclo[4.1.0]heptane-2-carboxylate (455 mg) and 4-dimethylaminopyridine (600 mg) were dissolved in N-methylpyrrolidone (5 mL). The reaction solution was stirred at 120° C. for 12 hours, then poured into 50 mL of water, extracted with ethyl acetate (20 mL×2), and washed with 15 mL of saturated sodium chloride solution. The organic phase was dried and desolventized to obtain a crude product. The crude product was separated and purified by silica gel column chromatography (PE:EA=1:1-1:2) to obtain 400 mg of a yellow solid.

g)(5R)-4-(2,5-diazabicyclo[4.1.0]heptan-2-yl)-5-methyl-5,8-dihydropyrido[2,3-d]pyrimidin-7(6H)-one 5-((R)-5-methyl-7-oxo-5,6,7,8-tetrahydropyrido[2,3-d]pyrimidin-4-yl)-2,5-diazabicyclo[4.1.0]heptane-2-carboxylate (400 mg) was dissolved in dioxane (5 mL), and hydrogen chloride/dioxane solution (5 mL) was added dropwise. The reaction solution was stirred at 25° C. for 2 hours. After the reaction was completed, the reaction solution was directly concentrated to obtain a crude yellow solid, which was directly used in the next step.

h) tert-butyl ((S)-2-(4-chlorophenyl)-3-((1R,6S)-5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(cyclopropyl) carbamate Under the protection of nitrogen, (5R)-4-(2,5-diazabicyclo[4.1.0]heptan-2-yl)-5-methyl-5,8-dihydropyrido[2,3-d]pyrimidin-7(6H)-one (270 mg), compound 5 (389 mg), 2-(7-benzotriazole oxide)-N,N,N',N'-tetramethylurea hexafluorophosphate (474 mg) and diisopropylethylamine (671 mg) were dissolved in N,N-dimethylformamide (10 mL). The reaction solution was stirred at 25° C. for 3 hours until the reaction was completed. Then the reaction solution was poured into 50 mL of water, extracted with ethyl acetate (20 mL×2), and washed with saturated sodium chloride solution (10 mL×3), and the organic phase was dried and concentrated to obtain a crude product. The crude product was separated and purified by column chromatography (PE:EA=1:2) to obtain 320 mg of a yellow solid.

i) (R)-4-((1R,6S)-5-((S)-2-(4-chlorophenyl)-3-(cyclopropylamino)propionyl)-2,5-diazabicyclo[4.1.0]heptan-2-yl)-5-methyl-5,8-dihydropyrido[2,3-d]pyrimidin-7(6H)-one and (R)-4-((1S,6R)-5-((S)-2-(4-chlorophenyl)-3-(cyclopropylamino)propionyl)-2,5-diazabicyclo[4.1.0]heptan-2-yl)-5-methyl-5,8-dihydropyrido[2,3-d]pyrimidin-7(6H)-one Tert-butyl((S)-2-(4-chlorophenyl)-3-((1R,6S)-5-((R)-5-methyl-7-oxo-5,6,7,8-tetrahydropyrido[2,3-d]pyrimidin-4- yl)-2,5-diazabicyclo[4.1.0]heptan-2-yl)-3-oxopropyl)(cyclopropyl)carbamate (320 mg) was dissolved in dioxane (2.5 mL), and hydrogen chloride/dioxane solution (2.7 mL) was added dropwise. The reaction solution was stirred at 25° C. for 14 h, and the reaction was completed. Then the reaction solution was concentrated to obtain a crude product, adjusted to pH=13-14 with a saturated potassium carbonate solution, extracted with DCM (10 mL×2), washed with water (10 mL), and desolventized. The product was resolved by supercritical fluid chromatography to obtain an isomer 1 (61.2 mg) and an isomer 2 (31.2 mg).

Resolution instrument and conditions: waters SFC200; Column: Daicel Chiralcel AS, 250×30 mm ID, 5 μm; Mobile phase: A is $CO_2$, B is isopropanol (0.1% $NH_3H_2O$); A:B=70:30 (volume ratio); flow rate 60 mL/min, column temperature 38° C.

UltraPerformance Convergence Chromatographic conditions: Column: Daicel Chiralcel AD, 2.1×150 mm ID, 3 μm, mobile phase A: $CO_2$, mobile phase B: isopropanol (0.1% DEA), gradient: time 0-8 min, phase B 5-40% (volume ratio); flow rate: 1 mL/min; column temperature 40° C. Isomer 1: RT=3.7 min; Isomer 2: RT=4.6 min.

isomer 1: LCMS(ESI) m/z 481 M+H). $^1$H NMR (400 MHz, DMSO-$d_6$) δ (ppm): 0.03-0.12 (m, 2H), 0.25-0.30 (m, 2H), 0.66-0.70 (m, 1H), 0.96-1.05 (m, 3H), 1.35-1.40 (m, 1H), 1.93-2.11 (m, 2H), 2.29-235 (m, 1H), 2.67-2.77 (m, 2H), 2.80-2.86 (m, 1H), 3.03-3.25 (m, 4H), 0.39-3.48 (m, 1H), 3.69-3.79 (m, 1H), 4.24-4.34 (m, 2H), 7.34-7.41 (m, 4H), 8.17 (s, 1H), 10.52 (s, 1H).

isomer 2: LCMS (ESI) m/z: 481 (M+H) $^1$H NMR 400 MHz, DMSO-$d_6$) δ (ppm): 0.14-0.21 m, 2H), 0.30-0.37 m, 2H), 0.93-1.07 (m, 4H) 2.03-2.34 (m, 3H) 2.66-2.8 (m, 2H), 3.10-3.25 (m, 4H), 3.36-3.94 (m, 4H), 4.07-4.15 (m, 1H), 4.41-4.45 (m, 1H), 7.32-7.42 (m, 4H), 8.19 (s, 1H), 10.48 (s, 1H).

Example 38

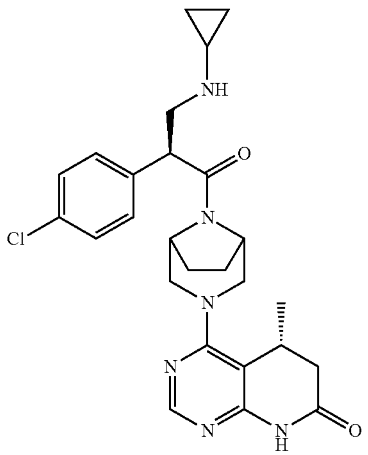 [SMILES: C[C@@H]1CC(=O)Nc2ncnc(N3CC4CCC(C3)N4C(=O)[C@H](CNC3CC3)c3ccc(Cl)cc3)c21]

Preparation was in accordance with the method as described in Process N, wherein tert-butyl 3,8-diazabicyclo[3.2.1]octan-8-carboxylate was used instead of tert-butyl 2,5-diazabicyclo[4.1.0]heptane-2-carboxylate to prepare the target compound.

LCMS (ESI) m/z: 495 (M+H). $^1$HNMR (400 MHz, DMSO-$d_6$) δ (ppm) 0.11-0.22 (m, 2H), 0.29-0.37 (m, 2H), 1.01 (dd, J=30.8, 6.8 Hz, 3H), 1.52-1.69 (m, 1H), 1.72-0.93 (m, 3H), 2.04-2.14 (m, 1H), 2.15 (d, J=16 Hz, 1H), 2.32 (d, J=13.2 Hz, 1H), 2.66-2.83 (m, 3H), 3.11-3.26 (m, 3H), 3.52 (d, J=16 Hz, 1H), 3.75-3.83 (m, 1H), 4.09-4.15 (m, 1H), 4.45-4.63 (m, 2H, 7.33-7.41 (m, 4H), 8.14 (d, J=32 Hz, 1H), 10.57 (d, J=96 Hz, 1H).

Example 39

Process P:

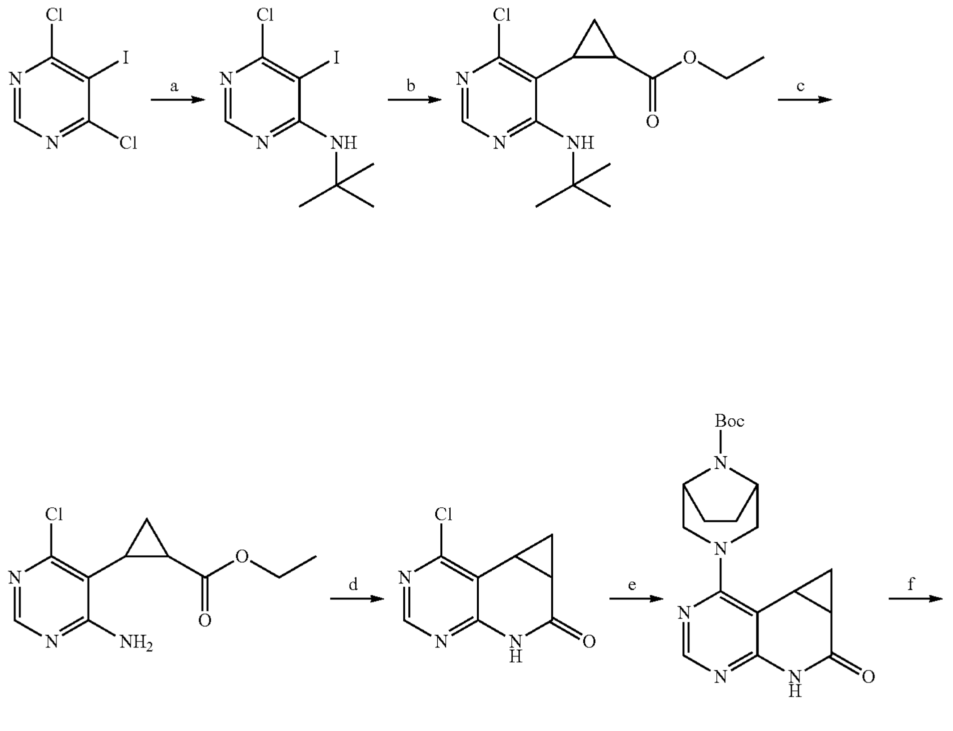

-continued

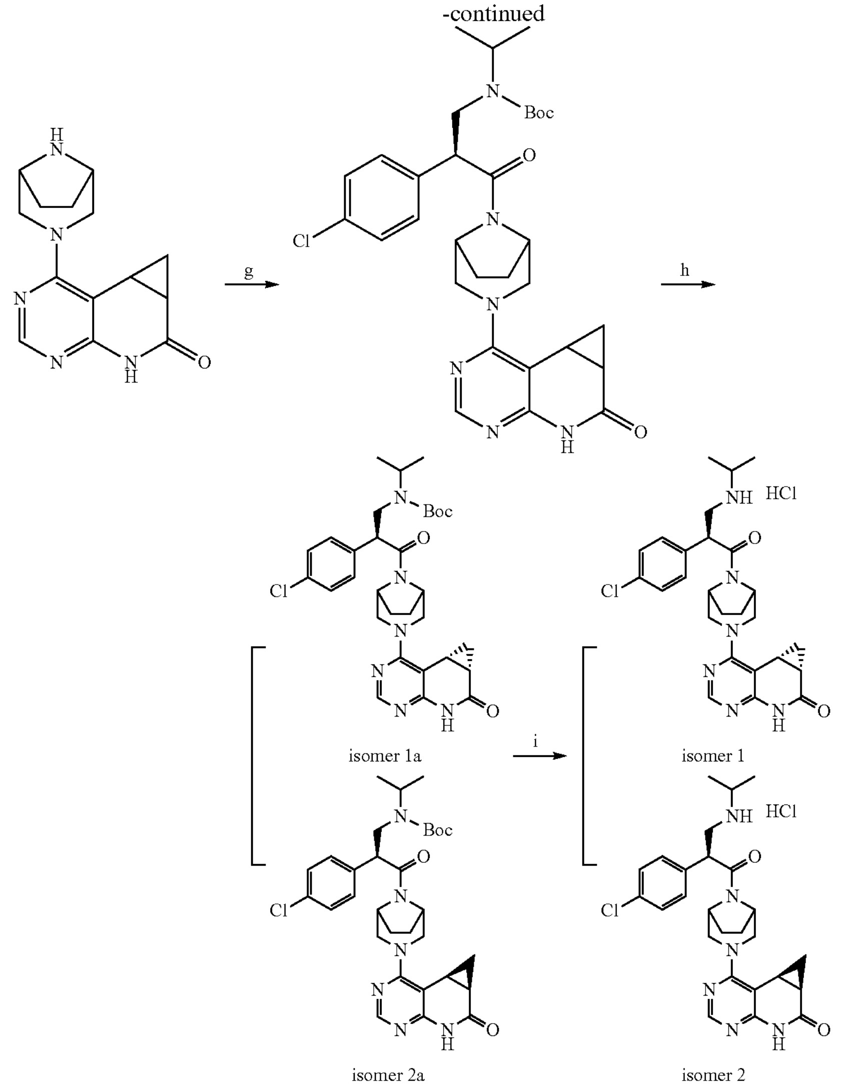

Reaction conditions: a) tert-butylamine, N,N-dimethylformamide; b) ethyl 2-(4,4,5,5-tetramethyl-1,3,2-dioxaboran-2-yl)cyclopropane carboxylate, palladium acetate, tricyclohexylphosphine, potassium carbonate, toluene, water; c) sulfuric acid, dichloromethane; d) triethylamine, ethanol; e) tert-butyl 3,8-diazabicyclo[3.2.1]octane-8-carboxylate, N,N-diisopropylethylamine, N,N-dimethylformamide; f) hydrogen chloride/dioxane solution; g) (S)-3-((tert-butoxycarbonyl)(isopropyl)amino)-2-(4-chlorophenyl)propionic acid, diisopropylethylamine, 2-(7-benzotriazole oxide)-N,N,N',N'-tetramethylurea hexafluorophosphate, N,N-dimethylformamide h) SFC; i) hydrogen chloride/dioxane solution.

a) N-(tert-butyl)-6-chloro-5-iodopyrimidin-4-amine 4,6-dichloro-5-iodopyrimidine (4.00 g) was mixed with N,N-dimethylformamide (60 ml) under stirring, and tert-butylamine (5.32 g) was added at room temperature under nitrogen protection. The mixture was stirred overnight at room temperature. The mixture was then poured into water (300 mL) and extracted with ethyl acetate (2×50 mL). The organic phases were combined and dried with anhydrous sodium sulfate. After filtration, the filtrate was concentrated under reduced pressure to obtain a pale yellow solid (4.1 g).

b) ethyl 2-(4-(tert-butyl)-6-chloropyrimidin-5-yl) cyclopropyl carboxylate

Under the protection of nitrogen, N-tert-butyl-6-chloro-5-iodopyrimidin-4-amine (4.10 g) and 2-(4,4,5,5-tetramethyl-1,3,2-dioxaboro-2-yl)cyclopropane-1-carboxylate (6.32 g) were dissolved in toluene (64.00 mL) and water (16.00 mL). Tricyclohexylphosphine (1.475 g), palladium acetate (1.475 g), and potassium carbonate (0.59 g) were added respectively, and the mixture was stirred at 90° C. overnight. The mixture was then cooled to room temperature, diluted with water (100 mL), and extracted with ethyl acetate (2×100 mL). The organic phases were combined and dried with anhydrous sodium sulfate. After filtration, the filtrate was concentrated under reduced pressure, and the product was purified by silica gel plate chromatography (petroleum ether: ethyl acetate=10:1) to obtain 2.50 g of a dark yellow solid.

c) ethyl 2-(4-amino-6-chloropyrimidin-5-yl)cyclopropyl carboxylate

Ethyl 2-(4-(tert-butyl)-6-chloropyrimidin-5-yl)cyclopropyl carboxylate (2.50 g) was added to dichloromethane (40.00 mL). Under the protection of nitrogen at 0-5° C., sulfuric acid (4.94 g) was added dropwise. The reaction solution was stirred at room temperature for 1 hour, then cooled to 0° C., and the mixture was neutralized to pH=8 with saturated sodium bicarbonate solution. The reaction solution was extracted with dichloromethane (2×50 ml). The organic phases were combined and dried with anhydrous magnesium sulfate. After filtration, the filtrate was concentrated under reduced pressure to obtain 2.4 g of yellow liquid.

d) 1-chloro-7,7a-dihydro-5H-cyclopropane[4,5]pyrido[2,3-d]pyrimidin-6(6aH)-one

Under nitrogen protection at room temperature, ethyl 2-(4-amino-6-chloropyrimidin-5-yl)cyclopropyl carboxylate (2.40 g) and triethylamine (6.03 g) were added to 200.00 mL of ethanol solution. The reaction mixture was stirred at 80° C. overnight. The mixture was then cooled to room temperature and concentrated in vacuum. The product was purified by silica gel plate chromatography (petroleum ether: ethyl acetate=1:1) to obtain 1.05 g of a pale yellow solid.

e) tert-Butyl 3-(6-oxo-6,6a,7,7a-tetrahydro-5H-cyclopropanepyrido[4,5]pyrimidin-1-yl)-3,8-diazabicyclo[3.2.1]octan-8-carboxylate Tert-butyl 3,8-diazabicyclo[3.2.1]octane-8-carboxylate (0.43 g) and N,N-diisopropylethylamine (0.39 g) were added to a solution of 1-chloro-7,7a-dihydro-5H-cyclopropane[4,5]pyrido[2,3-d]pyrimidin-6(6aH)-one (0.20 g) in N,N-dimethylformamide (5 mL) at 20° C. The reaction mixture was stirred at 110° C. for 24 hours. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel chromatography (petroleum ether: ethyl acetate=1:1) to obtain 0.30 g of a white solid.

f) 1-3,8-diazabicyclo[3.2.1]octan-3-yl)-7,7-dihydro-5H-cyclopropane[4,5]pyrido[2,3-d]pyrimidin-6(6aH)-one 4M hydrogen chloride/dioxane solution (2 mL) was added to tert-butyl3-(6-oxo-6,6a,7,7a-tetrahydro-5H-cyclopropanepyridin[4,5]pyrimidin-1-yl)-3,8-diazabicyclo[3.2.1]octane-8-carboxylate (0.15 g) at 20° C. The reaction mixture was stirred at 20° C. for 3 hours. The reaction solution was spin-dried to obtain a near-white solid (0.12 g).

g) tert-butyl ((2R)-2-(4-chlorophenyl)-3-oxo-3-3-(6-oxo-6,6a,7,7a-tetrahydro-5H-cyclopropyl-4,5]pyrido[2,3-d]pyrimidin-1-yl)-3,8-diazabicyclo[3.2.1]octane-8-yl)propyl carbamate (isopropyl)ester (S)-3-((tert-butoxycarbonyl)(isopropyl)amino)-2-(4-chlorophenyl)propionic acid (0.18 g) and diisopropylethylamine (0.17 g) were added to a solution of 1-3,8-diazabicyclo[3.2.1]octan-3-yl)-7,7-dihydro-5H-cyclopropane[4,5]pyrido[2,3-d]pyrimidin-6 (6aH)-one (0.12 g) in N,N-dimethylformamide (5 mL) at 20° C. The reaction mixture was stirred for 2 min. 2-(7-benzotriazole oxide)-N,N,N',N'-tetramethylurea hexafluorophosphate (0.20 g) was added at 20° C., and the reaction mixture was stirred at 20° C. for 1 hour. The reaction solution was poured into water (100 mL), and ethyl acetate (100 mL) was added for extraction. The organic phase was washed with saturated sodium chloride solution (100 mL×3), dried with anhydrous sodium sulfate, and spin-dried. The product was purified by silica gel plate chromatography (petroleum ether: ethyl acetate=1:1.5) to obtain 0.20 g of a white solid.

h) Chiral Resolution

Resolution instrument and conditions: Waters SFC200; Column: Daicel Chiralcel AS, 250×50 mm ID, 10 μm; Mobile phase: A is $CO_2$, B is methanol (0.1% $NH_3H_2O$), A:B=60:40 (volume ratio); flow rate 60 mL/min, column temperature 38° C.

i) Preparation of Isomer 1 and Isomer 2

4M Hydrogen chloride/dioxane solution (1 mL) was added to isomer 1a (20 mg) at 20° C. The reaction mixture was stirred at 20° C. for 3 hours. The reaction solution was spin-dried and the resultant was separated by HPLC to obtain a near-white solid (10 mg).

In the same way, isomer 2 was prepared from isomer 2a.

isomer 1: LCMS (ESI) m/z: 495 (M+H) $^1H$ NMR (400 MHz, DMSO-$d_6$) δ 8.69-8.59 (m, 1H), 7.34-7.52 (m, 4H) 5.39-5.53 (m, 1H), 4.69-4.81 (m, 3H), 4.52-4.67 (m, 1H), 4.09-4.38 (m, 2H), 3.75-3.81 (m, 1H), 3.64-3.73 (m, 2H), 3.45-3.53 (m, 2H), 3.26-3.36 (m, 1H), 2.95-3.06 (m, 1H), 1.96-2.07 (m, 1H), 50-1.66 (m, 21H), 1.21-1.30 (m, 8H) 1.01-1.11 (m, 1H), 0.83-0.90 (m, 1H).

isomer 2: LCMS (ESI) n/z: 495 (M+H) $^1H$ NMR (400 MHz, DMSO-$d_6$) δ 10.43 (d, J=15.9 Hz, 1H), 8.20 (d, J=26.6 Hz, 1H), 7.37-7.51 (m, 4H), 4.64-4.74 (m, 1H), 4.46-4.61 (m, 2H), 4.19-4.23 (m, 2H), 4.09-4.14 (m, 2H), 3.67-3.73 (m, 2H), 3.56-3.62 (m, 2H), 2.97-3.13 (m, 2H), 2.17-2.28 (m, 1H), 1.96-2.10 (m, 2H), 1.75-1.84 (m, 1H), 1.62-1.68 (m, 1H), 1.20-1.30 (m, 6H), 0.67-6.77 (m, 1H).

Example 40

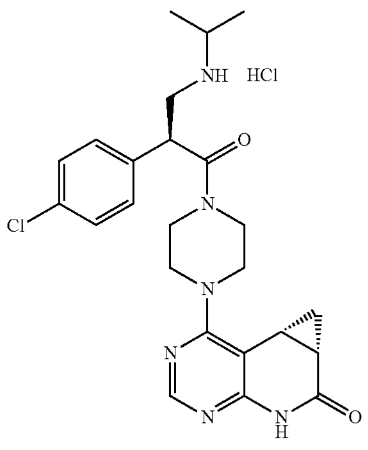
and isomer 1

-continued

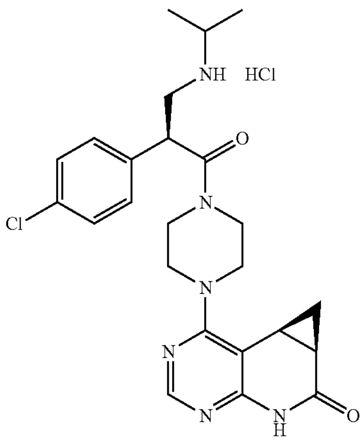

isomer 1

Preparation was in accordance with the method described in Process P of Example 39, wherein tert-butylpiperazine-1-carboxylate was used instead of tert-butyl 3,8-diazabicyclo[3.2.1]octane-8-carboxylate. After separation by supercritical fluid chromatography, the Boc protective group was removed to obtain an isomer 1 and an isomer 2, respectively. Resolution instrument and conditions: Waters SFC200; Column: Daicel Chiralcel AS, 250×50 mm ID, 10 μm; Mobile phase: A is $CO_2$, B is isopropanol (0.1% $NH_3H_2O$), A:B=60:40 (volume ratio); flow rate 60 mL/min, column temperature 38° C.

Isomer 1:

LCMS (ESI) m/z: 469 (M+H) $^1$H NMR (400 MHz, DMSO-$d_6$) 10.49 (s, 1H), 8.24 (s, 1H), 7.34-7.52 (m, 4H), 4.66-4.74 (m, 1H), 3.77-3.85 (m, 1H), 3.60-3.73 (m, 4H), 3.49-3.51 (m, 1H). 3.43-3.48 (m, 2H), 3.24-3.35 (m, 2H), 2.95-3.04 (m, 1H), 2.80-2.92 (m, 1H), 2.62-2.73 (m, 1H), 2.21-2.29 (m, 1H), 2.01-2.11 (m, 1H), 1.66-1.76 (m, 1H), 1.21-1.27 (m, 6H), 0.72 (q, J=4.9 Hz, 1H).

Isomer 2;

LCMS (ESI) m/z: 469 (M+H) $^1$H NMR (400 MHz, DMSO-$d_6$) δ 10.48 (s, 1H), 8.22 (s, 1H), 7.33-7.57 (m, 4H), 4.59-4.68 (m, 1H), 3.64-3172 (m, 4H), 3.45-3.53 (m, 3H), 3.27-3.36 (m, 2H), 3.16-3.24 (m, 1H), 3.04-3.12 (m, 1H), 2.93-3.03 (m, 1H), 2.17-2.28 (m, 1H), 1.99-2.09 (m, 1H), 1.67-1.76 (m, 1H), 1.19-1.31 (m, 6H), 0.72 (q, J=4.4 Hz, 11H).

Experimental Example 1: In Vitro Enzyme Activity Test

1. Materials and Reagents
   - Envision reader (Molecular Devices)
   - White 384-well plate (Art. No. #264706, Thermo)
   - The main reagents included in the HTRF kinEASE TK kit (Art. No. #62TKOPEC, Cisbio)
     - TK-Biotin Substrate
     - Streptavidin-XL665
     - Europium-labeled tyrosine kinase substrate antibody
     - 5× enzyme reaction buffer
     - SEB
     - HTRF detection buffer
     - AKT1 (Art. No. #01-101, Carna)
     - AKT2 (Art. No. #01-102, Carna)
     - AKT3 (Art. No. #PV3185, Invitrogen)
     - ATP 10 mM (Art. No. #PV3227, Invitrogen)
     - DTT 1M (Art. No. #D5545, Sigma)
     - $MgCl_2$ 1M (Art. No. #M8266, Sigma)
     - Compound of the invention
     - Positive control: GDC-0068
2. Experimental Procedure 2.1 Preparation of Reagents

TABLE 1

The components and concentrations of the kinase reaction system

| Reagent | | AKT1 | AKT2 | AKT3 |
|---|---|---|---|---|
| Concentration of enzyme | Final concentration in the enzyme reaction step (10 μL) | 0.6 ng/well | 0.1 ng/well | 0.3 ng/well |
| concentration of ATP | | 2 μM | 20 μM | 10 nM |
| Concentration of TK-Biotin Substrate | | 2 μM | 2 μM | 2 μM |
| Enzyme reaction time | | 50 min | 50 min | 50 min |
| Concentration of Streptavidin-XL665 | Final concentration in the total reaction (20 μL) | 125 nM | 125 nM | 125 nM |
| Concentration of Europium-labeled tyrosine kinase substrate antibody | | 1:100 diluted | 1:100 diluted | 1:100 diluted |

1× Kinase Reaction Buffer 1 mL 1× Kinase Reaction Buffer of Kinase AKT1, AKT2 and AKT3 contain 200 μL 5× Kinase Reaction Buffer, 5 μL 1 M $MgCl_2$, 1 μL 1 M DTT and 794 μL ultrapure water.

5× TK-Biotin Substrate and ATP Working Solution

The specific concentrations of TK-biotin substrate and ATP are shown in Table 1.

The substrate and ATP were diluted to 5 times of the reaction concentration with 1× kinase reaction buffer.

5× Kinase Working Solution

The concentration used in enzyme screening is shown in Table 1. 1× Kinase Reaction Buffer was used to prepare 5× enzyme working solution.

4× Streptavidin-XL665 Working Solution

The concentration of streptavidin-XL665 in the reaction is shown in Table 1. Detection buffer was used to prepare 4× Streptavidin-XL665 working solution.

4× Europium-Labeled Tyrosine Kinase Substrate Antibody Working Solution

The europium-labeled tyrosine kinase substrate antibody was diluted 100 times with detection reaction buffer as a working solution.

2.2 Experiment Process

All reagents were prepared according to the above method. These reagents were equilibrated to room temperature, except for enzymes, followed by sample loading.

a) First, the compound stock solution (10 mM DMSO solution) was diluted with DMSO to 100 μM compound solution, and then diluted with 1× kinase reaction buffer to 2.5 μM compound working solution (comprising 2.5% DMSO). 1× kinase reaction buffer was used to prepare 2.5% DMSO solution, and then 2.5% DMSO solution was used to dilute the 2.5 μM compound working solution, which was diluted seven times in a four-fold ratio to obtain compound working solutions with 8 concentrations (2500 nM, 625 nM, 156 nM, 39 nM, 9.8 nM, 2.4 nM, 0.6 nM and 0.15 nM). In addition to the control wells, 4 μL of the diluted compound working solutions were added to all reaction wells. 4 μL of the previously prepared 2.5% DMSO/kinase buffer solution was added to the control wells.

b) 2 μL of the previously prepared TK-biotin substrate solution was added to all reaction wells. The concentrations of substrate used in enzyme screening are shown in Table 1.

c) 2 μL of the previously prepared enzyme solution was added to all reaction wells, except the negative wells. The concentrations of enzyme are shown in Table 1. The volume of the negative well was filled with 2 μL of enzyme corresponding to 1× kinase reaction buffer. The plate was sealed with sealing film. After mixing, the plate was incubated at room temperature for 10 min to allow the compound and enzyme to fully combined.

d) 2 μL of ATP solution was added to all reaction wells to start the kinase reaction. The ATP concentration and reaction time during enzyme screening are shown in Table 1.

e) The test solution was prepared 5 min before the end of the kinase reaction. The detection buffer in the kit was used to prepare streptavidin-XL665 and europium-labeled tyrosine kinase substrate antibody (1:100) detection solution. The concentrations of the detection reagent during enzyme screening are shown in Table 1.

f) After the kinase reaction was completed, 5 μL of diluted streptavidin-XL665 were added to all reaction wells, and immediately the diluted europium-labeled tyrosine kinase substrate antibody detection solution was added after mixing.

g) The plate was sealed and mixed well. After reacting at room temperature for 1 hour, ENVISION (Perkinelmer) instrument was used to detect the fluorescence signal (320 nm excitation, 665 nm, 615 nm emission). The inhibition rate of each well was calculated through the fully active wells and the background signal wells, taking the average value in case of multiple wells. Meanwhile, the professional drawing analysis software PRISM 6.0 was used to fit the half maximal inhibitory concentration ($IC_{50}$) of each test compound.

TABLE 2

Table of the sample loading process in the experiment

| Enzyme reaction (10 μL) | Kinase reaction system Sample group | Control group: Negative control | Control group: Positive control |
|---|---|---|---|
| Compound | 4 μL | 4 μL of 2.5% DMSO/kinase buffer | 4 μL of 2.5% DMSO/kinase buffer |
| TK-Biotin labeled substrate | 2 μL | 2 μL | 2 μL |
| Kinase | 2 μL | 2 μL of kinase buffer | 2 μL |
| Sealed with films and incubated at room temperature for 10 min | | | |
| ATP | 2 μL | 2 μL | 2 μL |
| Sealed with films and incubated at room temperature for 50 min | | | |
| Detection (10 μL) | | | |
| Streptavidin-XL665 | 5 μL | 5 μL | 5 μL |
| Europium-labeled tyrosine kinase substrate antibody | 5 μL | 5 μL | 5 μL |
| Sealed with films and incubated at room temperature for 1 h | | | |
| Detection light: 320 nm, emission light: 665 nm, 615 nm | | | |

2.3 Data Analysis $$ER = 665\ \text{nm fluorescence value}/615\ \text{nm fluorescence value Inhibition rate} = (ER_{positive\ control} - ER_{sample})/(ER_{positive\ control} - ER_{negative\ control}) * 10000$$

3. Experimental Results

The experimental results are shown in Table 3:

TABLE 3

AKT inhibitory activity

| Title compounds in Examples | Chemical structure | AKT1 enzyme activity IC50 (nM) | AKT2 enzyme activity IC50 (nM) | AKT3 enzyme activity IC50 (nM) |
|---|---|---|---|---|
| Example 1 | 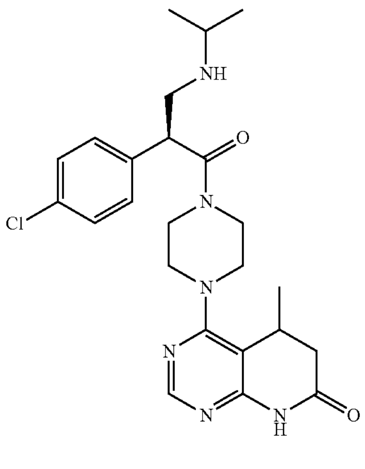 | 2.4 | 6.0 | 1.6 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 2 (R) Configuration product | 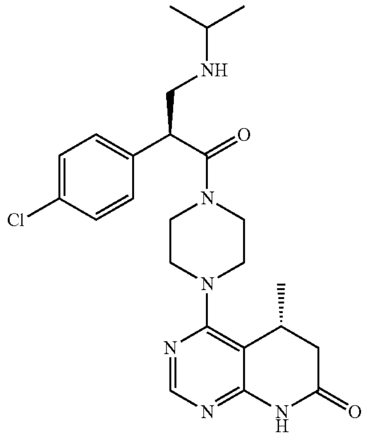 [SMILES: CC(C)NC[C@@H](C(=O)N1CCN(c2ncnc3c2C(C)CC(=O)N3)CC1)c1ccc(Cl)cc1] | 2.4 | 4.3 | 0.4 |
| Example 3 | 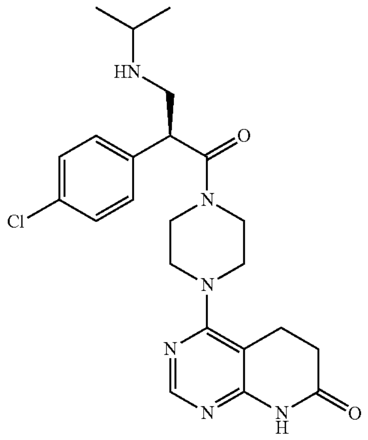 [SMILES: CC(C)NC[C@@H](C(=O)N1CCN(c2ncnc3c2CCC(=O)N3)CC1)c1ccc(Cl)cc1] | 52.4 | 21.2 | 7.5 |
| Example 7 | 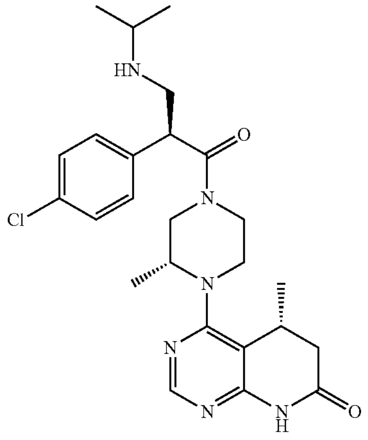 [SMILES: CC(C)NC[C@@H](C(=O)N1CCN(c2ncnc3c2[C@H](C)CC(=O)N3)[C@H](C)C1)c1ccc(Cl)cc1] | 26.4 | 292.9 | 7.4 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 8 | 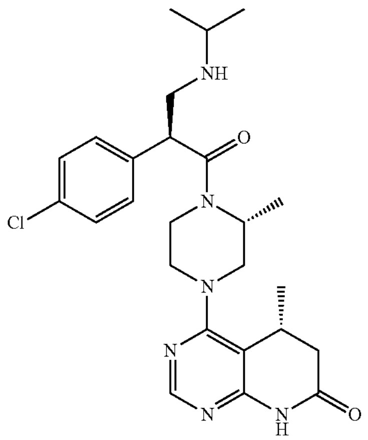 [SMILES: CC(C)NC[C@@H](C(=O)N1CCN(c2ncnc3c2[C@H](C)CC(=O)N3)C[C@H]1C)c1ccc(Cl)cc1] | 28.7 | 15.5 | 2.7 |
| Example 9 | 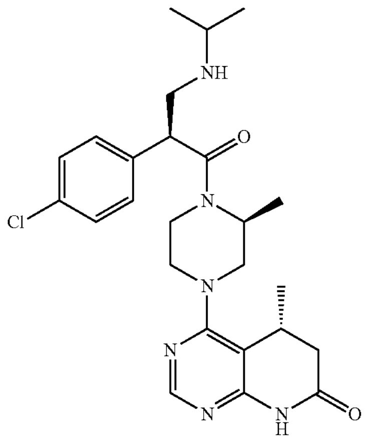 [SMILES: CC(C)NC[C@@H](C(=O)N1CCN(c2ncnc3c2[C@H](C)CC(=O)N3)C[C@@H]1C)c1ccc(Cl)cc1] | 166.6 | 206.2 | 3.3 |
| Example 10 | 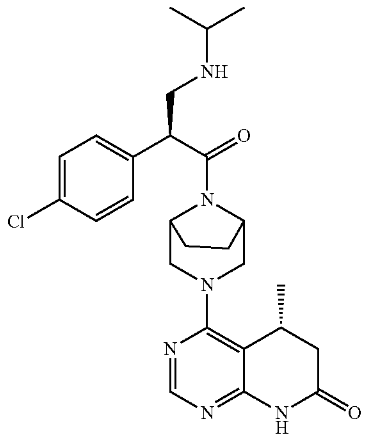 [SMILES: CC(C)NC[C@@H](C(=O)N1C2CCC1CN(c1ncnc3c1[C@H](C)CC(=O)N3)C2)c1ccc(Cl)cc1] | 2.8 | 63 | 0.21 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 11 | 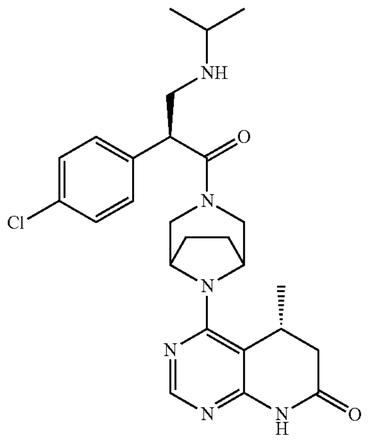 [SMILES: CC(C)NC[C@@H](C(=O)N1CC2CCC(C1)N2c1ncnc2c1[C@H](C)CC(=O)N2)c1ccc(Cl)cc1] | 3.5 | 71.0 | 0.25 |
| Example 12 | 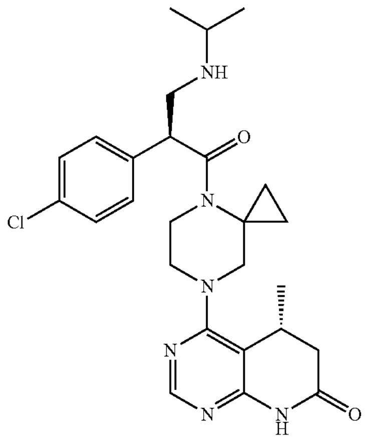 [SMILES: CC(C)NC[C@@H](C(=O)N1CCN(c2ncnc3c2[C@H](C)CC(=O)N3)CC12CC2)c1ccc(Cl)cc1] | 55.1 | 40.4 | 4.8 |
| Example 13 cis-isomer | 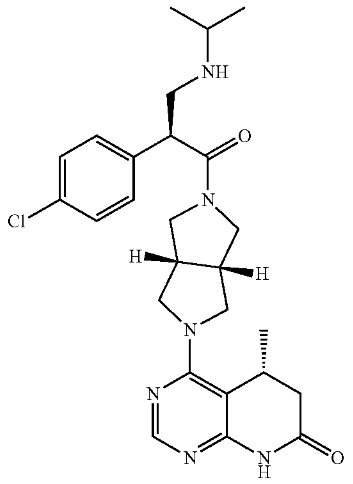 [SMILES: CC(C)NC[C@@H](C(=O)N1C[C@@H]2CN(c3ncnc4c3[C@H](C)CC(=O)N4)C[C@@H]2C1)c1ccc(Cl)cc1] | 285.0 | 166.6 | 6.6 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 15 | 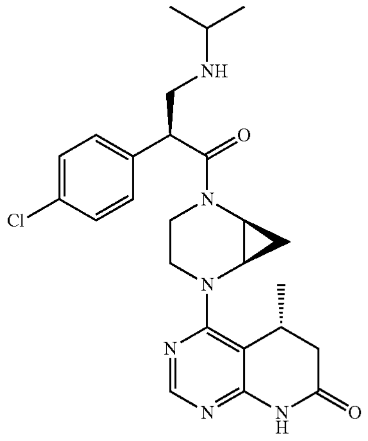 Isomer 1 | 62 | 542 | 13 |
| Example 15 | 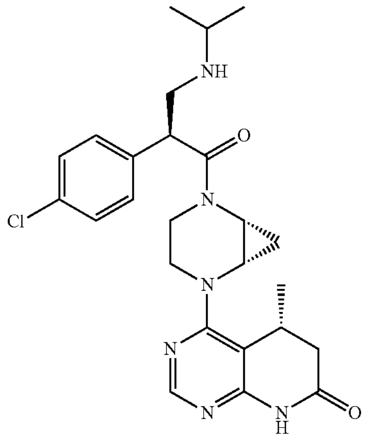 Isomer 2 | 0.35 | 6.3 | 0.09 |
| Example 16 | 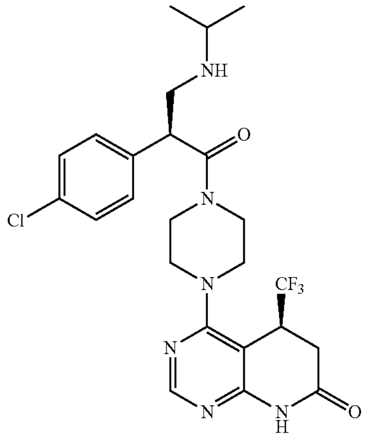 [SMILES: CC(C)NC[C@@H](C(=O)N1CCN(c2ncnc3c2[C@@H](C(F)(F)F)CC(=O)N3)CC1)c1ccc(Cl)cc1] Isomer 1 | 776 | 1000 | 139 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 16 | 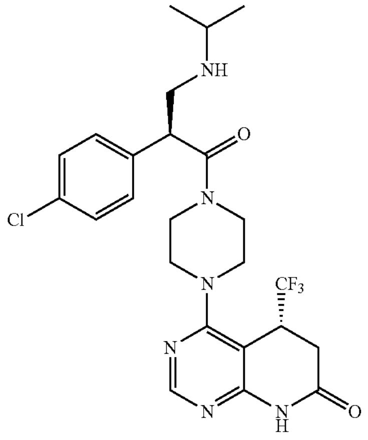 [SMILES: CC(C)NC[C@@H](C(=O)N1CCN(c2ncnc3c2[C@H](C(F)(F)F)CC(=O)N3)CC1)c1ccc(Cl)cc1] Isomer 2 | 12 | 15 | 1 |
| Example 18 | 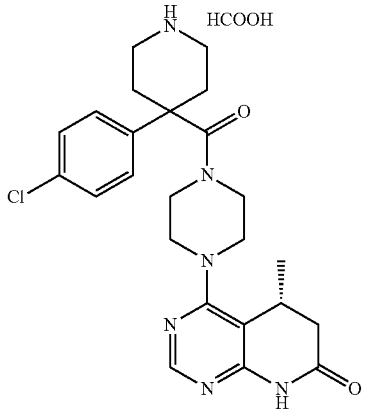 [SMILES: C[C@@H]1CC(=O)Nc2ncnc(N3CCN(C(=O)C4(c5ccc(Cl)cc5)CCNCC4)CC3)c21 ; "HCOOH"] | 590.0 | 256.5 | 20.1 |
| Example 19 | 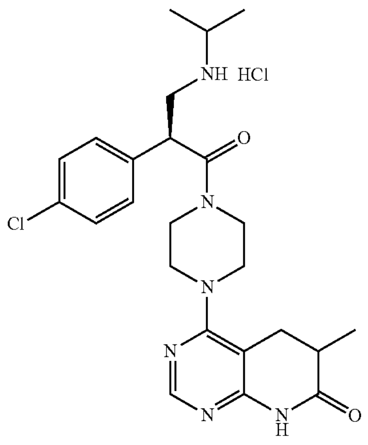 [SMILES: CC(C)NC[C@@H](C(=O)N1CCN(c2ncnc3c2CC(C)C(=O)N3)CC1)c1ccc(Cl)cc1 ; Cl] | 58.5 | 29.4 | 7.4 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 19 | 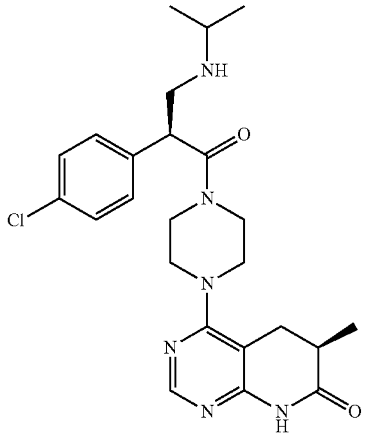 [SMILES: CC(C)NC[C@@H](C(=O)N1CCN(c2ncnc3c2C[C@@H](C)C(=O)N3)CC1)c1ccc(Cl)cc1] Isomer 1 | 82 | 504 | 18 |
| Example 19 | 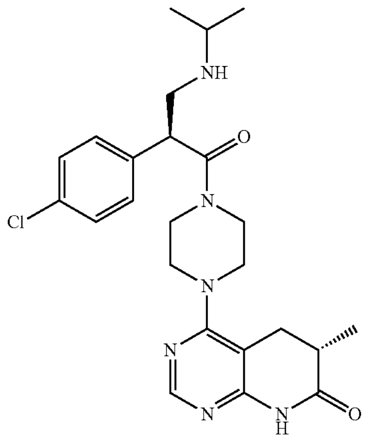 [SMILES: CC(C)NC[C@@H](C(=O)N1CCN(c2ncnc3c2C[C@H](C)C(=O)N3)CC1)c1ccc(Cl)cc1] Isomer 2 | 25 | 314 | 9.1 |
| Example 20 | 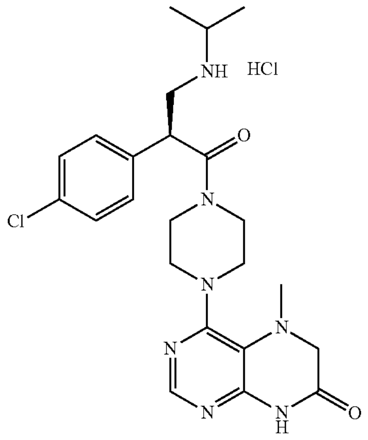 [SMILES: CC(C)NC[C@@H](C(=O)N1CCN(c2ncnc3c2N(C)CC(=O)N3)CC1)c1ccc(Cl)cc1 ; Cl] | 1.1 | 23 | 0.4 |

TABLE 3-continued
AKT inhibitory activity
| Title compounds in Examples | Chemical structure | AKT1 enzyme activity IC50 (nM) | AKT2 enzyme activity IC50 (nM) | AKT3 enzyme activity IC50 (nM) |
|---|---|---|---|---|
| Example 21 | 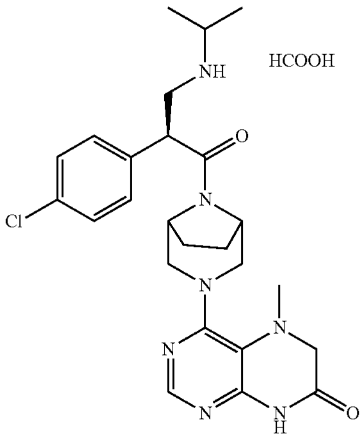 [SMILES: CC(C)NC[C@@H](C(=O)N1C2CCC1CN(c1ncnc3c1N(C)CC(=O)N3)C2)c1ccc(Cl)cc1 ; "HCOOH"] HCOOH | 1.9 | 46.0 | 0.2 |
| Example 22 | 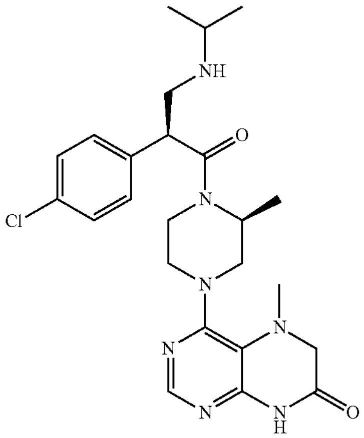 [SMILES: CC(C)NC[C@@H](C(=O)N1CCN(c2ncnc3c2N(C)CC(=O)N3)C[C@@H]1C)c1ccc(Cl)cc1] | 39 | 334 | 0.56 |
| Example 23 | 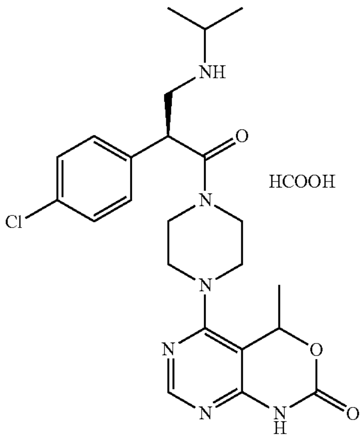 [SMILES: CC(C)NC[C@@H](C(=O)N1CCN(c2ncnc3c2C(C)OC(=O)N3)CC1)c1ccc(Cl)cc1 ; "HCOOH"] HCOOH | 6.0 | 10.9 | 1.2 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 23 | 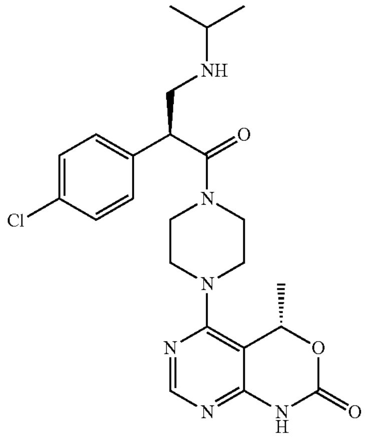 [SMILES: CC(C)NC[C@@H](C(=O)N1CCN(c2ncnc3c2[C@H](C)OC(=O)N3)CC1)c1ccc(Cl)cc1] Isomer 1 | 1.5 | 11 | 0.19 |
| Example 23 | 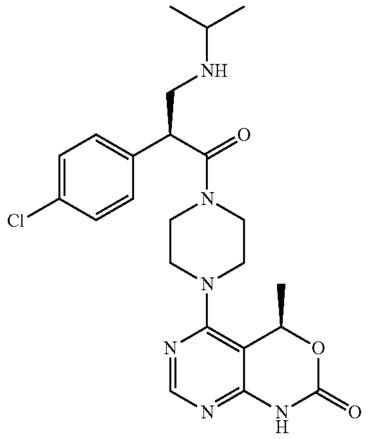 [SMILES: CC(C)NC[C@@H](C(=O)N1CCN(c2ncnc3c2[C@@H](C)OC(=O)N3)CC1)c1ccc(Cl)cc1] Isomer 2 | 201 | 1000 | 42 |
| Example 24 | 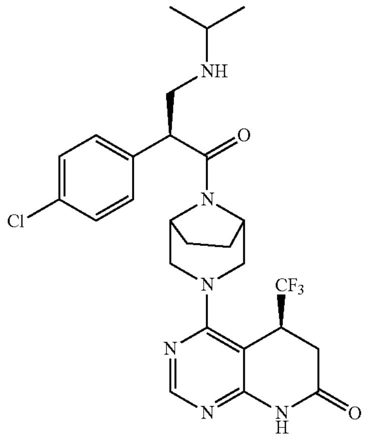 [SMILES: CC(C)NC[C@@H](C(=O)N1C2CCC1CN(c1ncnc3c1[C@@H](C(F)(F)F)CC(=O)N3)C2)c1ccc(Cl)cc1] Isomer 1 | 354 | 1000 | 61 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 24 | 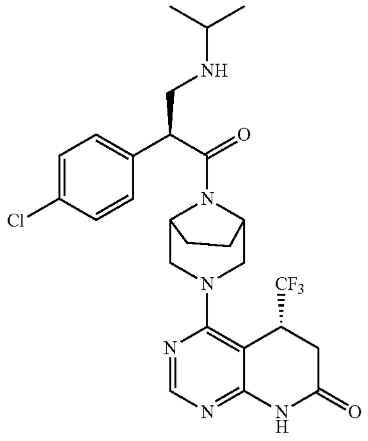 [SMILES: CC(C)NC[C@@H](C(=O)N1C2CCC1CN(c1ncnc3c1[C@H](C(F)(F)F)CC(=O)N3)C2)c1ccc(Cl)cc1] Isomer 2 | 116 | 1000 | 19 |
| Example 25 | 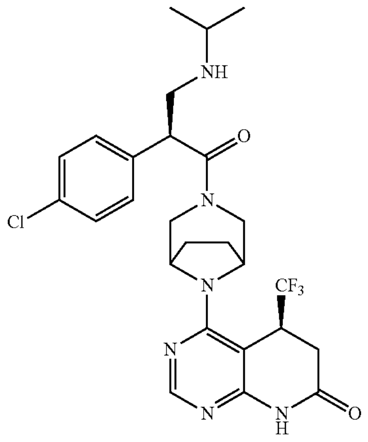 [SMILES: CC(C)NC[C@@H](C(=O)N1CC2CCC(C1)N2c1ncnc2c1[C@@H](C(F)(F)F)CC(=O)N2)c1ccc(Cl)cc1] Isomer 1 | 218 | 1000 | 20 |
| Example 25 | 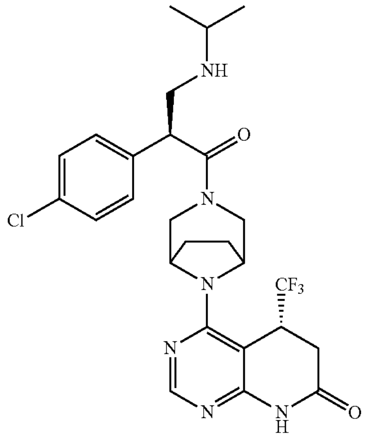 [SMILES: CC(C)NC[C@@H](C(=O)N1CC2CCC(C1)N2c1ncnc2c1[C@H](C(F)(F)F)CC(=O)N2)c1ccc(Cl)cc1] Isomer 2 | 0.59 | 20 | 0.19 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 26 | 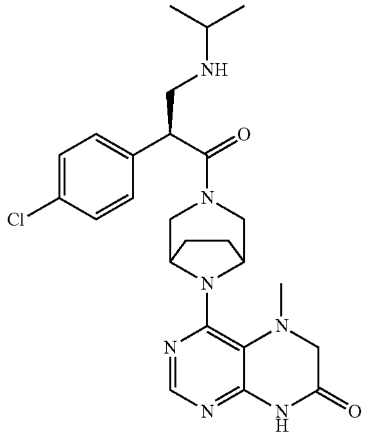 [SMILES: CC(C)NC[C@@H](C(=O)N1CC2CCC(C1)N2c1ncnc2c1N(C)CC(=O)N2)c1ccc(Cl)cc1] | 30 | 221 | 0.52 |
| Example 27 | 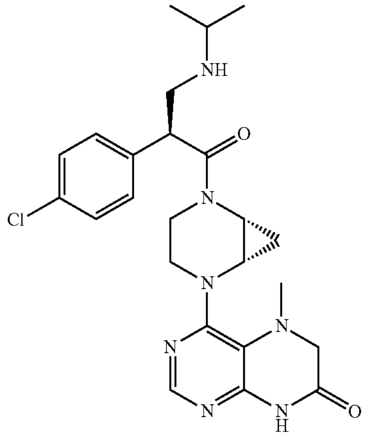 [SMILES: CC(C)NC[C@@H](C(=O)N1CCN(c2ncnc3c2N(C)CC(=O)N3)[C@H]2C[C@H]21)c1ccc(Cl)cc1] Isomer 1 | 22 | 169 | 0.48 |
| Example 27 | 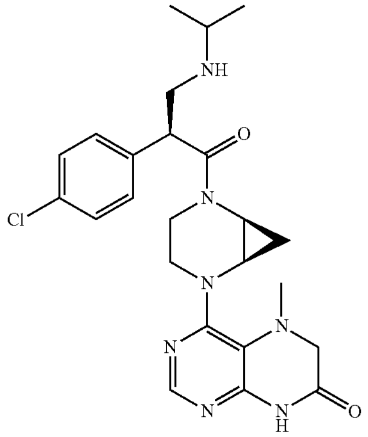 [SMILES: CC(C)NC[C@@H](C(=O)N1CCN(c2ncnc3c2N(C)CC(=O)N3)[C@@H]2C[C@@H]21)c1ccc(Cl)cc1] Isomer 2 | 147 | 1000 | 7.4 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 28 | 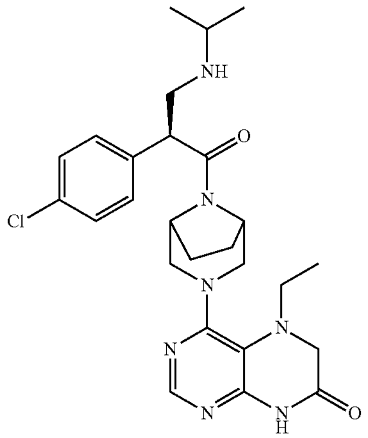 [SMILES: CCN1CC(=O)Nc2ncnc(N3CC4CCC(C3)N4C(=O)[C@H](CNC(C)C)c3ccc(Cl)cc3)c21] | 2.1 | 89 | 0.19 |
| Example 29 | 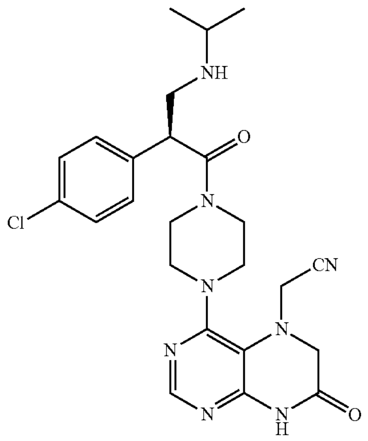 [SMILES: CC(C)NC[C@@H](C(=O)N1CCN(c2ncnc3c2N(CC#N)CC(=O)N3)CC1)c1ccc(Cl)cc1] | 40 | 227 | 1.1 |
| Example 30 | 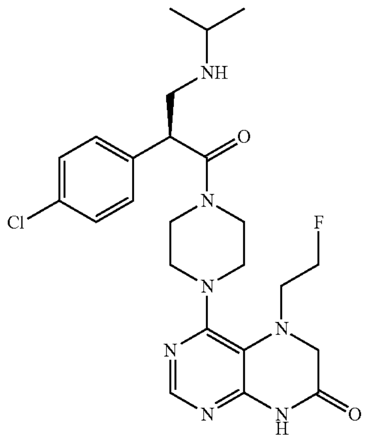 [SMILES: CC(C)NC[C@@H](C(=O)N1CCN(c2ncnc3c2N(CCF)CC(=O)N3)CC1)c1ccc(Cl)cc1] | 55 | 339 | 2.1 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 31 | 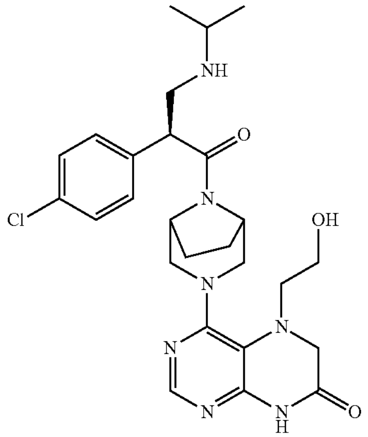 [SMILES: CC(C)NC[C@@H](C(=O)N1C2CCC1CN(c1ncnc3c1N(CCO)CC(=O)N3)C2)c1ccc(Cl)cc1] | 210 | 1000 | 1.8 |
| Example 32 | 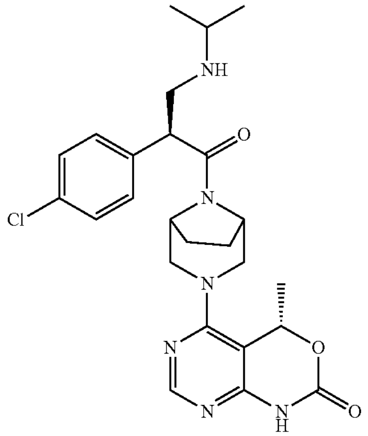 [SMILES: CC(C)NC[C@@H](C(=O)N1C2CCC1CN(c1ncnc3c1[C@H](C)OC(=O)N3)C2)c1ccc(Cl)cc1]<br>Isomer 1 | 0.63 | 4.9 | 0.41 |
| Example 32 | 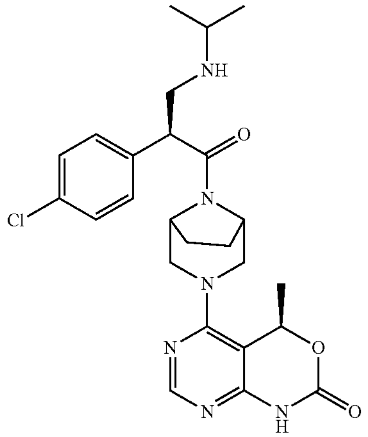 [SMILES: CC(C)NC[C@@H](C(=O)N1C2CCC1CN(c1ncnc3c1[C@@H](C)OC(=O)N3)C2)c1ccc(Cl)cc1]<br>Isomer 2 | 25 | 155 | 9.8 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 33 | 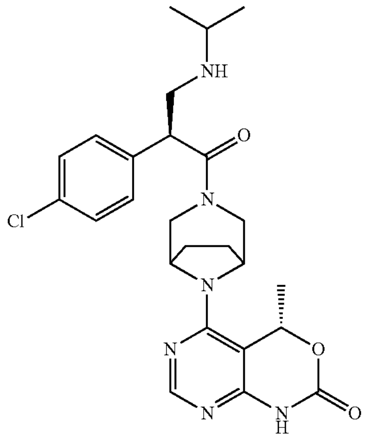 [SMILES: CC(C)NC[C@@H](C(=O)N1CC2CCC(C1)N2c1ncnc2c1[C@H](C)OC(=O)N2)c1ccc(Cl)cc1] Isomer 1 | 1.6 | 33 | 0.2 |
| Example 33 | 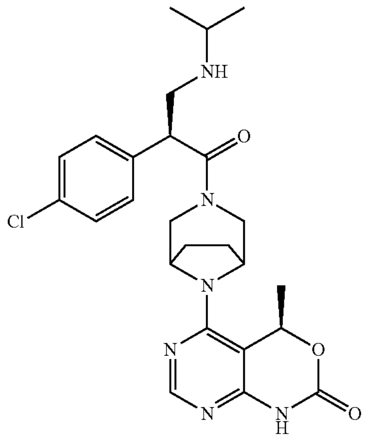 [SMILES: CC(C)NC[C@@H](C(=O)N1CC2CCC(C1)N2c1ncnc2c1[C@@H](C)OC(=O)N2)c1ccc(Cl)cc1] Isomer 2 | 260 | 1000 | 55 |
| Example 34 | 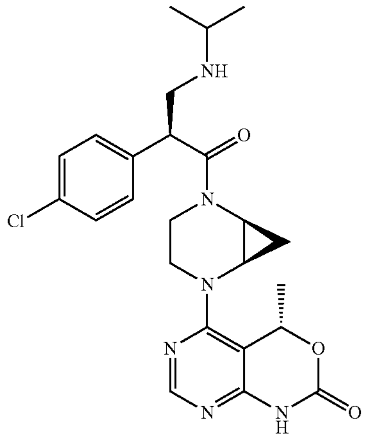 [SMILES: CC(C)NC[C@@H](C(=O)N1CCN(c2ncnc3c2[C@H](C)OC(=O)N3)[C@@H]2C[C@@H]21)c1ccc(Cl)cc1] Isomer 1 | 186 | 771 | 45 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 34 | 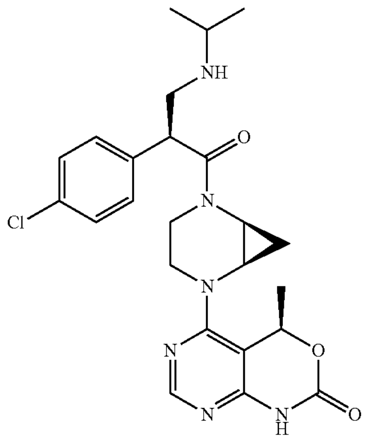 [SMILES: CC(C)NC[C@@H](C(=O)N1CCN(c2ncnc3c2[C@@H](C)OC(=O)N3)[C@@H]2C[C@@H]21)c1ccc(Cl)cc1] Isomer 2 | 613 | 1000 | 89 |
| Example 34 | 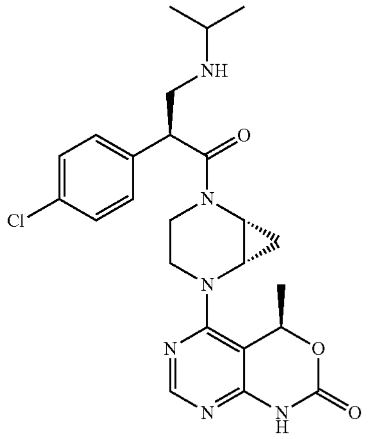 [SMILES: CC(C)NC[C@@H](C(=O)N1CCN(c2ncnc3c2[C@@H](C)OC(=O)N3)[C@H]2C[C@H]21)c1ccc(Cl)cc1] Isomer 3 | 429 | 1000 | 232 |
| Example 34 | 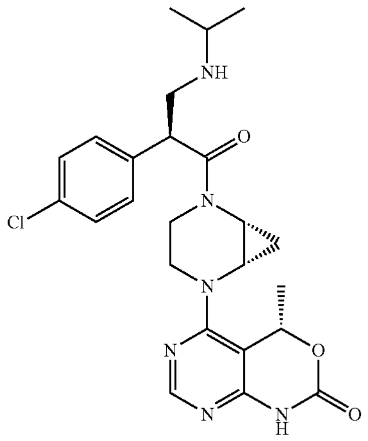 [SMILES: CC(C)NC[C@@H](C(=O)N1CCN(c2ncnc3c2[C@H](C)OC(=O)N3)[C@H]2C[C@H]21)c1ccc(Cl)cc1] Isomer 4 | 0.6 | 1.2 | 0.12 |

TABLE 3-continued
AKT inhibitory activity
| Title compounds in Examples | Chemical structure | AKT1 enzyme activity IC50 (nM) | AKT2 enzyme activity IC50 (nM) | AKT3 enzyme activity IC50 (nM) |
|---|---|---|---|---|
| Example 35 | 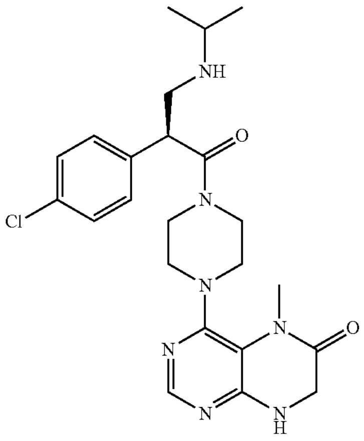 [SMILES: CC(C)NC[C@@H](C(=O)N1CCN(c2ncnc3c2N(C)C(=O)CN3)CC1)c1ccc(Cl)cc1] | 146 | 1000 | 212 |
| Example 36 | 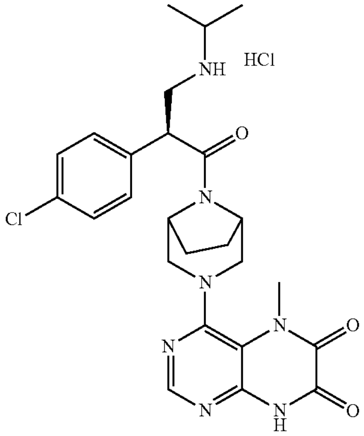 [SMILES: CC(C)NC[C@@H](C(=O)N1C2CCC1CN(c1ncnc3[nH]c(=O)c(=O)n(C)c13)C2)c1ccc(Cl)cc1 ; Cl] | 77 | 800 | 22 |
| Example 37 | 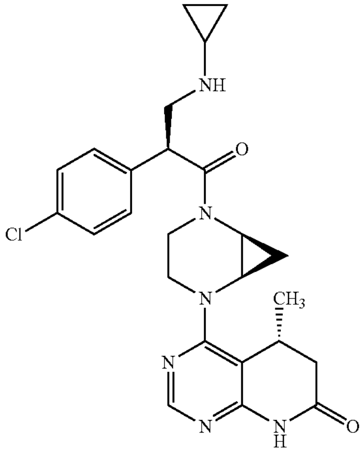 [SMILES: C[C@@H]1CC(=O)Nc2ncnc(N3CCN(C(=O)[C@H](CNC4CC4)c4ccc(Cl)cc4)[C@H]4C[C@H]43)c21] Isomer 1 | 442 | 1000 | 59 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 37 | 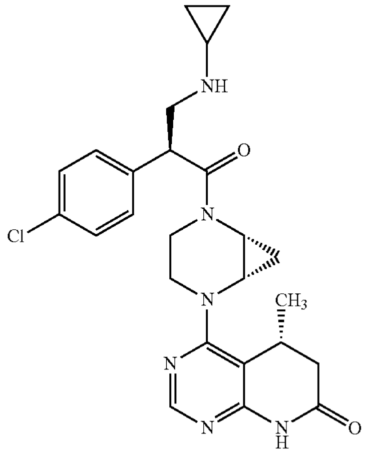 [SMILES: C[C@@H]1CC(=O)Nc2ncnc(N3CCN(C(=O)[C@H](CNC4CC4)c4ccc(Cl)cc4)[C@@H]4C[C@@H]43)c21] Isomer 2 | 0.65 | 5.7 | 0.12 |
| Example 38 | 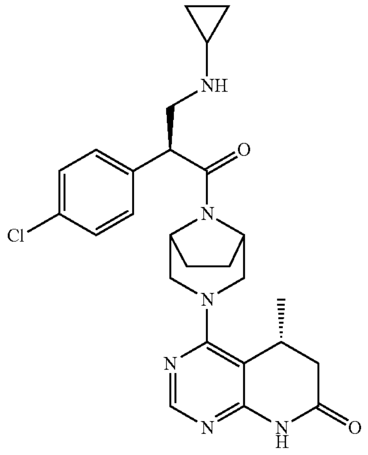 [SMILES: C[C@@H]1CC(=O)Nc2ncnc(N3CC4CCC(C3)N4C(=O)[C@H](CNC3CC3)c3ccc(Cl)cc3)c21] | 2.4 | 23 | 0.28 |
| Example 39 | 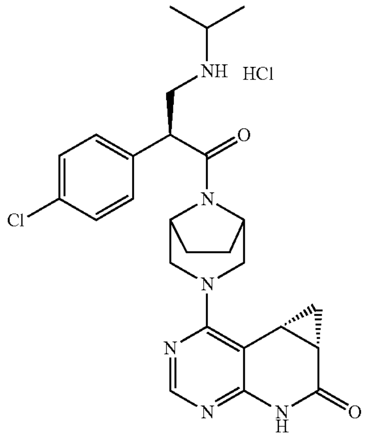 [SMILES: CC(C)NC[C@@H](C(=O)N1C2CCC1CN(c1ncnc3c1[C@@H]1C[C@@H]1C(=O)N3)C2)c1ccc(Cl)cc1 ; Cl] Isomer 1 | 13 | 75 | 7.6 |

TABLE 3-continued
| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Example 39 | 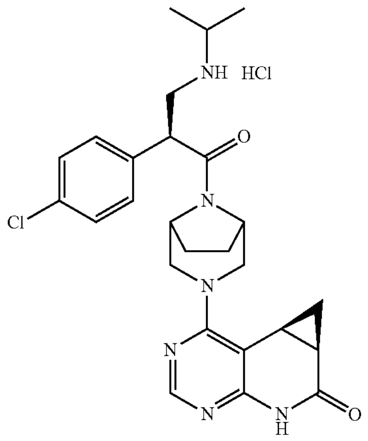 [SMILES: CC(C)NC[C@@H](C(=O)N1C2CCC1CN(c1ncnc3c1[C@H]1C[C@H]1C(=O)N3)C2)c1ccc(Cl)cc1 ; Cl] Isomer 2 | 151 | 756 | 43 |
| Example 40 | 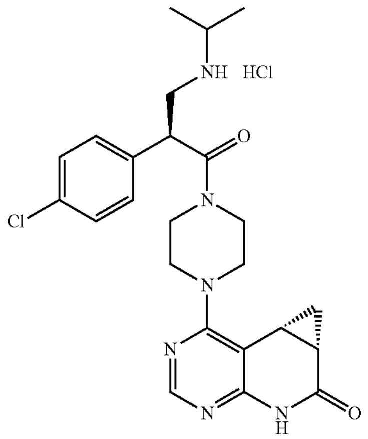 [SMILES: CC(C)NC[C@@H](C(=O)N1CCN(c2ncnc3c2[C@@H]2C[C@@H]2C(=O)N3)CC1)c1ccc(Cl)cc1 ; Cl] Isomer 1 | 14 | 95 | 12 |
| Example 40 | 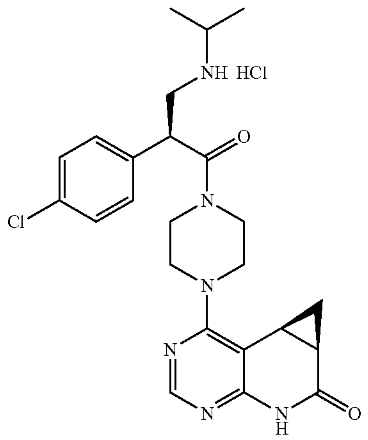 [SMILES: CC(C)NC[C@@H](C(=O)N1CCN(c2ncnc3c2[C@H]2C[C@H]2C(=O)N3)CC1)c1ccc(Cl)cc1 ; Cl] Isomer 2 | 82 | 475 | 61 |

TABLE 3-continued

| AKT inhibitory activity | | | | |
|---|---|---|---|---|
| Title compounds in Examples | Chemical structure | AKT1 enzyme activity IC50 (nM) | AKT2 enzyme activity IC50 (nM) | AKT3 enzyme activity IC50 (nM) |
| Positive control GDC-0068 | 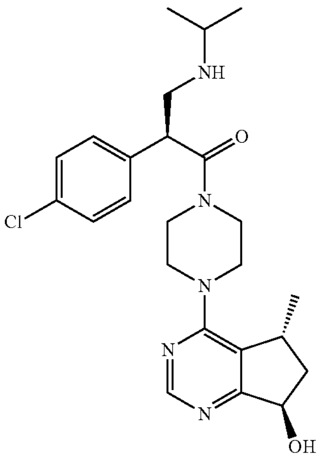 [SMILES: CC(C)NC[C@@H](C(=O)N1CCN(c2ncnc3c2[C@H](C)C[C@H]3O)CC1)c1ccc(Cl)cc1] | 3.2 | 1.7 | 2.5 |

Experimental Example 2 Pharmacokinetic Evaluation

The formulation of the compound of Example 10, Example 21, GDC-0068, and Example 34 Isomer 4:

Mixed menstruum: Tween 80: PEG400: water=1:9:90 (v/v/v)

The compounds were formulated into a 10 mg/mL stock solution with DMSO.

400 μl of stock solution with a concentration of 10 mg/mL was accurately pipetted into a glass bottle, and 3.6 mL of mixed menstruum was added. The ratio of the menstruum in the final formulation is DMSO:mixed menstruum (v/v)=10: 90. After vortexing (or sonication) and evenly distributed, 4 mL of a dosing solution with a concentration of 1 mg $mL^{-1}$ for each compound was obtained.

Formulation of Isomer 2 of the compound of Example 15:

Menstruum: DMSO: PEG400: ultrapure water=5:20:75 (v/v/v)

5.37 mg of test sample Isomer 2 of the compound of Example 15 was weighed into a glass bottle; 0.269 mL of DMSO was added, vortexed to completely dissolve the solid material; 1.074 mL of PEG400 was added, vortexed, and mixed; 4.028 mL of ultrapure water was added, vortexed and mixed to obtain a colorless solution with a concentration of 1 $mg \cdot mL^{-1}$.

Experimental animal: mouse, strain ICR, source: Weitong Lihua Laboratory Animal Technology Co., Ltd., age: 6-10 weeks, male.

Experimental Scheme

TABLE 4

| Table of animal experiment scheme | | | | | | | | |
|---|---|---|---|---|---|---|---|---|
| Compound | Group | Animal ID | dose ($mg \cdot kg^{-1}$) | volume ($mL \cdot kg^{-1}$) | Route of administration | Course of treatment | Fasted or not | Time point of sample collection |
| Example 10 | A | A1-A3 | 10 | 10 | intragastrically | single | Yes | Before administration, 1 h and 8 h after administration |
| | | A4-A6 | | | | | | 15 min, 2 h and 24 h after administration |
| | | A7-A9 | | | | | | 30 min and 4 h after administration |
| Example 21 | B | B1-B3 | 10 | 10 | intragastrically | single | Yes | Before administration, 1 h and 8 h after administration |
| | | B4-B6 | | | | | | 15 min, 2 h and 24 h after administration |
| | | B7-B9 | | | | | | 30 min and 4 h after administration |
| Isomer 2 of Example 15 | D | D1-D3 | 10 | 10 | intragastrically | single | Yes | Before administration, 1 h and 8 h after administration |
| | | D4-D6 | | | | | | 15 min, 2 h and 24 h after administration |
| | | D7-D9 | | | | | | 30 min and 4 h after administration |

TABLE 4-continued

| Table of animal experiment scheme | | | | | | | | |
|---|---|---|---|---|---|---|---|---|
| Compound | Group | Animal ID | dose ($mg \cdot kg^{-1}$) | volume ($mL \cdot kg^{-1}$) | Route of administration | Course of treatment | Fasted or not | Time point of sample collection |
| Isomer 4 of Example 34 | E | E1-E3 | 10 | 10 | intragastrically | single | Yes | Before administration, 1 h and 8 h after administration |
| | | E4-E6 | | | | | | 15 min, 2 h and 24 h after administration |
| | | E7-E9 | | | | | | 30 min and 4 h after administration |
| GDC-0068 | C | C2-C3 | 10 | 10 | intragastrically | single | Yes | Before administration, 1 h and 8 h after administration |
| | | C4-C6 | | | | | | 15 min, 2 h and 24 h after administration |
| | | C7-C9 | | | | | | 30 min and 4 h after administration |

The experimental animals were fed in the animal room of Suzhou Shengsu New Pharmaceutical Development Co., Ltd. The animal room was well ventilated and equipped with air conditioning. The temperature was maintained at 20-25° C. and the humidity was maintained at 40%-70%. Bright and dark lighting for 12 hours each, and the experimental animals ate and drank freely. After normal feeding for at least 5 days, mice with good physical signs were selected for this experiment after veterinary inspection. Each mouse was marked with a tag on its tail. Animal experiment scheme is shown in Table 4.

After weighing the body weight, the theoretical administration volume of each mouse is calculated according to the following formula.

$$\text{Theoretical dosing volume(mL)} = \left(\frac{\text{Dose}(\text{mg}\cdot\text{kg}^{-1})}{\text{Test solution concentration }(\text{mg}\cdot\text{mL}^{-1})}\right)\times \text{Animal weight(kg)}$$

On the day before the experiment, the mice were fasted overnight and were allowed to drink freely, and were fed 4 hours after the administration.

On the day of the experiment, mice in groups A to E were administered with 10 $mg \cdot kg^{-1}$ of the administration solution of Example 10, Example 21, GDC-0068, Isomer 2 of Example 15, and Isomer 4 of Example 34 by intragastric administration. After the administration, about 100 μL of blood was collected from the orbit of the mouse at each time point and placed in an EDTA-$K_2$ anticoagulation tube. The whole blood sample was centrifuged at 5500 rpm for 10 min, and the separated plasma was stored in a refrigerator at −40-−20° C. for biological sample analysis. An LC-MS/MS analytical method for determining the concentration of compounds in mouse plasma was established and used to determine the concentration of compounds in the biological samples obtained in this experiment. The non-compartmental model in Pharsight Phoenix 7.0 was used to calculate the pharmacokinetic parameters.

Experimental results: The experimental results are shown in Table 5.

TABLE 5

| Pharmacokinetic parameters of the compounds of the invention | | | | | |
|---|---|---|---|---|---|
| Pharmacokinetic parameters | GDC-0068 | Example 10 | Example 21 | Isomer 2 of Example 15 | Isomer 4 of Example 34 |
| $T_{1/2}$ (h) | 2.59 | 1.67 | NR | 3.16 | NR |
| $T_{max}$ (h) | 2 | 0.5 | 1 | 1.00 | 4.00 |
| $C_{max}$ (ng/mL) | 75.3 | 321 | 681 | 583 | 497 |
| AUC ($ng \cdot h/mL$) | 320 | 911 | 2290 | 2170 | 2580 |

NR: not calculated

The invention claimed is:

1. A compound represented by formula I or a pharmaceutically acceptable salt thereof,

I

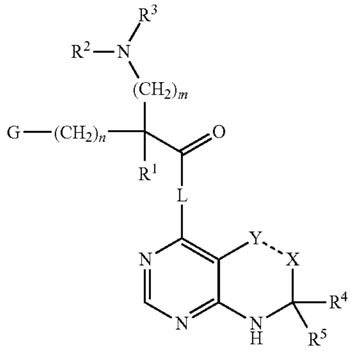

wherein $R^1$ is selected from the group consisting of H and $C_1$-$C_6$ alkyl, wherein the $C_1$-$C_6$ alkyl is optionally substituted by halogen or OH;

$R^2$ and $R^3$ are each independently selected from the group consisting of H, $C_1$-$C_6$ alkyl, and $C_3$-$C_6$ cycloalkyl; or $R^1$ and $R^2$, together with the atoms to which $R^1$ and $R^2$ are attached, form a 4-7 membered nitrogen-containing heterocyclic ring;

m is 1 or 2, n is 0;

$R^4$ and $R^5$ form =O together;

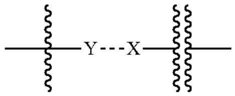

is selected from the group consisting of

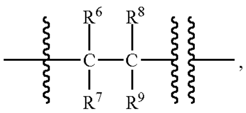, 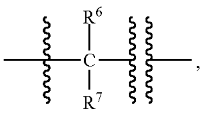,

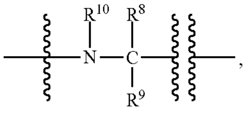, 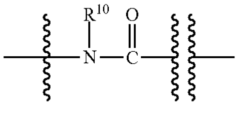 and

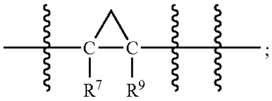;

$R^6$, $R^7$, $R^8$, and $R^9$ are each independently selected from the group consisting of H and $C_1$-$C_6$ alkyl, wherein the $C_1$-$C_6$ alkyl is optionally substituted by halogen;

$R^{10}$ is H or $C_1$-$C_6$ alkyl, wherein the $C_1$-$C_6$ alkyl is optionally substituted by halogen, OH or CN;

L is selected from the group consisting of

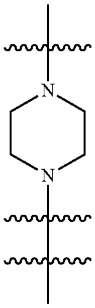, 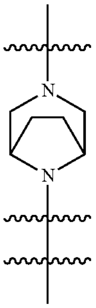, 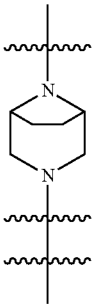, 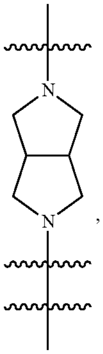,

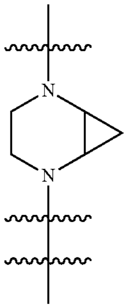, 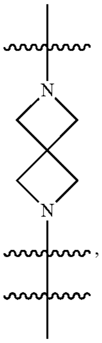, and 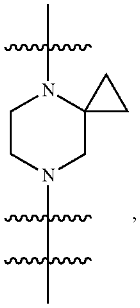, and is optionally substituted by one or more $R^{12}$; wherein a single wavy line is a position where L is connected to carbonyl, and a double wavy line is a position where L is connected to pyrimidine; and wherein $R^{12}$ is $C_1$-$C_6$ alkyl;

G is a 6-10 membered aryl optionally substituted by 1-5 $R^{11}$;

$R^{11}$ is halogen;

provided that neither $R^1$ nor $R^2$ is H if $R^1$ and $R^2$, together with the atoms to which $R^1$ and $R^2$ are attached, form a 4-7 membered nitrogen-containing heterocyclic ring; and when L is

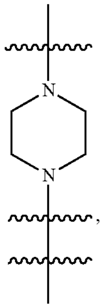, 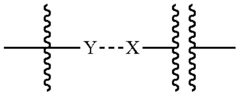

is not

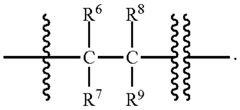.

2. The compound or a pharmaceutically acceptable salt thereof according to claim 1, wherein $R^1$ is H.

3. The compound or a pharmaceutically acceptable salt thereof according to claim 1, wherein $R^2$ and $R^3$ are each independently selected from the group consisting of H, isopropyl and cyclopropyl.

4. The compound or a pharmaceutically acceptable salt thereof according to claim 1, wherein $R^1$ and $R^2$, together with the atoms to which $R^1$ and $R^2$ are attached, form

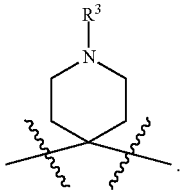.

5. The compound or a pharmaceutically acceptable salt thereof according to claim 1, wherein

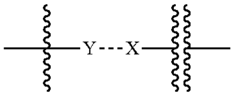

is selected from the group consisting of

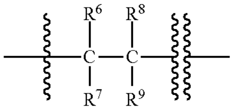, 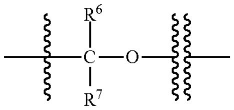 and

-continued

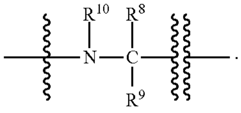.

6. The compound or a pharmaceutically acceptable salt thereof according to claim 1, wherein $R^6$, $R^7$, $R^8$, and $R^9$ are each independently selected from the group consisting of H, methyl and $CF_3$.

7. The compound or a pharmaceutically acceptable salt thereof according to claim 1, wherein $R^{10}$ is selected from the group consisting of H, methyl, ethyl, propyl, isopropyl, $CF_3$, $CH_2CF_3$, $CH_2CHF_2$, $CH_2CH_2F$, $CH_2CN$, $CH_2CH_2CN$, $CH_2OH$ and $CH_2CH_2OH$.

8. The compound or a pharmaceutically acceptable salt thereof according to claim 1, wherein L is optionally substituted by methyl.

9. The compound or a pharmaceutically acceptable salt thereof according to claim 8, wherein L is selected from the group consisting of:

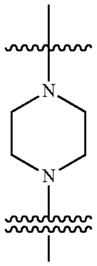, 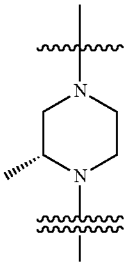, 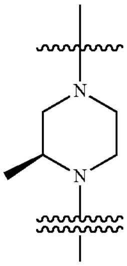, 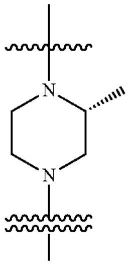, 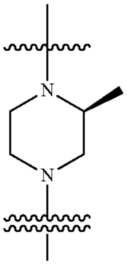, 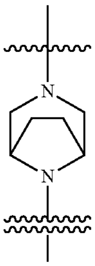, 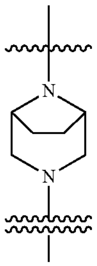, 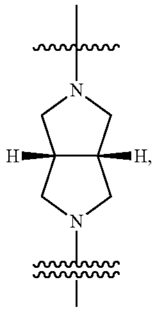, 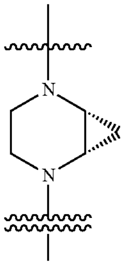, 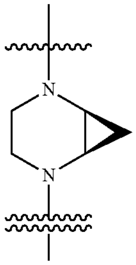 and 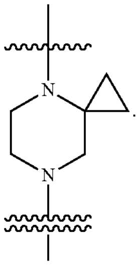.

10. The compound or a pharmaceutically acceptable salt thereof according to claim 1, wherein G is phenyl optionally substituted by 1-5 $R^{11}$; wherein $R^{11}$ is independently selected from the group consisting of F, Cl, Br and I.

11. The compound or a pharmaceutically acceptable salt thereof according to claim 1, wherein the compound is selected from the group consisting of:

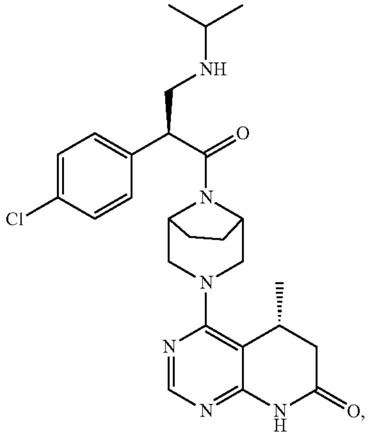,

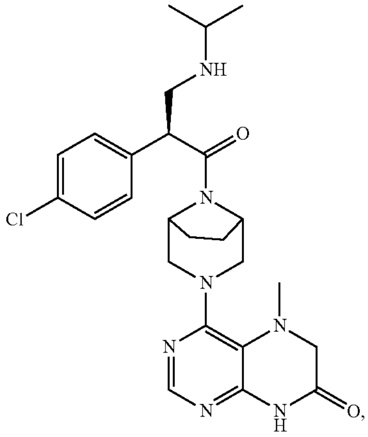,

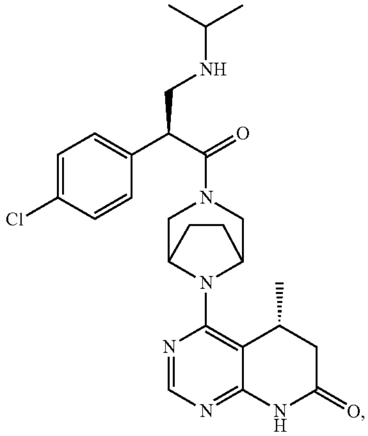,

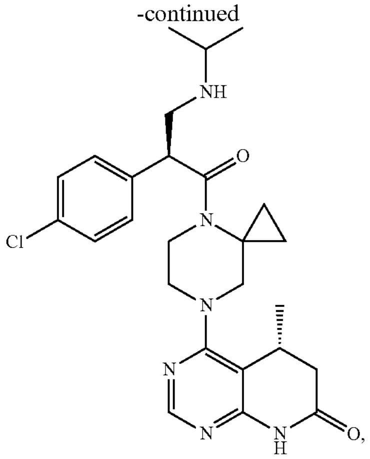
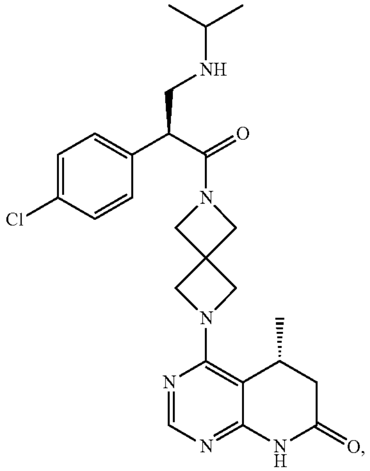
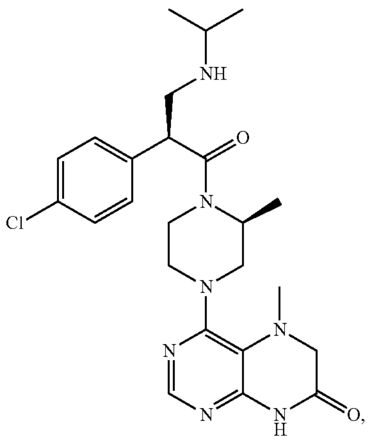
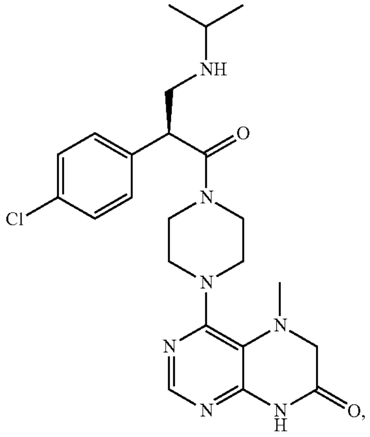
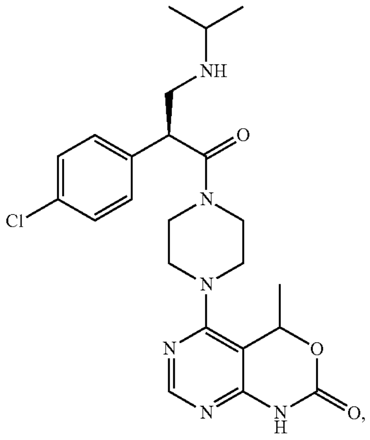
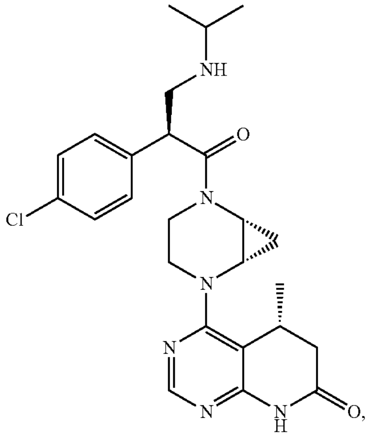

-continued
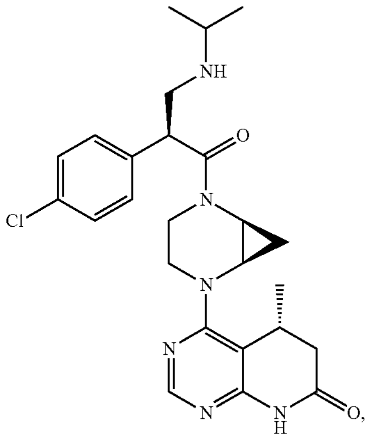,
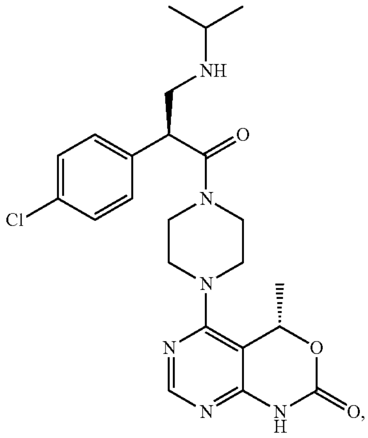,
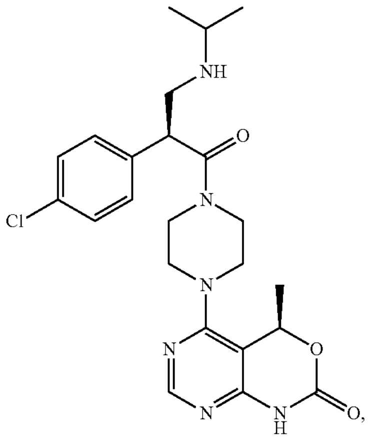,
-continued
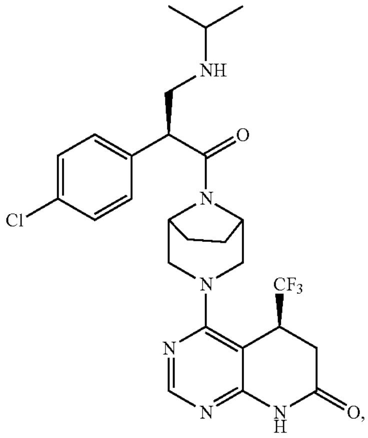,
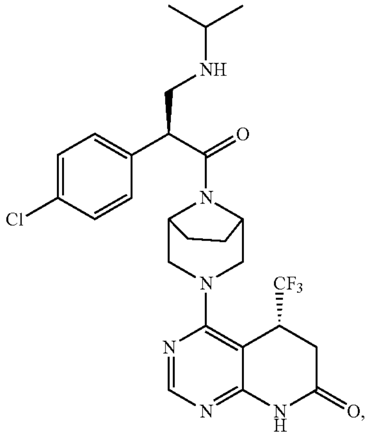,
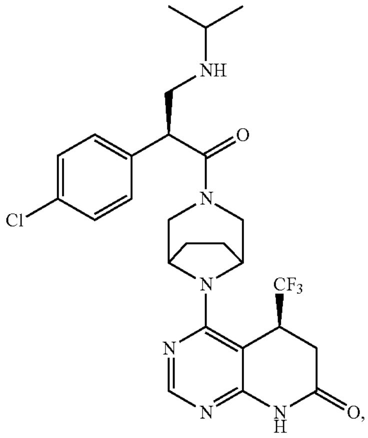, -continued
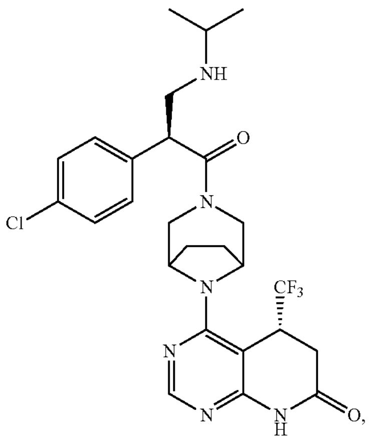
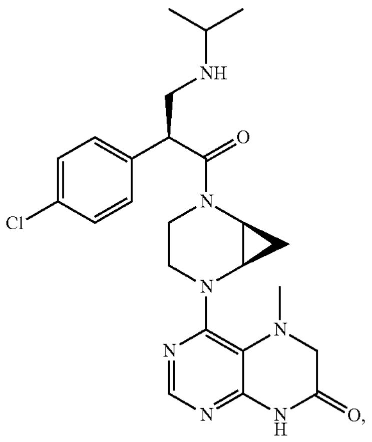
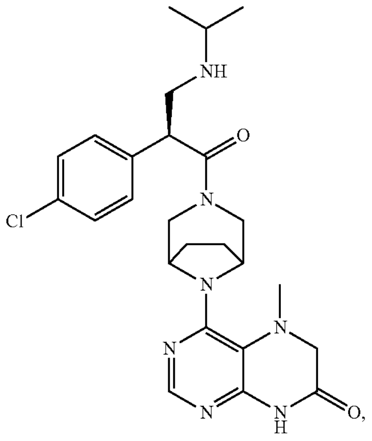
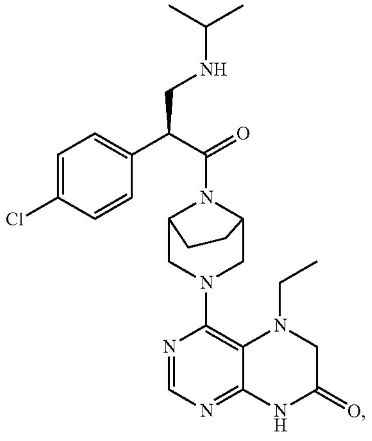
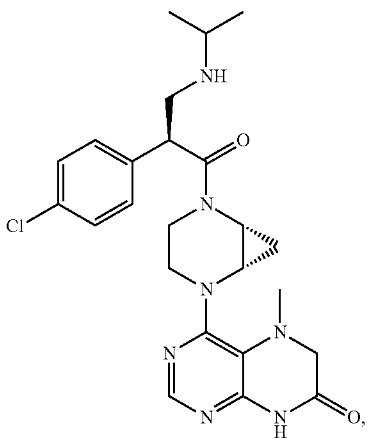
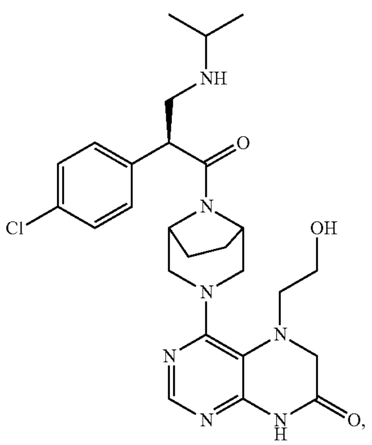
-continued -continued
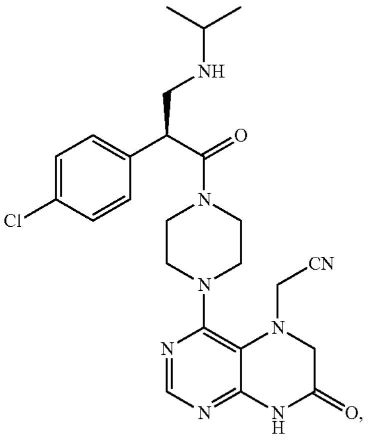
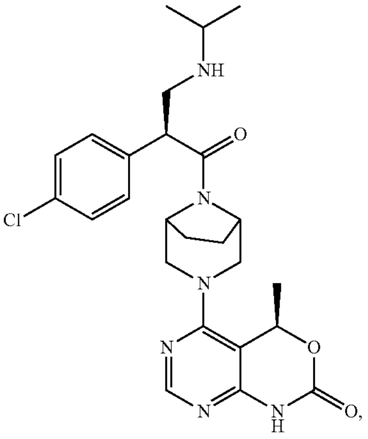
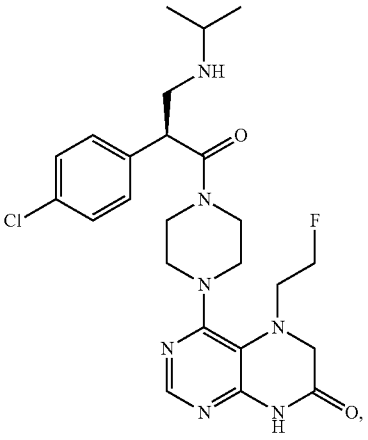
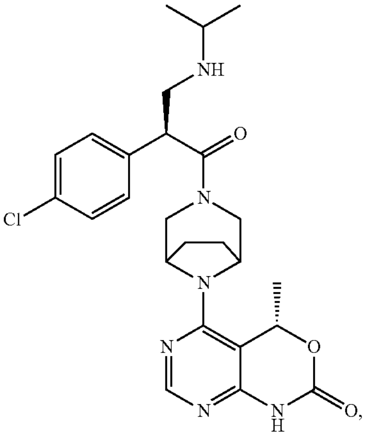
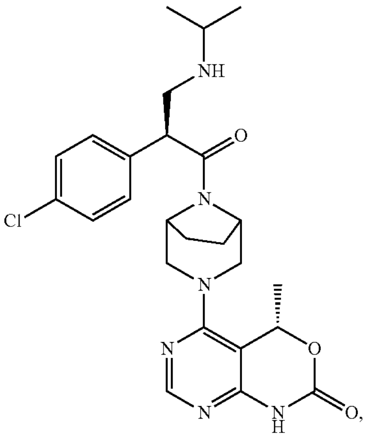
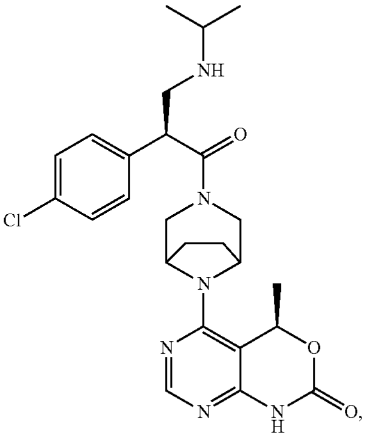

-continued
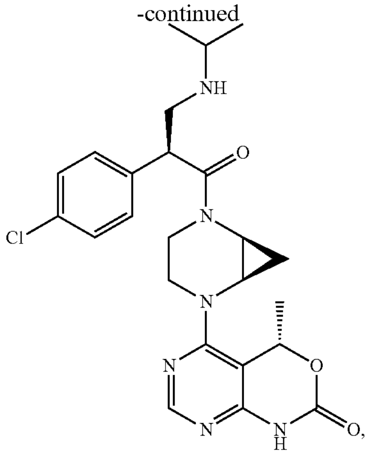
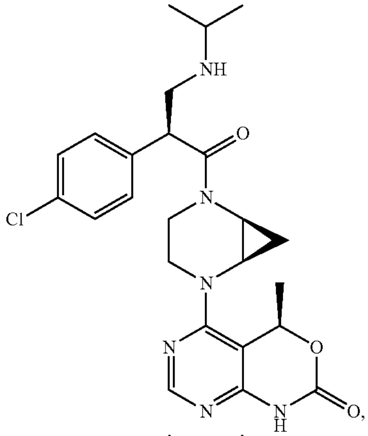
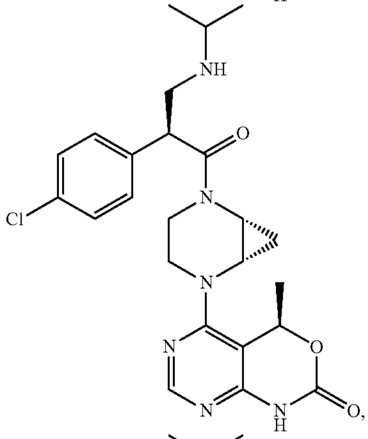
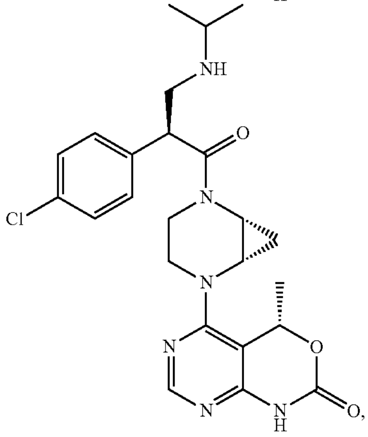
-continued
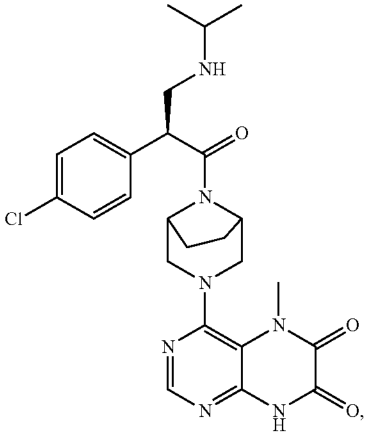
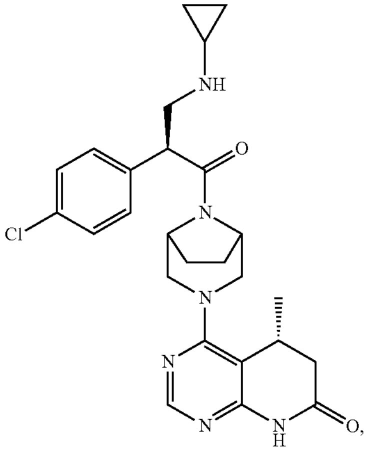
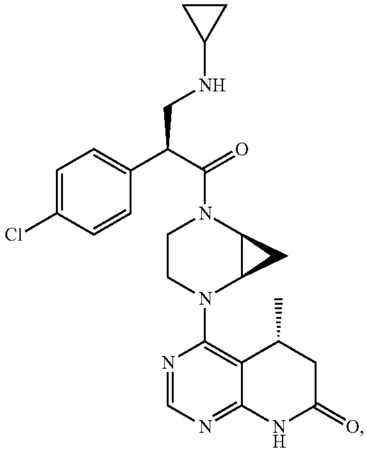

-continued

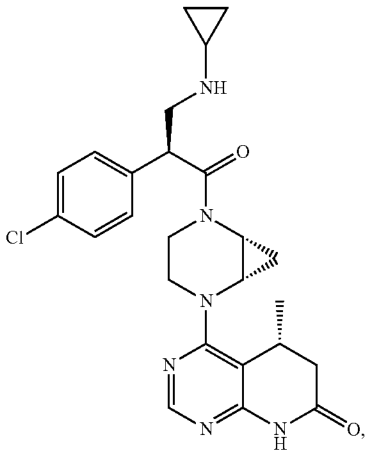

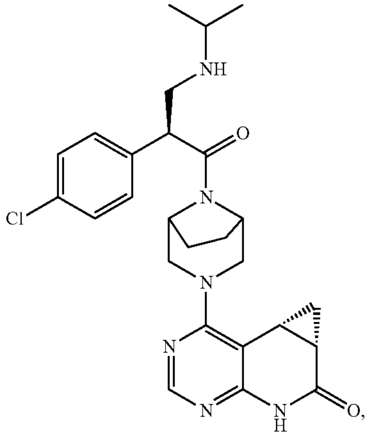

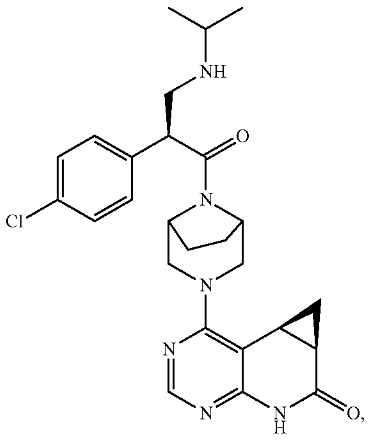 [SMILES: CC(C)NC[C@@H](C(=O)N1C2CCC1CN(c1ncnc3c1[C@H]1C[C@H]1C(=O)N3)C2)c1ccc(Cl)cc1]

-continued

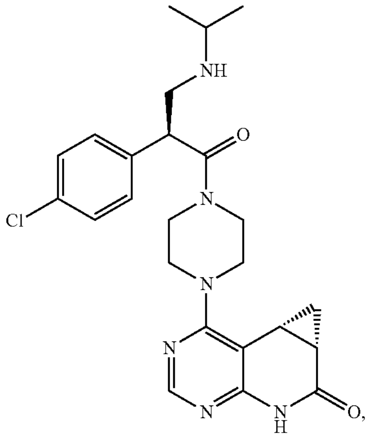

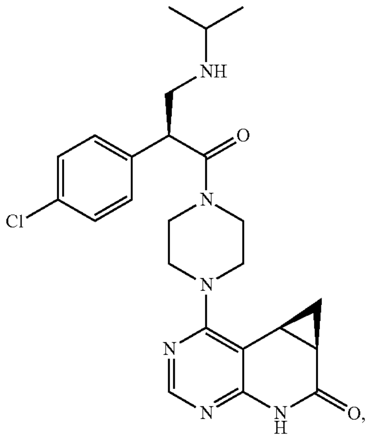

cis-(5R)-4-(5-((S)-2-(4-chlorophenyl)-3-(isopropylamino)propionyl)hexahydropyrrole[3,4-c]pyrrole-2(1H)-yl)-5-methyl-5,8-dihydropyrido[2,3-d]pyrimidin-7(6H)-one, and trans-(5R)-4-(5-((S)-2-(4-chlorophenyl)-3-(isopropylamino)propionyl)hexahydropyrrole[3,4-c]pyrrole-2(1H)-yl)-5-methyl-5,8-dihydropyrido[2,3-d]pyrimidin-7(6H)-one, or a pharmaceutically acceptable salt thereof.

12. The compound or a pharmaceutically acceptable salt thereof according to claim 1, wherein L is selected from the group consisting of

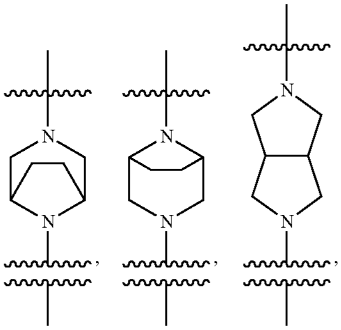

-continued

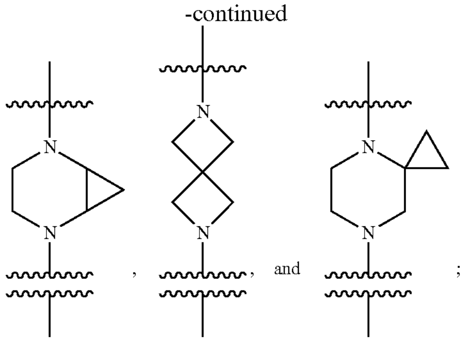

and wherein L is optionally substituted by methyl.

13. The compound or a pharmaceutically acceptable salt thereof according to claim 1, wherein L is selected from the group consisting of

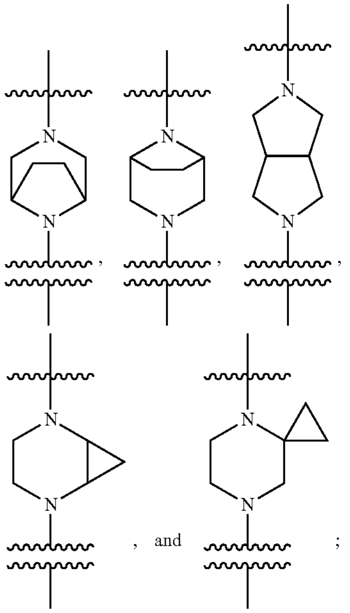

and wherein L is optionally substituted by methyl.

14. The compound or a pharmaceutically acceptable salt thereof according to claim 1, wherein the compound has the structure represented by Formula IV:

IV

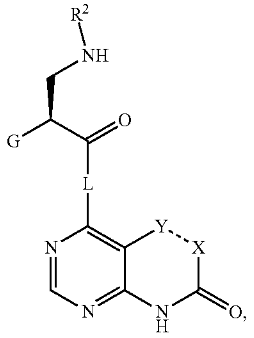

wherein $R^2$, L, G, and

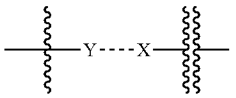

are as defined in claim 1.

15. The compound or a pharmaceutically acceptable salt thereof according to claim 1, wherein the compound has the structure represented by Formula V, Formula VIII, or Formula XI:

V

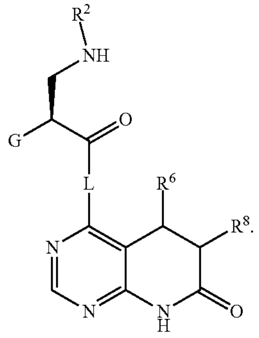

VIII

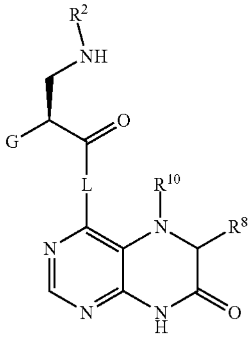

XI

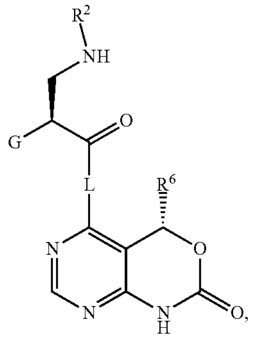

wherein $R^2$, $R^6$, $R^8$, $R^{10}$, L and G are as defined in claim 1.

16. The compound or a pharmaceutically acceptable salt thereof according to claim 1, wherein the compound has the structure represented by Formula VI, Formula IX, or Formula XII:

VI

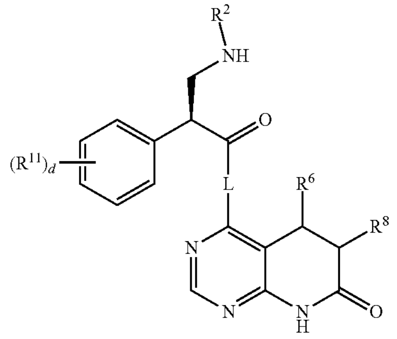

IX

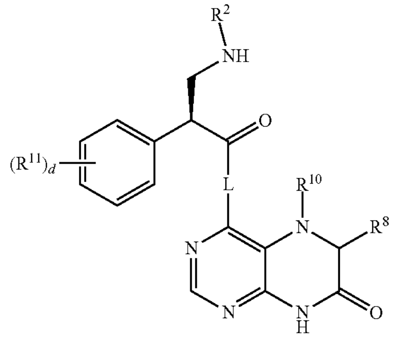

XII

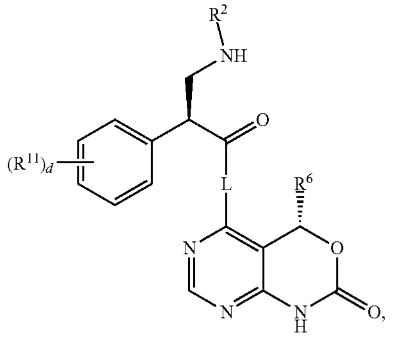

wherein $R^2$, $R^6$, $R^8$, $R^{10}$, $R^{11}$ and L are as defined in claim 1, and d is 0, 1 or 2.

17. The compound or a pharmaceutically acceptable salt thereof according to claim 1, wherein the compound has the structure represented by Formula VII:

VII

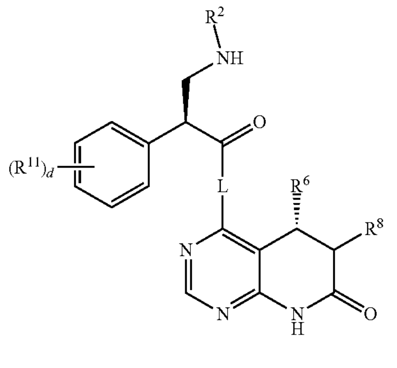

wherein, $R^2$, $R^6$, $R^8$, $R^{11}$ and L are as defined in claim 1, d is 0, 1 or 2.

18. The compound or a pharmaceutically acceptable salt thereof according to claim 1, wherein $R^2$ is $C_1$-$C_6$ alkyl or $C_3$-$C_6$ cycloalkyl; and/or $R^3$ is H.

19. The compound or a pharmaceutically acceptable salt thereof according to claim 1, wherein $R^2$ is isopropyl or cyclopropyl; and/or $R^3$ is H.

20. The compound or a pharmaceutically acceptable salt thereof according to claim 1, wherein $R^6$ is methyl or $CF_3$; and/or $R^7$ is H; and/or $R^8$ is H; and/or $R^9$ is H; and/or $R^{10}$ is methyl.

21. A compound selected from the group consisting of:

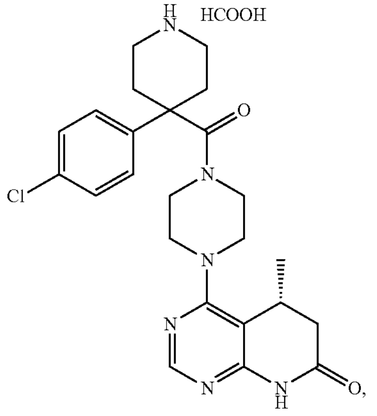

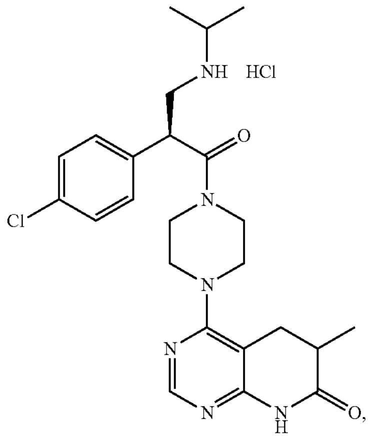

-continued
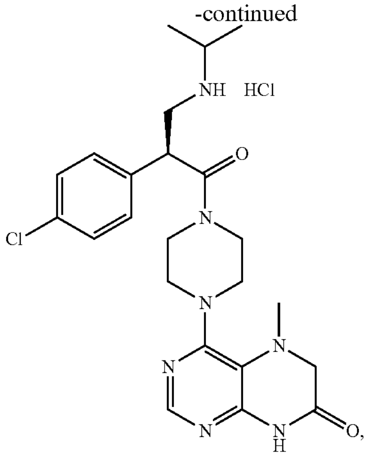
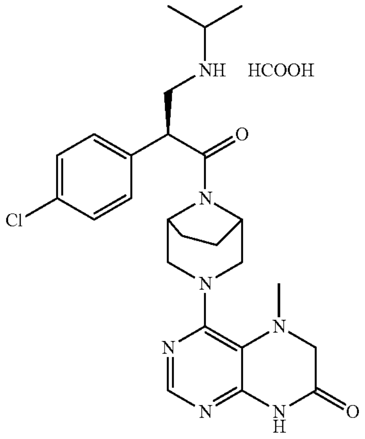
and
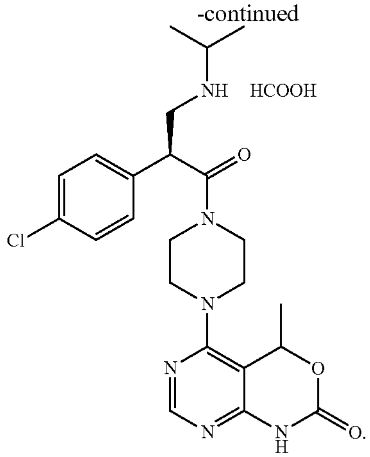
22. A method for treating breast cancer, prostate cancer or ovarian cancer, comprising administering the compound or a pharmaceutically acceptable salt thereof according to claim 1 or a pharmaceutical composition comprising the compound or a pharmaceutically acceptable salt thereof according to claim 1 to a subject in need.
* * * * *